US011091786B2

(12) United States Patent
Tam et al.

(10) Patent No.: US 11,091,786 B2
(45) Date of Patent: Aug. 17, 2021

(54) BUTELASE-MEDIATED PEPTIDE LIGATION

(71) Applicant: Nanyang Technological University, Singapore (SG)

(72) Inventors: James P Tam, Singapore (SG); Kien Truc Giang Nguyen, Singapore (SG); Yuan Cao, Singapore (SG); Chuan Fa Liu, Singapore (SG)

(73) Assignee: Nanyang Technological University, Singapore (SG)

( * ) Notice: Subject to any disclaimer, the term of this patent is extended or adjusted under 35 U.S.C. 154(b) by 476 days.

(21) Appl. No.: 15/765,156

(22) PCT Filed: Sep. 29, 2016

(86) PCT No.: PCT/SG2016/050481
§ 371 (c)(1),
(2) Date: Mar. 30, 2018

(87) PCT Pub. No.: WO2017/058114
PCT Pub. Date: Apr. 6, 2017

(65) Prior Publication Data
US 2018/0274003 A1    Sep. 27, 2018

(30) Foreign Application Priority Data

Oct. 1, 2015 (SG) .......................... 10201508158V

(51) Int. Cl.
*C07K 1/02* (2006.01)
*C07K 11/00* (2006.01)
(Continued)

(52) U.S. Cl.
CPC ................ *C12P 21/02* (2013.01); *C07K 1/02* (2013.01); *C07K 5/1019* (2013.01); *C07K 7/06* (2013.01);
(Continued)

(58) Field of Classification Search
None
See application file for complete search history.

(56) References Cited

FOREIGN PATENT DOCUMENTS

WO    90/11778 A1    10/1990
WO    94/18329 A2    8/1994
(Continued)

OTHER PUBLICATIONS

Antos et al., "Lipid Modification of Proteins through Sortase-Catalyzed Transpeptidation," *J. Am. Chem. Soc.* 130:16338-16343, 2008.

(Continued)

*Primary Examiner* — Kevin S Orwig
(74) *Attorney, Agent, or Firm* — Seed IP Law Group LLP

(57) ABSTRACT

The present invention relates to a method of forming a peptide of Formula (I) ($P^1$-$Xaa^1$-$Xaa^2$-$P^2$) by ligating a first peptide of Formula (II) ($P^1$-$Xaa^1$-X—R, wherein X is O or S) to a second peptide of Formula (III) ($Xaa^1$-$Xaa^2$-$P^2$) by enzymatically cleaving the bond between "Asx" and "X" in the first peptide of Formula (II) and ligating the fragment $P^1$-Asx of the first peptide to the second peptide of Formula (III), wherein the enzymatic cleavage and ligation reaction is catalyzed by butelase 1 (SEQ ID NO: 1) and the peptide of Formula (I) is a depsipeptide, preferably a thiodepsipeptide. Further encompassed are peptides and dendrimeric peptide assemblies prepared using the presently disclosed method, as well as use of the dendrimeric peptide assemblies as a vaccine, medicament, or diagnostic agent, particularly as an antimicrobial agent.

20 Claims, 25 Drawing Sheets
Specification includes a Sequence Listing.

(51) Int. Cl.
   C12P 21/02    (2006.01)
   C07K 7/06     (2006.01)
   C12N 9/00     (2006.01)
   C07K 5/11     (2006.01)
   C12N 9/50     (2006.01)
   A61K 38/00    (2006.01)

(52) U.S. Cl.
   CPC ............... *C07K 11/00* (2013.01); *C12N 9/50* (2013.01); *C12N 9/63* (2013.01); *C12N 9/93* (2013.01); *A61K 38/00* (2013.01)

(56) References Cited

FOREIGN PATENT DOCUMENTS

| WO | 2011/079817 A1 | 7/2011 |
| WO | 2015/163818 A1 | 10/2015 |

OTHER PUBLICATIONS

Antos et al., "Site-Specific N- and C-Terminal Labeling of a Single Polypeptide Using Sortases of Different Specificity,"*J. Am. Chem. Soc.* 131:10800-10801, 2009.
Aucagne et al., "Chemoselective Formation of Successive Triazole Linkages in One Pot: 'Click-Click' Chemistry," *Org. Lett.* 8(20):4505-4507, 2006.
Baker et al., "N-Terminally PEGylated Human Interferon-β-1a with Improved Pharmacokinetic Properties and in Vivo Efficacy in a Melanoma Angiogenesis Model," *Bioconjugate Chem.* 17:179-188, 2006.
Barber et al., "The Two-step Biosynthesis of Cyclic Peptides from Linear Precursors in a Member of the Plant Family Caryophyllaceae Involves Cyclization by a Serine Protease-like Enzyme," *Journal of Biological Chemistry* 288(18):12500-12510, 2013.
Beckmann et al., "One-Pot Procedure for Diazo Transfer and Azide-Alkyne Cycloaddition: Triazole Linkages from Amines," *Org. Lett.* 9(1):1-4, 2007.
Boman, "Antibacterial peptides: basic facts and emerging concepts," *Journal of Internal Medicine* 254:197-215, 2003.
Boman, "Peptide Antibiotics and Their Role in Innate Immunity," *Annu. Rev. Immunol.* 13:61-92, 1995.
Boutureira et al., "Advances in Chemical Protein Modification," *Chem. Rev.* 115:2174-2195, 2015.
Camarero, "Review Article: Recent Developments in the Site-Specific Immobilization of Proteins Onto Solid Supports," *Peptide Science* 90(3):450-458, 2007.
Cao et al., "Butelase-Mediated Ligation as an Efficient Bioconjugation Method for the Synthesis of Peptide Dendrimers," *Bioconjugate Chem.* 27:2592-2596, 2016.
Cao et al., "Butelase-mediated synthesis of protein thioesters and its application for tandem chemoenzymatic ligation," *Chem. Commun.* 51:17289-17292, 2015.
Chalker et al., "Chemical mutagenesis: selective post-expression interconversion of protein amino acid residues," *Current Opinion in Chemical Biology* 14:781-789, 2010.
Chan et al., "Covalent Attachment of Proteins to Solid Supports and Surfaces via Sortase-Mediated Ligation," *PLoS One* 2(11):e1164, 2007. (5 pages).
Chang et al., "Subtiligase: A tool for semisynthesis of proteins," *Proc. Natl. Acad. Sci. USA* 91:12544-12548, 1994.
Chen et al., "A Novel Method for the Rational Construction of Well-Defined Immunogens: The Use of Oximation to Conjugate Cholera Toxin B Subunit to a Peptide—Polyoxime Complex," *Bioconjugate Chem.* 14:614-618, 2003.
Clow et al., "Immobilization of proteins to biacore sensor chips using *Staphylococcus aureus* sortase A," *Biotechnol. Lett.* 30:1603-1607, 2008.
Cossart et al., "Sortase, a universal target for therapeutic agents against Gram-positive bacteria?" *PNAS* 97(10):5013-5015, 2000.

Craik et al., "Plant Cyclotides: A Unique Family of Cyclic and Knotted Proteins that Defines the Cyclic Cystine Knot Structural Motif," *J. Mol. Biol.* 294:1327-1336, 1999.
Dawson et al., "Synthesis of Proteins by Native Chemical Ligation," *Science* 266(5186):776-779, 1994.
De Koning et al., "Synthetic developments towards PNA-peptide conjugates," *Current Opinion in Chemical Biology* 7:734-740, 2003.
Defoort et al., "A rational design of synthetic peptide vaccine with a built-in adjuvant," *Int. J. Peptide Protein Res.* 40:214-221, 1992.
Dramsi et al., "Covalent attachment of proteins to peptidoglycan," *FEMS Microbiol. Rev.* 32:307-320, 2008.
Drijfhout et al., "A new synthetic functionalized antigen carrier," *Int. J. Peptide Protein Res.* 37:27-32, 1991.
Findlay et al., "Cationic Host Defence Peptides: Potential as Antiviral Therapeutics," *BioDrugs* 27:479-493, 2013.
Fujita et al., "Investigation Toward Multi-Epitope Vaccine Candidates Using Native Chemical Ligation," *Peptide Science* 90(5):624-632, 2008.
Galan et al., "Chemoselective derivatization of alkaloids in periwinkle," *Chem. Commun.* 43(31):3249-3251, 2007.
Gamblin et al., "Glyco-SeS: Selenenylsulfide-Mediated Protein Glycoconjugation—A New Strategy in Post-Translational Modification," *Angew. Chem. Int. Ed.* 43:828-833, 2004.
Gilmore et al., "N-Terminal Protein Modification through a Biomimetic Transamination Reaction," *Angew. Chem. Int. Ed.* 45:5307-5311, 2006.
Giuliani et al., "Antimicrobial peptides: an overview of a promising class of therapeutics," *Central European Journal of Biology* 2(1):1-33, 2007.
Hackenberger et al., "Chemoselective Ligation and Modification Strategies for Peptides and Proteins," *Angew. Chem. Int. Ed.* 47:10030-10074, 2008.
Ito et al., "Highly Oriented Recombinant Glycosyltransferases: Site-Specific Immobilization of Unstable Membrane Proteins by Using *Staphylococcus aureus* Sortase A," *Biochemistry* 49:2604-2614, 2010.
Kalia et al., "Advances in Bioconjugation," *Current Organic Chemistry* 14:138-147, 2010.
King et al., "Developments in the Field of Bioorthogonal Bond Forming Reactions—Past and Present Trends," *Bioconjugate Chem.* 25:825-839, 2014.
Kobashigawa et al., "Attachment of an NMR-invisible solubility enhancement tag using a sortase-mediated protein ligation method," *J. Biomol. NMR* 43:145-150, 2009.
Koh et al., "N-Lipidated Peptide Dimers: Effective Antibacterial Agents against Gram-Negative Pathogens through Lipopolysaccharide Permeabilization," *J. Med. Chem.* 58:6533-6548, 2015.
Kokryakov et al., "Protegrins: leukocyte antimicrobial peptides that combine features of corticostatic defensins and tachyplesins," *Federation of European Biochemical Societies Letters* 327(2):231-236, 1993.
Lee et al., "Using Marine Natural Products to Discover a Protease that Catalyzes Peptide Macrocyclization of Diverse Substrates," *J. Am. Chem. Soc.* 131:2122-2124, 2009.
Li et al., "A Direct Method for Site-Specific Protein Acetylation," *Angew. Chem. Int. Ed.* 50:9611-9614, 2011.
Li et al., "Direct preparation of peptide thioesters using an Fmoc solid-phase method," *Tetrahedron Letters* 39:8669-8672, 1998.
Liebscher et al., "N-Terminal Protein Modification by Substrate-Activated Reverse Proteolysis," *Angew. Chem. Int. Ed.* 53:3024-3028, 2014.
Lin et al., "A Chemoenzymatic Approach to Glycopeptide Antibiotics," *J. Am. Chem. Soc.* 126:13998-14003, 2004.
Liu et al., "Irreversible Sortase A-Mediated Ligation Driven by Diketopiperazine Formation," *J. Org. Chem.* 79:487-492, 2014.
Liu et al., "Multivalent Antimicrobial Peptides as Therapeutics: Design Principles and Structural Diversities," *Int. J Pept. Res. Ther.* 16:199-213, 2010. (16 pages).
Lok et al., "Differential regulation of RNF8-mediated Lys48- and Lys63-based poly-ubiquitylation," *Nucleic Acids Research* 40(1):196-205, 2012.

(56) References Cited

OTHER PUBLICATIONS

Lu et al., "Chemically Unambiguous Peptide Immunogen: Preparation, Orientation and Antigenicity of Purified Peptide Conjugated to the Multiple Antigen Peptide System," *Molecular Immunology* 28(6):623-630, 1991.
Lundquist, IV, et al., "Improved Solid-Phase Peptide Synthesis Method Utilizing α-Azide-Protected Amino Acids," *Org. Lett.* 3(5):781-783, 2001.
Mao et al., "Sortase-Mediated Protein Ligation: A New Method for Protein Engineering," *J. Am. Chem. Soc.* 126:2670-2671, 2004.
Marraffini et al., "Sortases and the Art of Anchoring Proteins to the Envelopes of Gram-Positive Bacteria," *Microbiol. Mol. Biol. Rev.* 70(1):192-221, 2006.
Matsumoto et al., "Site-specific tetrameric streptavidin-protein conjugation using sortase A," *Journal of Biotechnology* 152:37-42, 2011.
Mazmanian et al., "Sortase-catalysed anchoring of surface proteins to the cell wall of *Staphylococcus aureus*," *Molecular Microbiology* 40(5):1049-1057, 2001.
Mazmanian et al., "*Staphylococcus aureus* Sortase, an Enzyme that Anchors Surface Proteins to the Cell Wall," *Science* 285(5428):760-763, 1999.
Monsó et al., "Influence of Conjugation Chemistry and B Epitope Orientation on the Immune Response of Branched Peptide Antigens," *Bioconjugate Chemistry* 24(4):578-585, 2013.
Nguyen et al., "Butelase 1 is an Asx-specific ligase enabling peptide macrocyclization and synthesis," *Nature Chemical Biology* 10:732-740, 2014.
Nguyen et al., "Butelase 1: A Versatile Ligase for Peptide and Protein Macrocyclization," *J. Am. Chem. Soc.* 137:15398-15401, 2015.
Nguyen et al., "Discovery of Linear Cyclotides in Monocot Plant *Panicum laxum* of Poaceae Family Provides New Insights into Evolution and Distribution of Cyclotides in Plants," *Journal of Biological Chemistry* 288(5):3370-3380, 2013.
Nguyen et al., "Novel Cyclotides and Uncyclotides with Highly Shortened Precursors from *Chassalia chartacea* and Effects of Methionine Oxidation on Bioactivities," *Journal of Biological Chemistry* 287(21):17598-17607, 2012.
Nguyen et al., "Site-Specific N-Terminal Labeling of Peptides and Proteins using Butelase 1 and Thiodepsipeptide," *Angew. Chem.* 127:15920-15924, 2015.
Nyffeler et al., "The Chemistry of Amine-Azide Interconversion: Catalytic Diazotransfer and Regioselective Azide Reduction," *J. Am. Chem. Soc.* 124:10773-10778, 2002.
Parthasarathy et al., "Sortase A as a Novel Molecular 'Stapler' for Sequence-Specific Protein Conjugation," *Bioconjugate Chem.* 18:469-476, 2007.
Pasunooti et al., "Synthesis of 4-mercapto-L-lysine derivatives: Potential building blocks for sequential native chemical ligation," *Bioorg. Med. Chem. Lett.* 19:6268-6271, 2009.
Popp et al., "Making and Breaking Peptide Bonds: Protein Engineering Using Sortase," *Angew. Chem. Int. Ed.* 50:5024-5032, 2011.
Popp et al., "Sortagging: a versatile method for protein labeling," *Nature Chemical Biology* 3(11):707-708, 2007.
Posnett et al., "A Novel Method for Producing Anti-peptide Antibodies: Production of Site-Specific Antibodies to the T Cell Antigen Receptor β-Chain," *The Journal of Biological Chemistry* 263(4):1719-1725, 1988.
Pritz et al., "Synthesis of Biologically Active Peptide Nucleic Acid-Peptide Conjugates by Sortase-Mediated Ligation," *J. Org. Chem.* 72:3909-3912, 2007.
Pritz, "Enzymes in Protein Ligation: The Coupling of Peptides, Peptide Nucleic Acids and Proteins by Sortase A," *Mini-Reviews in Organic Chemistry* 5:47-52, 2008.

Proft, "Sortase-mediated protein ligation: an emerging biotechnology tool for protein modification and immobilisation," *Biotechnol. Lett.* 32:1-10, 2010.
Rao et al., "Synthesis of Peptide Dendrimer," *J. Am. Chem. Soc.* 116:6975-6976, 1994.
Rashidian et al. "Enzymatic Labeling of Proteins: Techniques and Approaches," *Bioconjugate Chemistry* 24:1277-1294, 2013.
Ritzefeld, "Sortagging: A Robust and Efficient Chemoenzymatic Ligation Strategy," *Chem. Eur. J.* 20:8516-8529, 2014.
Rose et al., "A Synthetic Peptide-Based Polyoxime Vaccine Construct of High Purity and Activity," *Molecular Immunology* 32(14/15): 1031-1037, 1995.
Sadler et al., "Peptide dendrimers: applications and synthesis," *Reviews in Molecular Biotechnology* 90:195-229, 2002.
Sakamoto et al., "Enzyme-Mediated Site-Specific Antibody-Protein Modification Using a ZZ Domain as a Linker," *Bioconjugate Chem.* 21:2227-2233, 2010.
Samantaray et al., "Peptide-Sugar Ligation Catalyzed by Transpeptidase Sortase: A Facile Approach to Neoglycoconjugate Synthesis," *J. Am. Chem. Soc.* 130:2132-2133, 2008.
Saska et al., "An Asparaginyl Endopeptidase Mediates in Vivo Protein Backbone Cyclization," *Journal of Biological Chemistry* 282(40):29721-29728, 2007.
Speers et al., "Activity-Based Protein Profiling in Vivo Using a Copper(I)-Catalyzed Azide-Alkyne [3+2] Cycloaddition," *J. Am. Chem. Soc.* 125:4686-4687, 2003.
Spetzler et al., "Unprotected peptides as building blocks for branched peptides and peptide dendrimers," *Int. J. Peptide Protein Res.* 45:78-85, 1995.
Tam et al., "Antimicrobial dendrimeric peptides," *Eur. J. Biochem.* 269:923-932, 2002.
Tam et al., "Design of Salt-Insensitive Glycine-Rich Antimicrobial Peptides with Cyclic Tricystine Structures," *Biochemistry* 39:7159-7169, 2000.
Tam et al., "Membranolytic selectivity of cystine-stabilized cyclic protegrins," *Eur. J. Biochem.* 267:3289-3300, 2000.
Tam, "Synthetic peptide vaccine design: Synthesis and properties of a high-density multiple antigenic peptide system," *Proc. Natl. Acad. Sci. USA* 85:5409-5413, 1988.
Tanaka et al., "Site-Specific Protein Modification on Living Cells Catalyzed by Sortase," *ChemBioChem* 9:802-807, 2008.
Tang et al., "A Cyclic Antimicrobial Peptide Produced in Primate Leukocytes by the Ligation of Two Truncated α-Defensins," *Science* 286(5439):498-502, 1999. (6 pages).
Theile et al., "Site-specific N-terminal labeling of proteins using sortase-mediated reactions," *Nature Protocols* 8(9):1800-1808, 2013.
Ton-That et al., "Purification and characterization of sortase, the transpeptidase that cleaves surface proteins of *Staphylococcus aureus* at the LPXTG motif," *Proc. Natl. Acad. Sci. USA* 96(22):12424-12429, 1999.
Tsukiji et al., "Sortase-Mediated Ligation: A Gift from Gram-Positive Bacteria to Protein Engineering," *ChemBioChem* 10:787-798, 2009.
Wang et al., "Bioconjugation by Copper(I)-Catalyzed Azide-Alkyne [3+2] Cycloaddition," *J. Am. Chem. Soc.* 125:3192-3193, 2003.
Williamson et al., "Depsipeptide substrates for sortase-mediated N-terminal protein ligation," *Nature Protocols* 9(2):253-262, 2014.
Williamson et al., "Efficient N-Terminal Labeling of Proteins by Use of Sortase," *Angew. Chem. Int. Ed.* 51:9377-9380, 2012.
Xie et al., "A chemical toolkit for proteins—an expanded genetic code," *Nature Reviews Molecular Cell Biology* 7:775-782, 2006.
Yamamura et al., "Enhancement of sortase A-mediated protein ligation by inducing a β-hairpin structure around the ligation site," *Chem. Commun.* 47:4742-4744, 2011.
Yang et al., "Dual Native Chemical Ligation at Lysine," *J. Am. Chem. Soc.* 131:13592-13593, 2009.
Yang et al., "Synthesis of K48-linked diubiquitin using dual native chemical ligation at lysine," *Chem. Commun.* 46:7199-7201, 2010.

a) Previous work: Butelase-mediated ligation using peptide substrate b) This work: Butelase-mediated ligation using thiodepsipeptide substrate $Y_1$ = All natural amino acids except Pro
$Y_2$ = Ile/Val/Leu/Cys R = H or A) Butelase-mediated ligation using native peptide as acyl donor B) Butelase-mediated ligation using thiodepsipeptide as acyl donor

A) Dimer assembly using thiodepsipeptide 1 after 30 min

B) Dimer assembly using normal peptide 4

A) Tetramer assembly after 45 min

B) Octamer assembly after 180 min

BUTELASE-MEDIATED PEPTIDE LIGATION

CROSS-REFERENCE TO RELATED APPLICATION

This application makes reference to and claims the benefit of priority of a Singapore Application for "Site-specific N-terminal Labelling of Peptides and Proteins using butelase 1 and Thiodepsipeptide" filed on Oct. 1, 2015, and duly assigned application Ser. No. 10201508158V. The content of said application filed on Oct. 1, 2015, is incorporated herein by reference for all purposes, including an incorporation of any element or part of the description, claims or drawings not contained herein and referred to in Rule 20.5(a) of the PCT, pursuant to Rule 4.18 of the PCT.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_540USPC_SEQUENCE_LISTING.txt. The text file is 446 KB, was created on Mar. 30, 2018, and is being submitted electronically via EFS-Web.

FIELD OF THE INVENTION

The present invention relates generally to a method of enzymatically ligating peptides.

BACKGROUND OF THE INVENTION

Site-specific protein modifications with tags and probes offer useful tools for various biochemical studies involving protein-protein interactions (J. Biotechnol. 2011, 152, 37; Bioconjug Chem 2010, 21, 2227; J. Am. Chem. Soc: 2008, 130, 16338), structure-function relationships (J Biomol NMR 2009, 43, 145), biomaterials (Biopolymers 2008, 90, 450; PLoS One 2007, 2, e1164; Biotechnology letters 2008, 30, 1603; Biochemistry (Most.) 2010, 49, 2604; Bioconjug. Chem. 2007, 18, 469) and therapeutics (Curr Opin Chem Biol 2003, 7, 734; J Org Chem 2007, 72, 3909). A common approach is by chemical means (Angew Chem Int Ed Engl 2008, 47, 10030). Many employ N-terminal amino acid- or side chain functional group-specific methods (Bioconjug Chem 2003, 14, 614; Science 1994, 266, 776; Angewandte Chemie International Edition 2006, 45, 5307) which include cysteine-directed derivatization (Science 1994, 266, 776; Curr Opin Chem Biol 2010, 14, 781; Angew Chem Int Ed Engl 2004, 43, 828; Angew Chem Int Ed Engl 2011, 50, 9611), conjugation of lysine side chain (Bioorg Med Chem Lett 2009, 19, 6268; J Am Chem Soc 2009, 131, 13592; Chem Commun (Camb) 2010, 46, 7199), and Click reaction (Bioconjug Chem 2003, 14, 614; Science 1994, 266, 776; Angewandte Chemie International Edition 2006, 45, 5307; Org Lett 2006, 8, 4505; Org Left 2007, 9, 1; Chem Commun (Camb) 2007, 3249; J Am Chem Soc 2004, 126, 13998; Org Lett 2001, 3, 781; J Am Chem Soc 2002, 124, 10773; J Am Chem Soc 2003, 125, 4686; J Am Chem Soc 2003, 125, 3192). Despite being powerful and robust, chemical methods generally require an excess amount of a labeling reagent, and a carefully controlled reaction condition (Bioconjug Chem 2006, 17, 179). Often, site specificity becomes a challenge when multiple copies of a targeted amino acid or functional group are present in a protein substrate (Angewandte Chemie International Edition 2006, 45, 5307). Recently, enzymatic approaches using peptide ligases under mild reaction conditions provide an attractive alternative with exquisite site-specificity (J Org Chem 2007, 72, 3909; J Am Chem Soc 2004, 126, 2670; Nat Chem Biol 2007, 3, 707; Angew Chem Int Edit 2011, 50, 5024; Mini-Rev Org Chem 2008, 5, 47; Biotechnology Letters 2010, 32, 1; J Am Chem Soc 2008, 130, 2132; Chembiochem 2008, 9, 802; ChemBioChem 2009, 10, 787; Angew. Chem. Int. Ed. Engl. 2014, 53, 3024). Enzymatic ligation is C-terminal-amino-acid-specific and orthogonal to chemical approaches in achieving protein labeling and conjugation reactions. Currently, sortase A is the most popular ligase (Proc. Natl. Acad. Sci. U.S.A. 2000, 97, 5013; FEMS Microbiol Rev 2008, 32, 307; Microbiol Mol Biol Rev 2006, 70, 192; Science 1999, 285, 760; Mol. Microbiol. 2001, 40, 1049; Proc. Natl. Acad. Sci. U.S.A 1999, 96, 12424), but it has low catalytic efficiency, requires a long reaction time and a high molar equivalent of enzyme (typically 0.1 to 1 molar ratio) (Angew Chem Int Ed Engl 2008, 47, 10030; J Am Chem Soc 2009, 131, 10800; J Org Chem 2014, 79, 487; Angew. Chem. Int. Ed. Engl. 2012, 51, 9377; Chem Commun (Camb) 2011, 47, 4742; Nat. Protoc. 2013, 8, 1800). In addition, sortase A has a stringent substrate requirement, leaving behind an additional sorting sequence LPXTG in the resulting modified proteins (Proc. Natl. Acad. Sci. U.S.A. 1999, 96, 12424). A ligase with a broad substrate specificity, efficient kinetics, and traceless ligation would be highly desirable.

Recently, as disclosed in the International Patent Publication No. WO2015163818 A1, which is hereby incorporated by reference in its entirety, the inventors of the present invention isolated an Asn/Asp(Asx)-specific ligase called butelase 1 from the medicinal plant *Clitoria ternatea* (Nat Chem Biol 2014, 10, 732). Butelase 1 is a cysteine ligase mediating the backbone cyclization in the biosynthesis of cyclotides, a family of circular plant defense peptides (J Mol Biol 1999, 294, 1327; J. Biol. Chem. 2013, 288, 3370; J. Biol. Chem. 2012, 287, 17598; J. Biol. Chem. 2007, 282, 29721). Butelase 1 has three attractive features: (1) it is the fastest known ligase with high catalytic efficiencies of up to 542,000 $M^{-1}$ $s^{-1}$ (Nat Chem Biol 2014, 10, 732; J. Biol. Chem. 2013, 288, 12500; J Am Chem Soc 2009, 131, 2122), (2) it is C-terminal specific for Asx with a sorting signal not more than two amino acids after Asx, and (3) it displays a very broad specificity for the acceptor nucleophilic amino acids (all natural amino acids except Pro) to form a new Asx-Xaa peptide bond. These features make butelase 1 an attractive new tool for protein engineering. However, while the butelase-mediated intramolecular ligation proceeds with high efficiency and is irreversible, the intermolecular peptide ligation is reversible and requires an excess amount of substrate to drive the reaction to completion (Nat Chem Biol 2014, 10, 732), a condition also found in sortase A (J Am Chem Soc 2004, 126, 2670; Nat Chem Biol 2007, 3, 707; Angew Chem Int Edit 2011, 50, 5024; Mini-Rev Org Chem 2008, 5, 47; Biotechnology Letters 2010, 32, 1).

Therefore, there is still need in the art for alternative methods that overcome the drawbacks of existing techniques.

SUMMARY OF THE INVENTION

The present invention satisfies the aforementioned need in the art by providing the presently disclosed method.

In a first aspect, the present invention provides a method of forming a peptide of Formula (I)

$$P^1\text{-Asx-Xaa}^1\text{-Xaa}^2\text{-}P^2 \qquad (I)$$

by ligating a first peptide of Formula (II)

P¹-Asx-X—R  (II)

to a second peptide of Formula (III)

Xaa¹-Xaa²-P²  (III), wherein P¹ and P² are each independently any peptide, modified or unmodified; Asx is Asp or Asn, preferably Asn; X is O or S, preferably S; R is a substituted or unsubstituted alkyl, preferably selected from the group consisting of —(CH$_2$)$_n$—CONH$_2$, —(CH$_2$)$_n$—COOH, —(CH$_2$)$_n$CO-AA¹,

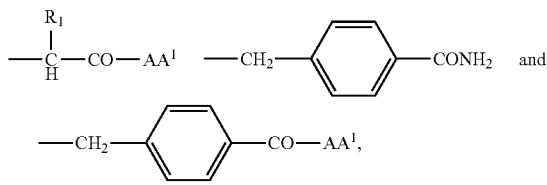

wherein n is an integer of 1 to 10, R$_1$ is H, or any other side chain of a naturally occurring amino acid, and AA¹ is any amino acid or is absent; Xaa¹ is any naturally occurring amino acid with the exception of Pro; Xaa² is any naturally occurring amino acid, but preferably is a hydrophobic amino acid or Cys, more preferably Val, Ile, Leu, or Cys, by enzymatically cleaving the bond between "Asx" and "X" in the first peptide of Formula (II) and ligating the fragment P¹-Asx of the first peptide to the second peptide of Formula (III) to form a ligated peptide of Formula (I), wherein the enzymatic cleavage and ligation reaction is catalyzed by a polypeptide having the activity of butelase 1 (SEQ ID NO:1) under conditions allowing said ligation.

In various embodiments, Asx is Asn, X is S, R is —CH (R$_1$)—CO-AA¹, R$_1$ is H, and AA¹ is any amino acid or absent.

In various embodiments, Asx is Asn, X is S, R is —CH (R$_1$)—CO-AA¹, R$_1$ is H, and AA¹ is Val.

In various embodiments, the polypeptide having the ligase activity of butelase 1 (SEQ ID NO:1) comprises or consists of:
(a) the amino acid sequence as set forth in SEQ ID NO:1 (butelase 1);
(b) an amino acid sequence that shares at least 60, preferably at least 70, even more preferably at least 80, most preferably at least 90% sequence identity with the amino acid sequence as set forth in SEQ ID NO:1; or
(c) an amino acid sequence that shares at least 80, preferably at least 90, more preferably at least 95% sequence homology with the amino acid sequence as set forth in SEQ ID NO:1; or
(d) a fragment of any one of (a)-(c).

In various embodiments, the polypeptide having the ligase activity of butelase 1 (SEQ ID NO:1) comprises or consists of the amino acid sequence as set forth in SEQ ID NO:2.

In various embodiments, the polypeptide having the ligase activity of butelase 1 (SEQ ID NO:1) comprises
(a) the amino acid residue Asn at the position corresponding to position 19 of SEQ ID NO:1; and/or
(b) the amino acid residue His at the position corresponding to position 124 of SEQ ID NO:1; and/or
(c) the amino acid residue Cys at the position corresponding to position 166 of SEQ ID NO:1.

In various embodiments, the polypeptide having the ligase activity of butelase 1 (SEQ ID NO:1) is the polypeptide as described above or comprises or consists of
(a) any one of the amino acid sequences as set forth in SEQ ID Nos:3-109;
(b) an amino acid sequence that shares at least 60, preferably at least 70, more preferably at least 80, most preferably at least 90% sequence identity with any one of the amino acid sequences of (a) over its entire length;
(c) an amino acid sequence that shares at least 80, preferably at least 90, more preferably at least 95% sequence homology with any one of the amino acid sequences of (a) over its entire length; or
(d) a fragment of any one of (a)-(c).

In various embodiments, P¹ or P² is modified by an affinity tag, a detectable label, a solid support material, or a scaffold molecule.

In various embodiments, P¹ or P² is modified by a biotin, a fluorescent marker, a polymer resin, or a dendrimer.

In various embodiments, P¹ or P² is modified by a dendrimer.

In various embodiments, each dendrimer is conjugated to 2 or more copies of the second peptide via P², such that the ligation of the first peptide and the second peptide results in a dendrimeric peptide assembly comprising 2 or more copies of the ligated peptide P¹-Asx-Xaa¹-Xaa²-P².

In various embodiments, the dendrimer is a lysyl dendrimer.

In various embodiments, the first peptide is P¹-Asn-thioglc-Val, and P¹ is an antimicrobial peptide.

In various embodiments, P¹ is an antimicrobial peptide comprising a BHHB tetrapeptide motif.

In various embodiments, P¹ is an antimicrobial peptide comprising an Arg-Leu-Tyr-Arg (SEQ ID NO:121) tetrapeptide.

In various embodiments, the first peptide is Ac-Arg-Leu-Tyr-Arg-Asn-thioglc-Val (SEQ ID NO:120).

In various embodiments, the second peptide is Arg-Ile-βAla conjugated to a lysyl dendrimer via βAla.

In various embodiments, the first peptide is Ac-Arg-Leu-Tyr-Arg-Asn-thioglc-Val (SEQ ID NO:120), and each lysyl dendrimer is conjugated to 2 or more copies of the second peptide Arg-Ile-βAla via βAla, such that the ligation of the first peptide and the second peptide results in a dendrimeric peptide assembly comprising 2 or more copies of Ac-Arg-Leu-Tyr-Arg-Asn-Arg-Ile-βAla (SEQ ID NO:131).

In a second aspect, the invention provides peptides prepared using the presently disclosed method.

In a third aspect, the invention provides dendrimeric peptide assembly prepared using the presently disclosed method.

In various embodiments, the presently disclosed dendrimeric peptide assembly comprises 2 or more copies of Ac-Arg-Leu-Tyr-Arg-Asn-Arg-Ile-βAla (SEQ ID NO:131).

In a fourth aspect, the invention provides use of the presently disclosed dendrimeric peptide assembly as a vaccine, medicament, or diagnostic agent.

In a final aspect, the invention provides use of the presently disclosed dendrimeric peptide assembly as an antimicrobial agent.

BRIEF DESCRIPTION OF THE DRAWINGS

The invention will be better understood with reference to the detailed description when considered in conjunction with the non-limiting examples and the accompanying drawings.

Figure 1:
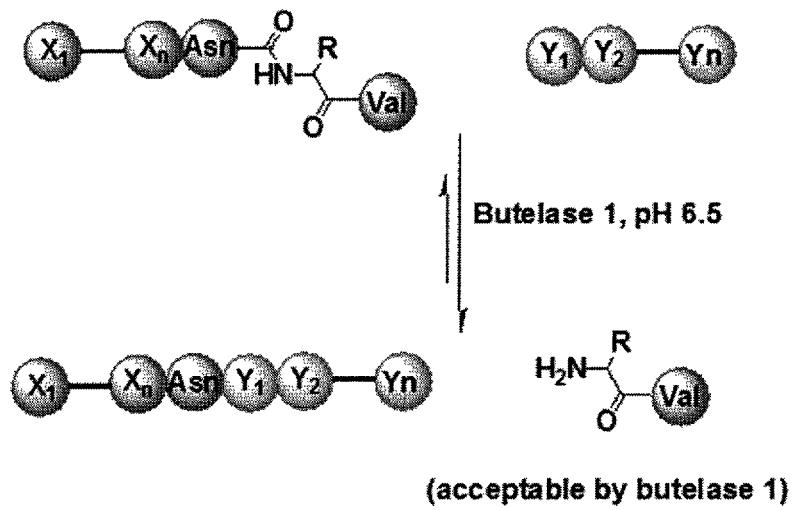
FIG. 1. Butelase 1 ligation using a) natural peptide and b) thiodepsipeptide.
Figure 1:
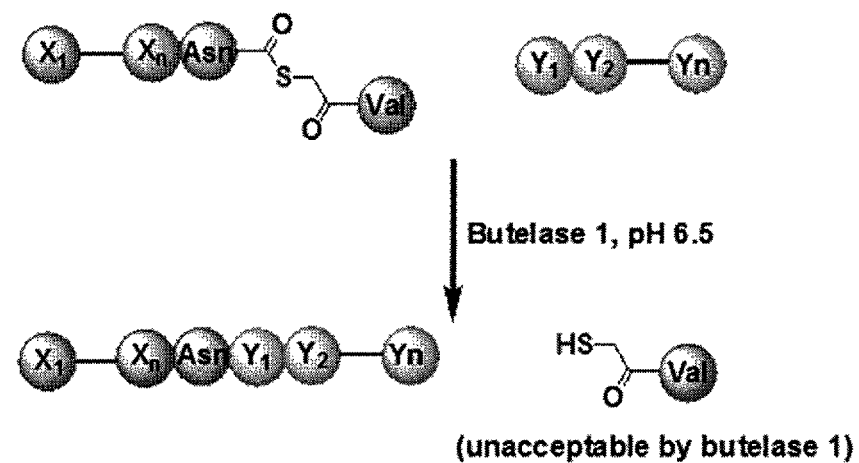
Figure 1:
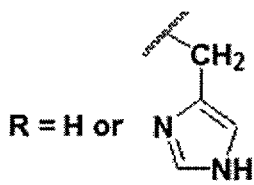

It should be noted that a significant percentage of peptide being hydrolyzed or reacting with glycerol instead of intramolecular cyclization as the model peptide contains an Arg at the second position which is not preferred by butelase 1 for cyclization.

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

The object of the present invention is to provide a technique for ligating peptides, taking advantage of the superior site specificity and catalytic efficiency of butelase 1-like Asx-specific protein ligases.

To this end, provided in a first aspect of the present disclosure is a method of forming a peptide of Formula (I)

P$^1$-Asx-Xaa$^1$-Xaa$^2$-P$^2$     (I)

by ligating a first peptide of Formula (II)

P$^1$-Asx-X—R     (II)

to a second peptide of Formula (III)

Xaa$^1$-Xaa$^2$-P$^2$     (III), wherein P$^1$ and P$^2$ are each independently any peptide, modified or unmodified; Asx is Asp or Asn, preferably Asn; X is O or S, preferably S; R is a substituted or unsubstituted alkyl, preferably selected from the group consisting of —(CH$_2$)$_n$—CONH$_2$, —(CH$_2$)$_n$—COOH, —(CH$_2$)—CO-AA$^1$,

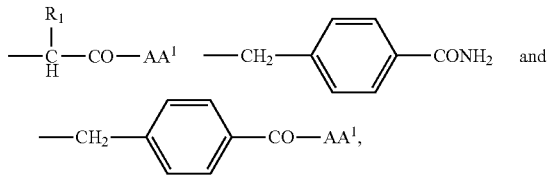

wherein n is an integer of 1 to 10, R$_1$ is H, or any other side chain of a naturally occurring amino acid, and AA$^1$ is any amino acid or is absent; Xaa$^1$ is any naturally occurring amino acid with the exception of Pro; Xaa$^2$ is any naturally occurring amino acid, but preferably is a hydrophobic amino acid or Cys, more preferably Val, Ile, Leu, or Cys, by enzymatically cleaving the bond between "Asx" and "X" in the first peptide of Formula (II) and ligating the fragment P$^1$-Asx of the first peptide to the second peptide of Formula (III) to form a ligated peptide of Formula (I), wherein the enzymatic cleavage and ligation reaction is catalyzed by a polypeptide having the activity of butelase 1 (SEQ ID NO:1) under conditions allowing said ligation.

It is also envisaged that, when the first peptide and the second peptide are the same peptide, the presently disclosed method cyclizes said peptide.

In the whole context of the present application, the terms "polypeptide", "peptide" and "protein" are used interchangeably to refer to polymers of amino acids of any length connected by peptide bonds. The polymer may comprise modified amino acids, it may be linear or branched, and it may be interrupted by non-amino acids. The terms also encompass an amino acid polymer that has been modified naturally or by intervention; for example, disulfide bond formation, glycosylation, lipidation, acetylation, phosphorylation, or any other manipulation, such as conjugation to a labeling component.

The term "amino acid" refers to natural and/or unnatural or synthetic amino acids, including both the D and L optical isomers, amino acid analogs (for example norleucine is an analog of leucine) and peptidomimetics. The term "naturally occuring amino acid", as used herein, relates to the 20 naturally occuring L-amino acids, namely Gly, Ala, Val, Leu, Ile, Phe, Cys, Met, Pro, Thr, Ser, Glu, Gln, Asp, Asn, His, Lys, Arg, Tyr, and Trp. The term "peptide bond" refers to a covalent amide linkage formed by loss of a molecule of water between the carboxyl group of one amino acid and the amino group of a second amino acid. For example, the "-" between P$^1$ and Asx in Formula (II), as well as all "-" in Formulae (I) and (III) represent peptide bonds. The "-" between X and R in Formula (II) represents a covalent bond. In addition, the "-" between C(O) and AA$^1$ in —(CH$_2$)—CO-AA$^1$, —CH(R$_1$)—CO-AA$^1$, and —CH$_2$—C$_6$H$_4$—CO-AA$^1$ represents a covalent bond between the carbonyl group and the amino group of AA$^1$, i.e. the carbonyl group shown and the amino group of AA$^1$ also form a peptide bond.

Generally, in all formulae depicted herein, the peptides are shown in the N- to C-terminal orientation.

The term "hydrophobic amino acid", as used herein, refers to an amino acid selected from the group consisting of Ala, Gly, Ile, Leu, Met, Phe, Pro, Trp, and Val.

The term "amino acid side chain" as used herein refers to a moiety attached to the α-carbon in an amino acid, preferably a naturally occuring amino acid. For example, the amino acid side chain may be methyl, isopropyl, 1-methylpropyl, 2-methylpropyl, benzyl, methyl(4-hydroxyphenyl), hydroxymethyl, 1-hydroxy-ethyl, carboxymethyl, 2-carboxyethyl, etc.

The term "alkyl", as used herein, refers to a linear, branched, or cyclic saturated hydrocarbon group. The term "unsubstituted" means that the specified group bears no substituents but the respective positions are occupied by hydrogen atoms only. By "substituted" as in "substituted alkyl" is meant that in the alkyl at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonate (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl). In addition, the aforementioned functional groups may, if a particular group permits, be further substituted with one or more additional functional groups. By "($C_x$-$C_y$)" (x and y being two different integers) is meant that the group contains x to y carbon atoms.

Without wishing to be bound to any particular theory, applicant believes that, the sorting signal HX—R, e.g. HXC(HR$_1$)C(O)-AA$^1$, cleaved off from the first peptide is a non-substrate of the polypeptide having the ligase activity of butelase 1 (SEQ ID NO:1), consequently rendering the ligation process essentially irreversible.

In various embodiments, Asx is Asp or Asn, X is O or S, R is —CH(R$_1$)—CO-AA$^1$, R$_1$ is H, or any other side chain of a naturally occurring amino acid, and AA$^1$ is any amino acid or is absent. Accordingly, the sorting signal HX—R (i.e. HX—C(HR$_1$)—C(O)-AA$^1$) is a modified peptide wherein the amino group of the first amino acid is substituted by —O— or —S—. When AA$^1$ is absent, the sorting signal HX—C(HR$_1$)C(O)-AA$^1$ is HXC(HR$_1$)C(O)OH.

In preferred embodiments, Asx is Asn, X is S, R is —CH(R$_1$)—CO-AA$^1$, R$_1$ is H, and AA$^1$ is any amino acid or absent. In this case, the sorting signal is HS—CH$_2$C(O)-AA$^1$, which is a thiodepsipeptide.

In particularly preferred embodiments, Asx is Asn, X is S, R is —CH(R$_1$)—CO-AA$^1$, R$_1$ is H, and AA$^1$ is Val. In this case, the sorting signal is H—S—CH$_2$C(O)-Val, herein denoted as H-thioglc-Val. Accordingly, "thioglc", as used herein, represents the structure —S—CH$_2$C(O)—.

A polypeptide according to the present invention possesses the ligase activity of butelase 1 (SEQ ID NO:1) as described in International Patent Publication No. WO2015163818 A1, which is hereby incorporated by reference in its entirety.

The polypeptide is utilizable for enzymatic coupling and has an ability to site-specifically break a peptide bond and then reform a new bond with an incoming nucleophile. It is "Asx-specific" in that the amino acid C-terminal to which ligation occurs, i.e. the C-terminal end of the peptide that is ligated, is either Asn or Asp, preferably Asn. As set forth above, it recognizes the motif Asx-X—R, at the C-terminus of the first peptide of Formula (II), and mediates peptide ligation by cleaving off the sorting signal HX—R and ligating P$^1$-Asx to the N-terminal residue of the second peptide Xaa$^1$-Xaa$^2$-P$^2$ to form a ligated peptide P$^1$-Asx-Xaa$^1$-Xaa$^2$-P$^2$.

In various embodiments, the polypeptide comprises or consists of the amino acid sequence as set forth in SEQ ID NO:1 (butelase 1).

In various embodiments, the polypeptide comprises or consists of an amino acid sequence that is at least 60%, 65%, 70%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:1 over its entire length. In some embodiments, it has an amino acid sequence that shares at least 60, preferably at least 70, more preferably at least 80, most preferably at least 90% sequence identity with the amino acid sequence set forth in SEQ ID NO:1 over its entire length or has an amino acid sequence that shares at least 80, preferably at least 90, more preferably at least 95% sequence homology with the amino acid sequence set forth in SEQ ID NO:1 over its entire length.

In various embodiments, the polypeptide may be a precursor of the mature enzyme. In such embodiments, it may comprise or consist of the amino acid sequence set forth in SEQ ID NO:2. Also encompassed are polypeptides having an amino acid sequence that is at least 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:2 over its entire length.

The identity of nucleic acid sequences or amino acid sequences is generally determined by means of a sequence comparison. This sequence comparison is based on the BLAST algorithm that is established in the existing art and commonly used (cf. for example Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, i.e. the proportion of identical nucleotides or amino acid residues at the same positions or at positions corresponding to one another in an alignment. The more broadly construed term "homology", in the context of amino acid sequences, also incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous and identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity and homology herein refer to the full length of the respectively indicated nucleic acid sequence or amino acid sequence.

In various embodiments, the polypeptide described herein comprises the amino acid residue Asn at the position corresponding to position 19 of SEQ ID NO:1; and/or the amino acid residue His at the position corresponding to position 124 of SEQ ID NO:1; and/or the amino acid residue Cys at the position corresponding to position 166 of SEQ ID NO:1. It has been found that these amino acid residues putatively play a role in the catalytic activity of the polypeptide. In preferred embodiments, the polypeptides thus comprise at least two, more preferably all three of the above indicated residues at the given or corresponding positions.

While it is recognized that various polypeptides as described above may be suitable for the practice of the present invention, it is preferable to use one with potent protein ligase actively. In various embodiments, this means that it can ligate a given peptide with an efficiency of at least 50%, more preferably at least 70%, most preferably at least 90%. The protein ligation reaction is preferably comparably fast, i.e. said polypeptide can ligate two given peptides with a $K_m$ of 500 µM or less, preferably 250 µM or less; and/or a $k_{cat}$ of at least 0.05 s$^{-1}$, preferably at least 0.5 s$^{-1}$, more preferably at least 1.0 most preferably at least 1.5 s$^{-1}$. Preferred polypeptides satisfy both requirements, i.e. the $K_m$ and $k_{cat}$ requirement. Methods to determine such Michaelis-Menten kinetics are well known in the art and can be routinely applied by those skilled in the art. It is preferred that the polypeptides of the invention have at least 50%, more preferably at least 70%, most preferably at least 90% of the protein ligase activity of the enzyme having the amino acid sequence of SEQ ID NO:1.

Polypeptides according to the present application can comprise amino acid modifications, in particular amino acid substitutions, insertions, or deletions. Such polypeptides are, for example, further developed by targeted genetic modification, i.e. by way of mutagenesis methods, and optimized for specific purposes or with regard to special properties (for example, with regard to their catalytic activity, stability, etc.). The objective may be to introduce targeted mutations, such as substitutions, insertions, or deletions, into the known molecules in order, for example, to alter substrate specificity and/or improve the catalytic activity. For this purpose, in particular, the surface charges and/or isoelectric point of the molecules, and thereby their interactions with the substrate, can be modified. Alternatively or additionally, the stability of the polypeptide can be enhanced by way of one or more corresponding mutations, and its catalytic performance thereby improved. Advantageous properties of individual mutations, e.g. individual substitutions, can supplement one another.

In various embodiments, the polypeptide may be characterized in that it is obtainable from a polypeptide as described above as an initial molecule by single or multiple conservative amino acid substitution. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I=V=L=M, D=E, N=Q, K=R, Y=F, and S=T.

Alternatively or additionally, the polypeptide may be characterized in that it is obtainable from a polypeptide contemplated herein as an initial molecule by fragmentation or by deletion, insertion, or substitution mutagenesis, and encompasses an amino acid sequence that matches the initial molecule over a length of at least 150, 160, 170, 180, 190, 200, 210, 220, 230, 240, 250, 260, 270, 280, 290, 300, 310, 320, 325, 330, 331, 332, 333, 334, 335, 336, 337, 338, 339, 340, 341, or 342 continuously connected amino acids. It is preferred that in such embodiments, the amino acids Asn19, His124 and Cys166 contained in the initial molecule are still present.

In various embodiments, the present invention thus also relates to fragments of the polypeptides described herein, with said fragments retaining enzymatic activity. It is preferred that they have at least 50%, more preferably at least 70, most preferably at least 90% of the protein ligase and/or cyclase activity of the initial molecule, preferably of the polypeptide having the amino acid sequence of SEQ ID NO:1. The fragments are preferably at least 150 amino acids in length, more preferably at least 200 or 250, most preferably at least 300. It is further preferred that these fragments comprise the amino acids Asn, His and Cys at positions corresponding to positions 19, 124 and 166 of SEQ ID NO: 1. Preferred fragments therefore comprise amino acids 19-166, more preferably 10-200, most preferably 1-277 of the amino acid sequence set forth in SEQ ID NO:1.

As set forth above, the peptides to be ligated in accordance with the present application may be modified by, for example, conjugation to a labeling component, either covalently or non-covalently. A labeling component may be any molecules such as, without limitation, an affinity tag, detectable label, solid support material, or scaffold molecule. The modified peptides may be prepared using standard techniques known to those skilled in the art of synthetic organic chemistry, or may be deduced by reference to the pertinent literature.

In various embodiments, $P^1$ or $P^2$ is modified by an affinity tag, a detectable label, a solid support material, a scaffold molecule.

In various embodiments, $P^1$ or $P^2$ is modified by a biotin, a fluorescent marker, a polymer resin, or a dendrimer.

In various embodiments, $P^1$ or $P^2$ is modified by a dendrimer.

In various embodiments, each dendrimer is conjugated to 2 or more copies of the second peptide via $P^2$, such that the ligation of the first peptide and the second peptide results in a dendrimeric peptide assembly comprising 2 or more copies of the ligated peptide $P^1$-Asx-Xaa$^1$-Xaa$^2$-$P^2$.

The term "affinity tag" as used herein refers to a moiety such as biotin that can be used to separate a molecule to which the affinity tag is attached from other molecules that do not contain the affinity tag.

The term "detectable label" is intended to mean at least one label capable of directly or indirectly generating a detectable signal. In non-limiting examples, a detectable label can be an enzyme producing a detectable signal, for example by colorimetry, fluorescence or luminescence; a chromophore, such as a fluorescent, luminescent or dye compound, e.g. GFP; a group with an electron density detectable by electron microscopy or by virtue of their electrical property, such as conductivity, amperometry, voltammetry or impedance; detectable group, for example the molecules of which are sufficiently large to induce detectable modifications of their physical and/or chemical characteristics (this detection can be carried out by optical methods such as diffraction, surface plasmon resonance, surface variation or contact angle variation, or physical methods such as atomic force spectroscopy or the tunnel effect; or a radioactive molecule such as $^{32}P$, $^{35}S$ or $^{125}I$.

The term "solid support material" as used herein refers to conventional solid supports for the synthesis of peptides, which are well known for the skilled in the art. The nature of the solid support is not particularly restricted and may be an inorganic substance or an organic substance such as a cross-linked polymer.

The term "scaffold molecule" as used herein refers to a compound to which other moieties are attached (e.g., conjugated). Various scaffold molecules, e.g. dendrimers, are well known in the art.

The term "dendrimer" refers to polymers having a regular branched structure of a fractal nature. Dendrimers are well known in the art. For the purpose of this application, dendrimers include, without limitation, hyperbranched polymers, dendrigraft polymers, tecto-dendrimers, core-shell (tecto)dendrimers, hybrid linear-dendritic copolymers, dendronized polymers, dendrimer-based supramolecular assemblies, and dendrimer-functionalized solid particles, which are within the purview of one of skill in the art.

Dendrimers have a core from which the inner branches emanate. Further branches may emanate from the inner branches and so forth. Distal from the core are the terminal branches, i.e., branches from which no further branches emanate. The periphery is defined as that portion of the dendrimeric polymer attached to the distal branches from which no further branches emanate. The periphery consists of the collection of terminal chains, i.e., that portion of the dendrimeric polymer distal from the terminal branches and ending with the chain ends. As an inherent consequence of their fractal nature, dendrimers may have a large number of functional groups at their chain ends. It is the chain ends that interact with the environment of the dendrimer and impart the properties of the dendrimer. The terms "chain end" and "functional group" are somewhat synonymous. However, the term "chain end" emphasizes the physical location of a section of the dendrimer; and the term "functional group" emphasizes the physical properties imparted by the "chain end". The "functional group" may be any chemical moiety compatible for use as "chain end".

Dendrimers possess many advantages including well-defined structure, mono-dispersity, multi-valency and ease of surface functionalization and provide a flexible polymeric scaffold to incorporate one or more types of peptides for enzymatic conjugation thereto.

In preferred embodiments, the dendrimer is a lysyl dendrimer.

Lysyl dendrimers according to the present invention are, as well known in the art, molecules with a tree-like structure whereby the branching is formed of repetitive lysine units. However, lysyl dendrimers may not exclusively consist of lysine units only, but may also involve other units as linkers such as 1,6-hexandiamine or dithioacetylhexan diamine between two lysine branches.

In accordance with the present application, every terminal lysine of a lysyl dendrimer provides two amino groups that may be used for coupling of a second peptide of the present application, to which a first peptide carrying a C-terminal Asx motif of Formula (II) may be ligated as mediated by a polypeptide having the ligase activity of butelase 1 (SEQ ID NO:1) to generate a bi- or multi-valent peptide-dendrimer conjugate. Alternatively, the lysyl dendrimer may comprise a first peptide having a C-terminal Asx motif, while the peptide for conjugation to said dendrimer may bear a N-terminal acceptor sequence as described above.

In addition, one skilled in the art would readily appreciate that, using the presently disclosed method, a dendrimer may be conjugated to 2 or more different types of peptides.

In various embodiments, the first peptide is $P^1$-Asn-thioglc-Val, and $P^1$ is an antimicrobial peptide.

The term "antimicrobial peptide" as used herein refers to any peptide with antimicrobial activity. The term "antimicrobial activity" refers to the ability of a peptide of the present invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of a peptide to kill at least one bacterial species. Non-limiting examples of antimicrobial peptides include all those available in the APD (http://aps.unmc.edu/AP/main.php) and LAMP (http://biotechlab.fudan.edu.cn/database/lamp/) databases, which are hereby incorporated by reference in their entirety.

In various embodiments, $P^1$ is an antimicrobial peptide comprising a BHHB (each B represents a basic amino acid; each H represents a hydrophobic amino acid) tetrapeptide motif.

In various embodiments, P¹ is an antimicrobial peptide comprising an Arg-Leu-Tyr-Arg (SEQ ID NO:121) tetrapeptide.

In various embodiments, the first peptide is Ac-Arg-Leu-Tyr-Arg-Asn-thioglc-Val (SEQ ID NO:120). By "Ac-Arg" is meant acetyl Arginine.

In various embodiments, the second peptide is Arg-Ile-βAla conjugated to a lysyl dendrimer via βAla.

In various embodiments, the first peptide is Ac-Arg-Leu-Tyr-Arg-Asn-thioglc-Val (SEQ ID NO:120), and each lysyl dendrimer is conjugated to 2 or more copies of the second peptide Arg-Ile-βAla via βAla, such that the ligation of the first peptide and the second peptide results in a dendrimeric peptide assembly comprising 2 or more copies of Ac-Arg-Leu-Tyr-Arg-Asn-Arg-Ile-βAla (SEQ ID NO:112).

In a second aspect, the invention provides peptides prepared using the presently disclosed method.

In a third aspect, the invention provides dendrimeric peptide assembly prepared using the presently disclosed method.

In a fourth aspect, the invention provides use of the presently disclosed dendrimeric peptide assembly as a vaccine, medicament, or diagnostic agent. For administration, the composition may be dispersed in a pharmaceutically acceptable adjuvant or carrier.

In a final aspect, the invention provides use of the presently disclosed dendrimeric peptide assembly as an antimicrobial agent.

The present invention is further illustrated by the following examples. However, it should be understood, that the invention is not limited to the exemplified embodiments.

EXAMPLES

Example 1: Site-Specific N-Terminal Labeling of Peptides and Proteins Using Butelase 1 and Thiodepsipeptide A. Materials and Reagents Amino acids, coupling reagents and resins were obtained from Chemimpex, Novabiochem and GL Biochem. All other chemical reagents were of analytical grade, and were obtained from Sigma Aldrich, Alfa Aesar and Acros Organics. All solvents and chemicals were used as received without purification unless otherwise indicated. Mouse anti-ubiquitin antibody was obtained from Santa Cruz biotechnology, anti-mouse secondary antibody was purchased from Dako, and anti-biotin, HRP-linked antibody was from Cell Signaling Technology.

B. High Performance Liquid Chromatography (HPLC)

Analytical RP-HPLC was run on a Nexera LC-30AD instrument (Shimadzu) with an analytical column (Aeris peptide XB—C18, 4.6×250 mm). Semi-preparative HPLC was performed on a Shimadzu system using a Jupiter C18 column (5 micron, 10×250 mm). All HPLC runs were done using the mixture of two solutions, A (0.045% TFA in water) and B (0.045% TFA in acetonitrile). UV detection was carried out at 220 Inn wave length.

C. Mass Spectrometry

Electrospray ionisation mass spectrometry (ESI-MS) was performed on a Thermo Finnigan LCQ DECA XP MAX or a Q Exative hybrid quadrupole-Orbitrap (Thermo Fisher). The deconvoluted data were obtained using the software of MegTran 1.03 and ESIProt 1.0.

D. Cloning and Expression of Recombinant Proteins

```
Ubiquitin (Met-Gly-Ile-Ubiquitin-His6)
(SEQ ID NO: 122):
MGIMQIFVKTLIGKTITLEVEPSDTIENVKAKIQDKEGIPPDQQRLIFAG

KQLEDGRTLSDYNIQKESTLHLVLRLRGGHHHHHH

Green fluorescent protein (Met-Ile-His6-GFP):
(SEQ ID NO: 123):
MIHHHHHHSGVDLGTENLYFQSMSKGEELFTGVVPILVELDGDVNGHK

FSVSGEGEGDATYGKLTLKFICTTGKLPVPWPTLVTTLTYGVQCFSRYPD

HMKQHDFFKSAMPEGYVQERTIFFKDDGNYKTRAEVKFEGDTLVNRIELK

GIDFKEDGNILGHKLEYNYNSHNVYIMADKQKNGIKVNFIIRHNIEDGSV

QLADHYQQNTPIGDGPVLLPDNHYLSTQSALSKDPNEKRDHMVLLEFVTA

AGITLGMDELYK

Ubiquitin (Met-GISGSGS-Ubiquitin-His6)
(SEQ ID NO: 124):
MGISGSGSQIFVKTLTGKTITLEVEPSDTIENVKAKIQDKEGIPPDQQRL

IFAGKQLEDGRTLSDYNIQKESTLHLVLRLRGGHHHHHH
```

Ubiquitin with two residues Gly-Ile added after the start codon (SEQ ID NO:122) was cloned into the pET3b vector (inserted residues were underlined). Green fluorescent protein with an additional Ile residue inserted after the start codon (SEQ ID NO:123) was cloned into the pNIC28-Bsa4 vector. The constructed plasmids were transformed into E. coli BL21 (DE3) competent cells for expression. Single colony was inoculated into 10 ml LB medium supplemented with ampicillin (for pET3b vector) or kanamycin (for pNIC28-Bsa4 vector) at 37° C. overnight. The cultures were transferred into 1 l of LB medium containing antibiotics until the OD600 reached ~0.6. IPTG was then added to a final concentration of 0.3 mM to induce the expression of the recombinant proteins at 18° C. overnight. Cells were harvested and lysed in PBS buffer (10 mM sodium phosphate, 150 mM NaCl, pH 7.4) by sonication. The lysates were filtered and loaded into the Ni-NTA column (Qiagen) for affinity purification.

E. Isolation and Purification of Butelase 1

Figure 12:
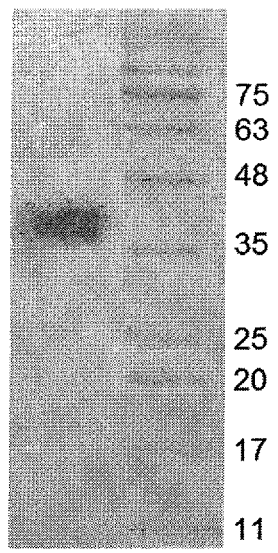
FIG. 12. SDS-PAGE analysis of butelase 1. The gel was visualized by silver staining. The left lane is the purified butelase 1 and the right lane is the protein ladder with molecular weight labeled in kDa.
Figure 13:
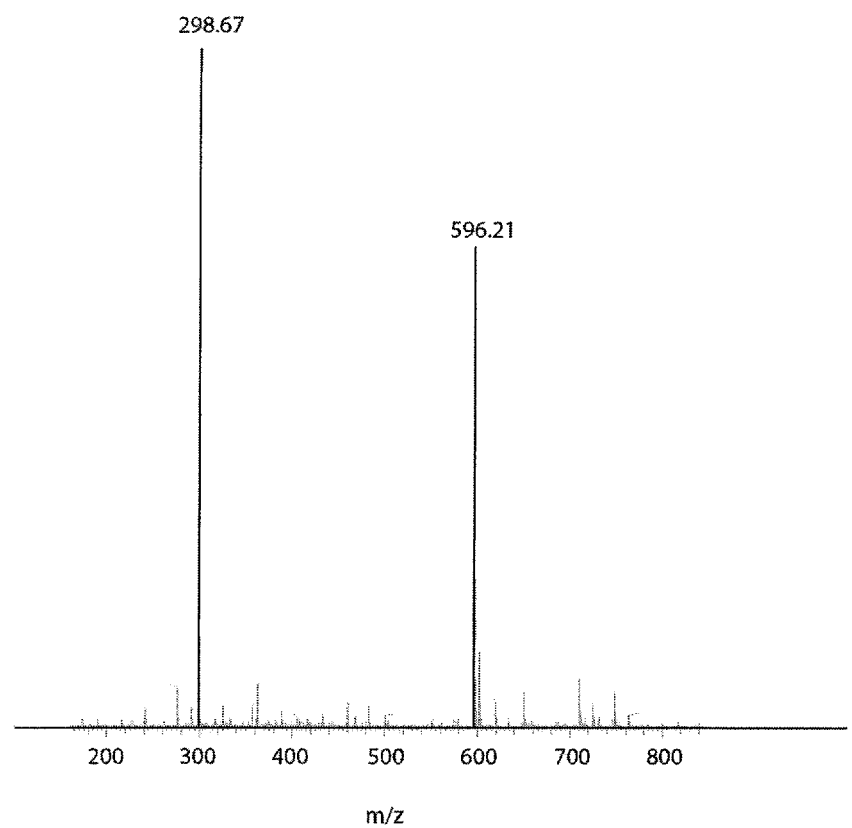
FIG. 13. Mass spectrum of Peptide 1 YKN-thioglc-V (SEQ ID NO:110). ESI-MS (positive) 595.71 (observed, M+H) 596.21 (calculated, M).
Figure 14:
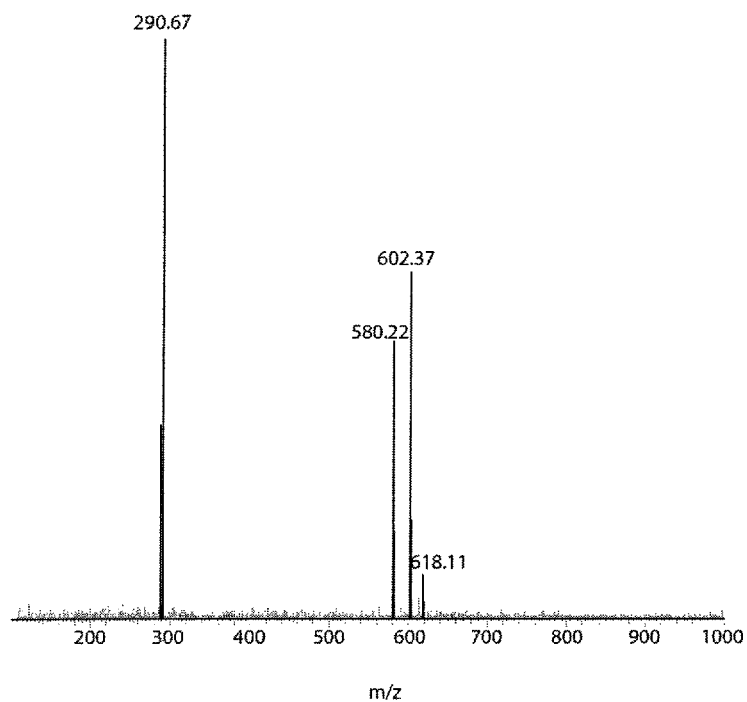
FIG. 14. Mass spectrum of Peptide 2 YKN-glc-V (SEQ ID NO:111). ESI-MS (positive) 580.22 (observed, M+H) 602.37 (observed, M+Na) 618.11 (observed, M+K) 579.30 (calculated, M).
Figure 15:
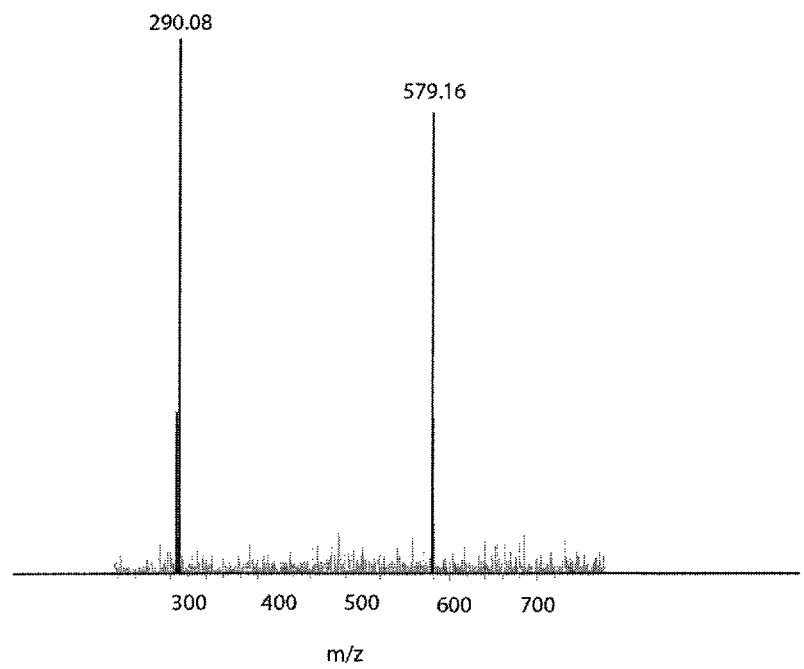
FIG. 15. Mass spectrum of Peptide 4 YKNGV (SEQ ID NO:113). ESI-MS (positive) 579.16 (observed, M+H) 578.66 (calculated, M).
Figure 16:
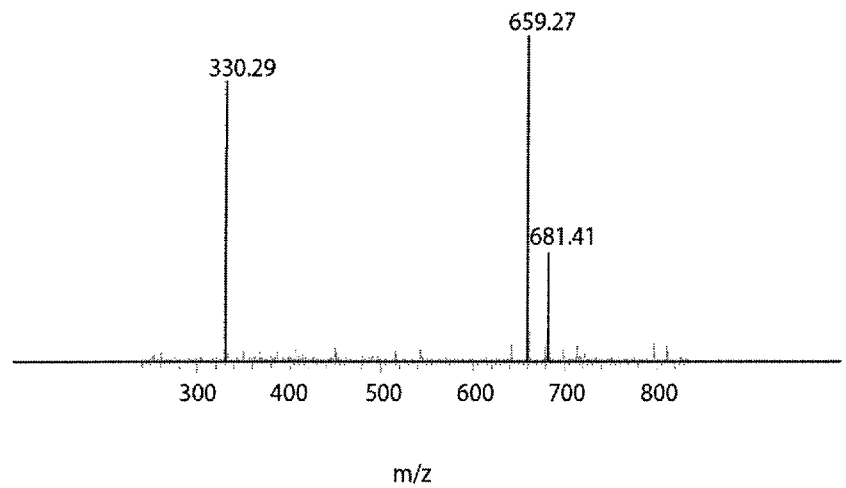
FIG. 16. Mass spectrum of Peptide 3 YKNGV (SEQ ID NO:112). ESI-MS (positive) 659.27 (observed, M+H) 681.41 (observed, M+Na) 659.36 (calculated, M).
Figure 17:
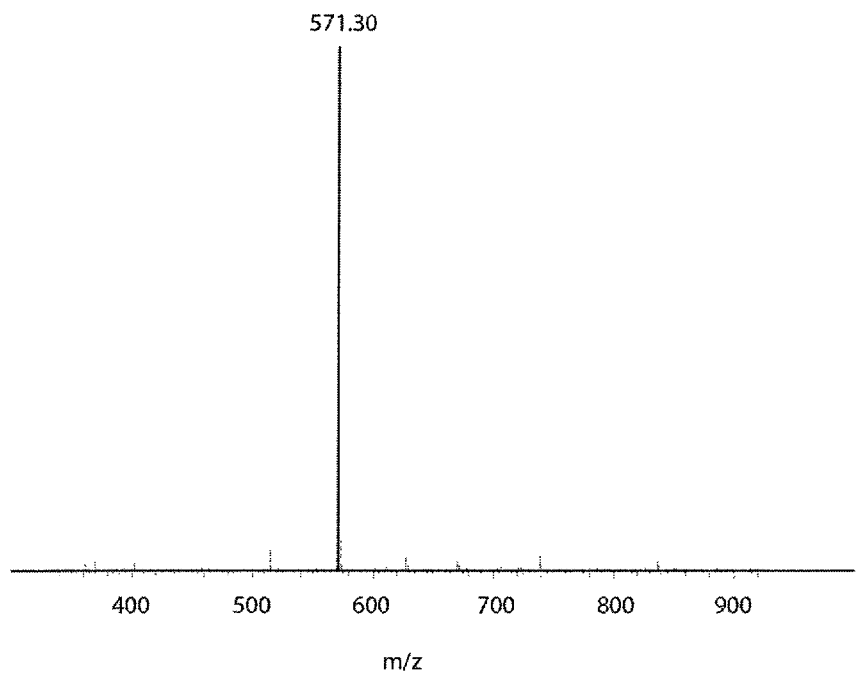
FIG. 17. Mass spectrum of Peptide 5 GIGGIR (SEQ ID NO:114). ESI-MS (positive) 571.30 (observed, M+H) 570.69 (calculated, M).
Figure 18:
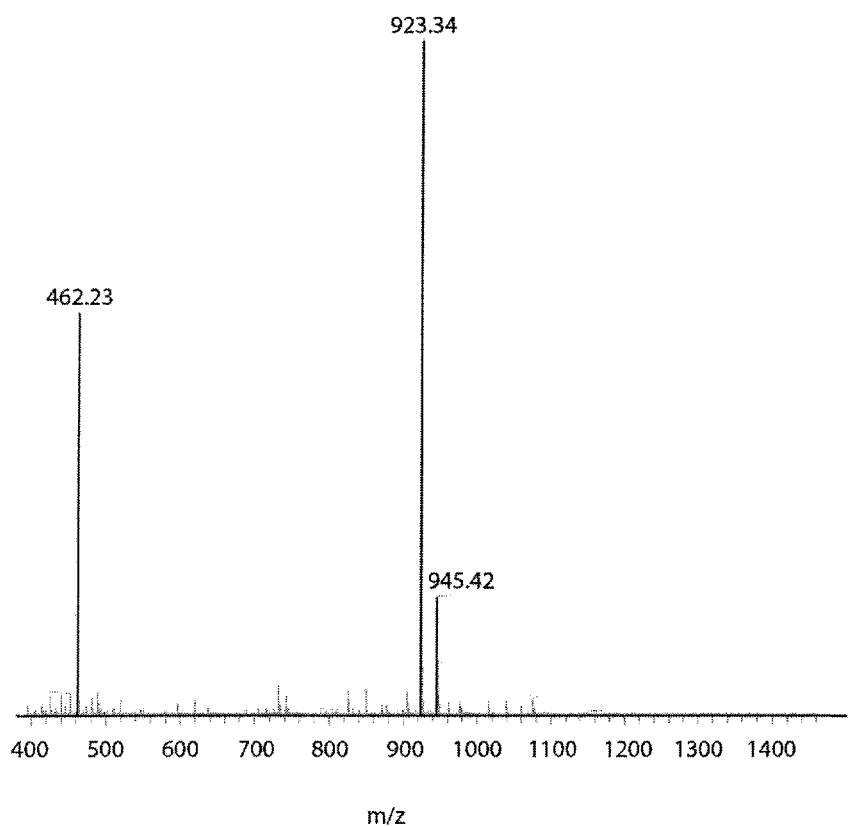
FIG. 18. Mass spectrum of Peptide 8 biotin-TYKN-thioglc-V (SEQ ID NO:117). ESI-MS (positive) 923.34 (observed, M+H) 945.42 (observed, M+Na) 922.40 (calculated, M).

The entire purification process of butelase 1 was conducted at 4° C. to minimize protein degradation. About 500 gram pods of Clitoria ternatea was blended with one liter of extraction buffer (20 mM sodium phosphate, 1 mM EDTA, 1 mM PMSF, and 5 mM mercaptoethanol (β-ME), pH 6.0). The homogenate was centrifuged at 9000 rpm for 15 minutes by using Beckman coulter Avanti™ J-25 centrifuge, with JA-10 rotor. The supernatant was then filtered and ammonium sulfate was added to reach 15% saturation. The supernatant was then centrifuged and the precipitated proteins were discarded. Ammonium sulfate was further added to reach the final concentration of 85%. The solution was then centrifuged and the precipitated proteins were redissolved in 500 ml of extraction buffer. The dissolved solution was dialyzed against extraction buffer using Snakeskin dialysis tubing with a 10 kDa molecular weight cut-off (MWCO). The dialyzed extract was filtered and loaded to the flash chromatography column with Q Sepharose Fast Flow anion exchange resin (GE Healthcare). The column was washed with one litre of wash buffer (10 mM sodium phosphate, 1 mM EDTA and 5 mM β-ME, pH 6.0) and eluted with 500 ml elution buffer (0.5 M NaCl, 10 mM sodium phosphate, 1 mM EDTA and 5 mM β-ME, pH 6.0). The eluent was dialyzed against wash buffer and subject to fractionation by HPLC using a preparative anion exchange column (PolyWAX LP, PolyLC). Fractions contain ligase activity were pooled and concentrated to a final volume of 3 ml using Amicon Ultra centrifugal filter (Millipore Ireland Ltd) of 10 kDa MWCO. The concentrated solution was subjected to size exclusion chromatography using a Biosuite HPLC column (21.5×300 mm) and further purified by anion exchange chromatography using analytical PolyWax HPLC column (Poly LC, 4.6×250 mm). The purity of the isolated butelase 1 was determined by SDS-PAGE and silver staining (FIG. 12). Approximately 0.5 mg butelase 1 can be obtained from 500 gram plant materials.

F. Synthesis of Trityl-Protected Thioglycolic Acid

Triphenylmethanol (805 mg, 3 mmol) was mixed with thioglycolic acid (208.4 µl, 3 mmol) in the presence of neat trifluoroacetic acid (TFA, 4 mL). The reaction was stirred at room temperature for 30 min. After removal of TFA in vacuo, toluene was added to removal the residual water. After complete removal of solution in the reaction mixture, desired product was obtained as white powder in quantitative yield and it was used in the following SPPS without further purification.

G. Peptide Synthesis

All native peptides 3, 4, 5 were synthesized using standard Fmoc chemistry on rink-amide-MBHA resin (0.7 mmol/g). Before the synthesis, the resin was pre-swelled in dichloromethane (DCM) for 10 min. Fmoc group removal was done using 20% piperidine in dimethylformamide (DMF) for 2 min and another 20 min. After deprotection, the resin was washed with DMF, DCM, and DMF alternatively. For the coupling reaction, 4 eq. of Fmoc-AA-OH, 4 eq. of PyBOP were first dissolved in DMF/DCM mixture and added to the resin. 8 eq. of DIEA was then added in. Coupling reaction was carried out for about 60-90 min. Coupling efficiency could be monitored by using Kaiser test After the whole sequence was assembled, the peptide was cleaved from the solid support using a cleavage solution of 95% TFA, 2.5% water and 2.5% TIS for 1 h. Precipitated by cold ether, the crude peptides were purified by HPLC. The desired products were identified using ESI-MS. After lypholization, peptides were obtained in powder form, which could be used freshly or stored at −20° C. for further use.

The depsipeptide 2 and 6 were also synthesized using standard Fmoc chemistry on rink amide MBHA resin. Building block used were Fmoc-Tyr(tBu)-OH, Fmoc-Lys(Boc)-OH, Fmoc-Asn(Trt)-OH, glycolic acid, Fmoc-Val-OH. The difference of this synthesis from the above native peptide synthesis was the coupling of glycolic acid and the subsequent Fmoc-Asn(Trt)-OH. As for glycolic acid coupling, 4 eq. of glycolic acid and 4 eq. of PyBOP dissolved in DMF/DCM were first added to the resin. 8 eq. of DIEA was subsequently added in. After coupling for 2 h, a 30 min treatment of 10% hydrazine/DMF was used for removal of the over-coupled glycolic acid. To couple the next amino acid Fmoc-Asn(Trt)-OH, instead of PyBOP, a stronger coupling condition DIC/HOBT was employed. The resin was first suspended in DCM/DMF mixture (9:1 v/v). 5 eq. of Fmoc-Asn(Trt)-OH and 5 eq. of HOBT were dissolved in a minimum amount of DMF facilitated by vortex and sonication. After adding the solution to the resin, 5 eq. of DIC was added followed by 0.1 eq. of DMAP. The reaction was shaken for overnight. 5% acetic anhydride in pyridine was used to cap the uncoupled hydroxyl groups for 30 min.

Both thiodepsipeptides 1 and 8 were synthesized using standard Boc chemistry on MBHA resin (1.03 mmol/g). The Boc chemistry differs from Fmoc chemistry in the way of deprotection and final cleavage. For Boc deprotection, 30% TFA in DCM was used to remove Boc protecting group for 2 min and 20 min. For trityl removal, besides 30% TFA in DCM, TIS was also used. For substrate 1, the building blocks used were Boc-Tyr(2-Br—Z)—OH, Boc-Lys(2-Cl—Z)—OH, Boc-Asn(Trt)-OH, Trityl-protected thioglycolic acid, Boc-Val-OH. For substrate 6, building blocks used were biotin, Boc-Thr(Bzl)-OH, Boc-Tyr(2-Br—Z)—OH, Boc-Lys(2-Cl—Z)—OH, Boc-Asn(Trt)-OH, Trityl-protected thioglycolic acid, Boc-Val-OH. For cleavage (scale of 250 mg resin), first add 750 µl thioanisole/ethanedithiol mixture (2:1) on the ice, then add 5 ml TFA followed by 500 µl TFMSA. The cleavage was allowed to proceed for 1 h at room temperature.

Fmoc chemistry has also been applied for the synthesis of the thiodepsipeptide 1. Since the thioester moiety is susceptible towards the nucleophilic piperidine, inventors used the modified Fmoc deprotection cocktail containing 25% 1-methylpyrrolidine, 2% hexamethyleneimine, 2% HOBT in NMP/DMSO (1:1) mixture as described previously (Tetrahedron Lett. 1998, 39, 8669).

H. Butelase-Mediated Ligation and Kinetic Characterization

Ligation assays were performed in 50-µl mixtures containing reaction buffer (1 mM EDTA, 20 mM phosphate buffer, pH 6.5), 0.1 µINA butelase 1, 1 mM GIGGIR (SEQ ID NO:114) and varying concentrations of peptides 1-4 (25 to 400 µM). The reactions were performed in triplicate at 42° C. and quenched by adding 5 µl of 1 M HCl solution. The peptides were separated by using a reversed-phase C18 analytical column (150×2.1 mm, Vydac) with a linear gradient from 5% to 40% acetonitrile over 15 min on a Nexera UHPLC system (Shimadzu). The ligation velocities were calculated by converting the HPLC-peak areas of remained linear precursors or the ligated products into concentrations. The identity of each HPLC peak was analyzed by MALDI-TOF MS (ABI 4800 MALDI TOF/TOF). The kinetic parameters ($k_{cat}$ and $K_m$) for each peptide were obtained by the LineweaverBurk plot.

I. Proteins Labeling with Thiodepsipeptides 1 and 8

The labeling of proteins were performed in reaction buffer (1 mM EDTA, 20 mM phosphate buffer, pH 6.5) containing 100 µM protein and 0.1 µM butelase 1. One equivalent of thiodepsipeptide substrate was added every 30 min. For ubiquitin, 5 equivalents of thiodepsipeptide were added in total, as for GFP, 4 equivalents were added. The labeling reactions were monitored by HPLC and ESI-MS.

Here inventors report the use of thiodepsipeptide as an acceptable sorting signal but a poor competing nucleophile after its release to render the butelase-mediated intermolecular ligation irreversible (FIG. 1). Inventors obtained quantitative ligation yields of >95% for a model peptide at 0.0005 molar equivalent of butelase 1 and two molar equivalents of the thiodepsipeptide. Inventors also successfully applied the proposed method to label ubiquitin and GFP with high yields. This method is based on inventors' previous work that incubation of butelase 1 with a model peptide KALVINHV (SEQ ID NO:125) with the dipeptide HV as a leaving group in the presence of various alkyl and aryl thiols did not lead to any detectable amount of peptide thioester (Nat Chem Biol 2014, 10, 732). This result suggested that thiol groups are poor competing nucleophiles than the HV dipeptide sorting signal. Thus, inventors hypothesized that intermolecular ligation reactions would be irreversible if the scissile asparaginyl amide bond is replaced by a thioester linkage. For comparison, inventors also synthesized a depsipeptide because it has been demonstrated that ligation yields were improved for sortase A using a depsipeptide substrate (Angew. Chem. Int. Ed. Engl. 2012, 51, 9377). However, the applications of depsipeptide for N-terminal protein labeling required 0.1-0.2 molar equivalents of sortase A and a time-consuming solution-phase synthesis of a depsipeptide precursor.

Figure 2:
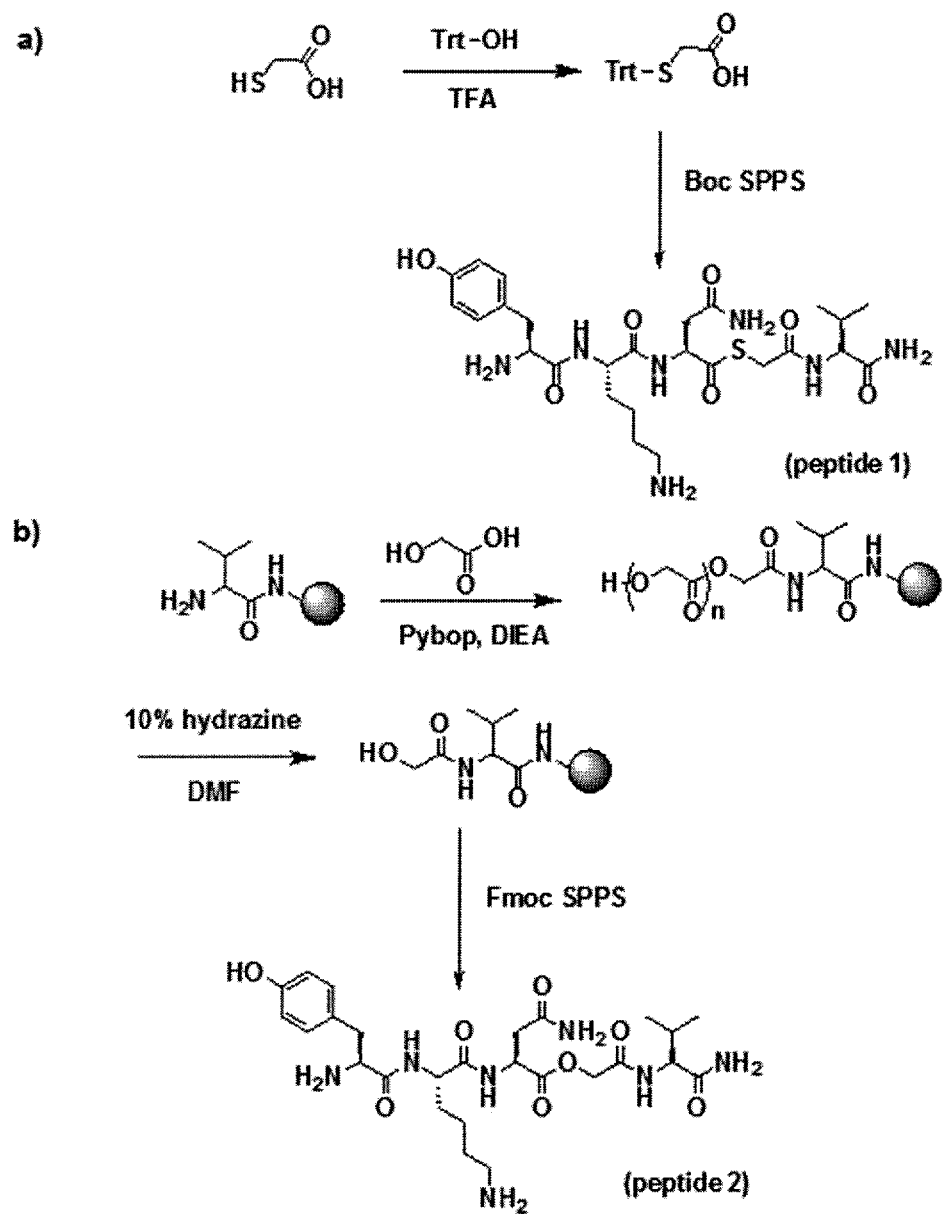
FIG. 2. Synthetic strategy for a) thiodepsipeptide 1 and b) depsipeptide 2.

To support this hypothesis, inventors prepared four different peptide substrates sharing a common sequence YKNXV (SEQ ID NO:126) 1-4 with a XV as a sorting signal (X=thio- or glycolic acid, His and Gly, respectively). Thiodepsipeptide 1 and depsipeptide 2 contain a S- and O-ester bond as a (S)GV and (O)GV analog, respectively, at the scissile bond compared with an amide bond in the two control peptides 3 (HV) and 4 (GV). Thiodepsipeptide 1 was prepared by a standard solid-phase synthesis (FIG. 2a). First, a mixture of an equal equivalent of thioglycolic acid and triphenylmethanol in the presence of neat trifluoroacetic acid yielded trityl-protected thioglycolic acid after solvent removal. This compound was used without further purification. Thiodepsipeptides were synthesized on MBHA resin with Boc-protected amino acids and the pre-made building block by Boc chemistry. Alternatively, the thiodepsipeptide 1 can also be prepared by Fmoc chemistry. Since the thioester moiety is susceptible towards piperidine, inventors used the modified Fmoc deprotection cocktail containing 25% 1-methylpyrrolidine, 2% hexamethyleneimine, 2% HOBT in NMP/DMSO (1:1) mixture (Tetrahedron Lett. 1998, 39, 8669). For depsipeptide 2, unlike previously reported method that required a carefully controlled solution-phase synthesis (Angew. Chem. Int. Ed. Engl. 2012, 51, 9377), inventors developed a fully solid-phase compatible and straightforward approach (FIG. 2b). The depsipeptides were synthesized on Rink amide MBHA resin with Fmoc amino acids and glycolic acid.

Hydrazinolysis of the glycolic acid-coupled product removed all side products of oligomers because of their susceptibility to hydrazine, leaving only one glycolic acid attached to the preceding residue as a stable amide bond. Inventors' synthesis scheme provides a new convenient method for preparing depsipeptides.

TABLE 1

List of peptide substrates and their corresponding molecular weight

| Peptide | SEQ ID NO: | Sequence | MW (MH$^+$) Calc. | Obs. |
|---|---|---|---|---|
| 1 | 110 | YKN(S)GV | 596.28 | 596.28 |
| 2 | 111 | YKN(O)GV | 580.30 | 580.19 |
| 3 | 112 | YKNHV | 659.36 | 659.27 |
| 4 | 113 | YKNGV | 579.32 | 579.16 |
| 5 | 114 | GIGGIR | 571.36 | 571.3 |
| 6 | 115 | (O)GVYKV | 565.33 | 565.28 |
| 7 | 116 | ERLYRGRLYRRNHV | 1888.05 | 1888.2 |
| 8 | 117 | biotin-TYKN-thioglc-V | 923.4 | 923.31 |

Figure 3:
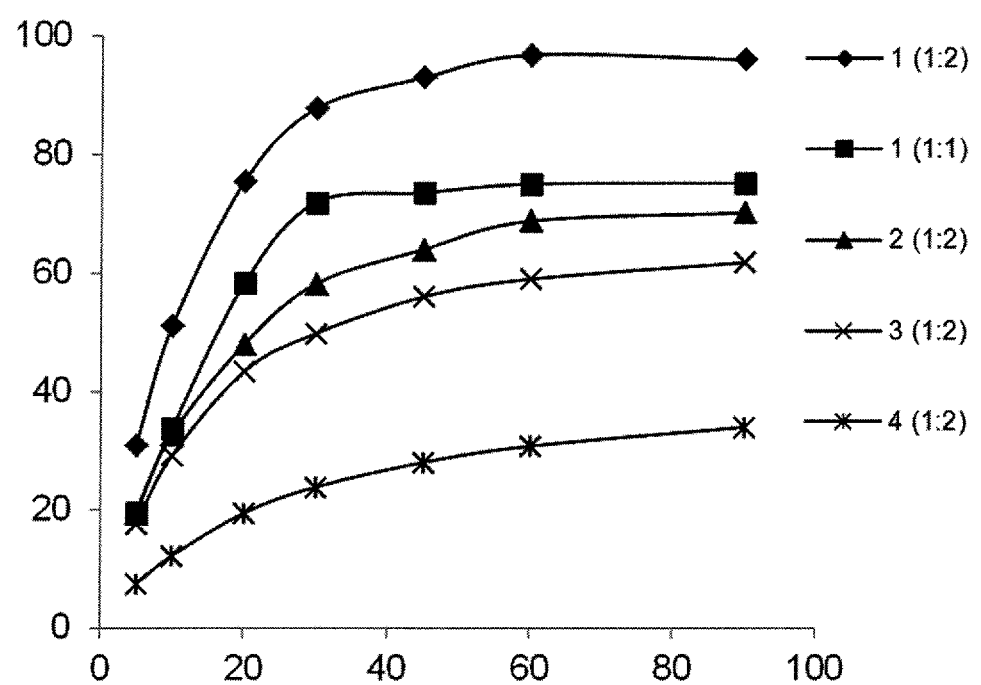
FIG. 3. Time-course of butelase-mediated ligation of peptides 1-4 with peptide 5. The reaction was monitored by HPLC. Reaction conditions: 50 nM butelase 1, 100 peptide 5, corresponding ratios of peptide 1-4, 20 mM phosphate buffer, 1 mM EDTA, pH 6.5, 42° C.

Inventors evaluated the ligation efficiency of each peptide substrate to a model peptide GIGGIR (SEQ ID NO:114) 5 to form the ligated product YKNGIGGIR (SEQ ID NO:127) by HPLC. The reactions were performed in the presence of 100 μM GIGGIR (SEQ ID NO:114), one or two molar equivalents of each peptide substrate, and 50 nM of butelase 1 (0.0005 molar equivalent). Time-course analysis showed that thiodepsipeptide 1 was the most efficient substrate followed by depsipeptide 2. Peptide 3 and peptide 4 were the least efficient. All ligation reactions reached equilibrium after 60 min with marginal yield improvement after 90 min. At two molar equivalents of 1, >95% of peptide 5 was converted into the ligation product within 1 h (FIG. 3). In contrast, the ligation yields only reached 31%, 59% and 68%, respectively, for peptide 4, 3 and 2 under similar conditions.

Even at one molar equivalent of thiodepsipeptide 1, the ligation yield still reached 73%, confirming thiodepsipeptide is the best of the four substrates. Table 2 shows a kinetic study to quantify the difference among peptides 1-4. The result was in agreement with the time-course experiments with thiodepsipeptide 1 having the highest catalytic efficiency ($k_{cat}/K_m$) and peptide 4 being the lowest.

TABLE 2

Kinetic parameters of butelase 1 for peptides 1-4

| Peptide | SEQ ID NO: | Sequence | $k_{cat}$ (s$^{-1}$) | $K_m$ (mM) | $k_{cat}/K_m$ (M$^{-1}$ s$^{-1}$) |
|---|---|---|---|---|---|
| 1 | 110 | YKN-thioglc-V | 56.5 ± 7.5 | 2.76 ± 0.3 | 20,480 |
| 2 | 111 | YKN-glc-V | 12.4 ± 0.32 | 0.74 ± 0.01 | 16,840 |
| 3 | 112 | YKNHV | 4.1 ± 0.65 | 0.3 ± 0.01 | 13,490 |
| 4 | 113 | YKNGV | 7.9 ± 0.72 | 0.88 ± 0.08 | 8,900 |

Figure 7:
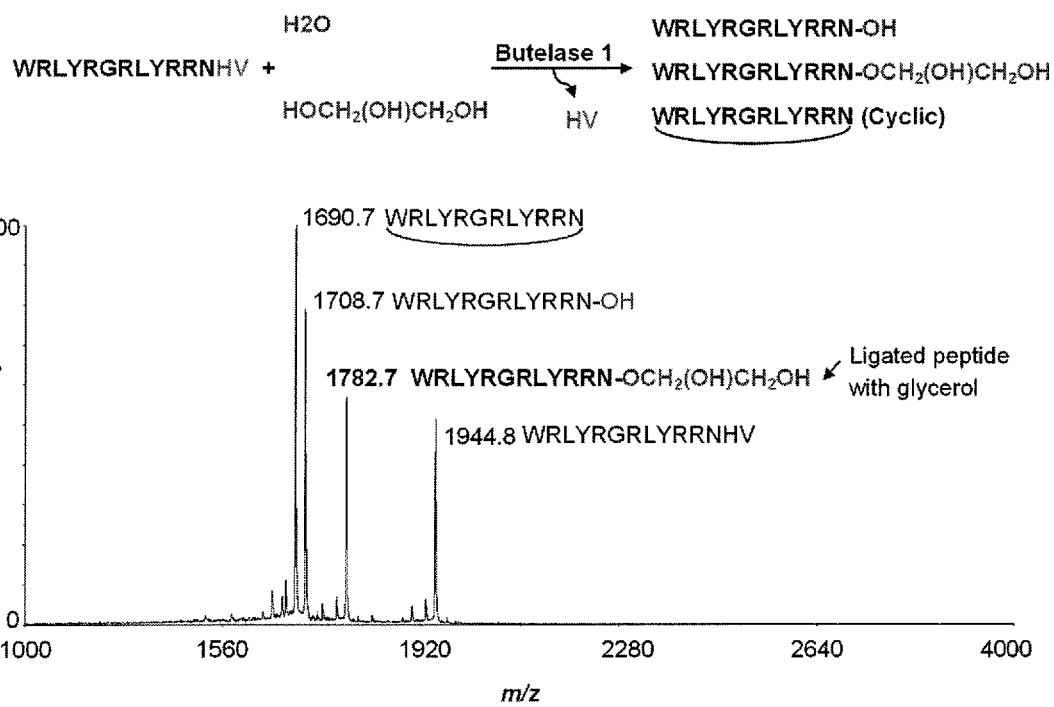
FIG. 7. Butelase-mediated ligation with glycerol. Incubation of a model peptide WRLYRGRLYRRNHV (SEQ ID NO:132) (100 μM) with butelase 1 in the present of 20% glycerol for 2 hours led to formation of three major products: a hydrolyzed product (WRLYRGRLYRRN) (SEQ ID NO:133), a cyclized product (WRLYRGRLYRRN) (SEQ ID NO: 134), and a ligated product with glycerol (WRLYRGRLYRRN—OCH$_2$(OH)CH$_2$OH) (SEQ ID NO:135).
Figure 8:
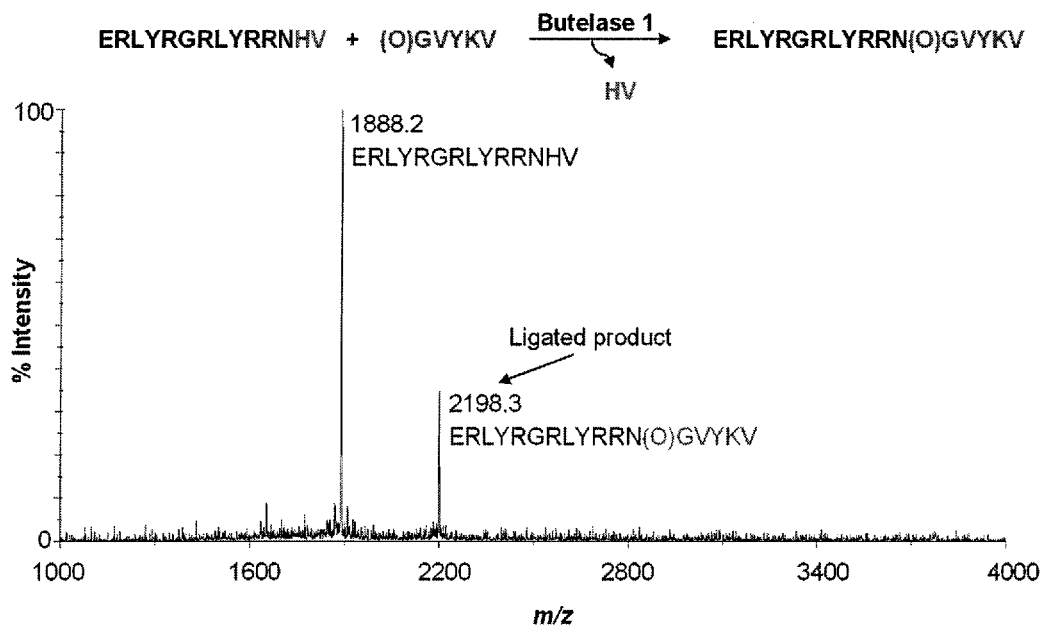
FIG. 8. Butelase-mediated ligation with (O)GVYKV peptide (SEQ ID NO:115). A model peptide ERLYRGRLYRRNHV (SEQ ID NO:116) (50 μM) was incubated butelase 1 (50 nM) and (O)GVYKV (SEQ ID NO:115) (5 mM) in 20 mM sodium phosphate buffer, pH 6.0 at 37° C. for 2 h. Analysis by mass spectrometry showed the formation of the ligated product with about 25% yield.

Next inventors sought to determine what shifts the equilibrium to a higher yield for thiodepsipeptide 1 as compared to depsipeptide 2, because their leaving groups are a thiol or an alcohol, both of which are poor nucleophiles in a butelase-mediated ligation. It was found that the model peptide accepts glycerol as a nucleophile to give about 20% of the ligated product (FIG. 7). This observation suggests that butelase 1 can recognize an alcohol as an acceptor nucleophile. To demonstrate that butelase 1 indeed accepts an alcohol group, inventors synthesized peptide 6, (O)GVYKV (SEQ ID NO:115), with glycolic acid as the N-terminal residue. Ligation of peptide 6 with peptide 7 (ERLYRGR-LYRRNHV; SEQ ID NO:116) led to a ligated product ERLYRGRLYRRN(O)GVYKV (SEQ ID NO:117) with about 25% yield (FIG. 8). No detectable ligation product was formed when ligated 7 with a (S)GV peptide under the same condition. These results indicate that the butelase-mediated ligation is reversible for depsipeptide and irreversible for thiodepsipeptide, which could explain for the higher yields of thiodepsipeptide 1 at equilibrium as compared to depsipeptide 2.

Figure 4:
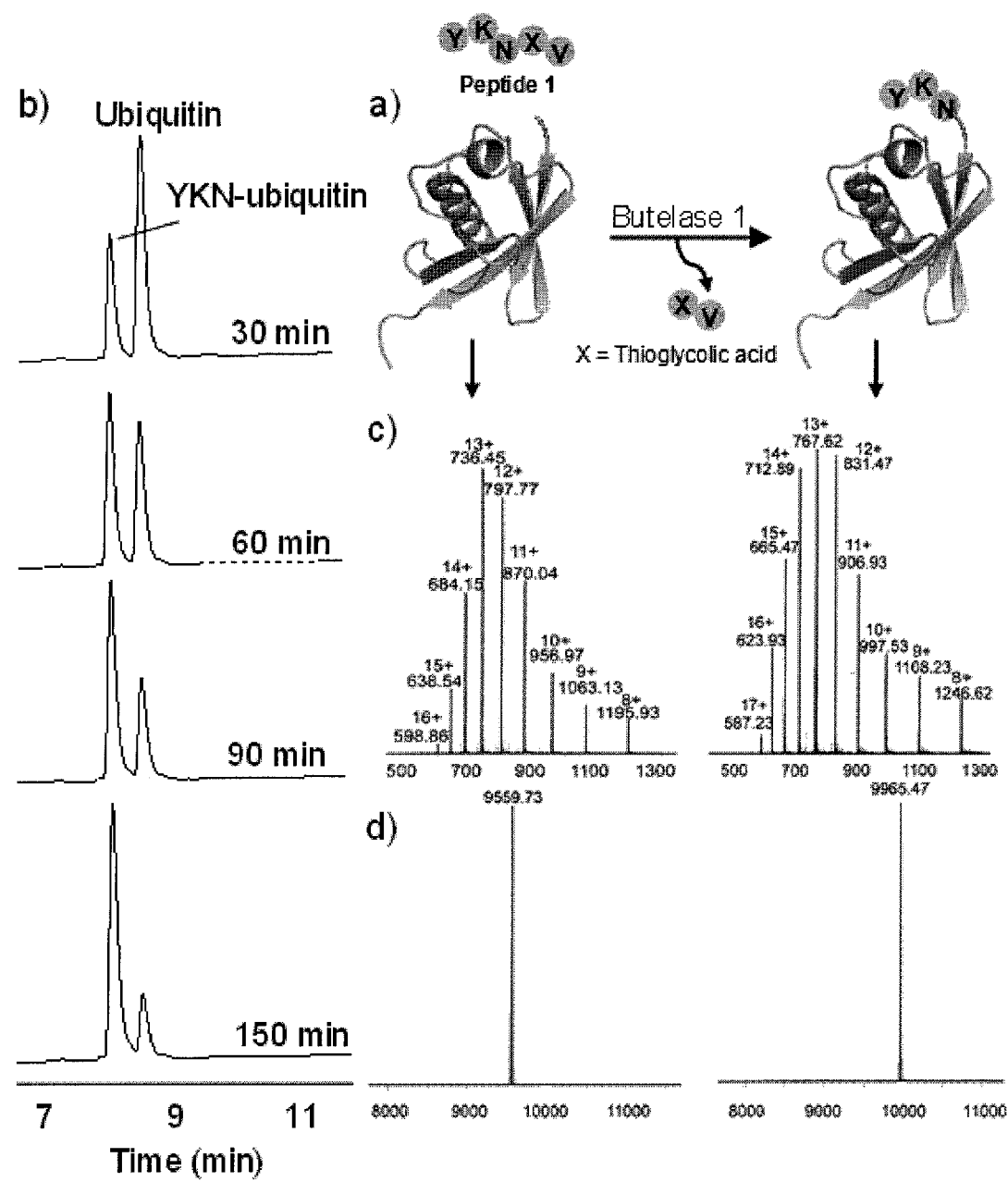
FIG. 4. a) Schematic illustration of the butelase-mediated N-terminal modification of ubiquitin by the use of thiodepsipeptide 1. b) Time-course analysis of ubiquitin labeling reaction. c) ESI spectra of unmodified and modified ubiquitin. d) Deconvoluted ESI spectra of unmodified and modified ubiquitin.
Figure 9:
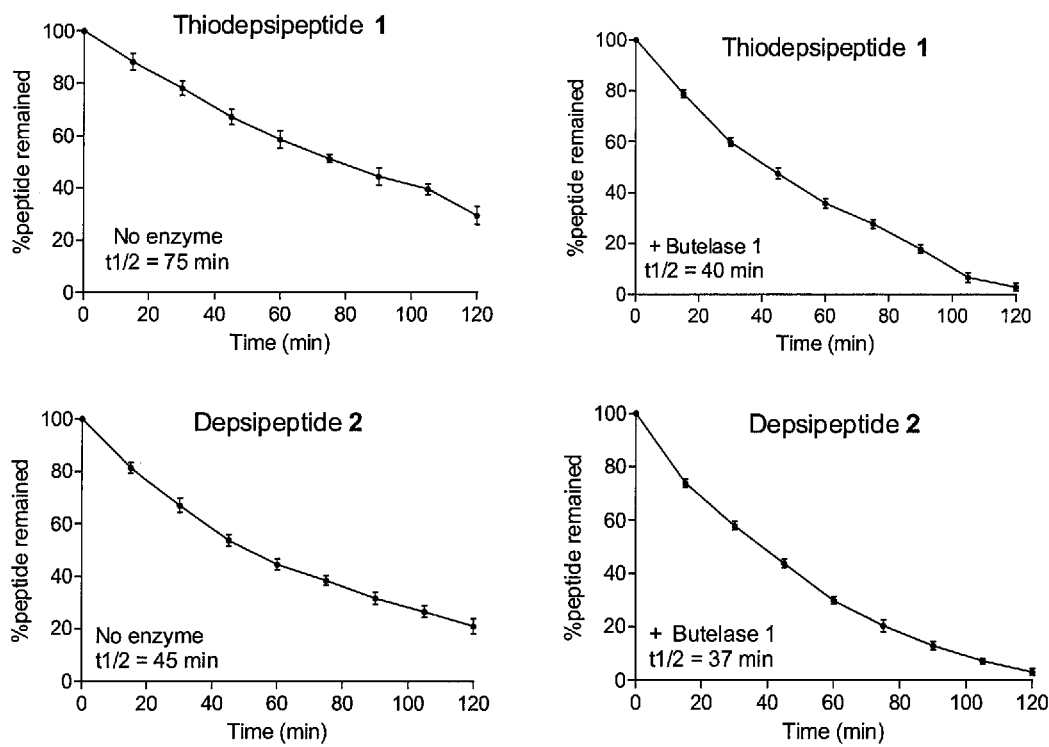
FIG. 9. Degradation time course for thiodepsipeptide 1 and depsipeptide 2. Each peptide (100 μM) was incubated in the absence or presence of butelase 1 (50 nM) at 42° C. The peptide stability was monitored by HPLC every 15 mM.
Figure 10:
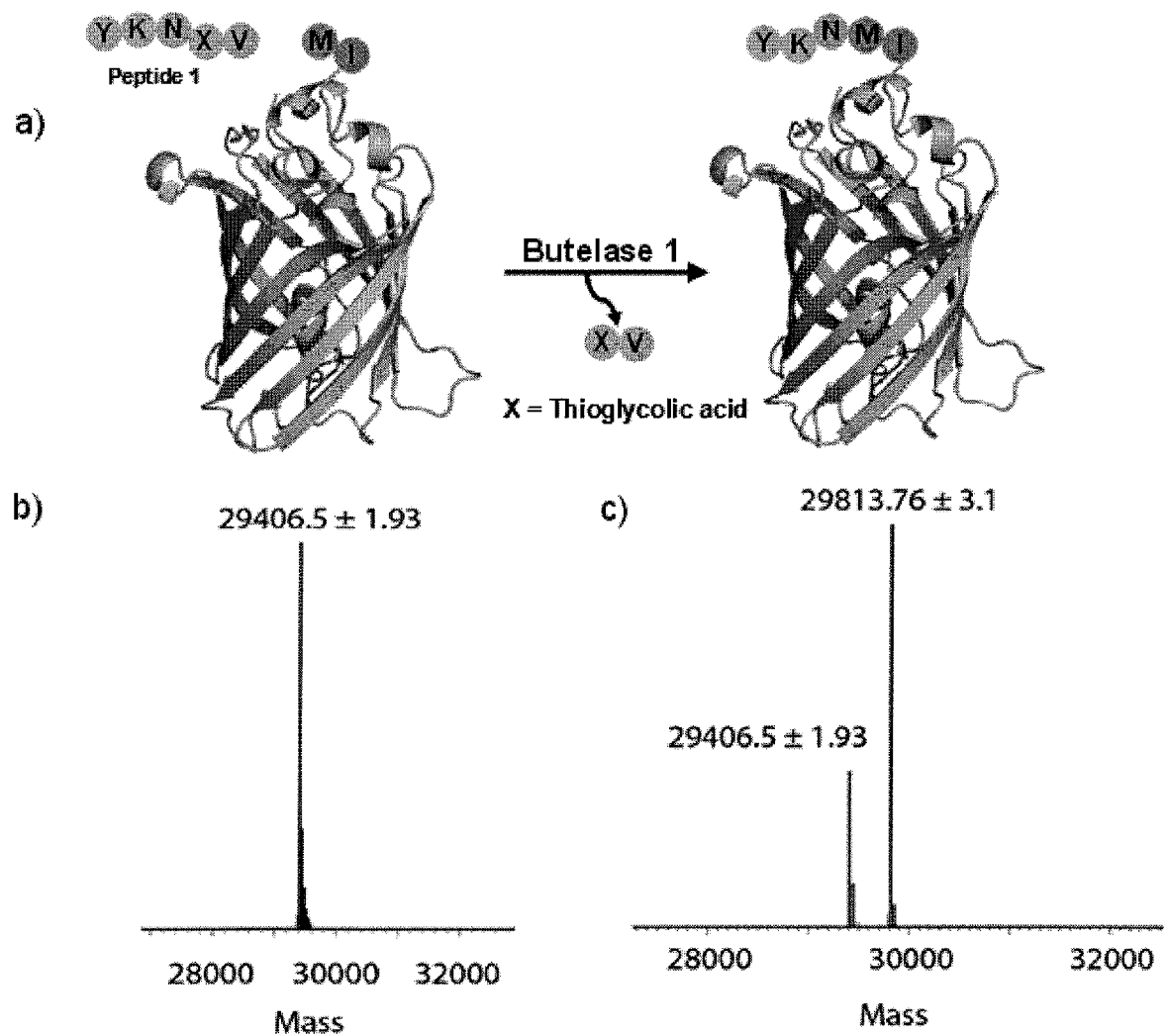
FIG. 10. a) Schematic illustration of the butelase-mediated N-terminal modification of GFP by the use of thiodepsipeptide 1. b, c) Deconvoluted ESI spectra of GFP before (b) and after (c) the ligation reaction. Unmodified and modified GFP have observed masses of 29406.5 and 29813.7 Da, respectively.

To apply butelase 1 for N-terminal labeling of proteins, inventors used ubiquitin and green fluorescent protein (GFP) as examples (FIG. 4). Since butelase 1 prefers a hydrophobic amino acid (Ile/Leu/Val) or Cys at the P2" position of an acceptor nucleophile, inventors prepared a recombinant ubiquitin protein (SEQ ID NO:122) with Gly-Ile at the N-terminus and His-tag at the C-terminus. It was also examined whether this method would work if His-tag was located at the N-terminus. Inventors thus prepared a recombinant GFP (SEQ ID NO:123) with an additional Ile inserted between the start codon and the N-terminal His-tag. Both proteins were labeled with the model thiodepsipeptide 1 in the presence of 0.001 molar equivalent of butelase 1. The labeling of proteins was slower as compared to the labeling of peptide 5, probably due to large differences in size between the model peptide and proteins. Furthermore, the N-terminal amino group of proteins may have a lower accessibility to butelase 1 as compared to peptides. Additionally, it was also found that the half-life of the thiodepsipeptide labeling reagent was relatively short mainly due to hydrolysis and aspartimide formation which was associated with the nature of the asparagine residue. The half-life of thiodepsipeptide 1 in inventors' reaction buffer is about 75 min in the absence of butelase 1 and 40 min in the presence of 0.0005 molar equivalent of butelase 1 (FIG. 9). For depsipeptide 2, the half-life is 45 min and 37 min in the absence and presence of butelase 1, respectively. This feature poses a problem when the ligation proceeds slowly, and a moderate yield (~60%) was obtained after five equivalents of thiodepsipeptide 1 being completely consumed in the reaction. Due to the instability of the thiodepsipeptide, one molar equivalent of the labeling reagent was added to the reaction every thirty minutes instead of adding them all at once. This strategy improved the ubiquitin labeling to 82% yield with five molar peptide equivalents after 2.5 h (FIG. 4). Comparatively, <10% ligation product observed when ligating ubiquitin with LPETGG peptide (SEQ ID NO:128) when using sortase A. This result suggests that the N-terminal of ubiquitin may be buried and less accessible for ligation than small peptides, a finding in agreement with a previous study that sortase A is unable to modify myoglobin and fly pumilio RNA binding domain (Angew. Chem. hit. Ed. Engl. 2012, 51, 9377). Using the same strategy, 70% of GFP was labelled with four molar peptide equivalents (FIG. 9). This is also first example to explore the application of butelase 1 for protein labeling.

Figure 5:
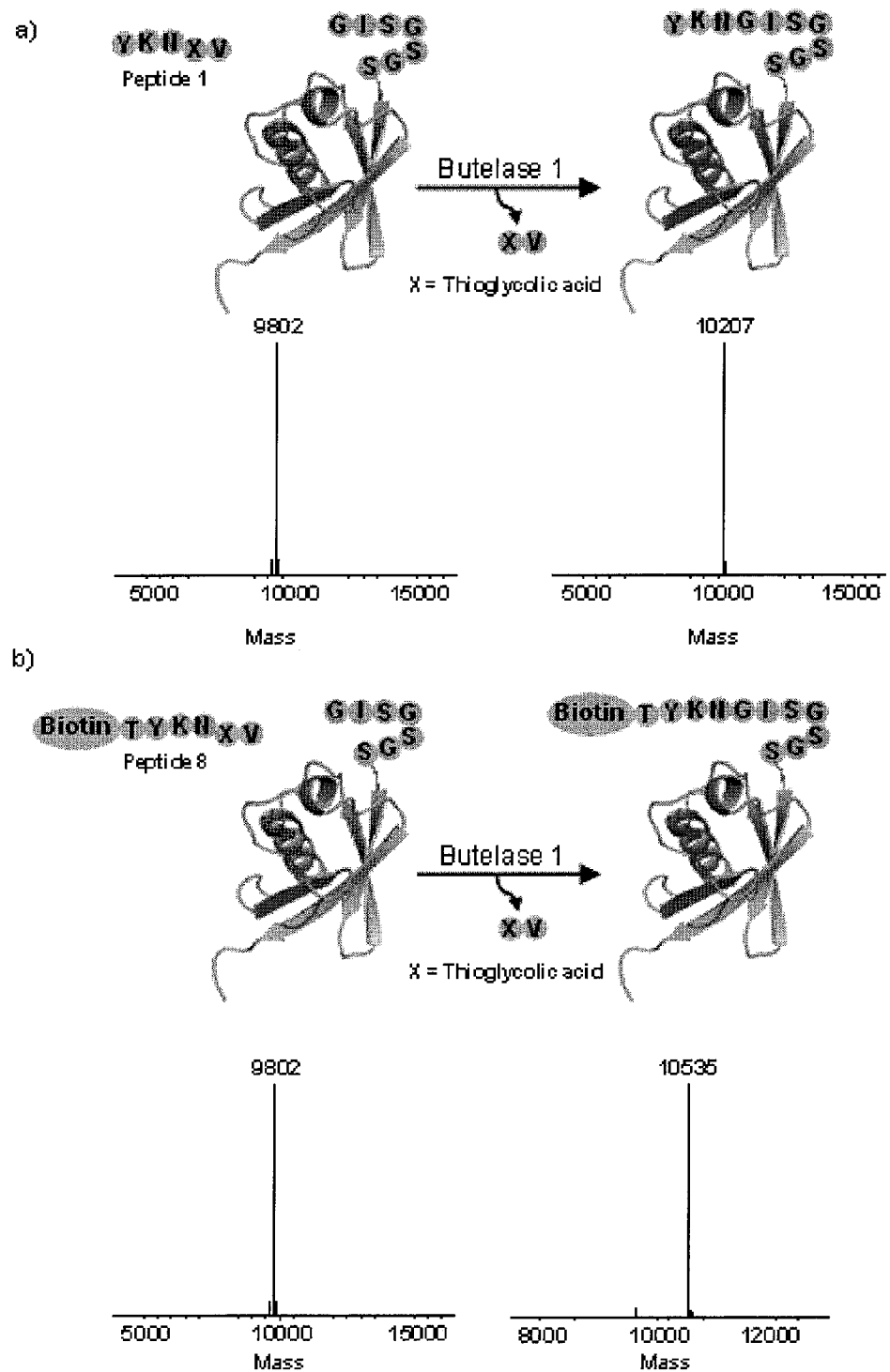
FIG. 5. a) Schematic illustration of the butelase-mediated N-terminal ligation of ubiquitin modified with a short linker peptide by the use of thiodepsipeptide 1. A quantitative ligation yield was obtained as shown by the deconvoluted ESI spectra. b) Schematic illustration of the butelase-mediated N-terminal modification of ubiquitin by the use of thiodepsipeptide 8 which carries a biotin tag. A quantitative ligation yield was obtained with four equivalent of peptide 8 and 0.001 molar equivalent of butelase 1.
Figure 6:
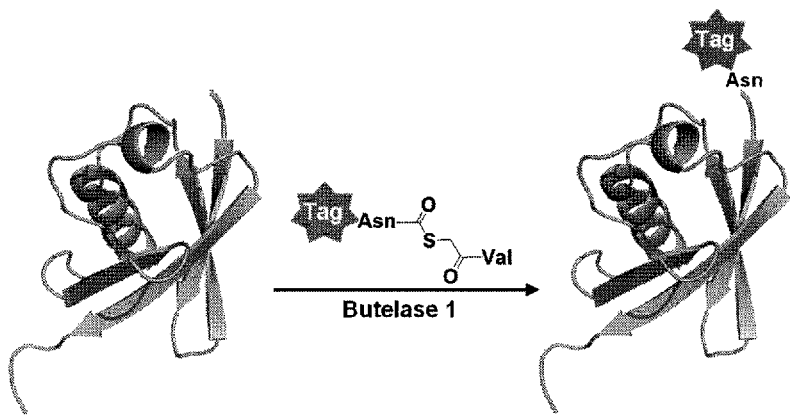
FIG. 6. Irreversible butelase-mediated ligation: A novel approach to render the ligation irreversible by using a thiodepsipeptide substrate. A ligation yield of >95% was achieved with a minimal excess of substrate and a low catalytic amount of butelase 1 (0.0005 to 0.001 molar equivalent). This method has been successfully applied to introduce a functional tag to ubiquitin and green fluorescent protein with high yields.

To improve the ligation yield by introducing an additional linker to the N-terminal of proteins, another recombinant ubiquitin (SEQ ID NO:124) with a short liker peptide GISGSGS (SEQ ID NO:129) was expressed. Inventors obtained quantitative labeling for ubiquitin (~95%) with four equivalents of the thiodepsipeptide 1 in the presence of 0.001 molar equivalent of butelase 1 in 100 min (FIG. 5a). The ligation yield also reached >90% yield for sortase A after introducing the linker peptide (GGSGSGS) (SEQ ID NO: 130), a result consistent with a literature precedent (Angew. Chem. Int. Ed. Engl. 2012, 51, 9377; Nat. Protoc. 2013, 8, 1800). However, sortase A required 0.1 molar equivalent of enzyme to catalyze the ligation as compared to 0.001 molar equivalent of butelase 1.

Figure 11:
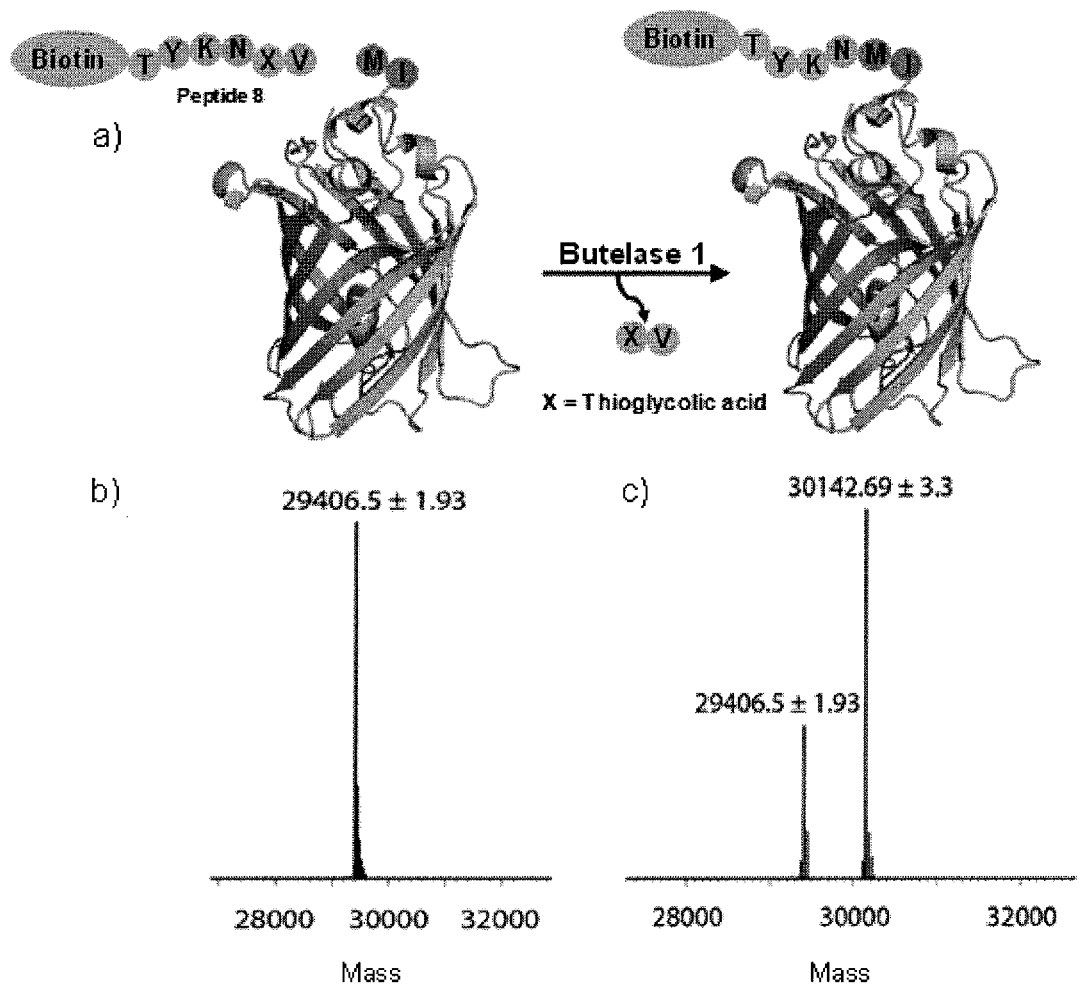
FIG. 11. a) Schematic illustration of the butelase-mediated N-terminal modification of GFP by the use of thiodepsipeptide 8 which carries a biotin tag. b, c) Deconvoluted ESI spectra of GFP before (b) and after (c) the ligation reaction. Unmodified and modified GFP have observed masses of 29406.5 and 30142.6 Da, respectively.

With the success on the model thiodepsipeptide, conjugation with biological functional groups was also investigated. A thiodepsipeptide 8 carrying a biotin functional group at its N-terminus was synthesized. Successful labeling was achieved on both ubiquitin and GFP with the biotinylated thiodepsipeptide 8 (FIGS. 5b, 11), demonstrating the applicability of the presently disclosed method to introduce a functional tag into peptides and proteins. The labeling yields are comparable between thiodepsipeptides 1 and 8, which indicates that the biotin group does not affect the labeling efficiency.

In conclusion, inventors have developed a novel method for butelase-mediated ligation using thiodepsipeptides as substrates. The ligation yield of >95% could be achieved for the model peptide and ubiquitin with a small excess of substrate. The developed method is also applicable for introducing a functional group such as biotin into proteins. The ligation efficiency was greatly improved as the (S)GV byproduct is a poor recognizing substrate in the reverse direction. Furthermore, the preparation of the labeling reagent and the use of this method are simple and straight forward. Inventors anticipate a broad application of this method for N-terminal modification of peptides and proteins.

Example 2: Bioconjugation: Efficient Butelase-Mediated Synthesis of Peptide Dendrimers and their Application as Antimicrobials A. Materials and Reagents For peptide synthesis, all the amino acids, coupling reagents and resins were obtained from chemimpex and GL biochem. All other chemical reagents were of analytical grade, obtained from Sigma Aldrich, alfa aesar and Acros Organics. All solvents and chemicals were used as received without purification unless otherwise indicated.

The materials for radial diffusion assay were prepared as following:

Trypticase soy broth (TSB): Full-strength broth contains 30 grams of TSB powder per liter of deionized water. It was autoclaved at 120° C. for 20 min and stored at room temperature.

Underlay gel: 50 mL of 100 mm sodium phosphate buffer, 5 ml full-strength TSB and 5 g agarose were mixed in a beaker followed by addition of deionized water to 500 mL. The medium was autoclaved at 120° C. for 20 min. Before use, it was maintained at 42° C. to prevent from solidifying.

Overlay gel: One liter of overlay gel contains 60 g of TSB powder and 10 g of agarose. The medium was autoclaved at 120° C. for 20 min. To prevent from solidifying, it was maintained at 42° C. before use.

B. High Performance Liquid Chromatography (HPLC)

The analytical HPLC analyses were carried out on a SHIMADZU NexraX$_2$ LC-30AD system with an analytical column (Aeris peptide XB—C18, 4.6×250 mm for peptide analysis. The peptide purifications were performed using Shimadzu HPLC equipped with a semi-preparative HPLC column (Jupiter C18, 5 μM, 10×250 mm). All the HPLC runs were done using the mixture of two solutions, A (0.045% TFA in water) and B (0.039% TFA in acetonitrile/water (9/1) mixture). Flow rate was 0.8 ml/min for analysis and 2.5 ml/min for purification. UV detection was carried out at 220 nm.

C. Mass Spectrometry

Peptides ESI mass spectra data were obtained on both ESI (Thermo Finnigan LCQ DECA XP MAX) and MALDI TOF MS (ABI 4800 MALDI TOF/TOF system).

D. Peptide Synthesis

The peptides RYRLNHV—NH$_2$ (SEQ ID NO:140), RLYR—NH$_2$ (SEQ ID NO:139), (RIβA)$_2$KY—NH$_2$, (RIβA)$_4$K$_2$KY—NH$_2$ and (RIβA)$_8$K$_4$K$_2$KY—NH$_2$ were prepared by standard Fmoc chemistry using Rink Amide MBHA resin. Prior to use, resin was swelled with DCM for 5 min. Before coupling the first residue, an Fmoc deprotection was performed using 20% piperidine in dimethylformamide (DMF) for 2 min, followed by another 20 min treatment. For standard coupling reactions, 4 eq. of Fmoc-AA-OH, 4 eq. of PyBOP were first mixed in DCM/DMF mixture and added to the resins. 8 eq. of DIEA was added subsequently. Coupling reaction mixtures were shaken on the belly dancer for 60 to 90 min, efficiency monitored by Kaiser test. Between couplings and deprotections, resins were washed with DMF and DCM alternatively. For efficient synthesis of the dendrons, it is recommended to perform acetic anhydride capping (0.5 eq to the coupling capacity) after the deprotection of the first residue. The building blocks used for the peptides mentioned above were Fmoc-Tyr(tbu)-OH, Fmoc-Arg(Pbf)-OH, Fmoc-Leu-OH, Fmoc-Asn(Trt)-OH, Fmoc-His(Trt)-OH, Fmoc-Val-OH, Fmoc-Ile-OH, Fmoc-βAla-OH, Fmoc-Lys(Fmoc)-OH. Upon completion of peptide assembling, peptides were cleaved from the resin using a mixture containing 95% TFA, 2.5%

TIS and 2.5% water. Peptides were precipitated from the cleavage reaction using cold ether.

Thiodepsipeptides RYRLN-thioglc-V (SEQ ID NO:142), Ac-RYRLN-thioglc-V—NH$_2$ (SEQ ID NO:137) and Ac-RLYRN-thioglc-V—NH$_2$ (SEQ ID NO:138) were prepared by Boc chemistry using MBHA resin. Coupling procedures were the same as Fmoc. For Boc deprotection, 30% TFA in DCM was used. The building blocks used were Boc-Arg (Mts)-OH, Boc-Leu-OH.H$_2$O, Boc-Asn(Trt)-OH, Boc-Tyr (2-Br—Z)—OH, trityl-protected thioglycolic acid, Boc-Val-OH. Acetic anhydride was used to introduce an acetyl group at the N-terminus. For the final cleavage (scale of 100 mg resin), 450 µl mixture of thioanisole/ethanethiol was first added to the resin, 3 ml of TFA was subsequently added to the reaction chilled on ice. After 10 min, 300 µl of TFMSA was added dropwise and the reaction was stirred at room temperature for 1 h.

E. Butelase 1 Preparation

A four-step chromatographic procedure was used to extract butelase 1 from the plant *Clitoria ternatea*. 1 kg of freshly collected *Clitoria ternatea* pods were homogenized with 1 l of extraction buffer EB1 (20 mM sodium phosphate, 2 ml of 0.5 M EDTA, 174 mg of PMSF, 0.35 ml of β-ME, pH 6.0). After removing the plant debris by filtration, ammonium sulfate solid was added to 15% saturation. The undesired large proteins were precipitated and removed by centrifuge. Ammonium sulfate was further added to 85% saturation and the precipitated proteins were collected after centrifuge. The extraction buffer EB1 was added to redissolve the proteins. The protein solution was dialyzed for overnight against extraction buffer EB2 (20 mM sodium phosphate, 1 mM EDTA and 5 mM (3-ME, pH 6.0).

Figure 24:
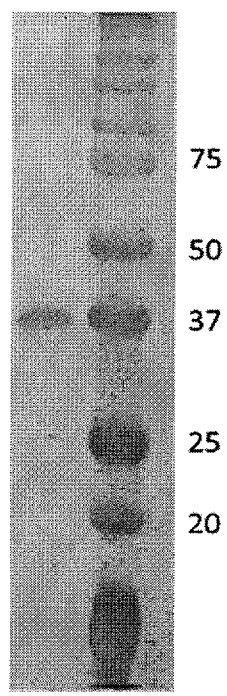
FIG. 24. SDS-PAGE (silver staining) of isolated butelase 1 (left lane) and protein markers (right lane).
Figure 25:
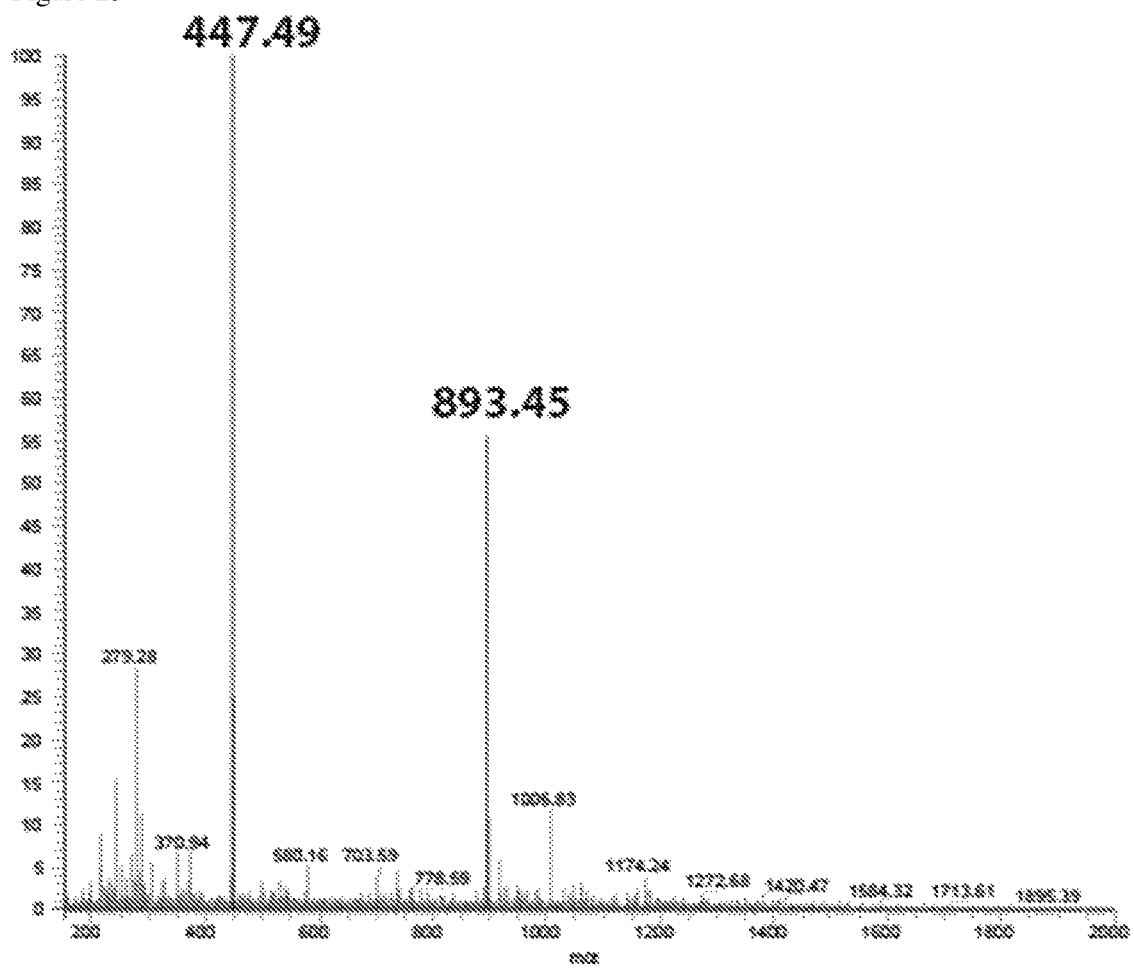
FIG. 25. Mass spectrum of RYRLN(S)GV-NH$_2$ (SEQ ID NO: 136). ESI-MS (positive) 893.45 (observed, M+H) 893.5 (calculated, M+H).
Figure 26:
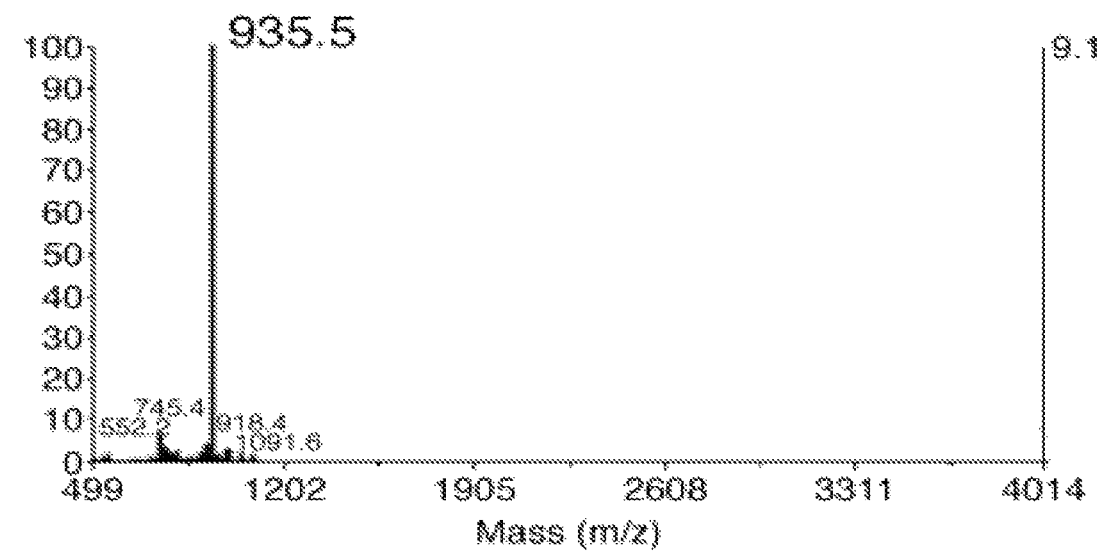
FIG. 26. Mass spectrum of Ac-RYRLN(S)GV-NH$_2$ (SEQ ID NO:137). MALDI-MS 935.5 (observed, M+H) 935.5 (calculated, M+H).
Figure 27:
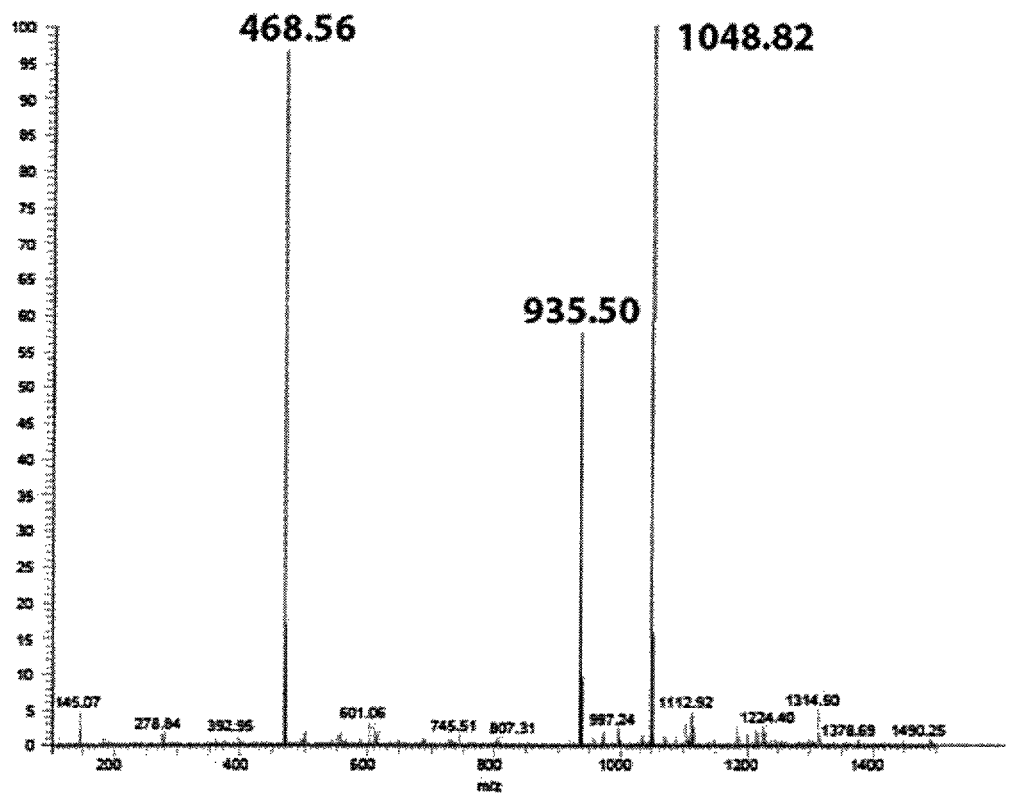
FIG. 27. Mass spectrum of Ac-RLYRN(S)GV—NH$_2$ (SEQ ID NO:138). ESI-MS (positive) 935.50 (observed, M+H) 1048.82 (observed, M+TFA) 935.5 (calculated, M+H).
Figure 28:
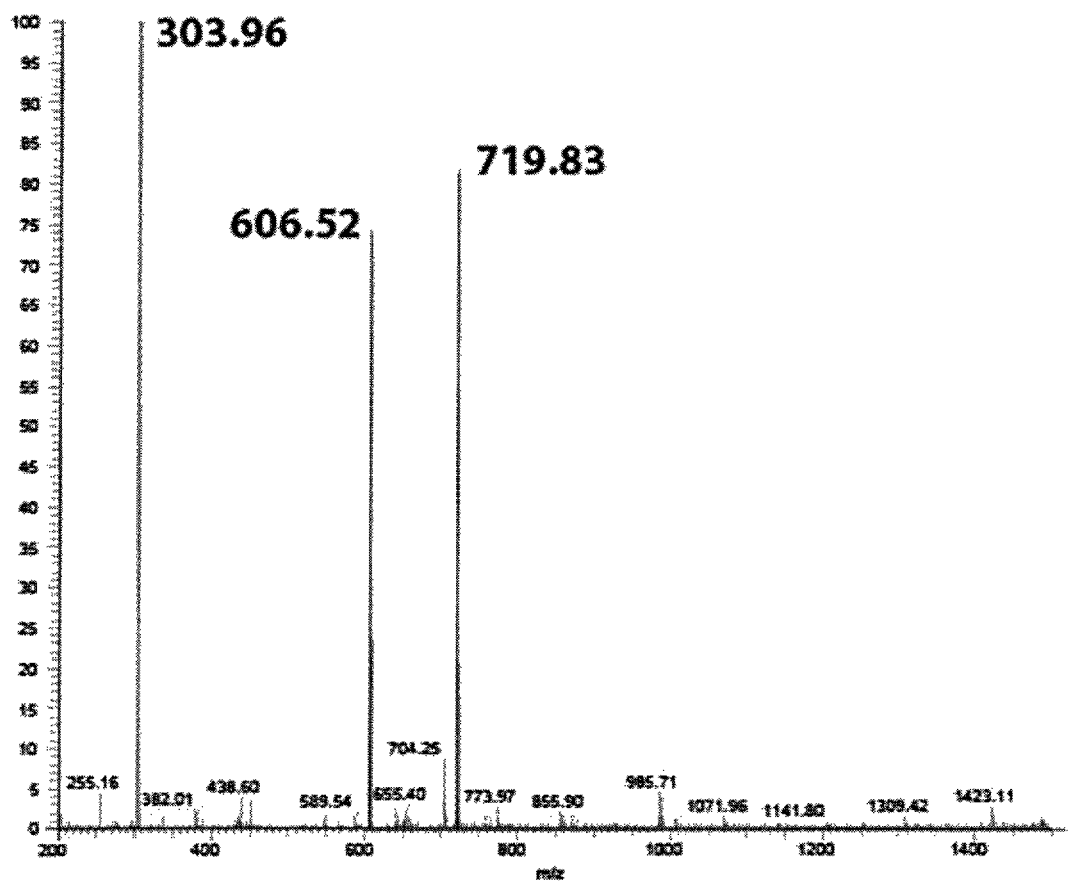
FIG. 28. Mass spectrum of RLRY—NH$_2$ (SEQ ID NO:139). ESI-MS (positive) 606.52 (observed, M+H) 719.83 (observed, M+TFA) 606.4 (calculated, M+H).
Figure 29:
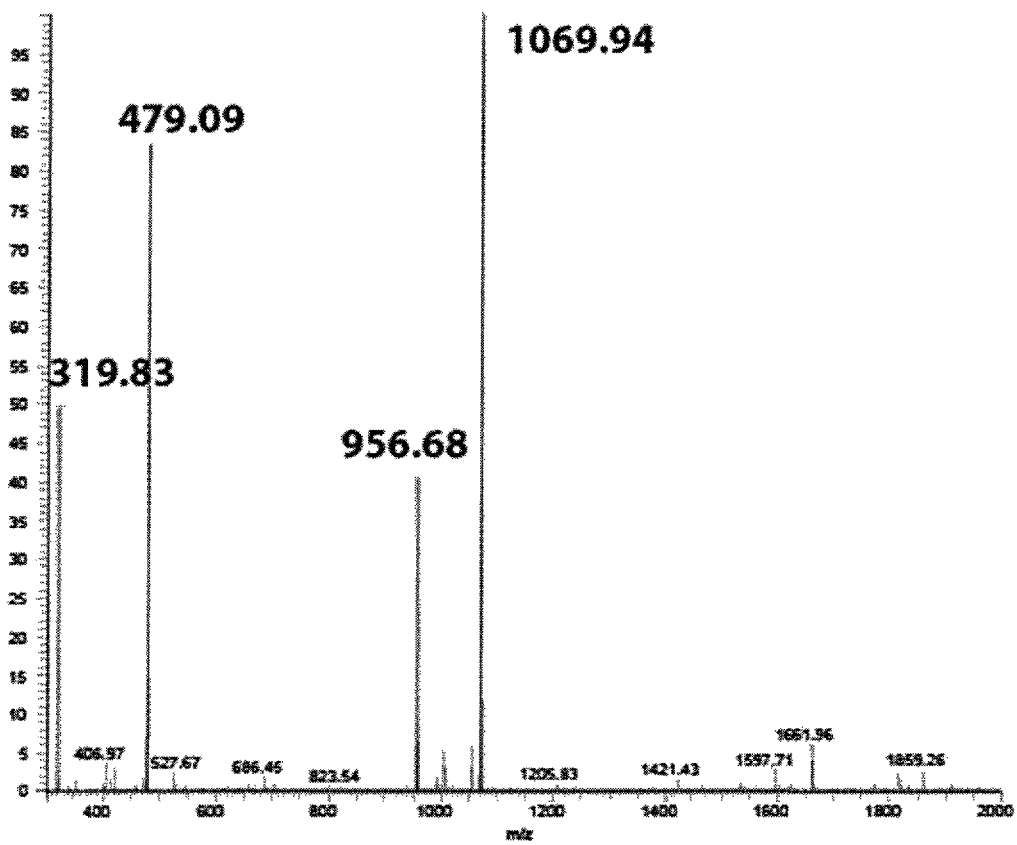
FIG. 29. Mass spectrum of RYRLNHV—NH$_2$ (SEQ ID NO:140). ESI-MS (positive) 956.68 (observed, M+H) 1069.94 (observed, M+Na) 956.5 (calculated, M).
Figure 30:
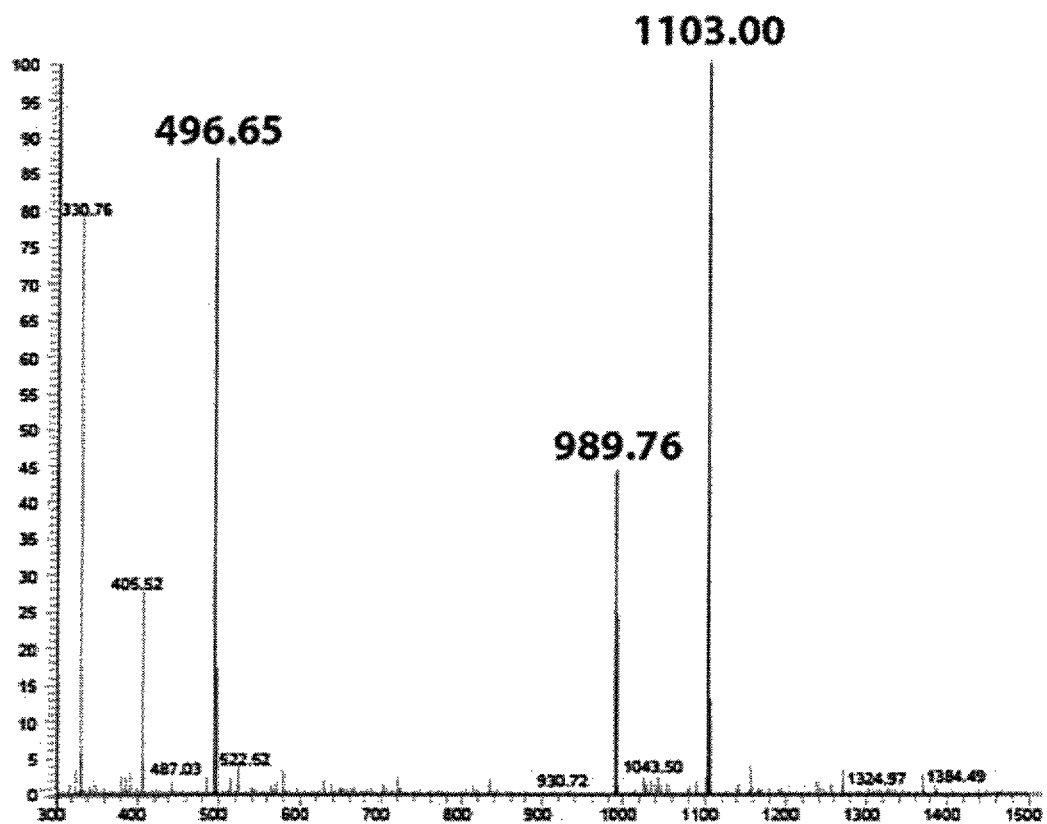
FIG. 30. Mass spectrum of (RIβA)$_2$KY—NH$_2$ ESI-MS (positive) 989.76 (observed, M+H) 1103.00 (observed, M+TFA) 989.6 (calculated, M+H).
Figure 31:
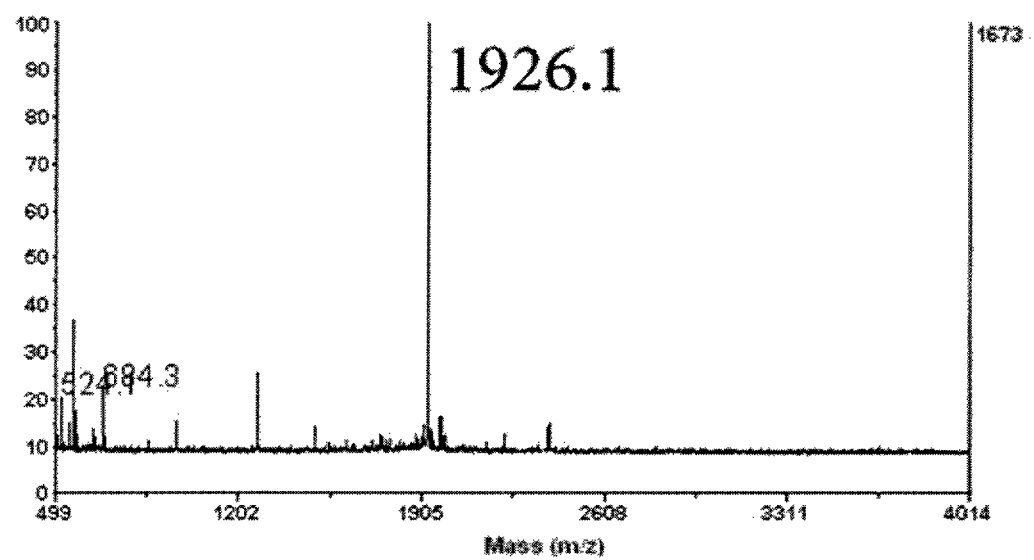
FIG. 31. Mass spectrum of (RIβA)$_8$K$_2$KY—NH$_2$ MALDI-MS 1926.1 (observed, M+H) 1926.3 (calculated, M).
Figure 32:
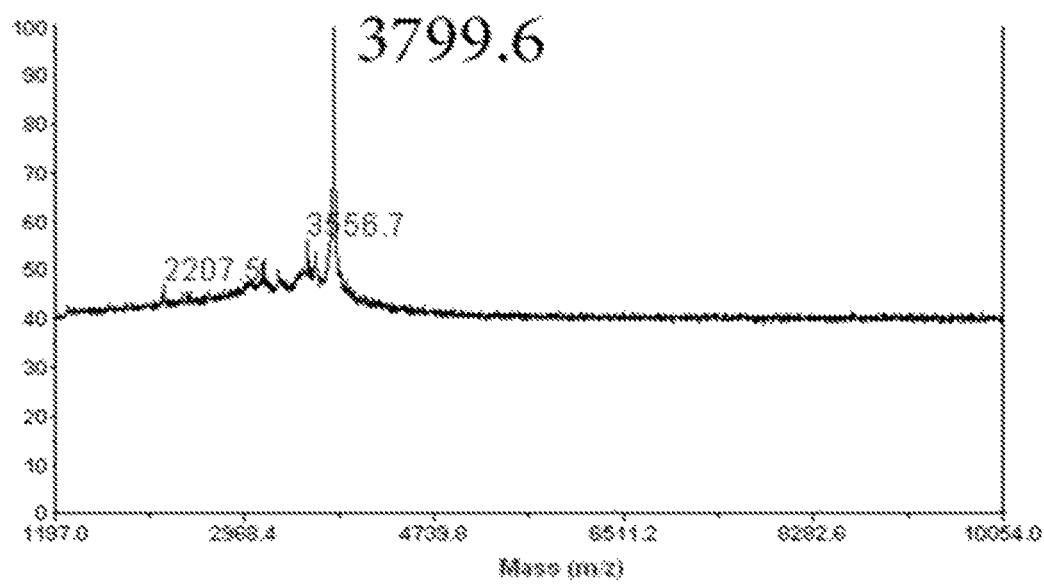
FIG. 32. Mass spectrum of (RIβA)$_8$K$_4$K$_2$KY—NH$_2$. MALDI-MS 3799.6 (observed, M+H) 3799.5 (calculated, M+H).
Figure 33:
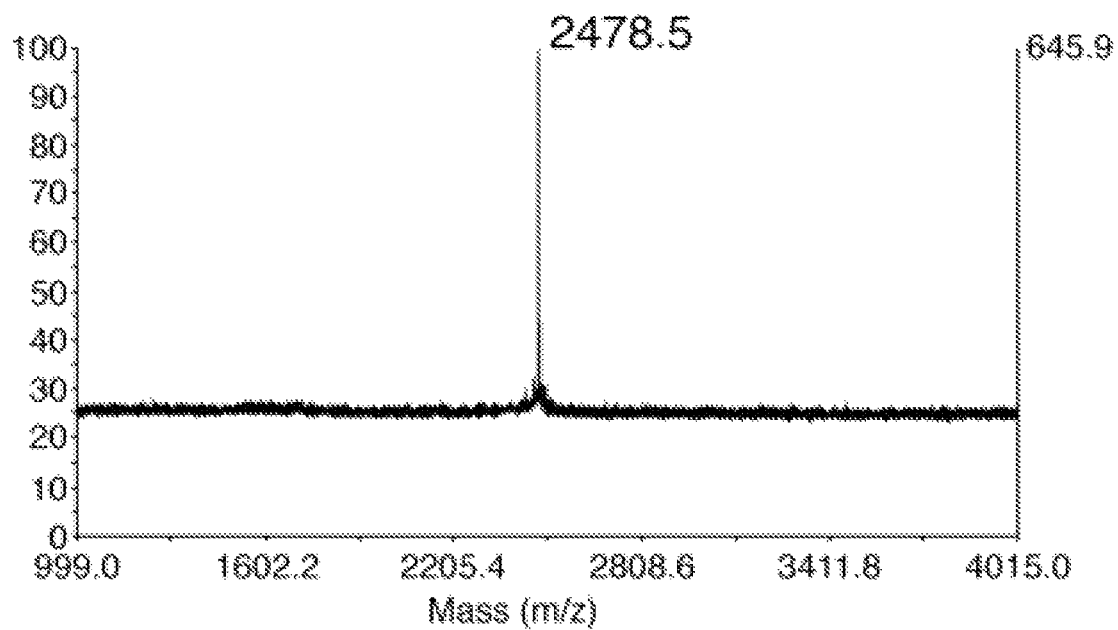
FIG. 33. Mass spectrum of (Ac-RLYRNRIβA)$_2$KY—NH$_2$. MALDI-MS 2478.5 (observed, M+H) 2478.4 (calculated, M+H).
Figure 34:
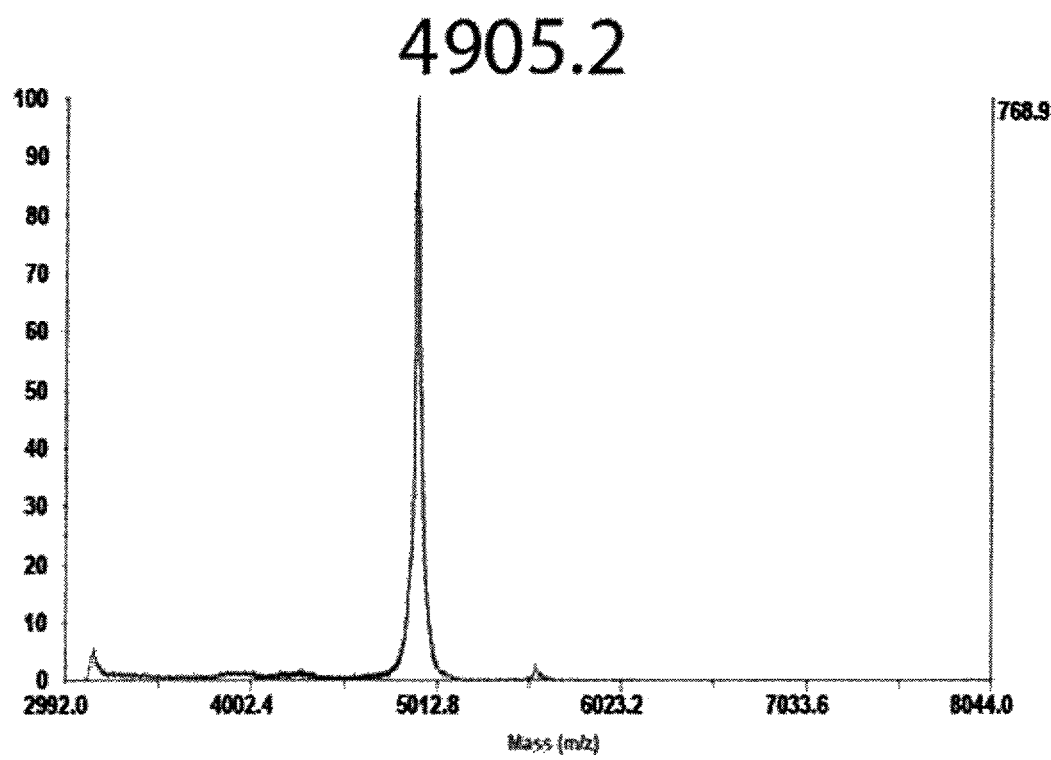
FIG. 34. Mass spectrum of (Ac-RLYRNRIβA)$_4$K$_2$KY—NH$_2$. MALDI-MS 4905.2 (observed, M+H) 4903.8 (calculated, M+H).

On the second day, the dialyzed protein solution was subjected to the flash chromatography column containing 300 ml slurry of Q Sepharose Fast Flow anion exchange resin (GE Healthcare). The column was first washed with EB2 and then eluted with 500 ml of elution buffer (EB2+200 mM NaCl). The eluent was dialyzed against EB2 for 4 h and fractionated using preparative PolyWax anion-exchange column (PolyLC, 21×250 mm). Fractions containing ligase activity were determined by testing on a cyclizable linear peptide substrate (GRCTKISPPICFPNHV, SEQ ID NO:141). All the fractions containing ligase activity were combined and concentrated using centrifugal filter with a MWCO of 10 kDa. The concentrated samples were first purified by a size-exclusion chromatography with Biosuite HPLC column and further purified by analytical anion-exchange chromatography using 4.6×200 mm PolyWax column. The purity of the isolated butelase 1 was determined by SBS-PAGE and silver staining, the enzyme showing a band at 37 kDa in SDS-gel. The concentration of butelase 1 was determined by OD280 based on the modeling. Around 5 mg of enzyme was obtained from the starting 1 kg of pods. FIG. 24 shows the SDS-PAGE (silver staining) of isolated butelase 1 (left lane) and protein markers (right lane).

F. Ligation Protocol

For all analytical reactions, a total system of 100 µl was used. Before the reaction, the stocks of thiodepsipeptides and butelase 1 were placed on the ice. The order of addition was: pH 6.5 phosphate buffer (20 mM), TCEP (1 mM), dendron core (50 µM), thiodepsipeptide (1.5 eq. per branch), butelase 1 (0.001 eq. per branch). After all reagents were added, the reaction was heated at 42° C. in a heating bath. A volume of 20 µl was taken out for HPLC analysis.

G. Radial Diffusion Assay

The following protocol was applied to the radial diffusion assay.

1. A single colony was picked and transferred into a 5 ml tube containing 2.5 ml TSB. The culture was shaken at 37° C. for 18 h.

2. 50 µl of the stationary phase culture was diluted to 2.5 mL of autoclaved TSB (1:50 dilution) and shaken at 37° C. for another 3 h.

3. This subculture was centrifuged at 5000 rpm for 5 min and the supernatant was discarded. The residual cells were washed with cold sterile 10 mM phosphate buffer, pH 7.4 and the buffer was discarded after centrifuge. 5 ml of the same buffer was added to resuspend the cells and its bacteria concentration was determined by measuring its optical density at 620 nm.

4. 10 ml of antoclaved, molten underlay gel agar was transferred to a 15-ml eppendorf tube and mixed with 4×10$^6$ CFU of bacteria by vortexing. The mixture was then poured into a petri dish and gelled in less than 3 mM. Wells were punched against the gel using a Pasteur pippette.

5. Peptides to be tested were serially diluted and 3.5 µl of each sample was added to the well. The plates were incubated at 37° C. for 3 h with gel-side up.

6. Next, each underlay gel was covered with 10 ml of overlay gel. After the gel solidified, the plates were turned gel-side up and incubated at 37° C. for overnight.

7. The following morning, all the plates were taken out and the zone diameters were measured with ruler. All the samples were tested in duplicates and the results were averaged. The final minimum inhibition concentration (MIC) was determined using excel.

Conjugation methods are enabling tools for biochemical studies. Their applications include labeling proteins with a biophysical probe or a bioactive cargo to enable structural studies, drug development as well as preparing biomaterials and immobilizing peptides and proteins on solid supports (Bioconjug Chem. 2014, 25, 825-839; Curr Org Chem. 2010, 14, 138-147).

Chemical strategies for a site-selective protein conjugation often utilize classic acylation or alkylation chemistries, taking advantages of the side-chain functionalities of Lys, Asp/Glu, and Cys residues (Chem Rev. 2015, 115, 2174-2195). A limitation of these methods is that they are not site-specific because proteins often carry multiple copies of these "selective" residues. Consequently, they lead to heterogeneous products. Recent advances have addressed this limitation including the use of recombinant methods to incorporate unnatural amino acids with unique chemical activities to allow both site-selective and site-specific conjugation on proteins in the presence of other natural amino acids to render a modified protein product homogenous (Nat Rev Mol Cell Biol. 2006, 7, 775-782).

Ligases, peptide-bond forming enzymes, provide an exciting complementary strategy through a ligase-mediated bioconjugation to the existing chemical conjugation methods. Bioconjugation, because of the inherent chemoselectivity of a ligase, produces exquisite site-selectivity and site-specificity (Bioconjug Chem. 2013, 24, 1277-1294). Current peptide ligases include sortase A (Chemistry. 2014, 20, 8516-8529) and subtiligase (Proc Natl Acad Sci USA. 1994, 91, 12544-12548). Recently, a new peptide ligase, namely butelase 1, was isolated from a cyclotide-producing plant *Clitoria ternatea* (Nat Chem Biol. 2014 10, 732-738). butelase 1 is the enzyme responsible for the macrocyclization of cliotides, cyclotides from *C. ternatea*, during their biosynthesis and recognizes a linear precursor with a C-terminal tripeptide motif Asn/Asp(Asx)-His-Val. It cleaves the bond between Asx and His to accept an N-terminal residue Xaa, resulting in a new Asx-Xaa bond in the cyclized peptide. butelase 1 exhibits not only the highest catalytic kinetics among all the peptide ligases found so far, but also a broad substrate specificity for the N-terminal amino acid, Xaa which can be any amino acid except Pro, making it an attractive tool for bioconjugation and peptide ligation (Chem Commun (Camb). 2015, 51, 17289-17292; Angew Chem Int Ed Engl. 2015, 54, 15694-15698; J Am Chem Soc. 2015, 137, 15398-15401).

Multiple antigen peptide system (MAP), a strategy to present multiple functional peptides in a clustered dendrimeric format, was first developed by Tam to amplify the immunogenecity of small antigenic peptides (J Biol Chem. 1988, 263, 1719-1725; Proc Natl Acad Sci USA. 1988, 85, 5409-5413). This chemical platform has also found wide applications in peptide-based therapeutics and biomaterials (J Biotechnol. 2002, 90, 195-229). A common MAP design contains a scaffold, a branching oligolysine dendron core, to which various copies of a functional peptide are attached. Often, stepwise solid phase peptide synthesis (SPPS) or a convergent synthetic strategy is used to prepare such peptide dendrimers (Mol Immunol. 1991, 28, 623-630). For many applications, stepwise SPPS suffices; however, as the size of a MAP increases, the likelihood of synthetic errors such as residue deletion also increases, making purification a challenge to arrive at a homogeneous product from a synthetic mixture. Although this problem could be partially mitigated by an optimized SPPS methodology, increased attentions have been focused on employing a convergent strategy in which the dendron core and the antigenic peptides are separately synthesized and purified to homogeneity and then brought together using chemoselective conjugation reactions. Conjugation chemistries developed thus far include disulfide (Int J Pept Protein Res. 1991, 37, 27-32), thioether (Int J Pept Protein Res. 1992, 40, 214-221), thiazolidine (J Am Chem Soc. 1994, 116, 6975-6976), oxime (Mol Immunol. 1995, 32, 1031-1037), hydrazine (Int J Pept Prot Res. 1995, 45, 78-85), maleimide (Bioconjug Chem. 2013, 24, 578-585) and native chemical ligation (Biopolymers. 2008, 90, 624-632). Compared with the stepwise SPPS method, the convergent strategy often gives higher yield and greater purity of the final MAP products.

Figure 19:
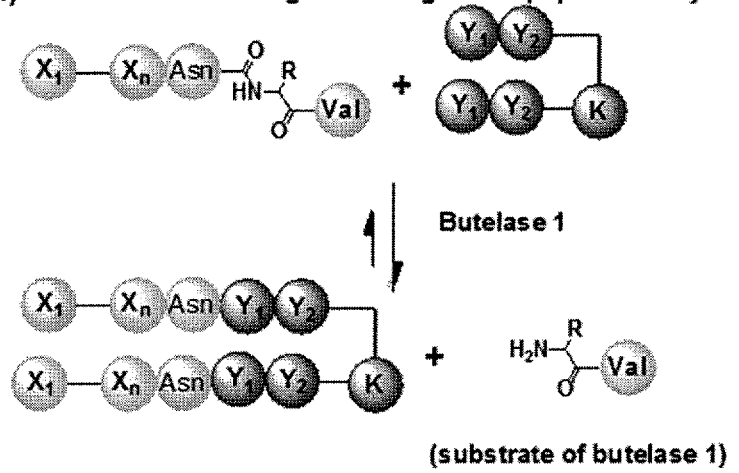
FIG. 19. Butelase-mediated peptide dendrimer synthesis (bivalent format as example), using A) native peptides and B) thiodepsipeptides as acyl donor substrates.
Figure 19:
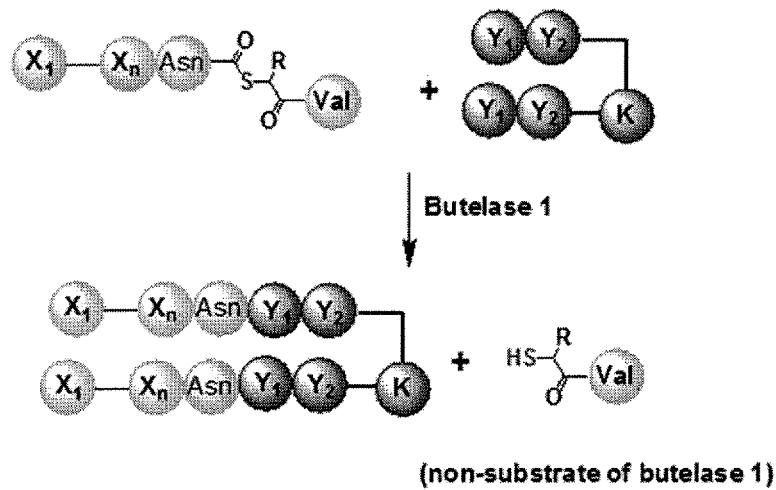
Figure 20:
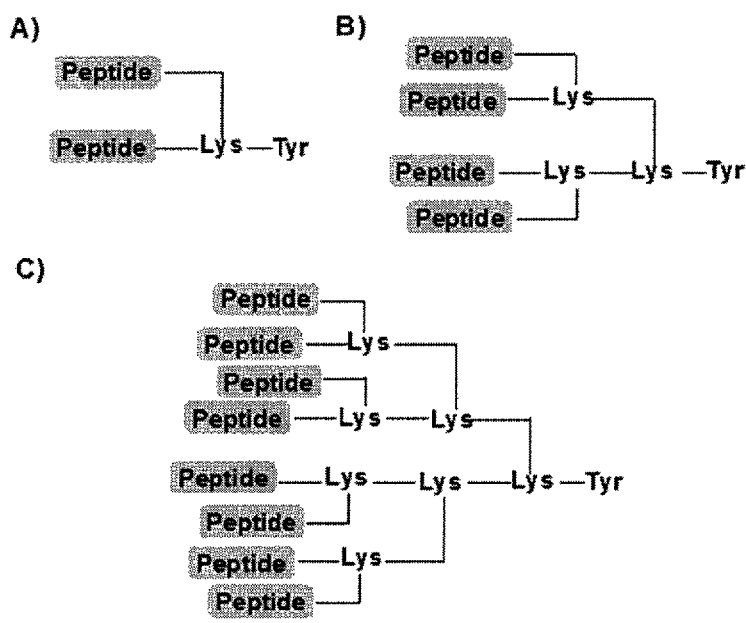
FIG. 20. Schematic presentation of selected peptide dendrimer structures assembled by butelase-mediated bioconjugation. A) bivalent peptide dendrimer (Ac-RYRLNRIβA)$_2$KY; B) tetravalent peptide dendrimer (Ac-RYRLNRIβA)$_4$K$_2$KY; C) octavalent peptide dendrimer (Ac-RYRLNRIβA)$_8$K$_4$K$_2$KY.

Inventors envisioned that, with its exquisite site-specificity and site selectivity, butelase 1 would be useful for peptide dendrimer synthesis whereby a peptide as an acyl donor could be bioconjuated to a lysyl dendron core containing appropriate N-terminal acceptor amino acids to form a multi-valent dendrimeric product (FIGS. 19 and 20). An enzymatic synthesis of a highly clustered peptide dendrimer (such as the octavalent one) would present a stringent test of a butelase-mediated ligation (BML) and help to advance the development of peptide-based vaccines and therapeutics.

In a trial reaction in which a conventional peptide substrate containing the C-terminal —NHV motif (peptide 4, Table 3) was used to bioconjugate to a bivalent lysyl dendron core (entry 2, Table 3), a sluggish reaction even with an excess of the monomeric peptide 4 and in a prolonged period was observed. Inventors attributed this poor outcome to the reversibility of the BML reaction because the released dipeptide His-Val acts as a competing nucleophile (FIG. 19A). Prompted by this observation, inventors sought to use thiodepsipeptides as acyl donors for peptide dendrimer synthesis to overcome the reversibility issue. It has been previously shown that thiodepsipeptides are superior substrates for butelase-mediated N-terminal labeling of proteins (Angew Chem Int Ed Engl. 2015, 54, 15694-15698). The use of thiodepsipeptide has two advantages. First, it contains a thioester linkage as the scissile bond which is more susceptible to enzymatic cleavage compared to its amide bond counterpart. Second, after the reaction, it releases a thiol byproduct which, unlike its native dipeptide counterpart, is a poor acyl-acceptor substrate of butelase 1, essentially rendering the BML reaction irreversible (FIG. 19B).

TABLE 3

Sequences of the used peptides.

| Number | SEQ ID NO: | Sequence |
|---|---|---|
| 1 | 118 | Ac-RYRLN-thioglc-V |
| 2 | | (RIβA)$_2$KY |
| 3 | | (Ac-RYRLNRIβA)$_2$KY |
| 4 | 119 | RYRLNHV |
| 5 | | (RYRLNRIβA)$_2$KY |
| 6 | | (RIβA)$_4$K$_2$KY |
| 7 | | (RIβA)$_8$ K$_4$K$_2$KY |
| 8 | | (Ac-RYRLNRIβA)$_4$K$_2$KY |
| 9 | | (Ac-RYRLNRIβA)$_8$K$_4$K$_2$KY |
| 10 | 120 | Ac-RLYRN-thioglc-V |
| 11 | 121 | RLYR |
| 12 | | (Ac-RLYRNRIβA)$_2$KY |
| 13 | | (Ac-RLYRNRIβA)$_4$K$_2$KY |

Figure 21:
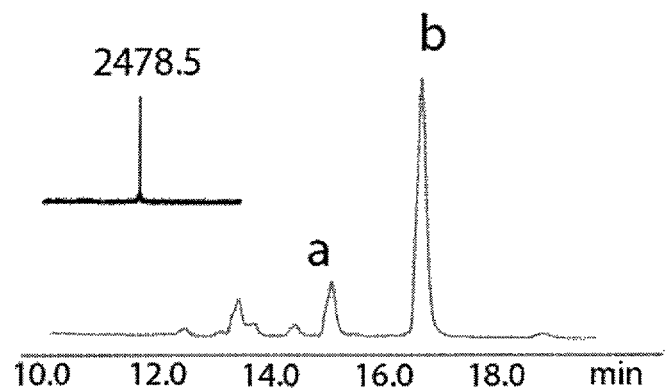
FIG. 21. Analytical HPLC monitoring of butelase-mediated peptide dendrimer bioconjugation using A) thiodepsipeptide—peak a: peptide Ac-RYRLN-thioglc-V (SEQ ID NO:118); peak b: desired bivalent product (Ac-RYRLNRIβA)$_2$KY with an observed mass of 2478.5 (calc. 2478.4 Da) or B) normal peptide—peak a': peptide RYRLNHV (SEQ ID NO:119); peak b': dendron core (RIβA)$_2$KY; peak c': the monovalent product; peak d': the desired bivalent product (RYRLNRIβA)$_2$KY.
Figure 21:
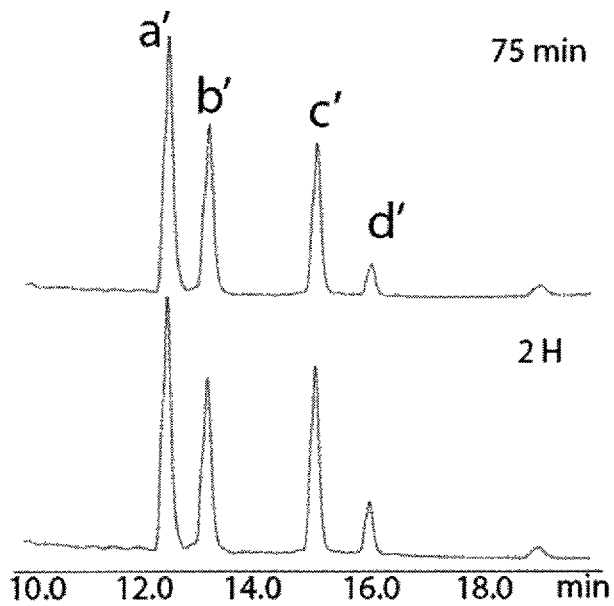
Figure 23:
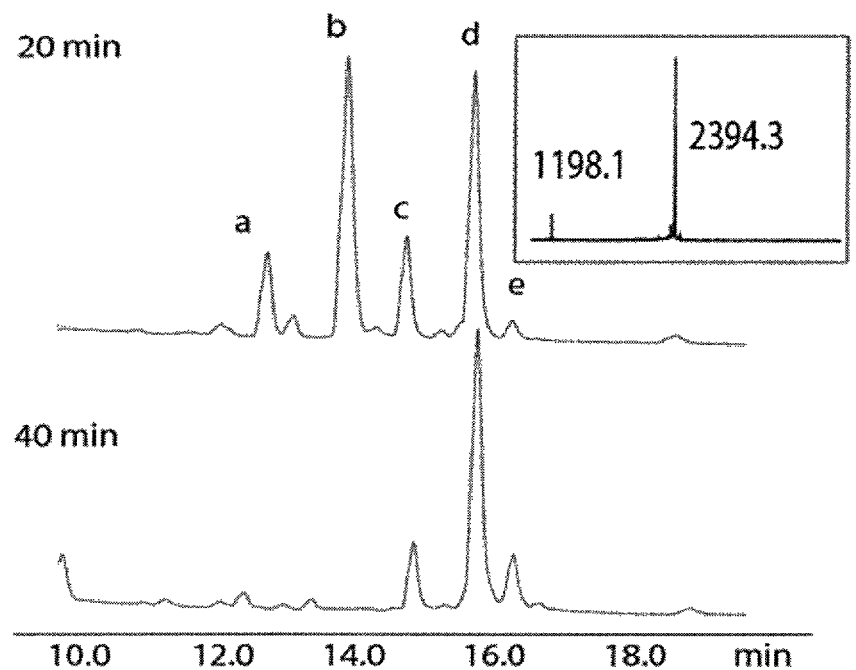
FIG. 23. HPLC profile of the ligation between the thiodepsipeptide RYRLN(S)GV (SEQ ID NO: 142) and the bivalent dendron core (RI)$_2$KY in the presence of butelase 1 (100 nM) and TCEP (1 mM) in pH 6.5 20 mM phosphate buffer, 42° C. Peak a refers to the dendron core, peak b refers to thiodepsipeptide, peak c refers to the monovalent product, peak d refers to bivalent product, peak e refers to byproduct caused by self-ligation (inset: MALDI mass spec of desired bivalent product).

To test this hypothesis, inventors first conducted a bioconjuation between an N-acetylated thiodepsipeptide 1 (Table 3) and the bivalent lysyl scaffold 2. The N-terminus of the thiodepsipeptide was acetylated because inventors found self-ligation of N-terminus-free thiodepsipeptide as a minor side reaction (FIG. 23) possibly due to high reactivity of the thioester. Thiodepsipeptide 1 was conveniently prepared by Boc chemistry as previously reported (Angew Chem Int Ed Engl. 2015, 54, 15694-15698). Using HPLC, the ligation reaction of 1 with 2 in forming the bivalent product 3 was evaluated (FIG. 20A). The reaction was performed in the presence of 50 μM scaffold 2, 150 μM thiodepsipeptide 1 (1.5 equiv. per branch), 100 nM butelase 1 (0.001 equiv. per branch), 1 mM TCEP, pH 6.5 phosphate buffer at 42° C. The dendron core was consumed in 30 min and the desired product 3 was formed in >95% yield based on HPLC analysis (FIG. 21A). This is in strong contrast to the sluggish ligation between the native peptide 4 which contains the NHV motif and the scaffold 2. Under similar conditions, >50% of the starting materials were not consumed after 2 h (FIG. 21B). HPLC analysis showed that the monovalent product was the major product (peak c' in FIG. 2B) whereas the desired bivalent product was a minor product (peak d' in FIG. 21B). Side reactions due to self-ligation of the unacetylated peptide 4 were not observed.

To further test enzymatic multimerization of peptides at a higher density level, tetra- and octavalent lysly dendron cores 6 and 7 with four and eight branches, respectively, were then prepared by SPPS using a low-loading resin.

Figure 22:
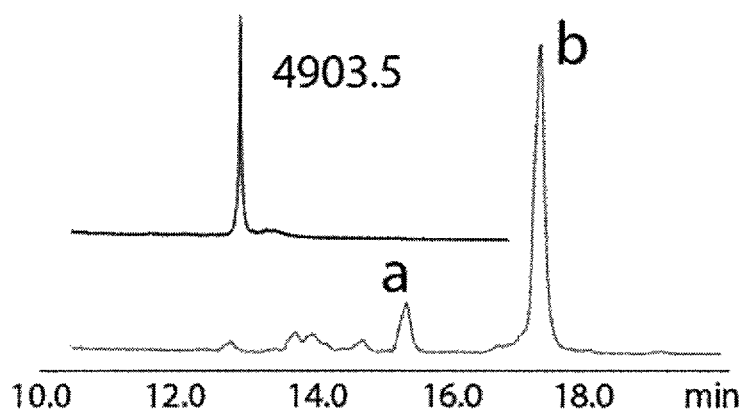
FIG. 22. Analytical HPLC monitoring of butelase-mediated preparation of (A) tetravalent dendrimer—peak a: linear peptide Ac-RYRLN-thioglc-V (SEQ ID NO:118); peak b: the desired tetravalent product (Ac-RYRLNRIβA)$_4$K$_2$KY with an observed mass of 4903.5 Da (calc. 4903.8 Da) and (B) octavalent dendrimer—peak a: linear peptide Ac-RYRLN-thioglc-V (SEQ ID NO:118); peak b': the desired octavalent product (Ac-RYRLNRIβA)$_8$K$_4$K$_2$KY with an observed mass of 9753.4 Da (calc. 9754.7 Da).
Figure 22:
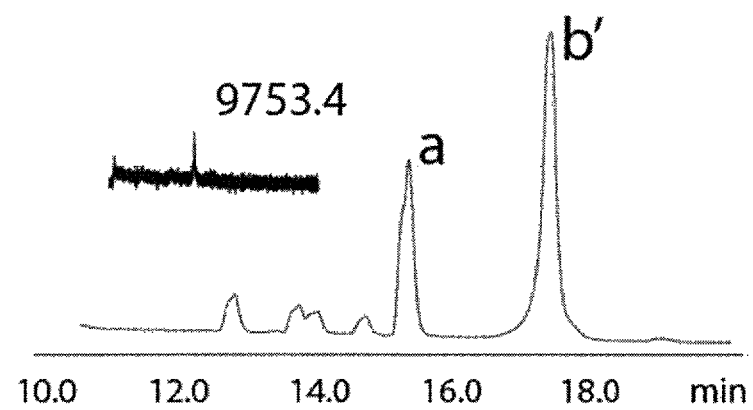

Under similar reaction conditions, clean and efficient ligations of thiodepsipeptide 1 with these two dendron cores were observed in HPLC profiles and dendron cores 6 and 7 were consumed after 45 min and 180 mM (FIG. 22), respectively, to give the corresponding tetra- and octavalent products 8 and 9 (peak b and b' in FIGS. 22A and B) in excellent yields (>85%). It should be noted that upon completion of the reaction, few intermediate low-order ligation products were found, a desirable scenario for purification purpose to achieve high product homogeneity. The synthesis of these MAPs with four and eight peptide branches showed the powerful nature of the butelase-mediated ligation reaction. To the best of inventors' knowledge, this is the first time that a peptide ligase has been used for the synthesis of an octabranched dendrimeric peptide. Moreover, the presently disclosed bioconjugation method forms native peptide bonds between the monomeric peptides and lysyl dendron cores, as opposed to most chemical conjugation methods which form non-peptidic linkages.

There is a growing interest to develop peptide-based antibiotics (Annu Rev Immunol. 1995, 13, 61-92; J Intern Med. 2003, 254, 197-215; Cent Eur J Biol 2007, 2, 1-33; Int J Pept Res Ther. 2010, 16, 199-213) because, compared with conventional antibiotics, they are less likely to develop drug resistance and have fewer side effects (J Med Chem. 2015, 58, 6533-6548; Biochemistry-Us. 2000, 39, 7159-7169; Eur J Biochem. 2000, 267, 3289-3300; Nucleic Acids Res. 2012, 40, W199-204). To apply the presently disclosed enzymatic method in preparing dendrimeric antimicrobials, inventors synthesized two antimicrobials 12 (bivalent) and 13 (tetravalent) (MS shown in supporting information) which harbored a tetrapeptide RLYR (SEQ ID NO:121) as the antibacterial sequence (Eur J Biochem. 2002, 269, 923-932) by ligating N-acetylated thiodepsipeptide 10 Ac-RLYRN-thioglc-V (SEQ ID NO:120) with dendron core 2 and 6 respectively. The RLYR (SEQ ID NO:121) tetrapeptide contains a BHHB motif (B=basic, H=hydrophobic) which is commonly found in certain potent and broad-spectrum β-stranded antimicrobial peptides (BioDrugs. 2013, 27, 479-493) such as PG (protegrins) (Febs Lett. 1993, 327, 231-236) and RTD-1 (rhesus monkey theta defensin) (Science. 1999, 286, 498-502). This consensus motif with positive charged and hydrophobic residues was successfully used as a dendrimeric antimicrobial in 2002 (Eur J Biochem. 2002, 269, 923-932). Such short peptide-based dendrimeric antimicrobials are broad-spectrum antibiotics and kill bacterial cells through electrostatic and hydrophobic interactions with the negatively charged microbial cytoplasmic membranes (Biochemistry-Us. 2009, 48, 5642-5657). Using a radial diffusion assay, inventors tested the antimicrobial activities against *E. coli* and *S. aureus* of these two dendrimeric peptides together with prototypical monomer 11 RLYR (SEQ ID NO:121), mono-, tri-lysine dendron core 2 and 6 for comparison. All assays were performed under a high-salt condition (100 mM NaCl) to simulate physiological conditions. The monomeric peptide 11 showed no appreciable activity against either *E. coli* or *S. aureus* (Table 4). However, significant antimicrobial activities were observed with the bivalent product 12 which had a MIC of 18.3 µM against *E. coli* and 3.4 µM against *S. aureus*. The tetravalent dendrimeric structure 13 had further improved antimicrobial activities with MICs<3 µM against both strains. When testing 13 against several drug-resistant strains under high-salt condition, the tetramer construct was broadly active against all six tested strains with MICs ranging from 0.87 to 4.8 µM. The results suggest that MAP-based dendrimeric peptides, which can be easily prepared using BML, are an effective platform for the design of antimicrobial agents. A possible reason for this success is that the dendrimeric structure increases the effective molarity of the functional monomeric units and reduces the entropy cost associated with peptide self-assembly on bacterial plasma membranes (Eur J Biochem. 2002, 269, 923-932).

TABLE 4

Antimicrobial activity of different peptides against *E. coli* and *S. aureus*.

| Peptide | MIC (µM) | |
|---|---|---|
| | E. coli | S. aureus |
| Monomer 11 | >300 | >300 |
| Bivalent dendron core 2 | >150 | >150 |
| Tetravalent dendron core 6 | >150 | >150 |
| Dimer 12 | 18.3 | 3.4 |
| Tetramer 13 | 2.4 | 1.4 |

TABLE 5

Antimicrobial activity of tetramer 13 against different drug-resistant strains.

| Organism | MIC (µM) |
|---|---|
| E. cloacae DM 09800 | 0.9 |
| K. species DR 13779 | 1.5 |
| E. coli DM 04604 | 4.5 |
| S. aureus DB 14329 | 4.8 |
| P. aeruginosa DM 14158 | 2.3 |
| E. coli DU 09777 | 2.2 |

In conclusion, inventors have developed a novel method to prepare peptide dendrimers using butelase 1 as the catalyst for bioconjugation of thiodepsipeptides with a lysyl dendron core. Using a small excessive of a monomeric peptide substrate (1.5 equiv. per branch to the dendron core) and a low catalytic amount of the enzyme butelase 1 (0.001 equiv.), inventors obtained very efficient synthesis of the bi-, tetra- and octavalent dendrimers. No other peptide ligases have been used for the synthesis of such dendrimeric peptides. Inventors further used this bioconjugation method to evaluate the polyvalent feature of peptide dendrimers as antimicrobials. Inventors found that a tetravalent dendrimer containing a tetrapeptide sequence with the BHHB motif is a potent broad-spectrum antimicrobial (MICs<5 µM), including several drug-resistant bacterial strains. The presently disclosed butelase-mediated bioconjugation method works under mild conditions and is user-friendly as it requires no complicated chemistry operations. Inventors anticipate this method to be a useful tool in preparing peptide dendrimers.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A method of forming a peptide of Formula (I) $P^1$-Asx-Xaa$^1$-Xaa$^2$-$P^2$ (I), the method comprising:
enzymatically cleaving a bond between "Asx" and "X" in a first peptide of Formula (II)

$$P^1\text{-Asx-X—R} \quad \text{(II); and}$$

ligating a $P^1$-Asx fragment of the first peptide of Formula (II) to a second peptide of Formula (III)
Xaa$^1$-Xaa$^2$-$P^2$ (III) to form the peptide of Formula (I);
wherein $P^1$ and $P^2$ are each independently any peptide, modified or unmodified; Asx is Asp or Asn; X is S; R is a substituted or unsubstituted alkyl selected from the group consisting of
—(CH$_2$)$_n$—CONH$_2$, —(CH$_2$)$_n$—COOH, —(CH$_2$)$_n$—CO-AA$^1$,

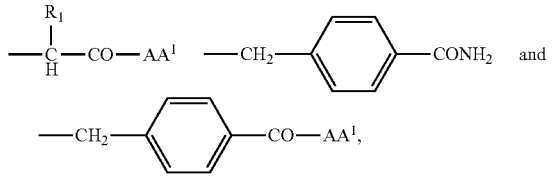

wherein n is an integer of 1 to 10, R$_1$ is H, or any other side chain of a naturally occurring amino acid, and AA$^1$ is any amino acid or is absent; Xaa$^1$ is any naturally occurring amino acid with the exception of Pro; Xaa$^2$ is a naturally occurring amino acid;
wherein the enzymatic cleavage and ligation are catalyzed by a polypeptide having at least 90% of the ligase activity of butelase 1 (SEQ ID NO:1).

2. The method according to claim 1, wherein Asx is Asn, R is —CH(R$_1$)—CO-AA$^1$, R$_1$ is H, and AA$^1$ is any amino acid or absent.

3. The method according to claim 1, wherein Asx is Asn, R is —CH(R$_1$)—CO-AA$^1$, R$_1$ is H, and AA$^1$ is Val.

4. The method according to claim 1, wherein the polypeptide having at least 90% of the ligase activity of butelase 1 (SEQ ID NO:1) comprises:
(a) the amino acid sequence as set forth in SEQ ID NO:1 (butelase 1);
(b) an amino acid sequence that shares at least 80% sequence identity with the amino acid sequence as set forth in SEQ ID NO:1; or
(c) a fragment of any one of (a)-(b).

5. The method according to claim 1, wherein the polypeptide having the ligase activity of butelase 1 (SEQ ID NO:1) comprises the amino acid sequence as set forth in SEQ ID NO:2.

6. The method according to claim 1, wherein the polypeptide having at least 90% of the ligase activity of butelase 1 (SEQ ID NO:1) comprises
(a) the amino acid residue Asn at the position corresponding to position 19 of SEQ ID NO:1; and/or
(b) the amino acid residue His at the position corresponding to position 124 of SEQ ID NO:1; and/or
(c) the amino acid residue Cys at the position corresponding to position 166 of SEQ ID NO:1.

7. The method according to claim 1, wherein the polypeptide having at least 90% of the ligase activity of butelase 1 (SEQ ID NO:1) comprises
(a) any one of the amino acid sequences as set forth in SEQ ID Nos:3-109;
(b) an amino acid sequence that shares at least 80% sequence identity with any one of the amino acid sequences of (a) over its entire length;
(c) a fragment of any one of (a)-(b).

8. The method according to claim 1, wherein $P^1$ or $P^2$ is modified by one or more of an affinity tag, a detectable label, a solid support material, a scaffold molecule, or any combination thereof.

9. The method according to claim 1, wherein $P^1$ or $P^2$ is modified by one or more of a biotin, a fluorescent marker, a polymer resin, a dendrimer, or any combination thereof.

10. The method according to claim 9, wherein $P^1$ or $P^2$ is modified by a dendrimer.

11. The method according to claim 10, wherein each dendrimer is conjugated to 2 or more copies of the second peptide via $P^2$, such that the ligation of the first peptide and the second peptide results in a dendrimeric peptide assembly comprising 2 or more copies of the ligated peptide $P^1$-Asx-Xaa$^1$-Xaa$^2$-$P^2$.

12. The method according to claim 10, wherein each dendrimer is a lysyl dendrimer.

13. The method according to claim 1, wherein the first peptide is $P^1$-Asn-thioglc-Val, and $P^1$ is an antimicrobial peptide.

14. The method according to claim 13, wherein $P^1$ is an antimicrobial peptide comprising a BHHB tetrapeptide motif.

15. The method according to claim 14, wherein $P^1$ is an antimicrobial peptide comprising an Arg-Leu-Tyr-Arg (SEQ ID NO:121) tetrapeptide.

16. The method according to claim 15, wherein the first peptide is Ac-Arg-Leu-Tyr-Arg-Asn-thioglc-Val (SEQ ID NO:120).

17. The method according to claim 1, wherein the second peptide is Arg-Ile-βAla conjugated to a lysyl dendrimer via βAla.

18. The method according to claim 12, wherein the first peptide is Ac-Arg-Leu-Tyr-Arg-Asn-thioglc-Val (SEQ ID NO:120), and each lysyl dendrimer is conjugated to 2 or more copies of the second peptide Arg-Ile-βAla via βAla, such that the ligation of the first peptide and the second peptide results in a dendrimeric peptide assembly comprising 2 or more copies of Ac-Arg-Leu-Tyr-Arg-Asn-Arg-Ile-βAla (SEQ ID NO:131).

19. A dendrimeric peptide assembly comprising 2 or more copies of Ac-Arg-Leu-Tyr-Arg-Asn-Arg-Ile-βAla (SEQ ID NO:131).

20. The method according to claim 1, wherein Xaa$^2$ is a hydrophobic amino acid or Cys.

* * * * *

SEQUENCE LISTING

```
<160> NUMBER OF SEQ ID NOS: 142

<210> SEQ ID NO 1
<211> LENGTH: 342
<212> TYPE: PRT
<213> ORGANISM: Clitoria ternatea

<400> SEQUENCE: 1

Val Glu Gly Thr Arg Trp Ala Val Leu Val Ala Gly Ser Lys Gly Tyr
1               5                   10                  15

Val Asn Tyr Arg His Gln Ala Asp Val Cys His Ala Tyr Gln Ile Leu
            20                  25                  30

Lys Lys Gly Gly Leu Lys Asp Glu Asn Ile Ile Val Phe Met Tyr Asp
        35                  40                  45

Asp Ile Ala Tyr Asn Glu Ser Asn Pro His Pro Gly Val Ile Ile Asn
    50                  55                  60

His Pro Tyr Gly Ser Asp Val Tyr Lys Gly Val Pro Lys Asp Tyr Val
65                  70                  75                  80

Gly Glu Asp Ile Asn Pro Pro Asn Phe Tyr Ala Val Leu Leu Ala Asn
                85                  90                  95

Lys Ser Ala Leu Thr Gly Thr Gly Ser Gly Lys Val Leu Asp Ser Gly
            100                 105                 110

Pro Asn Asp His Val Phe Ile Tyr Tyr Thr Asp His Gly Gly Ala Gly
        115                 120                 125

Val Leu Gly Met Pro Ser Lys Pro Tyr Ile Ala Ala Ser Asp Leu Asn
    130                 135                 140

Asp Val Leu Lys Lys Lys His Ala Ser Gly Thr Tyr Lys Ser Ile Val
145                 150                 155                 160

Phe Tyr Val Glu Ser Cys Glu Ser Gly Ser Met Phe Asp Gly Leu Leu
                165                 170                 175

Pro Glu Asp His Asn Ile Tyr Val Met Gly Ala Ser Asp Thr Gly Glu
            180                 185                 190

Ser Ser Trp Val Thr Tyr Cys Pro Leu Gln His Pro Ser Pro Pro Pro
        195                 200                 205

Glu Tyr Asp Val Cys Val Gly Asp Leu Phe Ser Val Ala Trp Leu Glu
    210                 215                 220

Asp Cys Asp Val His Asn Leu Gln Thr Glu Thr Phe Gln Gln Gln Tyr
```

```
                225                 230                 235                 240
Glu Val Val Lys Asn Lys Thr Ile Val Ala Leu Ile Glu Asp Gly Thr
                245                 250                 255

His Val Val Gln Tyr Gly Asp Val Gly Leu Ser Lys Gln Thr Leu Phe
                260                 265                 270

Val Tyr Met Gly Thr Asp Pro Ala Asn Asp Asn Thr Phe Thr Asp
                275                 280                 285

Lys Asn Ser Leu Gly Thr Pro Arg Lys Ala Val Ser Gln Arg Asp Ala
                290                 295                 300

Asp Leu Ile His Tyr Trp Glu Lys Tyr Arg Arg Ala Pro Glu Gly Ser
305                 310                 315                 320

Ser Arg Lys Ala Glu Ala Lys Lys Gln Leu Arg Glu Val Met Ala His
                325                 330                 335

Arg Met His Ile Asp Asn
                340

<210> SEQ ID NO 2
<211> LENGTH: 482
<212> TYPE: PRT
<213> ORGANISM: Clitoria ternatea

<400> SEQUENCE: 2

Met Lys Asn Pro Leu Ala Ile Leu Phe Leu Ile Ala Thr Val Val Ala
1               5                   10                  15

Val Val Ser Gly Ile Arg Asp Asp Phe Leu Arg Leu Pro Ser Gln Ala
                20                  25                  30

Ser Lys Phe Phe Gln Ala Asp Asp Asn Val Glu Gly Thr Arg Trp Ala
            35                  40                  45

Val Leu Val Ala Gly Ser Lys Gly Tyr Val Asn Tyr Arg His Gln Ala
        50                  55                  60

Asp Val Cys His Ala Tyr Gln Ile Leu Lys Lys Gly Leu Lys Asp
65                  70                  75                  80

Glu Asn Ile Ile Val Phe Met Tyr Asp Asp Ile Ala Tyr Asn Glu Ser
                85                  90                  95

Asn Pro His Pro Gly Val Ile Ile Asn His Pro Tyr Gly Ser Asp Val
                100                 105                 110

Tyr Lys Gly Val Pro Lys Asp Tyr Val Gly Glu Asp Ile Asn Pro Pro
            115                 120                 125

Asn Phe Tyr Ala Val Leu Leu Ala Asn Lys Ser Ala Leu Thr Gly Thr
130                 135                 140

Gly Ser Gly Lys Val Leu Asp Ser Gly Pro Asn Asp His Val Phe Ile
145                 150                 155                 160

Tyr Tyr Thr Asp His Gly Gly Ala Gly Val Leu Gly Met Pro Ser Lys
                165                 170                 175

Pro Tyr Ile Ala Ala Ser Asp Leu Asn Asp Val Leu Lys Lys Lys His
            180                 185                 190

Ala Ser Gly Thr Tyr Lys Ser Ile Val Phe Tyr Val Glu Ser Cys Glu
        195                 200                 205

Ser Gly Ser Met Phe Asp Gly Leu Leu Pro Glu Asp His Asn Ile Tyr
    210                 215                 220

Val Met Gly Ala Ser Asp Thr Gly Glu Ser Ser Trp Val Thr Tyr Cys
225                 230                 235                 240

Pro Leu Gln His Pro Ser Pro Pro Glu Tyr Asp Val Cys Val Gly
                245                 250                 255
```

```
Asp Leu Phe Ser Val Ala Trp Leu Glu Asp Cys Asp Val His Asn Leu
            260                 265                 270

Gln Thr Glu Thr Phe Gln Gln Gln Tyr Glu Val Val Lys Asn Lys Thr
        275                 280                 285

Ile Val Ala Leu Ile Glu Asp Gly Thr His Val Gln Tyr Gly Asp
    290                 295                 300

Val Gly Leu Ser Lys Gln Thr Leu Phe Val Tyr Met Gly Thr Asp Pro
305                 310                 315                 320

Ala Asn Asp Asn Asn Thr Phe Thr Asp Lys Asn Ser Leu Gly Thr Pro
                325                 330                 335

Arg Lys Ala Val Ser Gln Arg Asp Ala Asp Leu Ile His Tyr Trp Glu
            340                 345                 350

Lys Tyr Arg Arg Ala Pro Glu Gly Ser Ser Arg Lys Ala Glu Ala Lys
        355                 360                 365

Lys Gln Leu Arg Glu Val Met Ala His Arg Met His Ile Asp Asn Ser
    370                 375                 380

Val Lys His Ile Gly Lys Leu Leu Phe Gly Ile Glu Lys Gly His Lys
385                 390                 395                 400

Met Leu Asn Asn Val Arg Pro Ala Gly Leu Pro Val Val Asp Asp Trp
                405                 410                 415

Asp Cys Phe Lys Thr Leu Ile Arg Thr Phe Glu Thr His Cys Gly Ser
            420                 425                 430

Leu Ser Glu Tyr Gly Met Lys His Met Arg Ser Phe Ala Asn Leu Cys
        435                 440                 445

Asn Ala Gly Ile Arg Lys Glu Gln Met Ala Glu Ala Ser Ala Gln Ala
    450                 455                 460

Cys Val Ser Ile Pro Asp Asn Pro Trp Ser Ser Leu His Ala Gly Phe
465                 470                 475                 480

Ser Val

<210> SEQ ID NO 3
<211> LENGTH: 488
<212> TYPE: PRT
<213> ORGANISM: Clitoria ternatea

<400> SEQUENCE: 3

Met Ala Val Asp His Cys Phe Leu Lys Lys Lys Thr Cys Tyr Tyr Gly
1               5                   10                  15

Phe Val Leu Trp Ser Trp Met Leu Met Met Ser Leu His Ser Lys Ala
            20                  25                  30

Ala Arg Leu Asn Pro Gln Lys Glu Trp Asp Ser Val Ile Arg Leu Pro
        35                  40                  45

Thr Glu Pro Val Asp Ala Asp Thr Asp Glu Val Gly Thr Arg Trp Ala
    50                  55                  60

Val Leu Val Ala Gly Ser Asn Gly Tyr Glu Asn Tyr Arg His Gln Ala
65                  70                  75                  80

Asp Val Cys His Ala Tyr Gln Leu Leu Ile Lys Gly Gly Leu Lys Glu
                85                  90                  95

Glu Asn Ile Val Val Phe Met Tyr Asp Asp Ile Ala Trp His Glu Leu
            100                 105                 110

Asn Pro Arg Pro Gly Val Ile Ile Asn Asn Pro Arg Gly Glu Asp Val
        115                 120                 125

Tyr Ala Gly Val Pro Lys Asp Tyr Thr Gly Glu Asp Val Thr Ala Glu
    130                 135                 140
```

-continued

```
Asn Leu Phe Ala Val Ile Leu Gly Asp Arg Ser Lys Val Lys Gly Gly
145                 150                 155                 160

Ser Gly Lys Val Ile Asn Ser Lys Pro Glu Asp Arg Ile Phe Ile Phe
                165                 170                 175

Tyr Ser Asp His Gly Pro Gly Val Leu Gly Met Pro Asn Glu Gln
            180                 185                 190

Ile Leu Tyr Ala Met Asp Phe Ile Asp Val Leu Lys Lys Lys His Ala
        195                 200                 205

Ser Gly Gly Tyr Arg Glu Met Val Ile Tyr Val Glu Ala Cys Glu Ser
210                 215                 220

Gly Ser Leu Phe Glu Gly Ile Met Pro Lys Asp Leu Asn Val Phe Val
225                 230                 235                 240

Thr Thr Ala Ser Asn Ala Gln Glu Asn Ser Trp Gly Thr Tyr Cys Pro
                245                 250                 255

Gly Thr Glu Pro Ser Pro Pro Glu Tyr Thr Thr Cys Leu Gly Asp
            260                 265                 270

Leu Tyr Ser Val Ala Trp Met Glu Asp Ser Glu Ser His Asn Leu Arg
        275                 280                 285

Arg Glu Thr Val Asn Gln Gln Tyr Arg Ser Val Lys Glu Arg Thr Ser
290                 295                 300

Asn Phe Lys Asp Tyr Ala Met Gly Ser His Val Met Gln Tyr Gly Asp
305                 310                 315                 320

Thr Asn Ile Thr Ala Glu Lys Leu Tyr Leu Phe Gln Gly Phe Asp Pro
                325                 330                 335

Ala Thr Val Asn Leu Pro Pro His Asn Gly Arg Ile Glu Ala Lys Met
            340                 345                 350

Glu Val Val His Gln Arg Asp Ala Glu Leu Leu Phe Met Trp Gln Met
        355                 360                 365

Tyr Gln Arg Ser Asn His Leu Leu Gly Lys Lys Thr His Ile Leu Lys
370                 375                 380

Gln Ile Ala Glu Thr Val Lys His Arg Asn His Leu Asp Gly Ser Val
385                 390                 395                 400

Glu Leu Ile Gly Val Leu Leu Tyr Gly Pro Gly Lys Gly Ser Pro Val
                405                 410                 415

Leu Gln Ser Val Arg Asp Pro Gly Leu Pro Leu Val Asp Asn Trp Ala
            420                 425                 430

Cys Leu Lys Ser Met Val Arg Val Phe Glu Ser His Cys Gly Ser Leu
        435                 440                 445

Thr Gln Tyr Gly Met Lys His Met Arg Ala Phe Ala Asn Ile Cys Asn
450                 455                 460

Ser Gly Val Ser Glu Ser Ser Met Glu Glu Ala Cys Met Val Ala Cys
465                 470                 475                 480

Gly Gly His Asp Ala Gly His Leu
                485

<210> SEQ ID NO 4
<211> LENGTH: 359
<212> TYPE: PRT
<213> ORGANISM: Clitoria ternatea

<400> SEQUENCE: 4

Glu Asp Val Asn Ala His Asn Phe Phe Ala Val Leu Leu Gly Asn Lys
1               5                   10                  15

Ser Ala Leu Thr Gly Gly Ser Gly Lys Val Val Asp Ser Gly Pro Asp
            20                  25                  30
```

```
Asp His Ile Phe Ile Phe Tyr Ser Asp His Gly Gly Pro Gly Val Leu
        35                  40                  45

Gly Met Pro Thr His Pro Tyr Leu Tyr Ala Asp Asp Leu Asn Glu Val
    50                  55                  60

Leu Lys Lys Lys His Ala Ser Gly Thr Tyr Lys Arg Leu Val Phe Tyr
65                  70                  75                  80

Ile Glu Ala Cys Glu Ser Gly Ser Ile Phe Glu Gly Leu Leu Pro Glu
                85                  90                  95

Asp Ile Asp Ile Tyr Ala Thr Thr Ala Ser Asn Ala Thr Glu Ser Ser
            100                 105                 110

Ser Pro Thr Tyr Cys Pro Arg Pro Pro Ala Glu His Ala Pro Phe Pro
            115                 120                 125

Glu Tyr Thr Thr Cys Leu Gly Asp Leu Tyr Ser Ile Thr Trp Met Glu
        130                 135                 140

Asp Ser Asp Ile His Asn Leu Arg Thr Glu Thr Leu His Gln Gln Tyr
145                 150                 155                 160

Glu Leu Val Lys Gly Ile Thr Phe Ala Asp Ser Glu Gly Ser His Val
                165                 170                 175

Met Gln Tyr Gly Asp Ile Asp Leu Ser Ser Asp Val Leu Phe Gln Tyr
            180                 185                 190

Leu Gly Thr Asn Pro Ala Asn Asp Asn Phe Thr Phe Val Asp Glu Asn
        195                 200                 205

Tyr Leu Arg Ser Ser Ser Lys Pro Val Asn Gln His Asp Ala Asp Leu
    210                 215                 220

Ile His Phe Trp Asp Lys Phe Arg Lys Ala Pro Gly Asp Ser Ala Lys
225                 230                 235                 240

Lys Asn Thr Ala Gln Lys Gln Leu Leu Glu Val Met Ser His Arg Met
                245                 250                 255

His Ile Asp Asn Thr Val Gln Leu Ile Gly Lys Leu Leu Phe Gly Ile
            260                 265                 270

Glu Lys Gly Pro Glu Ile Leu Asn Asn Val Arg Pro Val Gly Ser Val
        275                 280                 285

Leu Val Asp Asp Trp Ala Cys Met Lys Ala Met Val Arg Thr Phe Glu
    290                 295                 300

Thr His Cys Gly Ser Leu Ser Gln Tyr Gly Met Lys His Met Arg Ser
305                 310                 315                 320

Phe Ala Asn Ile Cys Asn Ala Gly Ile Lys Asn Glu Gln Met Ala Glu
                325                 330                 335

Ala Ser Gly Gln Ala Cys Val Ser Ile Pro Ala Asn Pro Trp Ser Ser
            340                 345                 350

Leu Gln Arg Gly Phe Ser Ala
        355

<210> SEQ ID NO 5
<211> LENGTH: 193
<212> TYPE: PRT
<213> ORGANISM: Clitoria ternatea

<400> SEQUENCE: 5

Met Asp Thr Phe Pro Pro Leu Leu Leu Cys Leu Phe Val Leu Ala Ala
1               5                   10                  15

Val Val Ser Ala Arg Arg Gly Leu Ala Gly Glu Phe Arg Arg Leu Ala
            20                  25                  30

Ser Glu Pro Asp Ile Asp His Asn Phe Arg Gly Thr Lys Trp Ala Val
```

```
                35                  40                  45
Leu Leu Ala Gly Ser Arg Gly Phe Phe Asp Tyr Arg His Gln Ala Asp
 50                  55                  60

Val Cys His Ala Tyr Gln Leu Leu Arg Lys Gly Gly Leu Lys Glu Glu
65                  70                  75                  80

Asn Ile Ile Val Phe Met Tyr Asp Asp Ile Ala Asn Asn Glu Glu Asn
                85                  90                  95

Pro Arg Pro Gly Val Ile Ile Asn Ser Pro His Gly Asp Asn Val Tyr
            100                 105                 110

Lys Gly Val Pro Lys Asp Tyr Val Gly Glu Asp Val Asn Ala Asp Asn
        115                 120                 125

Phe Phe Ala Ala Ile Leu Gly Asn Lys Ser Ala Leu Thr Gly Gly Ser
130                 135                 140

Gly Lys Val Val Asp Ser Gly Pro Asn Asp His Ile Phe Ile Tyr Tyr
145                 150                 155                 160

Ser Asp His Gly Gly Pro Gly Val Leu Gly Met Pro Thr Ser Ser Tyr
                165                 170                 175

Val Phe Ala Ser Asp Leu Ile Glu Val Leu Lys Lys Lys His Ala Ser
            180                 185                 190

Gly
```

```
<210> SEQ ID NO 6
<211> LENGTH: 150
<212> TYPE: PRT
<213> ORGANISM: Clitoria ternatea

<400> SEQUENCE: 6

Met Asp Thr Phe Pro Pro Leu Leu Leu Cys Leu Phe Val Leu Ala Ala
1               5                   10                  15

Val Val Ser Ala Arg Arg Gly Leu Ala Gly Glu Phe Arg Arg Leu Ala
                20                  25                  30

Ser Glu Pro Asp Ile Asp His Asn Phe Arg Gly Thr Lys Trp Ala Val
            35                  40                  45

Leu Leu Ala Gly Ser Arg Gly Phe Phe Asp Tyr Arg His Gln Ala Asp
 50                  55                  60

Val Cys His Ala Tyr Gln Leu Leu Arg Lys Gly Gly Leu Lys Glu Glu
65                  70                  75                  80

Asn Ile Ile Val Phe Met Tyr Asp Asp Ile Ala Phe Asn Lys Lys Asn
                85                  90                  95

Pro Arg Pro Gly Val Ile Ile Asn Lys Pro Asp Gly Gly Asp Val Tyr
            100                 105                 110

Lys Gly Val Pro Lys Asp Tyr Thr Gly Glu Asn Val Asn Val Asn Asn
        115                 120                 125

Phe Leu Ala Val Leu Leu Gly Asn Lys Ser Ala Leu Thr Gly Gly Ser
130                 135                 140

Gly Lys Val Leu Asn Ser
145                 150
```

```
<210> SEQ ID NO 7
<211> LENGTH: 86
<212> TYPE: PRT
<213> ORGANISM: Clitoria ternatea

<400> SEQUENCE: 7

Ala Asp Leu Ile His Phe Trp Glu Lys Phe Arg Arg Ala Thr Lys Gly
1               5                   10                  15
```

```
Ser Pro Arg Lys Ala Glu Ala Glu Lys Gln Leu Arg Glu Val Thr Ser
             20                  25                  30

His Arg Met His Ile Asp His Ser Val Lys His Ile Gly Lys Leu Leu
             35                  40                  45

Phe Gly Ile Glu Lys Gly Ser Lys Met Leu Asn Ser Val Arg Pro Ala
             50                  55                  60

Gly Leu Pro Ile Val Asp Asp Trp Asp Cys Leu Lys Thr Met Val Arg
 65                  70                  75                  80

Thr Phe Glu Thr His Cys
                 85

<210> SEQ ID NO 8
<211> LENGTH: 473
<212> TYPE: PRT
<213> ORGANISM: Oldenlandia affinis

<400> SEQUENCE: 8

Met Val Arg Tyr Leu Ala Gly Ala Val Leu Leu Val Val Leu Ser
 1               5                  10                  15

Val Ala Ala Ala Val Ser Gly Ala Arg Asp Gly Asp Tyr Leu His Leu
             20                  25                  30

Pro Ser Glu Val Ser Arg Phe Phe Arg Pro Gln Glu Thr Asn Asp His
             35                  40                  45

Gly Glu Asp Ser Val Gly Thr Arg Trp Ala Val Leu Ile Ala Gly Ser
             50                  55                  60

Lys Gly Tyr Ala Asn Tyr Arg His Gln Ala Gly Val Cys His Ala Tyr
 65                  70                  75                  80

Gln Ile Leu Lys Arg Gly Gly Leu Lys Asp Glu Asn Ile Val Val Phe
             85                  90                  95

Met Tyr Asp Asp Ile Ala Tyr Asn Glu Ser Asn Pro Arg Pro Gly Val
                100                 105                 110

Ile Ile Asn Ser Pro His Gly Ser Asp Val Tyr Ala Gly Val Pro Lys
            115                 120                 125

Asp Tyr Thr Gly Glu Glu Val Asn Ala Lys Asn Phe Leu Ala Ala Ile
        130                 135                 140

Leu Gly Asn Lys Ser Ala Ile Thr Gly Gly Ser Gly Lys Val Val Asp
145                 150                 155                 160

Ser Gly Pro Asn Asp His Ile Phe Ile Tyr Tyr Thr Asp His Gly Ala
                165                 170                 175

Ala Gly Val Ile Gly Met Pro Ser Lys Pro Tyr Leu Tyr Ala Asp Glu
            180                 185                 190

Leu Asn Asp Ala Leu Lys Lys Lys His Ala Ser Gly Thr Tyr Lys Ser
        195                 200                 205

Leu Val Phe Tyr Leu Glu Ala Cys Glu Ser Gly Ser Met Phe Glu Gly
    210                 215                 220

Ile Leu Pro Glu Asp Leu Asn Ile Tyr Ala Leu Thr Ser Thr Asn Thr
225                 230                 235                 240

Thr Glu Ser Ser Trp Cys Tyr Tyr Cys Pro Ala Gln Glu Asn Pro Pro
                245                 250                 255

Pro Pro Glu Tyr Asn Val Cys Leu Gly Asp Leu Phe Ser Val Ala Trp
            260                 265                 270

Leu Glu Asp Ser Asp Val Gln Asn Ser Trp Tyr Glu Thr Leu Asn Gln
        275                 280                 285

Gln Tyr His His Val Asp Lys Arg Ile Ser His Ala Ser His Ala Thr
```

```
            290                 295                 300
Gln Tyr Gly Asn Leu Lys Leu Gly Glu Glu Gly Leu Phe Val Tyr Met
305                 310                 315                 320

Gly Ser Asn Pro Ala Asn Asp Asn Tyr Thr Ser Leu Asp Gly Asn Ala
                325                 330                 335

Leu Thr Pro Ser Ser Ile Val Val Asn Gln Arg Asp Ala Asp Leu Leu
            340                 345                 350

His Leu Trp Glu Lys Phe Arg Lys Ala Pro Glu Gly Ser Ala Arg Lys
        355                 360                 365

Glu Glu Ala Gln Thr Gln Ile Phe Lys Ala Met Ser His Arg Val His
    370                 375                 380

Ile Asp Ser Ser Ile Lys Leu Ile Gly Lys Leu Leu Phe Gly Ile Glu
385                 390                 395                 400

Lys Cys Thr Glu Ile Leu Asn Ala Val Arg Pro Ala Gly Gln Pro Leu
                405                 410                 415

Val Asp Asp Trp Ala Cys Leu Arg Ser Leu Val Gly Thr Phe Glu Thr
            420                 425                 430

His Cys Gly Ser Leu Ser Glu Tyr Gly Met Arg His Thr Arg Thr Ile
        435                 440                 445

Ala Asn Ile Cys Asn Ala Gly Ile Ser Glu Glu Gln Met Ala Glu Ala
    450                 455                 460

Ala Ser Gln Ala Cys Ala Ser Ile Pro
465                 470

<210> SEQ ID NO 9
<211> LENGTH: 486
<212> TYPE: PRT
<213> ORGANISM: Hedyotis biflora

<400> SEQUENCE: 9

Met Val Arg Tyr Pro Ala Gly Val Val Leu Leu Val Thr Ile Thr
1               5                   10                  15

Ile Ser Val Val Ala Glu Ala Arg Asp Gly Tyr Leu Lys Leu Pro Ser
                20                  25                  30

Glu Phe Ser Ala Phe Leu Arg Pro Asn Glu Thr Asn Asp Asn Ser Val
            35                  40                  45

Ser Thr Arg Trp Ala Val Leu Ile Ala Gly Ser Lys Asp Tyr Trp Asn
        50                  55                  60

Tyr Arg His Gln Ala Asp Val Cys His Ala Tyr Gln Ile Leu Lys Arg
65                  70                  75                  80

Gly Gly Leu Lys Asp Glu Asn Ile Val Val Phe Met Tyr Asp Asp Ile
                85                  90                  95

Ala Tyr Asn Glu Glu Asn Pro Arg Pro Gly Val Ile Ile Asn Ser Pro
            100                 105                 110

His Gly Ser Asp Val Tyr Ala Gly Val Pro Lys Asp Tyr Thr Gly Asp
        115                 120                 125

Glu Val Asn Ala Lys Asn Phe Leu Ala Ala Ile Leu Gly Asp Lys Ser
    130                 135                 140

Ala Ile Thr Gly Gly Ser Gly Lys Val Val Asp Ser Gly Pro Asn Asp
145                 150                 155                 160

His Ile Phe Ile Tyr Tyr Ser Asp His Gly Gly Pro Gly Val Leu Gly
                165                 170                 175

Met Pro Ser Gly Pro Tyr Leu Tyr Ala Asp Glu Leu Asn Asp Ala Leu
            180                 185                 190
```

```
Lys Lys Lys His Ala Ser Gly Thr Tyr Lys Ser Leu Val Phe Tyr Leu
            195                 200                 205

Glu Ala Cys Glu Ser Gly Ser Ile Phe Glu Gly Leu Leu Pro Glu Gly
210                 215                 220

Leu Asn Ile Tyr Ala Thr Thr Ala Ser Asn Ala Glu Glu Ser Ser Trp
225                 230                 235                 240

Gly Thr Tyr Cys Pro Gly Glu Tyr Pro Ser Pro Ser Glu Tyr Glu
            245                 250                 255

Thr Cys Leu Gly Asp Leu Tyr Ser Val Ala Trp Met Glu Asp Ser Glu
            260                 265                 270

Val His Asn Leu Arg Ser Glu Thr Leu Lys Gln Gln Tyr His Leu Val
            275                 280                 285

Lys Thr Arg Thr Ser Asn Gly Asn Ser Ala Tyr Gly Ser His Val Met
            290                 295                 300

Gln Tyr Gly Asp Leu Lys Leu Ser Val Asp Asn Leu Phe Leu Tyr Met
305                 310                 315                 320

Gly Thr Asn Pro Ala Asn Asp Asn Tyr Thr Phe Val Asp Asp Asn Ala
            325                 330                 335

Leu Arg Pro Ser Ser Lys Ala Ile Asn Gln Arg Asp Ala Asp Leu Val
            340                 345                 350

His Phe Trp Asp Lys Phe Arg Lys Ala Pro Glu Gly Ser Leu Arg Lys
            355                 360                 365

Glu Glu Ala Ala Lys Gln Val Phe Glu Ala Met Ser His Arg Met His
            370                 375                 380

Ile Asp Ser Ser Ile Lys Leu Val Gly Lys Leu Leu Phe Gly Ile Glu
385                 390                 395                 400

Arg Gly Ser Glu Ile Leu Asn Ala Val Arg Pro Ala Gly Gln Pro Leu
            405                 410                 415

Ala Asp Asp Trp Ala Cys Leu Lys Ser Leu Val Arg Thr Phe Glu Thr
            420                 425                 430

His Cys Gly Ser Leu Ser Gln Tyr Gly Met Lys His Met Arg Thr Val
            435                 440                 445

Ala Asn Ile Cys Asn Ala Gly Ile Thr Lys Glu Gln Met Ala Glu Ala
            450                 455                 460

Ala Ala Gln Ala Cys Val Ser Val Pro Ser Asn Pro Trp Ser Ser Leu
465                 470                 475                 480

Ser Gly Gly Phe Ser Ala
            485

<210> SEQ ID NO 10
<211> LENGTH: 483
<212> TYPE: PRT
<213> ORGANISM: Phaseolus vulgaris

<400> SEQUENCE: 10

Met Asp Gly Phe Pro Ile Leu Phe Leu Leu Ala Thr Leu Ile Thr Leu
1               5                   10                  15

Val Ser Gly Gly Arg Asp Glu Ile Leu Arg Leu Pro Ser Glu Ala Ser
            20                  25                  30

Arg Phe Phe Gln Ala Pro Ala Ala Asp Gln Asn Gln Glu Gly Thr Arg
            35                  40                  45

Trp Ala Leu Leu Ile Ala Gly Ser Asn Gly Tyr Trp Asn Tyr Arg His
50                  55                  60

Gln Ser Asp Val Cys His Ala Tyr Gln Leu Leu Arg Lys Gly Gly Leu
65                  70                  75                  80
```

```
Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Val Gly Glu Asp Val Thr
        115                 120                 125

Val Asn Asn Phe Phe Ala Ala Ile Leu Gly Asn Lys Ser Ala Leu Thr
130                 135                 140

Gly Gly Ser Gly Lys Val Ile Asp Ser Gly Pro Asn Asp His Ile Phe
145                 150                 155                 160

Ile Tyr Tyr Ser Asp His Gly Gly Pro Gly Val Leu Gly Met Pro Thr
                165                 170                 175

Ser Pro Tyr Met Tyr Ala Ser Asp Leu Ile Glu Val Leu Lys Lys Lys
            180                 185                 190

His Ala Ser Glu Thr Tyr Lys Ser Leu Val Phe Tyr Leu Glu Ala Cys
        195                 200                 205

Glu Ser Gly Ser Ile Phe Glu Gly Leu Leu Pro Glu Gly Met Asn Ile
210                 215                 220

Tyr Ala Thr Thr Ala Ala Asn Ala Glu Glu Ser Ser Trp Gly Thr Tyr
225                 230                 235                 240

Cys Pro Gly Glu Tyr Pro Ser Pro Pro Glu Tyr Glu Thr Cys Leu
                245                 250                 255

Gly Asp Leu Tyr Ser Val Ala Trp Met Glu Asp Ser Asp Ile His Asn
            260                 265                 270

Leu Gln Thr Glu Thr Leu His Gln Gln Phe Glu Leu Val Lys Gln Arg
        275                 280                 285

Thr Ile Asn Gly Asn Ser Ala Tyr Gly Ser His Val Met Gln Tyr Gly
290                 295                 300

Asp Ile Gly Leu Ser Lys Asn Asn Leu Ser Leu Tyr Leu Gly Thr Asn
305                 310                 315                 320

Pro Ala Asn Asp Asn Phe Ala Phe Arg Glu Lys Asn Ser Leu Val Pro
                325                 330                 335

Pro Ser Lys Ala Val Asn Gln Arg Asp Ala Asp Leu Val His Leu Trp
            340                 345                 350

Asp Lys Tyr Arg Lys Ala Pro Val Gly Ser Ser Arg Lys Ser Val Ala
        355                 360                 365

Gln Lys Gln Ile Leu Glu Ala Met Ser His Arg Met His Ile Asp Asp
370                 375                 380

Ser Met Lys Leu Ile Gly Lys Leu Leu Phe Gly Ile Glu Glu Gly Pro
385                 390                 395                 400

Lys Leu Leu Asn Ser Val Arg Pro Ala Gly Gln Pro Leu Val Asp Asp
                405                 410                 415

Trp Asp Cys Leu Lys Thr Leu Val Arg Thr Phe Glu Thr His Cys Gly
            420                 425                 430

Ser Leu Ser Gln Tyr Gly Met Lys His Met Arg Ser Phe Ala Asn Phe
        435                 440                 445

Cys Asn Ala Gly Ile Gly Lys Glu Gln Met Ala Glu Ala Ser Ala Gln
450                 455                 460

Ala Cys Val Ser Ile Pro Ala Thr Pro Trp Ser Ser Leu Arg Ser Gly
465                 470                 475                 480

Phe Ser Ala
```

```
<210> SEQ ID NO 11
<211> LENGTH: 484
<212> TYPE: PRT
<213> ORGANISM: Glycine max

<400> SEQUENCE: 11
```

| | | | | | | | | | | | | | | | |
|---|---|---|---|---|---|---|---|---|---|---|---|---|---|---|---|
| Met | Asp | Arg | Phe | Pro | Ile | Leu | Phe | Leu | Val | Ala | Thr | Leu | Ile | Thr | Leu |
| 1 | | | | 5 | | | | | 10 | | | | | 15 | |
| Ala | Ser | Gly | Ala | Arg | His | Asp | Ile | Leu | Arg | Leu | Pro | Ser | Glu | Ala | Ser |
| | | | 20 | | | | | 25 | | | | | 30 | | |
| Arg | Phe | Phe | Lys | Ala | Pro | Ala | Asn | Ala | Asp | Gln | Asn | Asp | Glu | Gly | Thr |
| | | 35 | | | | | 40 | | | | | 45 | | | |
| Arg | Trp | Ala | Val | Leu | Val | Ala | Gly | Ser | Asn | Gly | Tyr | Trp | Asn | Tyr | Arg |
| 50 | | | | | 55 | | | | | 60 | | | | | |
| His | Gln | Ser | Asp | Val | Cys | His | Ala | Tyr | Gln | Leu | Leu | Arg | Lys | Gly | Gly |
| 65 | | | | | 70 | | | | | 75 | | | | | 80 |
| Val | Lys | Glu | Glu | Asn | Ile | Val | Val | Phe | Met | Tyr | Asp | Asp | Ile | Ala | Phe |
| | | | | 85 | | | | | 90 | | | | | 95 | |
| Asn | Glu | Glu | Asn | Pro | Arg | Pro | Gly | Val | Ile | Ile | Asn | Ser | Pro | His | Gly |
| | | | 100 | | | | | 105 | | | | | 110 | | |
| Asn | Asp | Val | Tyr | Lys | Gly | Val | Pro | Lys | Asp | Tyr | Val | Gly | Glu | Asp | Val |
| | | | 115 | | | | | 120 | | | | | 125 | | |
| Thr | Val | Asp | Asn | Phe | Phe | Ala | Ala | Ile | Leu | Gly | Asn | Lys | Ser | Ala | Leu |
| 130 | | | | | 135 | | | | | 140 | | | | | |
| Thr | Gly | Gly | Ser | Gly | Lys | Val | Val | Asp | Ser | Gly | Pro | Asn | Asp | His | Ile |
| 145 | | | | | 150 | | | | | 155 | | | | | 160 |
| Phe | Ile | Tyr | Tyr | Ser | Asp | His | Gly | Gly | Pro | Gly | Val | Leu | Gly | Met | Pro |
| | | | | 165 | | | | | 170 | | | | | 175 | |
| Thr | Asn | Pro | Tyr | Met | Tyr | Ala | Ser | Asp | Leu | Ile | Glu | Val | Leu | Lys | Lys |
| | | | 180 | | | | | 185 | | | | | 190 | | |
| Lys | His | Ala | Ser | Gly | Thr | Tyr | Lys | Ser | Leu | Val | Phe | Tyr | Leu | Glu | Ala |
| | | | 195 | | | | | 200 | | | | | 205 | | |
| Cys | Glu | Ser | Gly | Ser | Ile | Phe | Glu | Gly | Leu | Leu | Pro | Glu | Gly | Leu | Asn |
| 210 | | | | | 215 | | | | | 220 | | | | | |
| Ile | Tyr | Ala | Thr | Thr | Ala | Ser | Asn | Ala | Glu | Glu | Ser | Ser | Trp | Gly | Thr |
| 225 | | | | | 230 | | | | | 235 | | | | | 240 |
| Tyr | Cys | Pro | Gly | Glu | Tyr | Pro | Ser | Pro | Pro | Glu | Tyr | Glu | Thr | Cys |
| | | | | 245 | | | | | 250 | | | | | 255 |
| Leu | Gly | Asp | Leu | Tyr | Ser | Val | Ala | Trp | Met | Glu | Asp | Ser | Asp | Ile | His |
| | | | 260 | | | | | 265 | | | | | 270 | | |
| Asn | Leu | Arg | Thr | Glu | Thr | Leu | His | Gln | Gln | Tyr | Asp | Leu | Val | Lys | Glu |
| | | | 275 | | | | | 280 | | | | | 285 | | |
| Arg | Thr | Met | Asn | Gly | Asn | Ser | Ile | Tyr | Gly | Ser | His | Val | Met | Gln | Tyr |
| | 290 | | | | | 295 | | | | | 300 | | | | |
| Gly | Asp | Ile | Gly | Leu | Ser | Lys | Asn | Asn | Leu | Val | Leu | Tyr | Leu | Gly | Thr |
| 305 | | | | | 310 | | | | | 315 | | | | | 320 |
| Asn | Pro | Ala | Asn | Asp | Asn | Phe | Thr | Phe | Val | His | Lys | Asn | Ser | Leu | Val |
| | | | | 325 | | | | | 330 | | | | | 335 | |
| Pro | Pro | Ser | Lys | Ala | Val | Asn | Gln | Arg | Asp | Ala | Asp | Leu | Ile | His | Phe |
| | | | 340 | | | | | 345 | | | | | 350 | | |
| Trp | Asp | Lys | Phe | Arg | Lys | Ala | Pro | Val | Gly | Ser | Ser | Arg | Lys | Ala | Ala |
| | | | 355 | | | | | 360 | | | | | 365 | | |
| Ala | Glu | Lys | Glu | Ile | Leu | Glu | Ala | Met | Ser | His | Arg | Met | His | Ile | Asp |
| | 370 | | | | | 375 | | | | | 380 | | | | |

-continued

Asp Asn Met Lys Leu Ile Gly Lys Leu Leu Phe Gly Ile Glu Lys Gly
385                 390                 395                 400

Pro Glu Leu Leu Ser Ser Val Arg Pro Ala Gly Gln Pro Leu Val Asp
            405                 410                 415

Asp Trp Asp Cys Leu Lys Thr Leu Val Arg Thr Phe Glu Thr His Cys
            420                 425                 430

Gly Ser Leu Ser Gln Tyr Gly Met Lys His Met Arg Ser Phe Ala Asn
            435                 440                 445

Phe Cys Asn Ala Gly Ile Arg Lys Glu Gln Met Ala Glu Ala Ser Ala
            450                 455                 460

Gln Ala Cys Val Ser Ile Pro Ala Ser Ser Trp Ser Ser Leu His Arg
465                 470                 475                 480

Gly Phe Ser Ala

<210> SEQ ID NO 12
<211> LENGTH: 483
<212> TYPE: PRT
<213> ORGANISM: Homo sapiens

<400> SEQUENCE: 12

Met Asp Arg Phe Pro Ile Leu Phe Leu Leu Ala Thr Leu Ile Thr Leu
1               5                   10                  15

Ala Ser Gly Ala Arg His Asp Ile Leu Arg Leu Pro Ser Glu Ala Ser
            20                  25                  30

Thr Phe Phe Lys Ala Pro Gly Gly Asp Gln Asn Asp Glu Gly Thr Arg
            35                  40                  45

Trp Ala Val Leu Ile Ala Gly Ser Asn Gly Tyr Trp Asn Tyr Arg His
50                  55                  60

Gln Ser Asp Val Cys His Ala Tyr Gln Leu Leu Arg Lys Gly Gly Leu
65                  70                  75                  80

Lys Glu Glu Asn Ile Val Val Phe Met Tyr Asp Asp Ile Ala Phe Asn
            85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Ile Gly Glu Asp Val Thr
            115                 120                 125

Val Gly Asn Phe Phe Ala Ala Ile Leu Gly Asn Lys Ser Ala Leu Thr
130                 135                 140

Gly Gly Ser Gly Lys Val Val Asp Ser Gly Pro Asn Asp His Ile Phe
145                 150                 155                 160

Ile Tyr Tyr Ser Asp His Gly Gly Pro Gly Val Leu Gly Met Pro Thr
            165                 170                 175

Asn Pro Tyr Val Tyr Ala Ser Asp Leu Ile Glu Val Leu Lys Lys Lys
            180                 185                 190

His Ala Ser Gly Ser Tyr Lys Ser Leu Val Phe Tyr Leu Glu Ala Cys
            195                 200                 205

Glu Ser Gly Ser Ile Phe Glu Gly Leu Leu Pro Glu Gly Leu Asn Ile
210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Ser Glu Tyr Glu Thr Cys Leu
            245                 250                 255

Gly Asp Leu Tyr Ser Val Ala Trp Met Glu Asp Ser Asp Ile His Asn
            260                 265                 270

-continued

```
Leu Gln Thr Glu Thr Leu His Gln Gln Tyr Glu Leu Val Lys Gln Arg
        275                 280                 285

Thr Met Asn Gly Asn Ser Ile Tyr Gly Ser His Val Met Gln Tyr Gly
    290                 295                 300

Asp Ile Gly Leu Ser Glu Asn Asn Leu Val Leu Tyr Leu Gly Thr Asn
305                 310                 315                 320

Pro Ala Asn Asp Asn Phe Thr Phe Val Leu Lys Asn Ser Leu Val Pro
                325                 330                 335

Pro Ser Lys Ala Val Asn Gln Arg Asp Ala Asp Leu Ile His Phe Trp
                340                 345                 350

Asp Lys Phe Arg Lys Ala Pro Val Gly Ser Ser Arg Lys Ala Ala Ala
            355                 360                 365

Glu Lys Gln Ile Leu Glu Ala Met Ser His Arg Met His Ile Asp Asp
        370                 375                 380

Ser Met Lys Arg Ile Gly Lys Leu Phe Phe Gly Ile Glu Lys Gly Pro
385                 390                 395                 400

Glu Leu Leu Ser Ser Val Arg Pro Ala Gly Gln Pro Leu Val Asp Asp
                405                 410                 415

Trp Asp Cys Leu Lys Thr Leu Val Arg Thr Phe Glu Thr His Cys Gly
                420                 425                 430

Ser Leu Ser Gln Tyr Gly Met Lys His Met Arg Ser Phe Ala Asn Phe
            435                 440                 445

Cys Asn Ala Gly Ile Arg Lys Glu Gln Met Ala Glu Ala Ser Ala Gln
        450                 455                 460

Ala Cys Val Asn Ile Pro Ala Ser Ser Trp Ser Ser Met His Arg Gly
465                 470                 475                 480

Phe Ser Ala

<210> SEQ ID NO 13
<211> LENGTH: 483
<212> TYPE: PRT
<213> ORGANISM: Vigna mungo

<400> SEQUENCE: 13

Met Asn Arg Phe Pro Ile Ile Phe Val Val Ala Asn Leu Ile Thr Leu
1               5                   10                  15

Val Ser Gly Gly Arg Asp Glu Ile Leu Arg Met Pro Ser Glu Ala Ser
            20                  25                  30

Arg Phe Phe Gln Ala Pro Ala Thr Asp Glu Asn Asp Glu Gly Thr Arg
        35                  40                  45

Trp Ala Val Leu Ile Ala Gly Ser Asn Gly Tyr Trp Asn Tyr Arg His
    50                  55                  60

Gln Ser Asp Val Cys His Ala Tyr Gln Leu Leu Thr Lys Gly Gly Leu
65                  70                  75                  80

Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Val Gly Glu Asp Val Thr
        115                 120                 125

Val Asn Asn Phe Phe Ala Ala Ile Leu Gly Asn Lys Ser Ala Leu Thr
    130                 135                 140

Gly Gly Ser Gly Lys Val Val Asn Ser Gly Pro Asn Asp His Ile Phe
145                 150                 155                 160
```

```
Ile Tyr Tyr Ser Asp His Gly Gly Pro Gly Val Leu Gly Met Pro Thr
            165                 170                 175

Ser Pro Tyr Met Tyr Ala Ser Asp Leu Ile Glu Val Leu Lys Lys Lys
        180                 185                 190

His Ala Ser Gly Thr Tyr Lys Ser Leu Ala Phe Tyr Leu Glu Gly Cys
        195                 200                 205

Glu Ser Gly Ser Ile Phe Gly Gly Leu Leu Pro Gly Gly Leu Asn Ile
        210                 215                 220

Tyr Ala Thr Thr Ala Ala Asn Ala Glu Glu Ser Ser Trp Gly Thr Tyr
225                 230                 235                 240

Cys Pro Gly Asp Asn Pro Ser Pro Pro Glu Tyr Glu Thr Cys Leu
                245                 250                 255

Gly Asp Leu Tyr Ser Val Ala Trp Met Glu Asp Ser Asp Ile His Asn
            260                 265                 270

Leu Arg Thr Glu Thr Leu His Gln Gln Phe Glu Leu Val Lys Gln Arg
            275                 280                 285

Thr Met Asn Gly Asn Ser Ala Tyr Gly Ser His Val Met Gln Tyr Gly
        290                 295                 300

Asp Val Gly Leu Ser Lys Asn Asn Val Ser Leu Tyr Leu Gly Thr Asn
305                 310                 315                 320

Pro Ala Asn Asp Asn Phe Pro Phe Arg Glu Lys Asn Ser Leu Val Pro
                325                 330                 335

Pro Ser Lys Ala Val Asn Gln Arg Asp Ala Asp Leu Val His Phe Trp
            340                 345                 350

Asp Lys Phe Pro Lys Ala Pro Leu Gly Ser Ser Arg Lys Ser Val Ala
        355                 360                 365

Gln Lys Gln Ile Leu Glu Ala Met Ser His Arg Met His Ile Asp Asp
    370                 375                 380

Ser Val Thr Leu Ile Gly Lys Leu Leu Phe Gly Ile Glu Glu Gly Pro
385                 390                 395                 400

Glu Leu Leu Ser Ser Val Arg Pro Ala Gly Gln Pro Leu Val Asp Asp
                405                 410                 415

Trp Asp Cys Leu Lys Thr Leu Val Arg Thr Phe Glu Thr His Cys Gly
            420                 425                 430

Ser Leu Ser Gln Tyr Gly Met Lys His Met Arg Ser Phe Ala Asn Leu
        435                 440                 445

Cys Asn Ala Gly Ile Arg Lys Glu Gln Met Ala Glu Ala Ser Ala Gln
        450                 455                 460

Ala Cys Val Ser Ile Pro Ala Thr Pro Trp Ser Ser Leu Ser Ser Gly
465                 470                 475                 480

Phe Ser Ala

<210> SEQ ID NO 14
<211> LENGTH: 488
<212> TYPE: PRT
<213> ORGANISM: Cicer arietinum

<400> SEQUENCE: 14

Met Tyr Arg Phe Pro Thr Pro Thr Leu Leu Phe Leu Ile Val Thr Leu
1               5                   10                  15

Ile Ala Leu Val Ser Ser Asn Pro Glu Asp Phe Leu Arg Leu Pro Ser
            20                  25                  30

Glu Ser Ser Arg Phe Phe His Ser Pro Ser Ala Asp Asp Lys Glu Asn
        35                  40                  45
```

-continued

Asn Glu Gly Thr Arg Trp Ala Ile Leu Ile Ala Gly Ser Asn Gly Tyr
    50                  55                  60

Trp Asn Tyr Arg His Gln Ser Asp Val Cys His Ala Tyr Gln Val Leu
65                  70                  75                  80

Arg Lys Gly Gly Leu Lys Glu Glu Asn Ile Val Val Phe Met Tyr Asp
                85                  90                  95

Asp Ile Ala Phe Asn Glu Glu Asn Pro Arg Pro Gly Val Ile Ile Asn
                100                 105                 110

Ser Pro His Gly Asp Asp Val Tyr Lys Gly Val Pro Lys Asp Tyr Thr
            115                 120                 125

Gly Glu Asp Val Asn Val Asp Asn Phe Phe Ala Ala Leu Leu Gly Asn
130                 135                 140

Lys Ser Ala Leu Thr Gly Gly Ser Gly Lys Val Val Asp Ser Gly Pro
145                 150                 155                 160

Asn Asp His Ile Phe Ile Tyr Tyr Ser Asp His Gly Gly Pro Gly Val
                165                 170                 175

Leu Gly Met Pro Thr Ser Pro Tyr Met Tyr Ala Ser Asp Leu Ile Glu
                180                 185                 190

Val Leu Lys Lys Lys His Ala Ser Gly Thr Tyr Lys Ser Leu Val Phe
            195                 200                 205

Tyr Leu Glu Ala Cys Glu Ser Gly Ser Ile Phe Glu Gly Leu Leu Pro
210                 215                 220

Glu Gly Leu Asn Ile Tyr Ala Thr Thr Ala Ala Asn Ala Asp Glu Ser
225                 230                 235                 240

Ser Trp Gly Thr Tyr Cys Pro Gly Glu Phe Pro Ser Pro Pro Pro Glu
                245                 250                 255

Tyr Glu Thr Cys Leu Gly Asp Leu Tyr Ser Val Ala Trp Met Glu Asp
            260                 265                 270

Ser Asp Met His Asn Leu Gln Ser Glu Thr Leu His Gln Gln Tyr Glu
        275                 280                 285

Leu Val Lys Glu Arg Thr Lys Asn Gly Asn Thr Leu Tyr Gly Ser His
            290                 295                 300

Val Met Gln Tyr Gly Asp Ile Gly Leu Ser Glu Asn Ser Leu Phe Leu
305                 310                 315                 320

Tyr Leu Gly Thr Asn Pro Ala Asn Glu Asn Phe Thr Phe Val Gly Arg
                325                 330                 335

Asn Ser Leu Val Pro Pro Ser Lys Ala Val Asn Gln Arg Asp Ala Asp
                340                 345                 350

Leu Val His Phe Trp Asp Lys Phe Arg Lys Ala Pro Gln Gly Ser Pro
            355                 360                 365

Arg Lys Ala Ala Ala Glu Lys Gln Val Leu Glu Ala Met Ser His Arg
370                 375                 380

Met His Ile Asp Asp Ser Ile Lys Leu Val Gly Lys Leu Leu Phe Gly
385                 390                 395                 400

Met Glu Lys Gly Pro Glu Val Leu Thr Ser Val Arg Pro Ala Gly Gln
                405                 410                 415

Pro Leu Ala Asp Asp Trp Asn Cys Leu Lys Thr Leu Val Arg Thr Phe
            420                 425                 430

Glu Thr Tyr Cys Gly Ser Leu Ser Gln Tyr Gly Met Lys His Met Arg
            435                 440                 445

Ser Phe Ala Asn Phe Cys Asn Ala Gly Ile His Lys Glu Gln Met Ala
450                 455                 460

Glu Ala Ser Ala Gln Ala Cys Val Asn Val Pro Ala Asn Pro Trp Ser

```
                465                 470                 475                 480
Ser Leu Arg Ser Gly Phe Ser Ala
                485

<210> SEQ ID NO 15
<211> LENGTH: 492
<212> TYPE: PRT
<213> ORGANISM: Ricinus communis

<400> SEQUENCE: 15

Met Thr Ile Arg Leu Ser Thr Gly Ile Ile Leu Ile Leu Leu Thr Leu
1               5                   10                  15

Cys Gly Val Val Ser Ser Arg Asp Ile Val Gly Asp Val Ile Arg
            20                  25                  30

Leu Pro Ser Glu Ala Ser Arg Phe Phe Arg Pro Ala Asp Gly Lys Asn
        35                  40                  45

Gly Asp Asp Asp Ser Ala Gly Thr Arg Trp Ala Ile Leu Ile Ala Gly
    50                  55                  60

Ser Asn Gly Tyr Trp Asn Tyr Arg His Gln Ala Asp Val Cys His Ala
65                  70                  75                  80

Tyr Gln Leu Leu Arg Lys Gly Gly Leu Lys Glu Glu Asn Ile Ile Val
                85                  90                  95

Phe Met Tyr Asp Asp Ile Ala Tyr Asn Glu Glu Asn Pro Arg Gln Gly
            100                 105                 110

Ile Ile Ile Asn Asn Pro His Gly Glu Asp Val Tyr Lys Gly Val Pro
        115                 120                 125

Lys Asp Tyr Thr Gly Glu Asn Val Thr Val Gly Asn Phe Phe Ala Ala
    130                 135                 140

Ile Leu Gly Asn Arg Thr Ala Leu Thr Gly Gly Arg Gly Lys Val Val
145                 150                 155                 160

Asp Ser Gly Pro Asn Asp His Ile Phe Val Tyr Tyr Thr Asp His Gly
                165                 170                 175

Gly Pro Gly Val Leu Gly Met Pro Thr Asn Pro Tyr Leu Tyr Ala Asn
            180                 185                 190

Asp Leu Ile Asp Val Leu Lys Lys Lys His Ala Ser Gly Thr Tyr Lys
        195                 200                 205

Ser Leu Val Phe Tyr Leu Glu Ala Cys Glu Ser Gly Ser Ile Phe Glu
    210                 215                 220

Gly Leu Leu Pro Glu Gly Leu Asn Ile Tyr Ala Thr Thr Ala Ser Asn
225                 230                 235                 240

Ala Glu Glu Ser Ser Trp Gly Thr Tyr Cys Pro Gly Glu Tyr Pro Ser
                245                 250                 255

Pro Pro Pro Glu Tyr Glu Thr Cys Leu Gly Asp Leu Tyr Ser Ile Ala
            260                 265                 270

Trp Met Glu Asp Ser Asp Val His Asn Leu Gln Thr Glu Thr Leu His
        275                 280                 285

Gln Gln Tyr Glu Leu Val Lys Arg Arg Thr Ser Asn Gly Asn Ser Ala
    290                 295                 300

Tyr Gly Ser His Val Met Gln Tyr Gly Asp Val Gly Leu Ser Arg Glu
305                 310                 315                 320

Asn Leu Phe Leu Tyr Met Gly Thr Asn Pro Ala Asn Asp Asn Tyr Thr
                325                 330                 335

Phe Val Asp Glu Asn Ser Leu Thr Pro Pro Ser Lys Ala Val Asn Gln
            340                 345                 350
```

```
Arg Asp Ala Asp Leu Val His Phe Trp Asp Lys Tyr Arg Lys Ala Pro
            355                 360                 365

Asp Gly Ser Ala Arg Lys Asp Gln Ala Gln Lys Gln Phe Val Glu Ala
            370                 375                 380

Met Ser His Arg Met His Ile Asp His Ser Val Lys Leu Ile Gly Lys
385                 390                 395                 400

Leu Leu Phe Gly Leu Glu Lys Ala Ser Glu Val Leu Ser Thr Val Arg
                405                 410                 415

Pro Ala Gly Gln Pro Leu Val Asp Trp Asp Cys Leu Lys Lys Leu
            420                 425                 430

Val Arg Thr Phe Glu Thr His Cys Gly Ser Ile Ser Gln Tyr Gly Met
            435                 440                 445

Lys His Met Arg Ser Leu Ala Asn Leu Cys Asn Ala Gly Ile Arg Glu
            450                 455                 460

Glu Gln Met Ala Glu Ala Ser Ala Gln Ala Cys Ile Thr Phe Pro Ser
465                 470                 475                 480

Gly Pro Trp Ser Ser Leu His Lys Gly Phe Ser Ala
                485                 490

<210> SEQ ID NO 16
<211> LENGTH: 487
<212> TYPE: PRT
<213> ORGANISM: Theobroma cacao

<400> SEQUENCE: 16

Met Thr Arg Leu Val Ser Gly Val Ile Leu Leu Leu Ser Leu Thr
1               5                   10                  15

Gly Ile Val Ser Ala Gly Arg Asp Ile Thr Gly Asp Val Leu Arg Leu
                20                  25                  30

Pro Ser Glu Ala Ser Lys Phe Phe Arg Gly Ser Asn Asp Asp Glu Val
            35                  40                  45

Glu Gly Thr Arg Trp Ala Val Leu Ile Ala Gly Ser Asn Gly Tyr Trp
        50                  55                  60

Asn Tyr Arg His Gln Ala Asp Val Cys His Ala Tyr Gln Leu Leu Lys
65                  70                  75                  80

Lys Gly Gly Leu Lys Asp Glu Asn Ile Ile Val Phe Met Tyr Asp Asp
                85                  90                  95

Ile Ala Phe Asn Glu Glu Asn Pro Arg Pro Gly Ile Ile Ile Asn Ser
            100                 105                 110

Pro His Gly Asp Val Tyr Glu Gly Val Pro Lys Asp Tyr Thr Gly
        115                 120                 125

Glu Asp Val Thr Val Asn Asn Leu Leu Ala Ala Ile Leu Gly Asn Lys
130                 135                 140

Thr Ala Leu Thr Gly Gly Ser Gly Lys Val Val Asp Ser Gly Pro Asn
145                 150                 155                 160

Asp His Ile Phe Ile Tyr Tyr Thr Asp His Gly Gly Pro Gly Val Leu
                165                 170                 175

Gly Met Pro Thr Phe Pro Tyr Leu Tyr Ala Asp Asp Leu Ile Glu Val
            180                 185                 190

Leu Lys Lys Lys His Ala Ser Gly Thr Tyr Lys Ser Leu Val Phe Tyr
        195                 200                 205

Leu Glu Ala Cys Glu Ser Gly Ser Ile Phe Glu Gly Leu Leu Pro Glu
    210                 215                 220

Gly Leu Asn Ile Tyr Ala Thr Thr Ala Ser Asn Ala Glu Glu Ser Ser
225                 230                 235                 240
```

```
Trp Gly Thr Tyr Cys Pro Gly Glu Tyr Pro Ser Pro Pro Glu Tyr
            245                 250                 255

Glu Thr Cys Leu Gly Asp Leu Tyr Ser Val Ala Trp Met Glu Asp Ser
        260                 265                 270

Asp Ile His Asn Leu Gln Thr Glu Thr Leu His Gln Gln Tyr Glu Leu
            275                 280                 285

Val Lys Arg Arg Thr Ile Asn Gly Asn Ser Ala Tyr Gly Ser His Val
    290                 295                 300

Met Gln Tyr Gly Asp Ile Gly Leu Ser Lys Asp Ile Val Phe Val Tyr
305                 310                 315                 320

Leu Gly Thr Asn Pro Ala Asn Asp Asn Phe Thr Phe Val Asp Glu Asn
                325                 330                 335

Ser Leu Gln Pro Pro Thr Lys Ala Val Asn Gln Arg Asp Ala Asp Leu
            340                 345                 350

Val His Phe Trp Asp Lys Tyr Arg Lys Ala Pro Asp Gly Ser Val Arg
        355                 360                 365

Lys Leu Glu Ala Gln Lys Gln Phe Val Glu Ala Met Ser His Arg Met
    370                 375                 380

His Ile Asp Asn Ser Met Lys Leu Ile Gly Lys Leu Leu Phe Gly Ile
385                 390                 395                 400

Glu Lys Gly Pro Glu Val Met Lys Thr Val Arg Pro Ala Gly Gln Pro
                405                 410                 415

Leu Val Asp Asp Trp Lys Cys Leu Lys Lys Met Val Arg Thr Phe Glu
            420                 425                 430

Thr His Cys Gly Ser Leu Ala Gln Tyr Gly Met Lys His Met Arg Ser
        435                 440                 445

Leu Ala Asn Ile Cys Asn Ala Gly Ile Gln Thr Glu Gln Met Ala Glu
    450                 455                 460

Ala Ser Ala Gln Ala Cys Val Ser Ile Pro Ser Gly His Trp Ser Ser
465                 470                 475                 480

Val Gln Lys Gly Phe Ser Ala
                485

<210> SEQ ID NO 17
<211> LENGTH: 484
<212> TYPE: PRT
<213> ORGANISM: Medicago truncatula

<400> SEQUENCE: 17

Met Ala Arg Phe Leu Phe Leu Ile Ile Ala Thr Leu Ile Pro Ile Phe
1               5                   10                  15

Ser Ala Ala Thr Ala Thr Ala Gly Asp Asp Phe Leu Arg Leu Pro Ser
            20                  25                  30

Gln Ala Ser Arg Phe Phe Gln Ser Asp Asp Asn Asn Glu Gly Thr
        35                  40                  45

Lys Trp Ala Ile Leu Ile Ala Gly Ser Asn Gly Tyr Trp Asn Tyr Arg
    50                  55                  60

His Gln Ser Asp Val Cys His Ala Tyr Gln Val Leu Arg Lys Gly Gly
65                  70                  75                  80

Leu Lys Glu Glu Asn Ile Ile Val Phe Met Tyr Asp Asp Ile Ala Asp
                85                  90                  95

Asn Gln Glu Asn Pro Arg Pro Gly Val Ile Ile Asn Ser Pro His Gly
            100                 105                 110

Asp Asp Val Tyr Lys Gly Val Pro Lys Asp Tyr Thr Gly Asp Asp Val
```

```
            115                 120                 125
Asn Val Asn Asn Phe Phe Ala Ala Leu Leu Gly Asn Lys Ser Ala Leu
    130                 135                 140

Thr Gly Gly Ser Gly Lys Val Val Asp Ser Gly Pro Asn Asp His Ile
145                 150                 155                 160

Phe Ile Tyr Tyr Ser Asp His Gly Gly Pro Gly Val Leu Gly Met Pro
                165                 170                 175

Thr Gly Pro Phe Met Tyr Ala Thr Asp Leu Ile Glu Val Leu Lys Lys
            180                 185                 190

Lys His Ala Ser Glu Thr Tyr Lys Ser Leu Val Phe Tyr Leu Glu Ala
        195                 200                 205

Cys Glu Ser Gly Ser Ile Phe Glu Gly Leu Leu Pro Glu Gly Leu Asn
    210                 215                 220

Ile Tyr Ala Thr Ala Ala Asn Ala Glu Ser Ser Trp Gly Thr
225                 230                 235                 240

Tyr Cys Pro Gly Glu Asn Pro Ser Pro Pro Glu Tyr Glu Thr Cys
                245                 250                 255

Leu Gly Asp Leu Tyr Ser Val Ala Trp Met Glu Asp Ser Asp Ile His
            260                 265                 270

Asn Leu Gln Thr Glu Thr Leu His Gln Gln Tyr Glu Leu Val Lys Glu
        275                 280                 285

Arg Thr Ser Asn Gly Asn Ser Ile Tyr Gly Ser His Val Met Gln Phe
    290                 295                 300

Gly Asp Ile Gly Leu Ser Arg Asp Ser Leu Phe Leu Tyr Leu Gly Ser
305                 310                 315                 320

Asn Pro Ala Asn Glu Asn Phe Thr Phe Met Gly Arg Asn Ser Leu Val
                325                 330                 335

Pro Pro Ser Lys Thr Val Asn Gln Arg Asp Ala Asp Leu Ile His Phe
            340                 345                 350

Trp Asp Lys Phe Arg Lys Ala Pro Gln Gly Ser Pro Arg Lys Val Ala
        355                 360                 365

Ala Gln Lys Gln Val Leu Glu Ala Met Ser His Arg Met His Ile Asp
    370                 375                 380

Glu Ser Ile Lys Leu Val Gly Lys Leu Leu Phe Gly Met Lys Lys Gly
385                 390                 395                 400

Pro Glu Val Leu Ala Ser Val Arg Pro Ala Gly Gln Pro Val Val Asp
                405                 410                 415

Asp Trp Asp Cys Leu Lys Ser Leu Val Arg Thr Phe Glu Thr Tyr Cys
            420                 425                 430

Gly Ser Leu Ser Gln Tyr Gly Met Lys His Met Arg Ser Phe Ala Asn
        435                 440                 445

Phe Cys Asn Ala Gly Ile His Ser Glu Gln Met Ala Glu Ala Ser Ala
    450                 455                 460

Gln Ala Cys Ile Asn Ile Pro Ala Asn Pro Trp Ser Ser Leu His Gly
465                 470                 475                 480

Gly Phe Ser Ala

<210> SEQ ID NO 18
<211> LENGTH: 493
<212> TYPE: PRT
<213> ORGANISM: Populus tomentosa

<400> SEQUENCE: 18

Met Thr Arg Leu Ile Ala Gly Val Ile Phe Leu Leu Ile Ala Phe Cys
```

-continued

```
1               5                   10                  15
Gly Ile Ala Val Gly Val Arg Asp Ile Val Gly Asp Val Leu Arg Leu
                20                  25                  30
Pro Ser Glu Ala Ser Arg Phe Phe Arg Ser Gly Lys Phe Asn Asp Asp
                35                  40                  45
Asn Ser Asp Asp Asp Ser Ser Gly Thr Arg Trp Ala Ile Leu Leu Ala
 50                 55                  60
Gly Ser Asn Gly Tyr Trp Asn Tyr Arg His Gln Ala Asp Val Cys His
 65                 70                  75                  80
Ala Tyr Gln Leu Leu Arg Lys Gly Gly Leu Lys Glu Glu Asn Ile Ile
                85                  90                  95
Val Phe Met Tyr Asp Asp Ile Ala Asp Asn Pro Glu Asn Pro Arg Pro
                100                 105                 110
Gly Val Ile Ile Asn Asn Pro Gln Gly Glu Asp Val Tyr Glu Gly Val
                115                 120                 125
Pro Lys Asp Tyr Thr Gly Gln Asp Val Thr Val Gly Asn Phe Phe Ala
                130                 135                 140
Ala Ile Leu Gly Asn Lys Thr Ala Leu Thr Gly Gly Ser Gly Lys Val
 145                150                 155                 160
Val Asp Ser Gly Pro Asn Asp His Ile Phe Ile Tyr Tyr Thr Asp His
                165                 170                 175
Gly Gly Pro Gly Val Leu Gly Met Pro Thr Asn Pro Tyr Leu Tyr Ala
                180                 185                 190
Asp Asp Leu Ile Asp Val Leu Lys Lys Lys His Ala Ser Gly Thr Tyr
                195                 200                 205
Lys Ser Leu Val Phe Tyr Leu Glu Ala Cys Glu Ser Gly Ser Ile Phe
 210                215                 220
Glu Gly Leu Leu Pro Gln Gly Leu Asn Ile Tyr Ala Thr Thr Ala Ser
 225                230                 235                 240
Asn Ala Glu Glu Ser Ser Trp Gly Thr Tyr Cys Pro Gly Glu Tyr Pro
                245                 250                 255
Ser Pro Pro Pro Glu Tyr Glu Thr Cys Leu Gly Asp Leu Tyr Ser Val
                260                 265                 270
Ala Trp Met Glu Asp Ser Asp Ile His Asn Leu Arg Thr Glu Thr Leu
                275                 280                 285
His Gln Gln Tyr Glu Leu Val Lys Arg Arg Thr Ser Asp Glu Asn Ser
                290                 295                 300
Ala Tyr Gly Ser His Val Met Gln Tyr Gly Asp Val Gly Leu Ser Lys
 305                310                 315                 320
Glu Asp Leu Phe Gln Tyr Met Gly Thr Asn Pro Ala Asn Asp Asn Phe
                325                 330                 335
Thr Phe Leu Glu Asp Asn Ser Leu Arg Pro Pro Ser Lys Ala Val Asn
                340                 345                 350
Gln Arg Asp Ala Asp Leu Val His Phe Trp Ala Lys Tyr Arg Lys Ala
                355                 360                 365
Pro Glu Gly Ser Ser Arg Lys Val Glu Ala Gln Lys Gln Phe Val Glu
                370                 375                 380
Ala Met Ser His Arg Met His Ile Asp His Ser Ile Lys Leu Ile Gly
 385                390                 395                 400
Lys Leu Leu Phe Gly Ile Glu Lys Ala Ser Glu Val Leu Asn Asn Val
                405                 410                 415
Arg Pro Ala Gly Gln Pro Leu Val Asp Asp Trp Val Cys Leu Lys Thr
                420                 425                 430
```

```
Leu Val Arg Thr Phe Glu Thr His Cys Gly Ser Ile Ser Gln Tyr Gly
            435                 440                 445

Met Lys His Met Arg Ser Leu Ala Asn Leu Cys Asn Ala Gly Ile Val
        450                 455                 460

Lys Glu Gln Met Ala Glu Ala Ser Ala Gln Ala Cys Val Ser Ile Pro
465                 470                 475                 480

Ser Gly Ser Trp Ser Ser Leu His Lys Gly Phe Ser Ala
                    485                 490

<210> SEQ ID NO 19
<211> LENGTH: 489
<212> TYPE: PRT
<213> ORGANISM: Populus trichocarpa

<400> SEQUENCE: 19

Met Thr Gly Leu Ala Thr Gly Ala Ile Phe Leu Leu Ile Ser Leu Cys
1               5                   10                  15

Gly Ile Ala Ala Ala Gly Arg Asp Thr Val Gly Asp Val Leu Arg Leu
            20                  25                  30

Pro Ser Glu Ala Ser Arg Phe Phe His Asn Asp Asp Asn Ser Asp Asp
        35                  40                  45

Asp Ser Thr Gly Thr Arg Trp Ala Ile Leu Leu Ala Gly Ser Asn Gly
    50                  55                  60

Tyr Trp Asn Tyr Arg His Gln Ala Asp Val Cys His Ala Tyr Gln Leu
65                  70                  75                  80

Leu Arg Lys Gly Gly Leu Lys Glu Glu Asn Ile Ile Val Phe Met Tyr
                85                  90                  95

Asp Asp Ile Ala Tyr Asn Ser Glu Asn Pro Arg Arg Gly Val Ile Ile
            100                 105                 110

Asn Ser Pro Gln Gly Glu Asp Val Tyr Lys Gly Val Pro Lys Asp Tyr
        115                 120                 125

Thr Gly Glu Asp Val Thr Val Gly Asn Phe Phe Ala Ala Ile Leu Gly
    130                 135                 140

Asn Lys Thr Ala Leu Thr Gly Gly Ser Gly Lys Val Val Asp Ser Gly
145                 150                 155                 160

Pro Asn Asp His Ile Phe Ile Tyr Tyr Thr Asp His Gly Gly Pro Gly
                165                 170                 175

Val Leu Gly Met Pro Thr Asn Pro Tyr Leu Tyr Ala Asp Asp Leu Ile
            180                 185                 190

Asp Val Leu Lys Lys Lys His Ala Ser Gly Thr Tyr Lys Ser Leu Val
        195                 200                 205

Phe Tyr Leu Glu Ala Cys Glu Ser Gly Ser Ile Phe Glu Gly Leu Leu
    210                 215                 220

Pro Gln Gly Leu Asn Ile Tyr Ala Thr Thr Ala Ser Asn Ala Glu Glu
225                 230                 235                 240

Ser Ser Trp Gly Thr Tyr Cys Pro Gly Glu Asn Pro Ser Pro Pro Pro
                245                 250                 255

Glu Tyr Glu Thr Cys Leu Gly Asp Leu Tyr Ser Val Ala Trp Met Glu
            260                 265                 270

Asp Ser Asp Ile His Asn Leu Gln Thr Glu Thr Leu His Gln Gln Tyr
        275                 280                 285

Glu Leu Val Lys Arg Arg Thr Ser Asn Asp Asn Ser Pro Tyr Gly Ser
    290                 295                 300

His Val Met Gln Tyr Gly Asp Val Gly Leu Ser Lys Asp Asn Ile Phe
```

305                 310                 315                 320

Leu Tyr Met Gly Thr Asn Pro Ala Asn Asp Asn Phe Thr Phe Met Asp
            325                 330                 335

Glu Asn Leu Leu Arg Pro Arg Ser Lys Ala Val Asn Gln Arg Asp Ala
            340                 345                 350

Asp Leu Val His Phe Trp Asp Lys Tyr Arg Lys Ala Pro Glu Gly Ser
            355                 360                 365

Ser Arg Lys Val Glu Ala Gln Lys Gln Phe Val Glu Ala Met Ser His
370                 375                 380

Arg Met His Ile Asp His Ser Ile Lys Leu Ile Gly Lys Leu Leu Phe
385                 390                 395                 400

Gly Ile Glu Lys Ala Ser Glu Val Leu Asn Ala Ile Arg Pro Ala Gly
            405                 410                 415

Gln Pro Leu Val Asp Asp Trp Asp Cys Leu Lys Thr Leu Val Arg Thr
            420                 425                 430

Phe Glu Thr His Cys Gly Ser Val Ser Gln Tyr Gly Met Lys His Met
            435                 440                 445

Arg Ser Leu Ala Asn Leu Cys Asn Ala Gly Ile Gly Lys Glu Gln Met
            450                 455                 460

Ala Glu Ala Ser Ala Gln Ala Cys Val Ser Phe Pro Ser Gly Pro Trp
465                 470                 475                 480

Ser Thr Leu His Lys Gly Phe Ser Ala
            485

<210> SEQ ID NO 20
<211> LENGTH: 494
<212> TYPE: PRT
<213> ORGANISM: Malus hupehensis var. mengshanensis
<220> FEATURE:
<221> NAME/KEY: MISC_FEATURE
<222> LOCATION: (264)..(264)
<223> OTHER INFORMATION: Xaa can be any naturally occurring amino acid

<400> SEQUENCE: 20

Met Thr Arg Leu Ala Ser Ala Val Val Leu Phe Leu Ala Ser Val
1               5                   10                  15

Leu Ala Ser Ala Ala Gly Ser Arg Asp Leu Ile Gly Asp Val Leu Arg
            20                  25                  30

Leu Pro Ser Glu Ala Ser Arg Phe Phe Gly Arg Gly Asp Asp Ala Pro
            35                  40                  45

Asp Gln Gln Asp Asp Gly Thr Val Gly Thr Arg Trp Ala Val Leu Ile
50                  55                  60

Ala Gly Ser Asn Gly Tyr Trp Asn Tyr Arg His Gln Ala Asp Ile Cys
65                  70                  75                  80

His Ala Tyr Gln Leu Leu Lys Lys Gly Gly Leu Lys Asp Glu Asn Ile
            85                  90                  95

Val Val Phe Met Tyr Asp Asp Ile Ala Tyr Asn Glu Glu Asn Pro Arg
            100                 105                 110

Gln Gly Val Ile Ile Asn Ser Pro His Gly Ser Asp Val Tyr Glu Gly
            115                 120                 125

Val Pro Lys Asp Tyr Thr Gly Glu Asp Val Thr Val Asn Asn Phe Phe
            130                 135                 140

Ala Ala Ile Leu Gly Asn Lys Thr Ala Leu Thr Gly Gly Ser Gly Lys
145                 150                 155                 160

Val Val Asp Ser Gly Pro Asn Asp His Ile Phe Ile Tyr Tyr Thr Asp
            165                 170                 175

His Gly Gly Pro Gly Ile Leu Gly Met Pro Thr Ser Pro Tyr Ile Tyr
            180                 185                 190

Ala Asn Asp Leu Ile Glu Val Leu Lys Lys His Ala Ala Gly Thr
        195                 200                 205

Tyr Lys Ser Leu Val Phe Tyr Leu Glu Ala Cys Glu Ser Gly Ser Ile
    210                 215                 220

Phe Glu Gly Leu Leu Pro Glu Gly Leu Asn Ile Phe Ala Thr Thr Ala
225                 230                 235                 240

Ser Asn Ala Glu Glu Ser Ser Trp Gly Thr Tyr Cys Pro Gly Glu Tyr
                245                 250                 255

Pro Ser Pro Pro Pro Glu Tyr Xaa Thr Cys Leu Gly Asp Leu Tyr Ser
            260                 265                 270

Val Val Trp Met Glu Asp Ser Asp Val His Asn Leu Arg Ser Glu Thr
    275                 280                 285

Leu His Gln Gln Tyr Glu Leu Val Lys Met Arg Thr Ala Asn Asp Asn
    290                 295                 300

Ser Gly Phe Gly Ser His Val Met Gln Tyr Gly Asp Val Gly Leu Ser
305                 310                 315                 320

Lys Asn Asn Leu Phe Val Tyr Met Gly Thr Asn Pro Ala Asn Asp Asn
                325                 330                 335

Tyr Thr Phe Leu Gly Glu Asn Ser Leu Arg Pro Ser Ser Lys Ala Val
            340                 345                 350

Asn Gln Arg Asp Ala Asp Leu Leu Arg Phe Trp His Lys Tyr Arg Lys
    355                 360                 365

Ala Pro Glu Gly Ser Ala Arg Lys Ile Gln Ala Gln Lys Asp Phe Val
    370                 375                 380

Glu Ala Met Ser His Arg Met His Ile Asp Gln Thr Met Lys Leu Ile
385                 390                 395                 400

Gly Lys Leu Leu Phe Gly Ile Glu Lys Gly Pro Gln Val Leu Asn Ala
                405                 410                 415

Val Arg Pro Ala Gly Gln Pro Leu Val Asp Asp Trp Asp Cys Leu Lys
            420                 425                 430

Thr Met Val Arg Ser Phe Glu Thr His Cys Gly Ser Leu Ser Gln Tyr
    435                 440                 445

Gly Met Lys His Met Arg Ser Leu Ala Asn Ile Cys Asn Ala Gly Met
    450                 455                 460

Thr Gln Glu Gln Met Ala Glu Ala Ser Ala Gln Ala Cys Val Ser Ala
465                 470                 475                 480

Pro Ser Gly Arg Trp Ser Ser Leu His Arg Gly Phe Ser Ala
                485                 490

<210> SEQ ID NO 21
<211> LENGTH: 480
<212> TYPE: PRT
<213> ORGANISM: Glycine max

<400> SEQUENCE: 21

Met Pro Thr Phe Phe Leu Pro Thr Leu Leu Leu Leu Ile Ala Phe
1               5                   10                  15

Ala Thr Ser Val Ser Gly Arg Arg Asp Leu Val Gly Asp Phe Leu Arg
            20                  25                  30

Leu Pro Ser Glu Thr Asp Asn Asp Asp Asn Phe Lys Gly Thr Arg Trp
        35                  40                  45

Ala Val Leu Leu Ala Gly Ser Asn Gly Tyr Trp Asn Tyr Arg His Gln

```
             50                  55                  60
Ala Asp Val Cys His Ala Tyr Gln Ile Leu Arg Lys Gly Gly Leu Lys
 65                  70                  75                  80

Glu Glu Asn Ile Ile Val Phe Met Tyr Asp Asp Ile Ala Phe Asn Gly
                 85                  90                  95

Glu Asn Pro Arg Pro Gly Val Ile Ile Asn Lys Pro Asp Gly Gly Asp
            100                 105                 110

Val Tyr Lys Gly Val Pro Lys Asp Tyr Thr Gly Glu Asp Val Thr Val
        115                 120                 125

Asp Asn Phe Phe Ala Ala Leu Leu Gly Asn Lys Ser Ala Leu Thr Gly
    130                 135                 140

Gly Ser Gly Lys Val Val Asp Ser Pro Asp Asp His Ile Phe Val
145                 150                 155                 160

Tyr Tyr Thr Asp His Gly Gly Pro Gly Val Leu Gly Met Pro Ala Gly
                165                 170                 175

Pro Tyr Leu Tyr Ala Asp Asp Leu Ile Glu Val Leu Lys Lys Lys His
            180                 185                 190

Ala Ser Gly Thr Tyr Lys Asn Leu Val Phe Tyr Leu Glu Ala Cys Glu
        195                 200                 205

Ser Gly Ser Ile Phe Glu Gly Leu Leu Pro Glu Asp Ile Asn Ile Tyr
    210                 215                 220

Ala Thr Thr Ala Ser Asn Ala Glu Glu Ser Ser Trp Gly Thr Tyr Cys
225                 230                 235                 240

Pro Gly Glu Tyr Pro Ser Pro Pro Glu Tyr Thr Thr Cys Leu Gly
                245                 250                 255

Asp Leu Tyr Ser Val Ala Trp Met Glu Asp Ser Asp Arg His Asn Leu
            260                 265                 270

Arg Thr Glu Thr Leu His Gln Gln Tyr Lys Leu Val Lys Glu Arg Thr
        275                 280                 285

Ile Ser Gly Asp Ser Tyr Tyr Gly Ser His Val Met Gln Tyr Gly Asp
    290                 295                 300

Val Gly Leu Ser Arg Asp Val Leu Phe His Tyr Leu Gly Thr Asp Pro
305                 310                 315                 320

Ala Asn Asp Asn Phe Thr Phe Val Asp Glu Asn Ser Leu Trp Ser Pro
                325                 330                 335

Ser Lys Pro Val Asn Gln Arg Asp Ala Asp Leu Ile His Phe Trp Asp
            340                 345                 350

Lys Phe Arg Lys Ala Pro Glu Gly Ser Leu Arg Lys Asn Thr Ala Gln
        355                 360                 365

Lys Gln Val Leu Glu Ala Met Ser His Arg Met His Val Asp Asn Ser
    370                 375                 380

Val Lys Leu Ile Gly Lys Leu Leu Phe Gly Ile Glu Lys Gly Pro Glu
385                 390                 395                 400

Val Leu Asn Ala Val Arg Pro Ala Gly Ser Ala Leu Val Asp Asp Trp
                405                 410                 415

His Cys Leu Lys Thr Met Val Arg Thr Phe Glu Thr His Cys Gly Ser
            420                 425                 430

Leu Ser Gln Tyr Gly Met Lys His Met Arg Ser Phe Ala Asn Ile Cys
        435                 440                 445

Asn Val Gly Ile Lys Asn Glu Gln Met Ala Glu Ala Ser Ala Gln Ala
    450                 455                 460

Cys Val Ser Ile Pro Ser Asn Pro Trp Ser Ser Leu Gln Arg Gly Phe
465                 470                 475                 480
```

<210> SEQ ID NO 22
<211> LENGTH: 481
<212> TYPE: PRT
<213> ORGANISM: Glycine max

<400> SEQUENCE: 22

```
Met Ala Thr Leu Leu Pro Thr Leu Leu Leu Ile Pro Phe Ala
1               5                   10                  15

Thr Leu Val Ser Ala Arg Pro His Leu Ala Gly Asp Phe Leu Arg Leu
            20                  25                  30

Pro Ser Glu Thr Asp Asn Asp Asn Val Gln Gly Thr Arg Trp Ala
        35                  40                      45

Val Leu Leu Ala Gly Ser Asn Gly Tyr Trp Asn Tyr Arg His Gln Ala
50                  55                  60

Asp Val Cys His Ala Tyr Gln Ile Leu Arg Lys Gly Gly Leu Lys Glu
65                  70                  75                  80

Glu Asn Ile Ile Val Phe Met Tyr Asp Asp Ile Ala Phe Asn Gly Glu
                85                  90                  95

Asn Pro Arg Pro Gly Val Ile Ile Asn Lys Pro Asp Gly Gly Asp Val
            100                 105                 110

Tyr Glu Gly Val Pro Lys Asp Tyr Thr Gly Glu Asp Val Thr Val Gly
        115                 120                 125

Asn Phe Phe Ala Ala Leu Leu Gly Asn Lys Ser Ala Leu Thr Gly Gly
130                 135                 140

Ser Gly Lys Val Val Asp Ser Gly Pro Asp Asp His Ile Phe Val Tyr
145                 150                 155                 160

Tyr Thr Asp His Gly Gly Pro Gly Val Leu Gly Met Pro Ala Gly Pro
                165                 170                 175

Tyr Leu Tyr Ala Asp Asp Leu Ile Glu Val Leu Lys Lys Lys His Ala
            180                 185                 190

Ser Gly Thr Tyr Lys Asn Leu Val Phe Tyr Leu Glu Ala Cys Glu Ser
        195                 200                 205

Gly Ser Ile Phe Glu Gly Leu Leu Pro Glu Asp Ile Asn Ile Tyr Ala
210                 215                 220

Thr Thr Ala Ser Asn Ala Glu Glu Ser Ser Trp Gly Thr Tyr Cys Pro
225                 230                 235                 240

Gly Glu Tyr Pro Ser Pro Pro Glu Tyr Ser Thr Cys Leu Gly Asp
                245                 250                 255

Leu Tyr Ser Val Ala Trp Met Glu Asp Ser Asp Arg His Asn Leu Arg
            260                 265                 270

Thr Glu Thr Leu His Gln Gln Tyr Lys Leu Val Lys Glu Arg Thr Ile
        275                 280                 285

Ser Gly Asp Ser Tyr Tyr Gly Ser His Val Met Gln Tyr Gly Asp Val
290                 295                 300

Arg Leu Ser Ser Asp Val Leu Phe His Tyr Leu Gly Thr Asp Pro Ala
305                 310                 315                 320

Asn Asp Asn Phe Thr Phe Val Asp Glu Asn Ser Leu Trp Ser Pro Ser
                325                 330                 335

Lys Pro Val Asn Gln Arg Asp Ala Asp Leu Ile His Phe Trp Asp Lys
            340                 345                 350

Phe Arg Lys Ala Pro Glu Gly Ser Leu Arg Lys Asn Ala Ala Gln Lys
        355                 360                 365

Gln Val Leu Glu Ala Met Ser His Arg Met His Val Asp Asn Ser Val
```

```
            370                 375                 380
Lys Leu Ile Gly Lys Leu Leu Phe Gly Ile Glu Lys Gly Pro Glu Val
385                 390                 395                 400

Leu Asn Ala Val Arg Pro Ala Gly Ser Ala Leu Val Asp Asp Trp His
                405                 410                 415

Cys Leu Lys Thr Met Val Arg Thr Phe Glu Thr His Cys Gly Ser Leu
                420                 425                 430

Ser Gln Tyr Gly Met Lys His Met Arg Ser Phe Ala Asn Ile Cys Asn
                435                 440                 445

Val Gly Ile Lys Asn Glu Gln Met Ala Glu Ala Ser Ala Gln Ala Cys
            450                 455                 460

Val Ser Ile Pro Ser Asn Pro Trp Ser Ser Leu Gln Arg Gly Phe Ser
465                 470                 475                 480

Ala

<210> SEQ ID NO 23
<211> LENGTH: 494
<212> TYPE: PRT
<213> ORGANISM: Prunus persica

<400> SEQUENCE: 23

Met Thr Arg Leu Ala Ser Ala Val Val Leu Leu Phe Leu Val Ser Leu
1               5                   10                  15

Ser Ser Phe Ala Ala Gly Ser Arg Asp Leu Ile Gly Asp Val Leu Arg
                20                  25                  30

Leu Pro Ser Glu Ala Ser Arg Phe Phe Gly Arg Gly Asp Asp Gly Pro
            35                  40                  45

Asp Glu Gln Asp Asp Gly Thr Val Gly Thr Arg Trp Ala Val Leu Ile
50                  55                  60

Ala Gly Ser Asn Gly Tyr Trp Asn Tyr Arg His Gln Ala Asp Ile Cys
65                  70                  75                  80

His Ala Tyr Gln Leu Leu Lys Lys Gly Gly Leu Lys Asp Glu Asn Ile
                85                  90                  95

Val Val Phe Met Tyr Asp Asp Ile Ala Tyr Asn Glu Glu Asn Pro Arg
                100                 105                 110

Pro Gly Val Ile Ile Asn Ser Pro His Gly Asp Asp Val Tyr Lys Gly
            115                 120                 125

Val Pro Lys Asp Tyr Thr Gly Asp Asp Val Thr Val Asn Asn Phe Phe
130                 135                 140

Ala Ala Ile Leu Gly Asn Lys Thr Ala Leu Thr Gly Gly Thr Gly Lys
145                 150                 155                 160

Val Val Asp Ser Gly Pro Asn Asp His Ile Phe Ile Tyr Tyr Ser Asp
                165                 170                 175

His Gly Gly Pro Gly Val Leu Gly Met Pro Thr Ser Pro Tyr Ile Tyr
                180                 185                 190

Ala Asn Asp Leu Ile Glu Val Leu Lys Lys His Ala Ala Gly Thr
            195                 200                 205

Tyr Lys Ser Leu Val Phe Tyr Leu Glu Ala Cys Glu Ser Gly Ser Ile
        210                 215                 220

Phe Glu Gly Leu Leu Pro Glu Gly Leu Asn Ile Phe Ala Thr Thr Ala
225                 230                 235                 240

Ser Asn Ala Glu Glu Ser Ser Trp Gly Thr Tyr Cys Pro Gly Glu Tyr
                245                 250                 255

Pro Ser Pro Pro Pro Glu Tyr Glu Thr Cys Leu Gly Asp Leu Tyr Ser
```

-continued

```
                 260                 265                 270
Val Ala Trp Met Glu Asp Ser Asp Ile His Asn Leu Arg Ser Glu Thr
            275                 280                 285

Leu His Gln Gln Tyr Glu Leu Val Lys Thr Arg Thr Ala Asn Asp Asn
        290                 295                 300

Ser Gly Phe Gly Ser His Val Met Gln Tyr Gly Asp Val Gly Leu Ser
305                 310                 315                 320

Lys Glu Asn Leu Phe Val Tyr Met Gly Thr Asn Pro Ala Asn Asp Asn
                325                 330                 335

Tyr Thr Phe Leu Gly Glu Asn Ser Leu Arg Pro Ser Thr Lys Ala Val
            340                 345                 350

Asn Gln Arg Asp Ala Asp Leu Val His Phe Trp His Lys Tyr Arg Lys
        355                 360                 365

Ala Pro Glu Gly Ser Pro Arg Lys Ile Gln Ala Gln Lys Asp Phe Val
370                 375                 380

Glu Ala Met Ser His Arg Met His Met Asp Gln Thr Met Lys Leu Ile
385                 390                 395                 400

Gly Lys Leu Leu Phe Gly Ile Lys Lys Gly Pro Glu Val Leu Asn Thr
                405                 410                 415

Val Arg Pro Ala Gly Gln Pro Leu Val Asp Asp Trp Asp Cys Leu Lys
            420                 425                 430

Thr Met Val Arg Ser Phe Glu Thr Tyr Cys Gly Ser Leu Ser Gln Tyr
        435                 440                 445

Gly Met Lys His Met Arg Ser Leu Ala Asn Ile Cys Asn Ala Gly Met
450                 455                 460

Thr Lys Glu Gln Met Thr Glu Ala Ser Ala Gln Ala Cys Thr Ser Val
465                 470                 475                 480

Pro Ser Ser Arg Trp Ser Ser Leu His Arg Gly Phe Ser Ala
                485                 490

<210> SEQ ID NO 24
<211> LENGTH: 487
<212> TYPE: PRT
<213> ORGANISM: Arachis diogoi

<400> SEQUENCE: 24

Met Glu Ser Leu Leu Arg Ile Thr Leu Leu Phe Phe Ala Phe Thr Thr
1               5                  10                  15

Phe Val Ala Ser Ala Ser Gly Arg Arg Asp Ile Val Gly Gly Thr Leu
            20                  25                  30

Arg Leu Pro Ser Glu Ala Ile Ser Arg Phe Phe His Glu Pro Glu Asn
        35                  40                  45

Glu Gly Thr Lys Trp Ala Val Leu Leu Ala Gly Ser Asn Gly Tyr Trp
    50                  55                  60

Asn Tyr Arg His Gln Ala Asp Ile Cys His Ala Tyr Gln Leu Leu Arg
65                  70                  75                  80

Ser Gly Gly Val Lys Glu Glu Asn Ile Ile Val Phe Met Phe Asp Asp
                85                  90                  95

Ile Ala Tyr Ser Glu Glu Asn Pro Arg Pro Gly Val Ile Ile Asn Lys
            100                 105                 110

Pro Asp Gly Gly Asp Val Tyr Lys Gly Val Pro Lys Asp Tyr Thr Gly
        115                 120                 125

Lys Asp Val Asn Val Asn Asn Phe Phe Ala Ala Leu Leu Gly Asn Lys
    130                 135                 140
```

```
Ser Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Ile Leu
            165                 170                 175

Gly Met Pro Val Gly Pro Tyr Leu Tyr Ala Asn Asp Leu Asn Glu Val
            180                 185                 190

Leu Lys Lys Lys His Ala Ser Gly Gly Tyr Lys Ser Leu Val Phe Tyr
            195                 200                 205

Leu Glu Ala Cys Glu Ser Gly Ser Ile Phe Glu Gly Leu Leu Pro Glu
210                 215                 220

Asp Ile Asn Ile Tyr Ala Thr Thr Ala Ser Asn Ala Val Glu Ser Ser
225                 230                 235                 240

Trp Gly Thr Tyr Cys Pro Gly Glu Asp Pro Ser Pro Pro Glu Tyr
            245                 250                 255

Ser Thr Cys Leu Gly Asp Leu Tyr Ser Ile Ser Trp Met Glu Asp Ser
            260                 265                 270

Asp Thr His Asn Leu Arg Thr Glu Thr Leu His Gln Gln Tyr Lys Leu
            275                 280                 285

Val Lys Asp Arg Thr Leu Asn Gly Asn Ala Tyr Tyr Gly Ser His Ala
290                 295                 300

Met Gln Tyr Gly Asp Val Gly Ile Ser Glu Asn Leu Leu Phe Gln Tyr
305                 310                 315                 320

Leu Gly Thr Asn Pro Ala Asn Asp Asn Tyr Thr Phe Val Asp Glu Asn
            325                 330                 335

Ser Leu Arg Thr Pro Ser Lys Ala Val Asn Gln Arg Asp Ala Asp Leu
            340                 345                 350

Ile His Phe Trp Glu Lys Phe Arg Lys Ala Pro Glu Gly Ser Ser Ser
            355                 360                 365

Lys Ile Thr Ala Gln Lys Gln Val Glu Val Met Ser His Arg Met
370                 375                 380

His Ile Asp Asn Ser Val Lys Leu Ile Gly Asn Leu Leu Phe Gly Thr
385                 390                 395                 400

Glu Lys Gly Pro Glu Leu Leu Ser Ala Val Arg Pro Ala Gly Lys Pro
            405                 410                 415

Leu Val Asp Asp Trp Asp Cys Leu Lys Asn Met Val Arg Thr Phe Glu
            420                 425                 430

Thr His Cys Gly Ser Leu Ser Gln Tyr Gly Met Lys His Met Arg Thr
            435                 440                 445

Phe Ala Asn Ile Cys Asn Ala Gly Ile His Lys Asp Gln Met Asp Glu
450                 455                 460

Ala Thr Ala Gln Ala Cys Val Ser Ile Pro Ser Asn Pro Trp Ser Ser
465                 470                 475                 480

Leu Glu Arg Gly Phe Ser Ala
                485

<210> SEQ ID NO 25
<211> LENGTH: 493
<212> TYPE: PRT
<213> ORGANISM: Populus trichocarpa

<400> SEQUENCE: 25

Met Thr Arg Leu Ile Ala Gly Val Ile Phe Leu Leu Ile Ser Phe Cys
1               5                   10                  15

Gly Ile Ala Val Gly Val Arg Asp Ile Val Gly Asp Val Leu Arg Leu
            20                  25                  30
```

```
Pro Ser Glu Ala Ser Arg Phe Phe Arg Pro Gly Lys Phe Asn Asp Asp
            35                  40                  45

Asn Ser Asp Asp Asp Ser Ser Gly Thr Arg Trp Ala Ile Leu Leu Ala
 50                  55                  60

Gly Ser Asn Gly Tyr Trp Asn Tyr Arg His Gln Ala Asp Val Cys His
 65                  70                  75                  80

Ala Tyr Gln Leu Leu Arg Gln Gly Gly Leu Lys Glu Glu Asn Ile Ile
                     85                  90                  95

Val Phe Met Tyr Asp Asp Ile Ala Asp Asn Pro Glu Asn Pro Arg Pro
                100                 105                 110

Gly Val Ile Ile Asn Asn Pro Gln Gly Glu Asp Val Tyr Lys Gly Val
                115                 120                 125

Pro Lys Asp Tyr Thr Gly Pro Asp Val Thr Val Gly Asn Phe Phe Ala
                130                 135                 140

Ala Ile Leu Gly Asn Lys Thr Ala Leu Thr Gly Gly Ser Gly Lys Val
145                 150                 155                 160

Ile Asp Ser Gly Pro Asn Asp His Ile Phe Ile Tyr Thr Asp His
                165                 170                 175

Gly Gly Pro Gly Val Leu Gly Met Pro Thr Asn Pro Tyr Leu Tyr Ala
                180                 185                 190

Asp Asp Leu Ile Asp Val Leu Lys Lys Lys His Ala Ser Gly Thr Tyr
                195                 200                 205

Lys Ser Leu Val Phe Tyr Leu Glu Ala Cys Glu Ser Gly Ser Ile Phe
210                 215                 220

Glu Gly Leu Leu Pro Gln Gly Leu Asn Ile Tyr Ala Thr Thr Ala Ser
225                 230                 235                 240

Asn Ala Glu Glu Ser Ser Trp Gly Thr Tyr Cys Pro Gly Glu Tyr Pro
                245                 250                 255

Ser Pro Pro Pro Glu Tyr Glu Thr Cys Leu Gly Asp Leu Tyr Ser Val
                260                 265                 270

Ala Trp Met Glu Asp Ser Asp Ile His Asn Leu Arg Thr Glu Thr Leu
            275                 280                 285

His Gln Gln Tyr Glu Leu Val Lys Arg Arg Thr Ser Tyr Asp Asn Ser
            290                 295                 300

Pro Tyr Gly Ser His Val Met Gln Tyr Gly Asp Val Gly Leu Ser Lys
305                 310                 315                 320

Asp Asp Leu Phe Gln Tyr Met Gly Thr Asn Pro Ala Asn Asp Asn Tyr
                325                 330                 335

Thr Phe Val Glu Glu Asn Ser Leu Arg Pro His Ser Lys Val Val Asn
                340                 345                 350

Gln Arg Asp Ala Asp Leu Val His Phe Trp Thr Lys Tyr Arg Lys Ala
            355                 360                 365

Pro Glu Gly Ser Ser Arg Lys Val Glu Ala Gln Lys Gln Phe Val Glu
            370                 375                 380

Ala Met Ser His Arg Met His Ile Asp His Ser Ile Lys Leu Ile Gly
385                 390                 395                 400

Lys Leu Leu Phe Gly Ile Glu Lys Ala Ser Glu Ala Leu Asn Thr Val
                405                 410                 415

Arg Pro Ala Gly Gln Pro Leu Val Asp Asp Trp Val Cys Leu Lys Thr
                420                 425                 430

Leu Val Arg Thr Phe Glu Thr His Cys Gly Ser Ile Ser Gln Tyr Gly
            435                 440                 445
```

```
Met Lys His Met Arg Ser Leu Ala Asn Leu Cys Asn Ala Gly Ile Val
            450                 455                 460

Lys Glu Gln Met Ala Glu Ala Ser Ala Gln Ala Cys Val Ser Phe Pro
465                 470                 475                 480

Ser Gly Ser Trp Ser Ser Leu His Lys Gly Phe Ser Ala
                485                 490

<210> SEQ ID NO 26
<211> LENGTH: 492
<212> TYPE: PRT
<213> ORGANISM: Cicer arietinum

<400> SEQUENCE: 26

Met Asp Arg Ser Lys Ile Ser Thr Leu Leu Phe Leu Ile Val Ala Leu
1               5                   10                  15

Thr Phe Leu Ala Ala Val Ser Ala Val Arg Asp Leu Pro Gly Asp Tyr
                20                  25                  30

Leu Arg Leu Pro Ser Asp Ala Ser Arg Phe Phe His Glu Pro Glu Asn
            35                  40                  45

Asp Asp Asn Val Gln Gly Thr Arg Trp Ala Ile Leu Leu Ala Gly Ser
50                  55                  60

Asn Gly Tyr Trp Asn Tyr Arg His Gln Ala Asp Val Cys His Ala Tyr
65                  70                  75                  80

Gln Ile Leu Arg Lys Gly Gly Leu Lys Glu Glu Asn Ile Ile Val Phe
                85                  90                  95

Met Tyr Asp Asp Ile Ala Phe Asp Ile Glu Asn Pro Arg Pro Gly Val
                100                 105                 110

Ile Ile Asn Lys Pro Asp Gly Gly Asp Val Tyr Ala Gly Val Pro Lys
            115                 120                 125

Asp Tyr Thr Gly Asp Asp Val Asn Val Asp Asn Phe Tyr Ala Ala Leu
130                 135                 140

Leu Gly Asn Lys Ser Ala Leu Thr Gly Gly Ser Gly Lys Val Val Asp
145                 150                 155                 160

Ser Gly Pro Asn Asp His Ile Phe Val Tyr Tyr Thr Asp His Gly Gly
                165                 170                 175

Pro Gly Val Leu Gly Met Pro Val Gly Pro Tyr Leu Tyr Ala Ser Asp
                180                 185                 190

Leu Asn Glu Val Leu Lys Lys His Ala Ser Gly Ser Tyr Lys Ser
                195                 200                 205

Leu Val Phe Tyr Leu Glu Ala Cys Glu Ser Gly Ser Ile Phe Glu Gly
210                 215                 220

Leu Leu Pro Glu Asn Ile Asn Ile Tyr Ala Thr Thr Ala Ser Asn Ala
225                 230                 235                 240

Asp Glu Ser Ser Trp Gly Thr Tyr Cys Pro Gly Glu Tyr Pro Pro Pro
                245                 250                 255

Pro Pro Glu Tyr Ser Thr Cys Leu Gly Asp Leu Tyr Ser Val Ala Trp
            260                 265                 270

Met Glu Asp Ser Asp Ile His Asn Leu Arg Thr Glu Ser Leu His Gln
                275                 280                 285

Gln Tyr Lys Val Val Lys Asp Arg Thr Ile Asn Gly Val Tyr Tyr Gly
            290                 295                 300

Ser His Val Met Glu Tyr Gly Asp Val Gly Leu Ser Asn Asn His Leu
305                 310                 315                 320

Phe Ile Tyr Leu Gly Thr Asn Pro Ala Asn Asp Asn Ile Ser Phe Val
                325                 330                 335
```

-continued

```
Asp Glu Ser Ser Leu Thr Leu Arg Ser Pro Ser Ala Ala Val Asn Gln
            340                 345                 350

Arg Asp Ala Asp Leu Ile His Phe Trp Asp Lys Phe Arg Lys Ala Pro
            355                 360                 365

Glu Gly Ser Ala Arg Lys Asn Glu Ala Glu Lys Gln Val Leu Glu Ala
            370                 375                 380

Met Ser His Arg Lys His Val Asp Asn Ser Val Glu Leu Ile Gly Lys
385                 390                 395                 400

Leu Leu Phe Gly Ile Glu Lys Gly Pro Glu Leu Phe Asn Thr Val Arg
                405                 410                 415

Pro Ala Gly Leu Pro Leu Val Asp Asn Trp Asp Cys Leu Lys Thr Met
            420                 425                 430

Val Arg Thr Phe Glu Thr His Cys Gly Ser Leu Ser Gln Tyr Gly Met
            435                 440                 445

Lys His Met Arg Ser Phe Ala Asn Ile Cys Asn Ala Gly Ile Gln Asn
            450                 455                 460

Glu Gln Met Ala Glu Ala Ser Ala Gln Ala Cys Ser Asn Ile Pro Ala
465                 470                 475                 480

Asn Pro Trp Ser Ser Leu His Arg Gly Phe Ser Ala
                485                 490

<210> SEQ ID NO 27
<211> LENGTH: 493
<212> TYPE: PRT
<213> ORGANISM: Vitis vinifera

<400> SEQUENCE: 27

Met Thr Ile Phe Pro Ala Ala Val Ala Ala Phe Leu Ala Leu Ser Thr
1               5                   10                  15

Leu Val Ala Gly Gly Arg His Phe Ala Gly Asp Asn Gly Leu Leu Leu
            20                  25                  30

Pro Ser Glu Ala Ser Arg Phe Phe Arg Pro Gly Gly Ala Ala Asp Asp
            35                  40                  45

Asp Thr Gly Ala Glu Ser Ala Gly Thr Arg Trp Ala Val Leu Ile Ala
            50                  55                  60

Gly Ser Asn Gly Tyr Trp Asn Tyr Arg His Gln Ala Asp Ile Cys His
65                  70                  75                  80

Ala Tyr Gln Leu Leu Lys Lys Gly Gly Leu Lys Asp Glu Asn Ile Ile
                85                  90                  95

Val Phe Met Tyr Asp Asp Ile Ser Phe Asn Glu Glu Asn Pro Arg Pro
                100                 105                 110

Gly Ile Ile Ile Asn Ser Pro His Gly Glu Asp Val Tyr Glu Gly Val
                115                 120                 125

Pro Lys Asp Tyr Thr Gly Glu Asp Val Thr Val Asp Asn Phe Phe Ala
            130                 135                 140

Val Ile Leu Gly Asn Lys Thr Ala Leu Ser Gly Gly Ser Gly Lys Val
145                 150                 155                 160

Leu Asp Ser Gly Pro Asn Asp His Ile Phe Ile Tyr Tyr Ser Asp His
                165                 170                 175

Gly Gly Pro Gly Val Leu Gly Met Pro Thr Ser Pro Tyr Leu Tyr Ala
                180                 185                 190

Asn Asp Leu Ile Glu Val Leu Lys Lys Lys His Ala Ser Gly Thr Tyr
            195                 200                 205

Asn Ser Leu Val Phe Tyr Leu Glu Ala Cys Glu Ser Gly Ser Ile Phe
```

```
               210                 215                 220
Glu Gly Leu Leu Pro Glu Gly Leu Asn Ile Tyr Ala Thr Thr Ala Ala
225                 230                 235                 240

Asn Ala Glu Glu Ser Ser Trp Gly Thr Tyr Cys Pro Gly Glu Asp Pro
                245                 250                 255

Ser Pro Pro Glu Tyr Glu Thr Cys Leu Gly Asp Leu Tyr Ser Val
            260                 265                 270

Ala Trp Met Glu Asp Ser Asp Val His Asn Leu Arg Thr Glu Thr Leu
            275                 280                 285

Arg Gln Gln Tyr Glu Leu Val Lys Lys Arg Thr Ala Asn Asp Asn Ser
            290                 295                 300

Val Tyr Gly Ser His Val Met Gln Tyr Gly Asp Leu Gly Leu Asn Lys
305                 310                 315                 320

Glu Asp Leu Val Leu Tyr Met Gly Thr Asn Pro Ala Asn Asp Asn Tyr
                325                 330                 335

Thr Phe Val Asp Asn Asn Ser Leu Arg Leu Pro Ser Lys Ala Val Asn
                340                 345                 350

Gln Arg Asp Ala Asp Leu Val His Phe Trp Asp Lys Phe Arg Lys Ala
                355                 360                 365

Pro Glu Gly Ser Pro Arg Lys Ala Glu Ala Gln Lys Gln Phe Leu Glu
370                 375                 380

Ala Met Ser His Arg Thr His Ile Asp His Ala Ile Lys Leu Val Gly
385                 390                 395                 400

Arg Leu Leu Phe Gly Met Lys Lys Gly Ser Glu Val Leu Lys Thr Val
                405                 410                 415

Arg Pro Ala Gly Gln Pro Leu Val Asp Asp Trp His Cys Leu Lys Thr
                420                 425                 430

Leu Val Arg Thr Phe Glu Ala His Cys Gly Ser Leu Ser Gln Tyr Gly
                435                 440                 445

Met Lys His Met Arg Ser Ile Ala Asn Ile Cys Asn Ala Gly Ile Glu
                450                 455                 460

Lys Glu Gln Met Ala Glu Ala Ser Ala Gln Ala Cys Val Thr Ile Pro
465                 470                 475                 480

Pro Gly Pro Trp Ser Ser Leu Asp Lys Gly Phe Ser Ala
                485                 490

<210> SEQ ID NO 28
<211> LENGTH: 484
<212> TYPE: PRT
<213> ORGANISM: Phaseolus vulgaris

<400> SEQUENCE: 28

Met Ala Thr Thr Thr Ala Thr Thr Ser Leu Leu Ala Leu Leu Leu Leu
1               5                   10                  15

Phe Leu Val Ala Leu Val Ser Ala Gly Arg Asp Leu Val Gly Asp Phe
                20                  25                  30

Leu Arg Leu Pro Ser Asp Ser Gly Asn Gly Asp Asn Val His Gly Thr
            35                  40                  45

Arg Trp Ala Ile Leu Phe Ala Gly Ser Ser Gly Tyr Trp Asn Tyr Arg
50                  55                  60

His Gln Ala Asp Ile Cys His Ala Tyr Gln Leu Leu Arg Lys Gly Gly
65                  70                  75                  80

Leu Lys Asp Glu Asn Ile Ile Val Phe Met Tyr Asp Asp Ile Ala Phe
                85                  90                  95
```

Asn Ser Glu Asn Pro Arg Arg Gly Val Ile Ile Asn Ser Pro Asn Gly
                100                 105                 110

Asp Asp Val Tyr Lys Gly Val Pro Lys Asp Tyr Thr Gly Glu Asp Val
            115                 120                 125

Thr Ala His Asn Phe Tyr Ala Ala Leu Leu Gly Asp Lys Ser Lys Leu
        130                 135                 140

Thr Gly Gly Ser Gly Lys Val Val Asn Ser Gly Pro Asn Asp His Ile
145                 150                 155                 160

Phe Ile Phe Tyr Ser Asp His Gly Gly Pro Gly Val Leu Gly Ser Pro
                165                 170                 175

Ala Gly Pro Tyr Ile Tyr Ala Ser Asp Leu Asn Glu Val Leu Lys Lys
            180                 185                 190

Lys His Ala Ser Gly Thr Tyr Lys Asn Leu Val Phe Tyr Leu Glu Ala
        195                 200                 205

Cys Glu Ser Gly Ser Ile Phe Glu Gly Leu Leu Pro Glu Asp Ile Asn
        210                 215                 220

Val Tyr Ala Thr Ala Ser Asn Ala Asp Glu Ser Ser Trp Gly Thr
225                 230                 235                 240

Tyr Cys Pro Gly Glu Asp Pro Ser Pro Pro Glu Tyr Ser Thr Cys
                245                 250                 255

Leu Gly Asp Leu Tyr Ser Val Ala Trp Met Glu Asp Ser Asp Arg His
            260                 265                 270

Asn Leu Arg Thr Glu Thr Leu His Gln Gln Tyr Lys Leu Val Lys Glu
        275                 280                 285

Arg Thr Ile Ser Gly Gly Leu Tyr Tyr Gly Ser His Val Met Gln Tyr
        290                 295                 300

Gly Asp Val Gly Leu Ser Lys Asp Ile Leu Phe His Tyr Leu Gly Thr
305                 310                 315                 320

Asp Pro Ala Asn Glu Asn Leu Thr Phe Val Asp Glu Asn Ser Leu Trp
                325                 330                 335

Ser Ser Ser Lys Ala Val Asn Gln Arg Asp Ala Asp Leu Val His Phe
            340                 345                 350

Trp Asp Lys Phe Arg Lys Ala Pro Glu Gly Ser Pro Lys Lys Asn Glu
        355                 360                 365

Ala Arg Lys Gln Val Leu Glu Val Met Ser His Arg Met His Ile Asp
        370                 375                 380

Asp Ser Val Glu Leu Val Gly Lys Leu Leu Phe Gly Ile Glu Lys Ala
385                 390                 395                 400

Pro Glu Leu Leu Asn Ala Val Arg Pro Ala Gly Ser Ala Leu Val Asp
                405                 410                 415

Asp Trp Asp Cys Leu Lys Thr Met Val Arg Thr Phe Glu Thr His Cys
            420                 425                 430

Gly Ser Leu Ser Gln Tyr Gly Met Lys His Met Arg Ser Phe Ala Asn
        435                 440                 445

Met Cys Asn Val Gly Ile Lys Lys Glu Gln Met Arg Glu Ala Ser Ala
        450                 455                 460

Gln Ala Cys Val Thr Ile Pro Ala Asn Pro Trp Ser Ser Leu Gln Arg
465                 470                 475                 480

Gly Phe Ser Ala

<210> SEQ ID NO 29
<211> LENGTH: 484
<212> TYPE: PRT
<213> ORGANISM: Phaseolus vulgaris

<400> SEQUENCE: 29

Met Ala Thr Thr Thr Ala Thr Thr Ser Leu Leu Ala Leu Leu Leu Leu
1               5                   10                  15

Phe Leu Val Ala Leu Val Ser Ala Gly Arg Asp Leu Val Gly Asp Phe
            20                  25                  30

Leu Arg Leu Pro Ser Asp Ser Gly Asn Gly Asp Asn Val His Gly Thr
        35                  40                  45

Arg Trp Ala Ile Leu Phe Ala Gly Ser Ser Gly Tyr Trp Asn Tyr Arg
    50                  55                  60

His Gln Ala Asp Ile Cys His Ala Tyr Gln Leu Leu Arg Lys Gly Gly
65                  70                  75                  80

Leu Lys Asp Glu Asn Ile Ile Val Phe Met Tyr Asp Asp Ile Ala Phe
                85                  90                  95

Asn Ser Glu Asn Pro Arg Arg Gly Val Ile Ile Asn Ser Pro Asn Gly
            100                 105                 110

Asp Glu Val Tyr Lys Gly Val Pro Lys Asp Tyr Thr Gly Glu Asp Val
        115                 120                 125

Thr Ala His Asn Phe Tyr Ala Ala Leu Leu Gly Asp Lys Ser Lys Leu
130                 135                 140

Thr Gly Gly Ser Gly Lys Val Val Asn Ser Gly Pro Asn Asp His Ile
145                 150                 155                 160

Phe Ile Phe Tyr Ser Asp His Gly Gly Pro Gly Val Leu Gly Ser Pro
                165                 170                 175

Ala Gly Pro Tyr Ile Tyr Ala Ser Asp Leu Asn Glu Val Leu Lys Lys
            180                 185                 190

Lys His Ala Ser Gly Thr Tyr Lys Asn Leu Val Phe Tyr Leu Glu Ala
        195                 200                 205

Cys Glu Ser Gly Ser Ile Phe Glu Gly Leu Leu Pro Glu Asp Ile Asn
    210                 215                 220

Val Tyr Ala Thr Thr Ala Ser Asn Ala Asp Glu Ser Ser Trp Gly Thr
225                 230                 235                 240

Tyr Cys Pro Gly Glu Asp Pro Ser Pro Pro Glu Tyr Ser Thr Cys
                245                 250                 255

Leu Gly Asp Leu Tyr Ser Val Ala Trp Met Glu Asp Ser Asp Arg His
            260                 265                 270

Asn Leu Arg Thr Glu Thr Leu His Gln Gln Tyr Lys Leu Val Lys Glu
        275                 280                 285

Arg Thr Ile Ser Gly Gly Leu Tyr Tyr Gly Ser His Val Met Gln Tyr
    290                 295                 300

Gly Asp Val Gly Leu Ser Lys Asp Ile Leu Phe His Tyr Leu Gly Thr
305                 310                 315                 320

Asp Pro Ala Asn Glu Asn Leu Thr Phe Val Asp Glu Asn Ser Leu Trp
                325                 330                 335

Ser Ser Ser Lys Ala Val Asn Gln Arg Asp Ala Asp Leu Val His Phe
            340                 345                 350

Trp Asp Lys Phe Arg Lys Ala Pro Glu Gly Ser Pro Lys Lys Asn Glu
        355                 360                 365

Ala Arg Lys Gln Val Leu Glu Val Met Ser His Arg Met His Ile Asp
    370                 375                 380

Asp Ser Val Glu Leu Val Gly Lys Leu Leu Phe Gly Ile Glu Lys Ala
385                 390                 395                 400

Pro Glu Leu Leu Asn Ala Val Arg Pro Ala Gly Ser Ala Leu Val Asp

```
                405                 410                 415
Asp Trp Asp Cys Leu Lys Thr Met Val Arg Thr Phe Glu Thr His Cys
            420                 425                 430
Gly Ser Leu Ser Gln Tyr Gly Met Lys His Met Arg Ser Phe Ala Asn
            435                 440                 445
Met Cys Asn Val Gly Ile Lys Lys Glu Gln Met Arg Glu Ala Ser Ala
            450                 455                 460
Gln Ala Cys Val Thr Ile Pro Ala Asn Pro Trp Ser Ser Leu Gln Arg
465                 470                 475                 480
Gly Phe Ser Ala

<210> SEQ ID NO 30
<211> LENGTH: 493
<212> TYPE: PRT
<213> ORGANISM: Vitis vinifera

<400> SEQUENCE: 30

Met Thr Ile Phe Pro Ala Ala Val Ala Ala Leu Leu Ala Leu Ser Thr
1                   5                   10                  15
Leu Val Ala Gly Gly Arg His Phe Ala Gly Asp Asn Gly Leu Leu Leu
            20                  25                  30
Pro Ser Glu Ala Ser Arg Phe Phe Arg Pro Gly Gly Ala Ala Asp Asp
            35                  40                  45
Asp Thr Gly Gly Glu Ser Ala Gly Thr Arg Trp Ala Val Leu Ile Ala
        50                  55                  60
Gly Ser Asn Gly Tyr Trp Asn Tyr Arg His Gln Ala Asp Ile Cys His
65                  70                  75                  80
Ala Tyr Gln Leu Leu Lys Lys Gly Gly Leu Lys Asp Glu Asn Ile Ile
                85                  90                  95
Val Phe Met Tyr Asp Asp Ile Ser Phe Asn Glu Glu Asn Pro Arg Pro
            100                 105                 110
Gly Ile Ile Ile Asn Ser Pro His Gly Glu Asp Val Tyr Glu Gly Val
            115                 120                 125
Pro Lys Asp Tyr Thr Gly Glu Asp Val Thr Val Asp Asn Phe Phe Ala
        130                 135                 140
Val Ile Leu Gly Asn Lys Thr Ala Leu Ser Gly Gly Ser Gly Lys Val
145                 150                 155                 160
Leu Asp Ser Gly Pro Asn Asp His Ile Phe Ile Tyr Tyr Ser Asp His
                165                 170                 175
Gly Gly Pro Gly Val Leu Gly Met Pro Thr Ser Pro Tyr Leu Tyr Ala
            180                 185                 190
Asn Asp Leu Ile Glu Val Leu Lys Lys His Ala Ser Gly Thr Tyr
            195                 200                 205
Asn Ser Leu Val Phe Tyr Leu Glu Ala Cys Glu Ser Gly Ser Ile Phe
        210                 215                 220
Glu Gly Leu Leu Pro Glu Gly Leu Asn Ile Tyr Ala Thr Thr Ala Ala
225                 230                 235                 240
Asn Ala Glu Glu Ser Ser Trp Gly Thr Tyr Cys Pro Gly Glu Asp Pro
                245                 250                 255
Ser Pro Pro Pro Glu Tyr Glu Thr Cys Leu Gly Asp Leu Tyr Ser Val
            260                 265                 270
Ala Trp Met Glu Asp Ser Asp Val His Asn Leu Arg Thr Glu Thr Leu
            275                 280                 285
Arg Gln Gln Tyr Glu Leu Val Lys Lys Arg Thr Ala Asn Asp Asn Ser
```

```
                290                 295                 300
Val Tyr Gly Ser His Val Met Gln Tyr Gly Asp Leu Gly Leu Asn Lys
305                 310                 315                 320

Glu Asp Leu Val Leu Tyr Met Gly Thr Asn Pro Ala Asn Asp Asn Tyr
                325                 330                 335

Thr Phe Val Asp Asn Asn Ser Leu Arg Leu Pro Ser Lys Ala Val Asn
                340                 345                 350

Gln Arg Asp Ala Asp Leu Val His Phe Trp Asp Lys Phe Arg Lys Ala
                355                 360                 365

Pro Glu Gly Ser Pro Arg Lys Ala Glu Ala Gln Lys Gln Phe Leu Glu
                370                 375                 380

Ala Met Ser His Arg Thr His Ile Asp His Ala Ile Lys Leu Val Gly
385                 390                 395                 400

Arg Leu Leu Phe Gly Met Lys Lys Gly Ser Glu Val Leu Lys Thr Val
                405                 410                 415

Arg Pro Ala Gly Gln Pro Leu Val Asp Asp Trp His Cys Leu Lys Thr
                420                 425                 430

Leu Val Arg Thr Phe Glu Ala His Cys Gly Ser Leu Ser Gln Tyr Gly
                435                 440                 445

Met Lys His Met Arg Ser Ile Ala Asn Ile Cys Asn Ala Gly Ile Glu
                450                 455                 460

Lys Glu Gln Met Ala Glu Ala Ser Ala Gln Ala Cys Val Thr Ile Pro
465                 470                 475                 480

Pro Gly Pro Trp Ser Ser Leu Asp Lys Gly Phe Ser Ala
                485                 490

<210> SEQ ID NO 31
<211> LENGTH: 493
<212> TYPE: PRT
<213> ORGANISM: Cucumis sativus

<400> SEQUENCE: 31

Met Ala Arg Ile Pro Thr Gly Val Leu Leu Ser Leu Leu Phe Leu Ala
1               5                   10                  15

Val Ile Gly Leu Pro Ala Gly Ala Arg Asp Leu Pro Gly Asp Phe Leu
                20                  25                  30

Arg Leu Pro Ser Glu Ala Leu Lys Phe Phe Arg Gly Gly Ala Ser Asp
                35                  40                  45

Ala Ser Asp Glu Asp Ser Val Gly Thr Arg Trp Ala Val Leu Ile Ala
50                  55                  60

Gly Ser Asn Gly Tyr Trp Asn Tyr Arg His Gln Ala Asp Ile Cys His
65                  70                  75                  80

Ala Tyr Gln Leu Leu Arg Lys Asn Gly Leu Lys Asp Glu Asn Ile Ile
                85                  90                  95

Val Phe Met Tyr Asp Asp Ile Ala Phe Asn Pro Glu Asn Pro Arg Pro
                100                 105                 110

Gly Val Ile Ile Asn His Pro Lys Gly Ser Asp Val Tyr His Gly Val
                115                 120                 125

Pro Lys Asp Tyr Thr Gly Glu Asp Val Thr Val Asn Asn Phe Phe Ala
                130                 135                 140

Ala Ile Leu Gly Asn Lys Thr Ala Leu Thr Gly Gly Ser Gly Lys Val
145                 150                 155                 160

Val Asp Ser Gly Pro Asn Asp His Ile Phe Ile Tyr Tyr Ser Asp His
                165                 170                 175
```

```
Gly Gly Pro Gly Val Leu Gly Met Pro Thr Tyr Pro Tyr Met Tyr Ala
            180                 185                 190

Asp Asp Leu Asn Lys Val Leu Lys Lys His Ala Ala Gly Ser Tyr
        195                 200                 205

Lys Ser Leu Val Phe Tyr Leu Glu Ala Cys Glu Ser Gly Ser Ile Phe
    210                 215                 220

Glu Gly Leu Leu Pro Glu Gly Leu Asn Ile Tyr Thr Thr Thr Ala Ser
225                 230                 235                 240

Asn Ala Tyr Glu Ser Ser Trp Gly Thr Tyr Cys Pro Gly Asp Tyr Pro
            245                 250                 255

Ser Pro Pro Pro Glu Tyr Asp Thr Cys Leu Gly Asp Leu Tyr Ser Val
            260                 265                 270

Ala Trp Leu Glu Asp Ser Asp Asn His Asn Leu Lys Thr Glu Ser Leu
        275                 280                 285

Arg Gln Gln Tyr Glu Leu Val Lys Lys Arg Thr Ile Ser Gly Gln Tyr
    290                 295                 300

Ala Tyr Gly Ser His Val Met Gln Tyr Gly Asp Leu Met Leu Asn Lys
305                 310                 315                 320

Asn Ala Leu Phe Ser Tyr Leu Gly Thr Asp Pro Ala Asn Glu Asn Asn
            325                 330                 335

Thr Phe Val Glu Glu Asn Ser Leu Arg Pro Ala Thr Lys Phe Thr Asn
            340                 345                 350

Gln Arg Asp Ala Asp Leu Val His Phe Trp Glu Lys Phe Arg Lys Ala
        355                 360                 365

Pro Glu Gly Ser Leu Thr Lys Val Glu Ala Gln Lys Lys Phe Val Glu
    370                 375                 380

Ala Met Ser His Arg Ala His Ile Asp Asn Ser Val Lys Leu Val Gly
385                 390                 395                 400

Lys Leu Leu Phe Gly Ile Lys Glu Gly Pro Glu Val Leu Glu Ala Ile
            405                 410                 415

Arg Pro Ala Gly Arg Pro Leu Val Asp Asp Trp Asn Cys Leu Arg Asn
            420                 425                 430

Met Val Arg Ser Phe Glu Ala Arg Cys Gly Ser Leu Ser Gln Tyr Gly
        435                 440                 445

Met Lys His Met Arg Ser Phe Ala Asn Leu Cys Asn Ala Gly Ile Ser
    450                 455                 460

Lys Glu Gln Met Ala Glu Ala Ser Ala Gln Ala Cys Met Ser Val Pro
465                 470                 475                 480

Pro Gly Pro Trp Ser Ser Leu Leu Lys Gly Phe Thr Ala
            485                 490

<210> SEQ ID NO 32
<211> LENGTH: 493
<212> TYPE: PRT
<213> ORGANISM: Cucumis sativus

<400> SEQUENCE: 32

Met Ala Arg Ile Pro Thr Gly Val Leu Leu Ser Leu Leu Phe Leu Ala
1               5                  10                  15

Val Ile Gly Leu Pro Ala Gly Ala Arg Asp Leu Pro Gly Asp Phe Leu
            20                  25                  30

Arg Leu Pro Ser Glu Ala Leu Lys Phe Phe Arg Gly Gly Ala Ser Asp
        35                  40                  45

Ala Ser Asp Glu Asp Ser Val Gly Thr Arg Trp Ala Val Leu Ile Ala
    50                  55                  60
```

```
Gly Ser Asn Gly Tyr Trp Asn Tyr Arg His Gln Ala Asp Ile Cys His
65                  70                  75                  80

Ala Tyr Gln Leu Leu Arg Lys Asn Gly Leu Lys Asp Glu Asn Ile Ile
                85                  90                  95

Val Phe Met Tyr Asp Asp Ile Ala Phe Asn Pro Glu Asn Pro Arg Pro
            100                 105                 110

Gly Val Ile Ile Asn His Pro Lys Gly Ser Asp Val Tyr His Gly Val
        115                 120                 125

Pro Lys Asp Tyr Thr Gly Glu Asp Val Thr Val Asn Asn Phe Phe Ala
    130                 135                 140

Ala Ile Leu Gly Asn Lys Thr Ala Leu Thr Gly Gly Ser Gly Lys Val
145                 150                 155                 160

Val Asp Ser Gly Pro Asn Asp His Ile Phe Ile Tyr Tyr Ser Asp His
                165                 170                 175

Gly Gly Pro Gly Val Leu Gly Met Pro Thr Tyr Pro Tyr Met Tyr Ala
            180                 185                 190

Asp Asp Leu Asn Lys Val Leu Lys Lys His Ala Ala Gly Ser Tyr
        195                 200                 205

Lys Ser Leu Val Phe Tyr Leu Glu Ala Cys Glu Ser Gly Ser Ile Phe
    210                 215                 220

Glu Gly Leu Leu Pro Glu Gly Leu Asn Ile Tyr Thr Thr Thr Ala Ser
225                 230                 235                 240

Asn Ala Tyr Glu Ser Ser Trp Gly Thr Tyr Cys Pro Gly Asp Tyr Pro
                245                 250                 255

Ser Pro Pro Pro Glu Tyr Asp Thr Cys Leu Gly Asp Leu Tyr Ser Val
            260                 265                 270

Ala Trp Leu Glu Asp Ser Asp Asn His Asn Leu Lys Thr Glu Ser Leu
        275                 280                 285

Arg Gln Gln Tyr Glu Leu Val Lys Lys Arg Thr Leu Ser Gly Gln Tyr
    290                 295                 300

Ala Tyr Gly Ser His Val Met Gln Tyr Gly Asp Leu Met Leu Asn Lys
305                 310                 315                 320

Asn Ala Leu Phe Ser Tyr Leu Gly Thr Asp Pro Ala Asn Glu Asn Asn
                325                 330                 335

Thr Phe Val Glu Glu Asn Ser Leu Arg Pro Ala Thr Lys Phe Thr Asn
            340                 345                 350

Gln Arg Asp Ala Asp Leu Val His Phe Trp Glu Lys Phe Arg Lys Ala
        355                 360                 365

Pro Glu Gly Ser Leu Thr Lys Val Glu Ala Gln Lys Lys Phe Val Glu
    370                 375                 380

Ala Met Ser His Arg Ala His Ile Asp Asn Ser Val Lys Leu Val Gly
385                 390                 395                 400

Lys Leu Leu Phe Gly Ile Lys Glu Gly Pro Glu Val Leu Glu Ala Ile
                405                 410                 415

Arg Pro Ala Gly Arg Pro Leu Val Asp Asp Trp Asn Cys Leu Arg Asn
            420                 425                 430

Met Val Arg Ser Phe Glu Ala Arg Cys Gly Ser Leu Ser Gln Tyr Gly
        435                 440                 445

Met Lys His Met Arg Ser Phe Ala Asn Leu Cys Asn Ala Gly Ile Ser
    450                 455                 460

Lys Glu Gln Met Ala Glu Ala Ser Ala Gln Ala Cys Met Ser Val Pro
465                 470                 475                 480
```

Pro Gly Pro Trp Ser Ser Leu Leu Lys Gly Phe Thr Ala
                485                 490

<210> SEQ ID NO 33
<211> LENGTH: 493
<212> TYPE: PRT
<213> ORGANISM: Vicia sativa

<400> SEQUENCE: 33

Met Gly Ser Ser Gln Leu Ser Thr Leu Leu Phe Phe Thr Ile Val Val
1               5                   10                  15

Thr Phe Leu Thr Val Val Ser Ser Gly Arg Asp Leu Pro Gly Asp Tyr
            20                  25                  30

Leu Arg Leu Pro Ser Glu Thr Ser Arg Phe Arg Glu Pro Lys Asn
        35                  40                  45

Asp Asp Asp Phe Glu Gly Thr Arg Trp Ala Ile Leu Leu Ala Gly Ser
    50                  55                  60

Asn Gly Tyr Trp Asn Tyr Arg His Gln Ser Asp Val Cys His Ala Tyr
65                  70                  75                  80

Gln Leu Leu Arg Lys Gly Gly Ser Lys Glu Glu Asn Ile Ile Val Phe
                85                  90                  95

Met Tyr Asp Asp Ile Ala Ser Asn Glu Glu Asn Pro Arg Pro Gly Val
            100                 105                 110

Ile Ile Asn Lys Pro Asp Gly Asp Val Tyr Ala Gly Val Pro Lys
        115                 120                 125

Asp Tyr Thr Gly Ala Glu Val His Ala Asp Asn Phe Tyr Ala Ala Leu
    130                 135                 140

Leu Gly Asn Lys Ser Ala Leu Thr Gly Gly Ser Gly Lys Val Val Asp
145                 150                 155                 160

Ser Gly Pro Asn Asp His Ile Phe Val Tyr Tyr Thr Asp His Gly Gly
                165                 170                 175

Pro Gly Val Leu Gly Met Pro Val Gly Pro Tyr Leu Tyr Ala Ser Asp
            180                 185                 190

Leu Asn Glu Val Leu Lys Lys Lys His Ala Ser Gly Thr Tyr Lys Ser
        195                 200                 205

Leu Val Phe Tyr Leu Glu Ala Cys Glu Ser Gly Ser Ile Phe Glu Gly
    210                 215                 220

Leu Leu Pro Asp Asp Leu Asn Ile Tyr Ala Thr Thr Ala Ser Asn Ala
225                 230                 235                 240

Glu Glu Ser Ser Trp Gly Tyr Tyr Cys Pro Gly Asp Lys Pro Pro Pro
                245                 250                 255

Pro Pro Glu Tyr Ser Thr Cys Leu Gly Asp Leu Tyr Ser Ile Ala Trp
            260                 265                 270

Met Glu Asp Ser Glu Val His Asn Leu Gln Thr Glu Ser Leu Gln Gln
        275                 280                 285

Gln Tyr Lys Leu Val Lys Asn Arg Thr Ile Ser Glu Pro Tyr Gly Ser
    290                 295                 300

His Val Met Glu Tyr Gly Asp Ile Gly Leu Ser Lys Asn Asp Leu Tyr
305                 310                 315                 320

Gln Tyr Leu Gly Thr Asn Pro Ala Asn Asp Asn Asn Ser Phe Val Asp
                325                 330                 335

Glu Thr Glu Asn Ser Leu Lys Leu Arg Thr Pro Ser Ala Ala Val Asn
            340                 345                 350

Gln Arg Asp Ala Asp Leu Ile His Phe Trp Glu Lys Phe Arg Lys Ala
        355                 360                 365

```
Pro Glu Gly Ser Ser Gln Lys Asn Glu Ala Glu Lys Gln Val Leu Glu
        370                 375                 380

Ala Met Ser His Arg Lys His Ile Asp Asn Ser Val Lys Leu Ile Gly
385                 390                 395                 400

Gln Leu Leu Phe Gly Ile Glu Lys Gly Thr Glu Leu Leu Asp Val Val
                405                 410                 415

Arg Pro Ala Gly Ser Pro Leu Val Asp Asn Trp Asp Cys Leu Lys Thr
                420                 425                 430

Met Val Lys Thr Phe Glu Thr His Cys Gly Ser Leu Ser Gln Tyr Gly
            435                 440                 445

Met Lys His Met Arg Ser Phe Ala Asn Ile Cys Asn Ala Gly Ile Pro
        450                 455                 460

Asn Glu Pro Met Ala Glu Ala Ser Ala Gln Ala Cys Ala Ser Ile Pro
465                 470                 475                 480

Ala Asn Pro Trp Ser Ser Leu Gln Gly Gly Phe Ser Ala
                485                 490

<210> SEQ ID NO 34
<211> LENGTH: 493
<212> TYPE: PRT
<213> ORGANISM: Medicago truncatula

<400> SEQUENCE: 34

Met Asp Phe Ser Gln Phe Ser Thr Ile Leu Phe Leu Thr Val Ile Leu
1               5                   10                  15

Thr Ile Phe Ala Ala Val Ser Gly Ser Arg Asp Leu Pro Gly Asp Tyr
                20                  25                  30

Ile Arg Leu Pro Ser Gln Ser Gln Ala Ser Arg Phe Phe His Glu Pro
            35                  40                  45

Glu Asn Asp Asp Asn Asp Gln Gly Thr Arg Trp Ala Ile Leu Leu Ala
50                  55                  60

Gly Ser Asn Gly Tyr Trp Asn Tyr Arg His Gln Ala Asp Val Cys His
65                  70                  75                  80

Ala Tyr Gln Leu Leu Arg Lys Gly Gly Leu Lys Glu Glu Asn Ile Ile
                85                  90                  95

Val Phe Met Tyr Asp Asp Ile Ala Ser Asn Val Glu Asn Pro Arg Pro
                100                 105                 110

Gly Val Ile Ile Asn Lys Pro Asp Gly Asp Val Tyr Glu Gly Val
            115                 120                 125

Pro Lys Asp Tyr Thr Gly Ala Glu Val His Ala Asp Asn Phe Tyr Ala
        130                 135                 140

Ala Leu Leu Gly Asn Lys Ser Ala Leu Thr Gly Gly Ser Gly Lys Val
145                 150                 155                 160

Val Asp Ser Gly Pro Asn Asp His Ile Phe Val Tyr Tyr Thr Asp His
                165                 170                 175

Gly Gly Pro Gly Val Leu Gly Met Pro Val Gly Pro Tyr Leu Tyr Ala
            180                 185                 190

Ser Asp Leu Asn Glu Val Leu Lys Lys Lys His Ala Ser Gly Ser Tyr
        195                 200                 205

Lys Ser Leu Val Phe Tyr Leu Glu Ala Cys Glu Ser Gly Ser Ile Phe
    210                 215                 220

Glu Gly Leu Leu Pro Glu Asp Ile Asn Ile Tyr Ala Thr Thr Ala Ser
225                 230                 235                 240

Asn Ala Val Glu Ser Ser Trp Gly Thr Tyr Cys Pro Gly Glu Tyr Pro
```

```
            245                 250                 255
Pro Pro Pro Pro Glu Tyr Ser Thr Cys Leu Gly Asp Leu Tyr Ser Ile
            260                 265                 270

Ala Trp Met Glu Asp Ser Asp Ile His Asn Leu Arg Thr Glu Ser Leu
        275                 280                 285

His Gln Gln Tyr Lys Leu Val Lys Asp Arg Thr Ile Asn Gly Tyr Tyr
    290                 295                 300

Gly Ser His Val Met Glu Tyr Gly Asp Val Gly Leu Ser Asn Asn His
305                 310                 315                 320

Leu Phe Leu Tyr Leu Gly Thr Asn Pro Ala Asn Asp Asn Ile Ser Phe
                325                 330                 335

Val Asp Glu Ser Ser Leu Lys Leu Arg Ser Pro Ser Thr Ala Val Asn
            340                 345                 350

Gln Arg Asp Ala Asp Leu Ile His Phe Trp Asp Lys Phe Arg Lys Ala
        355                 360                 365

Pro Glu Gly Ser Leu Arg Lys Asn Glu Ala Gln Lys Glu Val Leu Glu
    370                 375                 380

Ala Met Ser His Arg Met His Val Asp Asn Ser Ala Lys Leu Ile Gly
385                 390                 395                 400

Lys Leu Leu Phe Gly Ile Glu Lys Gly Thr Glu Leu Leu Gly Asn Val
                405                 410                 415

Arg Pro Ala Gly Ser Pro Leu Val Asp Asn Trp Asp Cys Leu Lys Thr
            420                 425                 430

Met Val Lys Thr Phe Glu Thr His Cys Gly Ser Leu Ser Gln Tyr Gly
        435                 440                 445

Met Lys His Met Arg Ser Phe Ala Asn Ile Cys Asn Ala Gly Ile Gln
    450                 455                 460

Thr Glu Gln Met Ala Glu Ala Ser Ala Gln Ala Cys Ala Ser Ile Pro
465                 470                 475                 480

Ala Asn Pro Trp Ser Ser Leu Gln Arg Gly Phe Ser Ala
                485                 490

<210> SEQ ID NO 35
<211> LENGTH: 494
<212> TYPE: PRT
<213> ORGANISM: Fragaria vesca subsp. vesca

<400> SEQUENCE: 35

Met Thr Arg Leu Ala Ala Val Val Ala Val Val Leu Phe Phe Leu Val
1               5                   10                  15

Ser Leu Phe Ser Ser Thr Ser Ala Arg Asp Leu Pro Gly Asp Val
            20                  25                  30

Leu Arg Leu Pro Ser Glu Thr Ser Arg Phe Phe Arg Ala Gly Asp Asp
        35                  40                  45

Gln Gln Asp Asp Gly Thr Val Gly Thr Arg Trp Ala Val Leu Ile Ala
    50                  55                  60

Gly Ser Asn Gly Tyr Trp Asn Tyr Arg His Gln Ala Asp Ile Cys His
65                  70                  75                  80

Ala Tyr Gln Leu Leu Lys Lys Gly Gly Leu Lys Asp Glu Asn Ile Val
                85                  90                  95

Val Phe Met Tyr Asp Asp Ile Ala Tyr Asn Glu Glu Asn Pro Arg Gln
            100                 105                 110

Gly Val Ile Ile Asn Ser Pro His Gly Asp Asp Val Tyr Lys Gly Val
        115                 120                 125
```

```
Pro Lys Asp Tyr Thr Gly Glu Asp Val Thr Val Gly Asn Phe Phe Ala
    130                 135                 140

Ala Ile Leu Gly Asn Lys Thr Ala Ile Ser Gly Gly Ser Gly Lys Val
145                 150                 155                 160

Val Asp Ser Gly Pro Asn Asp His Ile Phe Ile Tyr Tyr Ser Asp His
                165                 170                 175

Gly Gly Pro Gly Val Leu Gly Met Pro Thr Ser Pro Tyr Ile Tyr Ala
            180                 185                 190

Asp Arg Leu Ile Glu Val Leu Lys Lys His Ala Ala Gly Thr Tyr
                195                 200                 205

Glu Ser Leu Val Phe Tyr Leu Glu Ala Cys Glu Ser Gly Ser Ile Phe
    210                 215                 220

Glu Gly Leu Leu Pro Glu Gly Leu Asn Ile Phe Ala Thr Thr Ala Ser
225                 230                 235                 240

Asn Ala Glu Glu Ser Ser Trp Gly Thr Tyr Cys Pro Gly Glu Tyr Pro
                245                 250                 255

Ser Pro Pro Pro Glu Tyr Glu Thr Cys Leu Gly Asp Leu Tyr Ser Val
            260                 265                 270

Ala Trp Met Glu Asp Ser Asp Ile His Asn Leu Arg Ser Glu Thr Leu
                275                 280                 285

His Gln Gln Tyr Glu Leu Val Lys Ser Arg Thr Ala Ser Asp Asn Ser
    290                 295                 300

Pro Tyr Gly Ser His Val Met Gln Tyr Gly Asp Ile Pro Leu Ser Lys
305                 310                 315                 320

Asn Asn Leu Phe Met Tyr Met Gly Thr Asn Pro Ala Asn Asp Asn Tyr
                325                 330                 335

Thr Phe Met Pro Gln Asn Phe Leu Arg Pro Ser Ser Ser Lys Ala Val
            340                 345                 350

Asn Gln Arg Asp Ala Asp Leu Val His Phe Trp His Lys Tyr Arg Lys
                355                 360                 365

Ala Pro Glu Gly Ser Ala Arg Lys Ala Gln Ala Gln Lys Glu Phe Leu
    370                 375                 380

Glu Ala Met Ser His Arg Met His Ile Asp Glu Ser Val Lys Leu Ile
385                 390                 395                 400

Gly Lys Leu Leu Phe Gly Ile Lys Lys Gly Pro Glu Val Leu Ser Ala
                405                 410                 415

Val Arg Pro Ala Gly Gln Pro Leu Val Asp Asp Trp Asp Cys Leu Lys
            420                 425                 430

Thr Met Val Arg Ser Phe Glu Thr Tyr Cys Gly Ser Leu Ser Gln Tyr
                435                 440                 445

Gly Met Lys His Met Arg Ser Leu Ala Asn Ile Cys Asn Ala Gly Met
    450                 455                 460

Thr Lys Glu Gln Met Ala Glu Ala Ser Ala Gln Ala Cys Val Asn Val
465                 470                 475                 480

Pro Ser Gly Arg Trp Ser Ser Leu His Arg Gly Phe Ser Ala
            485                 490

<210> SEQ ID NO 36
<211> LENGTH: 482
<212> TYPE: PRT
<213> ORGANISM: Solanum tuberosum

<400> SEQUENCE: 36

Met Asn Arg Ser Ile Ala Gly Val Leu Phe Leu Ile Ala Leu Ser Leu
1               5                   10                  15
```

Asn Val Ser Val Ser Glu Ser Arg Asn Phe Leu Lys Leu Pro Ser Glu
            20                  25                  30

Gly Ser Arg Phe Phe Asp Ala Asp Glu Asn Asp Ser Val Gly Thr Arg
        35                  40                  45

Trp Ala Ile Leu Leu Ala Gly Ser Asn Gly Tyr Trp Asn Tyr Arg His
 50                  55                  60

Gln Ala Asp Ile Cys His Ala Tyr Gln Leu Leu Lys Lys Gly Leu
 65                  70                  75                  80

Lys Asp Glu Asn Ile Val Val Phe Met Tyr Asp Ile Ala Asn Asn
                 85                  90                  95

Glu Glu Asn Pro Arg Gln Gly Val Ile Ile Asn Ser Pro His Gly Glu
            100                 105                 110

Asp Val Tyr Lys Gly Val Pro Lys Asp Tyr Thr Gly Asp Asp Val Thr
            115                 120                 125

Val Asn Asn Phe Leu Ala Ala Leu Leu Gly Asn Lys Thr Ala Ile Thr
 130                 135                 140

Gly Gly Ser Gly Lys Val Val Asp Ser Gly Pro Asn Asp His Ile Phe
145                 150                 155                 160

Ile Phe Tyr Ser Asp His Gly Ala Gly Val Ile Gly Met Pro Thr
                 165                 170                 175

Asp Pro Tyr Leu Tyr Ala Asn Asp Leu Ile Asp Ala Leu Lys Lys Lys
            180                 185                 190

His Ala Ser Gly Thr Tyr Lys Ser Leu Val Phe Tyr Leu Glu Ala Cys
            195                 200                 205

Glu Ser Gly Ser Met Phe Glu Gly Leu Leu Pro Glu Gly Leu Asn Ile
            210                 215                 220

Tyr Ala Thr Thr Ala Ser Asn Ala Asp Glu Ser Ser Trp Gly Thr Tyr
225                 230                 235                 240

Cys Pro Gly Glu Phe Pro Ser Pro Ile Glu Tyr Gly Thr Cys Leu
                 245                 250                 255

Gly Asp Leu Tyr Ser Ile Ser Trp Met Glu Asp Ser Glu Arg His Asn
            260                 265                 270

Leu Arg Thr Glu Thr Leu Lys Gln Gln Tyr His Leu Val Lys Glu Arg
            275                 280                 285

Thr Ala Ser Gly Asn Pro Ala Tyr Gly Ser His Val Met Gln Tyr Gly
            290                 295                 300

Asp Val His Leu Ser Lys Asp Val Leu Phe Leu Tyr Met Gly Thr Asp
305                 310                 315                 320

Pro Ala Asn Asp Asn Ser Thr Phe Met Asp Asp Asn Ser Met Arg Val
                 325                 330                 335

Ser Lys Ala Val Asn Gln Arg Asp Ala Asp Leu Val His Phe Trp Tyr
            340                 345                 350

Lys Phe His Lys Ala Pro Glu Gly Ser Val Arg Lys Thr Glu Ala Gln
            355                 360                 365

Lys Gln Leu Asn Glu Ala Ile Ser His Arg Met His Leu Asp Asn Ser
            370                 375                 380

Ile Ala Leu Val Gly Lys Leu Phe Gly Ile Lys Lys Gly Pro Glu
385                 390                 395                 400

Val Leu Thr Ser Val Arg Pro Ala Gly Gln Pro Leu Val Asp Asp Trp
                 405                 410                 415

Asp Cys Leu Lys Ser Tyr Val Arg Thr Phe Glu Thr His Cys Gly Ser
            420                 425                 430

-continued

```
Leu Ser Gln Tyr Gly Met Lys His Met Arg Ser Val Ala Asn Ile Cys
        435                 440                 445

Asn Ala Gly Ile Lys Met Glu Gln Met Val Glu Ala Ser Ala Gln Ala
450                 455                 460

Cys Pro Ser Val Pro Ser Asn Thr Trp Ser Ser Leu Gln Arg Gly Phe
465                 470                 475                 480

Ser Ala

<210> SEQ ID NO 37
<211> LENGTH: 482
<212> TYPE: PRT
<213> ORGANISM: Solanum tuberosum

<400> SEQUENCE: 37

Met Asn Arg Ser Ile Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
                20                  25                  30

Gly Ser Arg Phe Phe Asp Ala Asp Glu Asn Asp Ser Val Gly Thr Arg
            35                  40                  45

Trp Ala Ile Leu Leu Ala Gly Ser Asn Gly Tyr Trp Asn Tyr Arg His
        50                  55                  60

Gln Ala Asp Ile Cys His Ala Tyr Gln Leu Leu Lys Lys Gly Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
            100                 105                 110

Asp Val Tyr Lys Gly Val Pro Lys Asp Tyr Thr Gly Asp Asp Val Thr
        115                 120                 125

Val Asn Asn Phe Leu Ala Ala Leu Leu Gly Asn Lys Thr Ala Ile Thr
130                 135                 140

Gly Gly Ser Gly Lys Val Val Asp Ser Gly Pro Asn Asp His Ile Phe
145                 150                 155                 160

Ile Phe Tyr Ser Asp His Gly Gly Ala Gly Val Ile Gly Met Pro Thr
                165                 170                 175

Asp Pro Tyr Leu Tyr Ala Asn Asp Leu Ile Asp Ala Leu Lys Lys Lys
            180                 185                 190

His Ala Ser Gly Thr Tyr Lys Ser Leu Val Phe Tyr Leu Glu Ala Cys
        195                 200                 205

Glu Ser Gly Ser Met Phe Glu Gly Leu Leu Pro Glu Gly Leu Asn Ile
210                 215                 220

Tyr Ala Thr Thr Ala Ser Asn Ala Asp Glu Ser Ser Trp Gly Thr Tyr
225                 230                 235                 240

Cys Pro Gly Glu Phe Pro Ser Pro Ile Glu Tyr Gly Thr Cys Leu
                245                 250                 255

Gly Asp Leu Tyr Ser Ile Ser Trp Met Glu Asp Ser Gly Arg His Asn
            260                 265                 270

Leu Arg Thr Glu Thr Leu Lys Gln Gln Tyr His Leu Val Lys Glu Arg
        275                 280                 285

Thr Ala Ser Gly Asn Pro Ala Tyr Gly Ser His Val Met Gln Tyr Gly
290                 295                 300

Asp Val His Leu Ser Lys Asp Val Leu Phe Leu Tyr Met Gly Thr Asp
305                 310                 315                 320
```

```
Pro Ala Asn Asp Asn Ser Thr Phe Met Asp Asp Asn Ser Met Arg Val
            325                 330                 335

Ser Lys Ala Val Asn Gln Arg Asp Ala Asp Leu Val His Phe Trp Tyr
        340                 345                 350

Lys Phe His Lys Ala Pro Glu Gly Ser Val Arg Lys Thr Glu Ala Gln
            355                 360                 365

Lys Gln Leu Asn Glu Ala Ile Ser His Arg Met His Leu Asp Asn Ser
        370                 375                 380

Ile Ala Leu Val Gly Lys Leu Leu Phe Gly Ile Lys Lys Gly Pro Glu
385                 390                 395                 400

Val Leu Thr Ser Val Arg Pro Ala Gly Gln Pro Leu Val Asp Asp Trp
            405                 410                 415

Asp Cys Leu Lys Ser Tyr Val Arg Thr Phe Glu Thr His Cys Gly Ser
        420                 425                 430

Leu Ser Gln Tyr Gly Met Lys His Met Arg Ser Val Ala Asn Ile Cys
            435                 440                 445

Asn Ala Gly Ile Lys Met Glu Gln Met Val Glu Ala Ser Ala Gln Ala
        450                 455                 460

Cys Pro Ser Val Pro Ser Asn Thr Trp Ser Ser Leu Gln Arg Gly Phe
465                 470                 475                 480

Ser Ala

<210> SEQ ID NO 38
<211> LENGTH: 454
<212> TYPE: PRT
<213> ORGANISM: Glycine max

<400> SEQUENCE: 38

Met Asp Arg Phe Pro Ile Leu Phe Leu Leu Ala Thr Leu Ile Thr Leu
1               5                   10                  15

Ala Ser Gly Ala Arg His Asp Ile Leu Arg Leu Pro Ser Glu Ala Ser
            20                  25                  30

Thr Phe Phe Lys Ala Pro Gly Gly Asp Gln Asn Asp Glu Gly Thr Arg
        35                  40                  45

Trp Ala Val Leu Ile Ala Gly Ser Asn Gly Tyr Trp Asn Tyr Arg His
    50                  55                  60

Gln Ser Asp Val Cys His Ala Tyr Gln Leu Leu Arg Lys Gly Gly Leu
65                  70                  75                  80

Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Ile Gly Glu Asp Val Thr
        115                 120                 125

Val Gly Asn Phe Phe Ala Ala Ile Leu Gly Asn Lys Ser Ala Leu Thr
    130                 135                 140

Gly Gly Ser Gly Lys Val Val Asp Ser Gly Pro Asn Asp His Ile Phe
145                 150                 155                 160

Ile Tyr Tyr Ser Asp His Gly Gly Pro Gly Val Leu Gly Met Pro Thr
                165                 170                 175

Asn Pro Tyr Met Tyr Ala Ser Asp Leu Ile Glu Val Leu Lys Lys Lys
            180                 185                 190

His Ala Ser Gly Ser Tyr Lys Ser Leu Val Phe Tyr Leu Glu Ala Cys
        195                 200                 205
```

```
Glu Ser Gly Ser Ile Phe Glu Gly Leu Leu Pro Glu Gly Leu Asn Ile
    210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Ser Glu Tyr Glu Thr Cys Leu
                245                 250                 255

Gly Asp Leu Tyr Ser Val Ala Trp Met Glu Asp Ser Asp Ile His Asn
                260                 265                 270

Leu Gln Thr Glu Thr Leu His Gln Gln Tyr Glu Leu Val Lys Gln Arg
            275                 280                 285

Thr Met Asn Gly Asn Ser Ile Tyr Gly Ser His Val Met Gln Tyr Gly
    290                 295                 300

Asp Ile Gly Leu Ser Glu Asn Asn Leu Val Leu Tyr Leu Asp Leu Ile
305                 310                 315                 320

His Phe Trp Asp Lys Phe Arg Lys Ala Pro Val Gly Ser Ser Arg Lys
                325                 330                 335

Ala Ala Ala Glu Lys Gln Ile Leu Glu Ala Met Ser His Arg Met His
                340                 345                 350

Ile Asp Asp Ser Met Lys Arg Ile Gly Lys Leu Phe Phe Gly Ile Glu
            355                 360                 365

Lys Gly Pro Glu Leu Leu Ser Ser Val Arg Pro Ala Gly Gln Pro Leu
    370                 375                 380

Val Asp Asp Trp Asp Cys Leu Lys Thr Leu Val Arg Thr Phe Glu Thr
385                 390                 395                 400

His Cys Gly Ser Leu Ser Gln Tyr Gly Met Lys His Met Arg Ser Phe
                405                 410                 415

Ala Asn Phe Cys Asn Ala Gly Ile Arg Lys Glu Gln Met Ala Glu Ala
                420                 425                 430

Ser Ala Gln Ala Cys Val Asn Ile Pro Ala Ser Ser Trp Ser Ser Met
            435                 440                 445

His Arg Gly Phe Ser Ala
    450

<210> SEQ ID NO 39
<211> LENGTH: 490
<212> TYPE: PRT
<213> ORGANISM: Papaver rhoeas

<400> SEQUENCE: 39

Met Val Lys Phe Leu Phe Ser Val Ile Leu Phe Phe Leu Leu Ser
1               5                   10                  15

Ala Val Gly Ser Ser Ala Arg Asn Ile Glu Glu Asp Gly Val Ile Arg
            20                  25                  30

Leu Pro Ser Glu Val Lys Asp Phe Ile Asn Gly Lys Asn Ile Asp Asp
        35                  40                  45

Asp Ser Val Gly Gly Thr Arg Trp Ala Val Leu Ile Ala Gly Ser Ser
    50                  55                  60

Gly Tyr Trp Asn Tyr Arg His Gln Ala Asp Val Cys His Ala Tyr Gln
65                  70                  75                  80

Val Leu Lys Arg Gly Gly Val Lys Asp Glu Asn Ile Val Val Phe Met
                85                  90                  95

Tyr Asp Asp Ile Ala Leu Asn Glu Glu Asn Pro Arg Pro Gly Val Ile
                100                 105                 110

Ile Asn His Pro Lys Gly Glu Asp Val Tyr Ala Gly Val Pro Lys Asp
            115                 120                 125
```

Tyr Thr Gly Arg Asp Val Thr Ala His Asn Phe Tyr Ser Val Leu Leu
            130                 135                 140

Gly Asn Lys Thr Ala Val Lys Gly Gly Ser Gly Lys Val Ile Asp Ser
145                 150                 155                 160

Gly Pro Asn Asp His Ile Phe Ile Tyr Tyr Ser Asp His Gly Gly Pro
                165                 170                 175

Gly Val Leu Gly Met Pro Thr Tyr Pro Tyr Leu Tyr Ala Asp Asp Leu
            180                 185                 190

Val Asn Val Leu Lys Gln Lys His Ala Leu Gly Ala Tyr Lys Ser Leu
        195                 200                 205

Val Phe Tyr Leu Glu Ala Cys Glu Ser Gly Ser Ile Phe Glu Gly Ile
    210                 215                 220

Leu Pro Lys Gly Leu Asn Ile Tyr Ala Thr Thr Ala Ser Asn Ala Glu
225                 230                 235                 240

Glu Ser Ser Trp Gly Thr Tyr Cys Pro Gly Glu Phe Pro Ser Pro Pro
                245                 250                 255

Ser Glu Tyr Glu Thr Cys Leu Gly Asp Leu Tyr Ser Val Ala Trp Met
            260                 265                 270

Glu Asp Ser Asp Val His Asn Leu Arg Ser Glu Thr Leu Lys Gln Gln
        275                 280                 285

Tyr His Leu Val Lys Glu Arg Thr Gln Asn Ala Asn Ser Ala Tyr Gly
    290                 295                 300

Ser His Val Met Gln Tyr Gly Asp Leu Glu Val Ser Lys Glu Asp Leu
305                 310                 315                 320

Phe Leu Tyr Met Gly Thr Asn Pro Ala Asn Asp Asn Asn Lys Phe Ile
                325                 330                 335

Glu Gln Asn Ser Leu Pro Ser Leu Ser Gly Ser Val Asn Gln Arg Glu
            340                 345                 350

Ala Asp Leu Ile His Phe Trp Gln Lys Tyr Arg Lys Ala Pro Glu Gly
        355                 360                 365

Ser Gln Arg Lys Ala Asp Ala Gln Lys Gln Phe Val Glu Val Met Ala
    370                 375                 380

His Arg Met His Val Asp His Ser Ile Lys Leu Ile Gly Lys Leu Leu
385                 390                 395                 400

Phe Gly Phe Glu Lys Gly Pro Gln Val Leu Glu Ala Val Arg Pro Ala
                405                 410                 415

Gly Gln Pro Leu Val Asp Asp Trp Asp Cys Leu Lys Thr Met Val Arg
            420                 425                 430

Thr Phe Glu Ala Gln Cys Gly Ser Leu Ser Gln Tyr Gly Met Lys His
        435                 440                 445

Met Arg Ser Val Ala Asn Ile Cys Asn Ala Gly Ile Lys Lys Glu Gln
    450                 455                 460

Met Ala Glu Ala Ala Ser Gln Ala Cys Val Thr Ile Pro Asn Gly Ser
465                 470                 475                 480

Trp Ser Ser Thr His Gln Gly Phe Ser Ala
                485                 490

<210> SEQ ID NO 40
<211> LENGTH: 483
<212> TYPE: PRT
<213> ORGANISM: Vigna radiata

<400> SEQUENCE: 40

Met Ala Thr Thr Thr Thr Ser Leu Ser Thr Leu Phe Leu Leu Phe Leu

-continued

```
1               5                   10                  15
Ala Thr Val Ala Leu Val Ala Ala Gly Arg Asp Leu Val Gly Asp Phe
                20                  25                  30

Leu Arg Leu Pro Ser Asp Ser Gly Asn Asp Asp Asn Val Lys Gly Thr
                35                  40                  45

Arg Trp Ala Ile Leu Phe Ala Gly Ser Asn Gly Tyr Trp Asn Tyr Arg
                50                  55                  60

His Gln Ala Asp Ile Cys His Ala Tyr Gln Ile Leu Arg Lys Gly Gly
 65                  70                  75                  80

Leu Lys Glu Glu Asn Ile Ile Val Phe Met Tyr Asp Asp Ile Ala Phe
                85                  90                  95

Asn Trp Asp Asn Pro Arg Pro Gly Val Ile Ile Asn Lys Pro Asp Gly
                100                 105                 110

Asp Asp Val Tyr Glu Gly Val Pro Lys Asp Tyr Thr Gly Glu Asp Ala
                115                 120                 125

Thr Ala His Asn Phe Tyr Ser Ala Leu Leu Gly Asp Lys Ser Ala Leu
                130                 135                 140

Thr Gly Gly Ser Gly Lys Val Val Asn Ser Gly Pro Asp Asp Arg Ile
145                 150                 155                 160

Phe Ile Phe Tyr Ser Asp His Gly Gly Pro Gly Val Leu Gly Thr Pro
                165                 170                 175

Ala Gly Pro Tyr Ile Tyr Ala Ser Asp Leu Val Glu Val Leu Lys Lys
                180                 185                 190

Lys His Ala Ser Gly Thr Tyr Lys Asn Leu Val Phe Tyr Leu Glu Ala
                195                 200                 205

Cys Glu Ala Gly Ser Ile Phe Glu Gly Leu Leu Pro Glu Asp Ile Asn
                210                 215                 220

Ile Tyr Ala Thr Thr Ala Ser Asn Ala Glu Glu Ser Ser Trp Gly Thr
225                 230                 235                 240

Tyr Cys Pro Gly Glu Tyr Pro Ser Pro Pro Glu Tyr Ser Thr Cys
                245                 250                 255

Leu Gly Asp Leu Tyr Ser Val Ala Trp Met Glu Asp Ser Asp Arg His
                260                 265                 270

Asn Leu Arg Thr Glu Ser Leu His Gln Gln Tyr Lys Val Val Lys Asp
                275                 280                 285

Arg Thr Leu Ser Gly Gly Trp Tyr Gly Ser His Val Met Gln Tyr Gly
                290                 295                 300

Asp Val Glu Phe Ser Lys Asp Thr Leu Phe Leu Tyr Leu Gly Thr Asp
305                 310                 315                 320

Pro Ala Asn Asp Asn Leu Thr Phe Val Asp Glu Asn Ser Leu Trp Ser
                325                 330                 335

Ser Ser Thr Ala Val Asn Gln Arg Asp Ala Asp Leu Val His Phe Trp
                340                 345                 350

His Lys Phe Arg Lys Ala Pro Glu Gly Ser Pro Lys Lys Asn Glu Ala
                355                 360                 365

Arg Lys Gln Val Leu Glu Val Met Ser His Arg Met His Ile Asp Asp
                370                 375                 380

Ser Val Lys Leu Val Gly Lys Leu Leu Phe Gly Phe Glu Lys Ala Pro
385                 390                 395                 400

Glu Val Leu Asn Ala Val Arg Pro Ala Gly Ser Ala Leu Val Asp Asp
                405                 410                 415

Trp Ala Cys Leu Lys Thr Met Val Arg Thr Phe Glu Thr His Cys Gly
                420                 425                 430
```

```
Ser Leu Ser Gln Tyr Gly Met Lys His Met Arg Ser Phe Ala Asn Ile
        435                 440                 445

Cys Asn Val Gly Ile Lys Lys Glu Gln Met Ala Glu Ala Ser Ala Gln
    450                 455                 460

Ala Cys Val Thr Val Pro Ala Ser Ser Trp Ser Ser Leu Gln Arg Gly
465                 470                 475                 480

Phe Ser Ala

<210> SEQ ID NO 41
<211> LENGTH: 489
<212> TYPE: PRT
<213> ORGANISM: Nicotiana tabacum

<400> SEQUENCE: 41

Met Ile Arg Tyr Val Ala Gly Thr Leu Phe Leu Ile Gly Leu Ala Leu
1               5                   10                  15

Asn Val Ala Val Ser Glu Ser Arg Asn Val Leu Lys Leu Pro Ser Glu
            20                  25                  30

Val Ser Arg Phe Phe Gly Ala Asp Glu Ser Asn Ala Gly Asp His Asp
        35                  40                  45

Asp Asp Ser Val Gly Thr Arg Trp Ala Ile Leu Leu Ala Gly Ser Asn
    50                  55                  60

Gly Tyr Trp Asn Tyr Arg His Gln Ala Asp Ile Cys His Ala Tyr Gln
65                  70                  75                  80

Leu Leu Lys Lys Gly Gly Leu Lys Asp Glu Asn Ile Val Val Phe Met
                85                  90                  95

Tyr Asp Asp Ile Ala Asn Asn Glu Glu Asn Pro Arg Arg Gly Val Ile
            100                 105                 110

Ile Asn Ser Pro His Gly Glu Asp Val Tyr Lys Gly Val Pro Lys Asp
        115                 120                 125

Tyr Thr Gly Asp Asp Val Thr Val Asp Asn Phe Phe Ala Val Ile Leu
    130                 135                 140

Gly Asn Lys Thr Ala Leu Ser Gly Gly Ser Gly Lys Val Val Asn Ser
145                 150                 155                 160

Gly Pro Asn Asp His Ile Phe Ile Phe Tyr Ser Asp His Gly Gly Pro
                165                 170                 175

Gly Val Leu Gly Met Pro Thr Asp Pro Tyr Leu Tyr Ala Asn Asp Leu
            180                 185                 190

Ile Asp Val Leu Lys Lys Lys His Ala Ser Gly Thr Tyr Lys Ser Leu
        195                 200                 205

Val Phe Tyr Leu Glu Ala Cys Glu Ser Gly Ser Ile Phe Glu Gly Leu
    210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Glu Tyr Pro Ser Pro Pro
                245                 250                 255

Ile Glu Tyr Met Thr Cys Leu Gly Asp Leu Tyr Ser Ile Ser Trp Met
            260                 265                 270

Glu Asp Ser Glu Leu His Asn Leu Arg Thr Glu Ser Leu Lys Gln Gln
        275                 280                 285

Tyr His Leu Val Lys Glu Arg Thr Ala Thr Gly Asn Pro Val Tyr Gly
    290                 295                 300

Ser His Val Met Gln Tyr Gly Asp Leu His Leu Ser Lys Asp Ala Leu
305                 310                 315                 320
```

```
Tyr Leu Tyr Met Gly Thr Asn Pro Ala Asn Asp Asn Tyr Thr Phe Met
                325                 330                 335

Asp Asp Asn Ser Leu Arg Val Ser Lys Ala Val Asn Gln Arg Asp Ala
            340                 345                 350

Asp Leu Leu His Phe Trp His Lys Phe Arg Thr Ala Pro Glu Gly Ser
        355                 360                 365

Val Arg Lys Ile Glu Ala Gln Lys Gln Leu Asn Glu Ala Ile Ser His
    370                 375                 380

Arg Val His Leu Asp Asn Ser Val Ala Leu Val Gly Lys Leu Leu Phe
385                 390                 395                 400

Gly Ile Glu Lys Gly Pro Glu Val Leu Ser Gly Val Arg Pro Ala Gly
                405                 410                 415

Gln Pro Leu Val Asp Asp Trp Asp Cys Leu Lys Ser Phe Val Arg Thr
            420                 425                 430

Phe Glu Thr His Cys Gly Ser Leu Ser Gln Tyr Gly Met Lys His Met
        435                 440                 445

Arg Ser Ile Ala Asn Ile Cys Asn Ala Gly Ile Lys Lys Glu Gln Met
    450                 455                 460

Val Glu Ala Ser Ala Gln Ala Cys Pro Ser Val Pro Ser Asn Thr Trp
465                 470                 475                 480

Ser Ser Leu His Arg Gly Phe Ser Ala
                485

<210> SEQ ID NO 42
<211> LENGTH: 482
<212> TYPE: PRT
<213> ORGANISM: Solanum lycopersicum

<400> SEQUENCE: 42

Met Asn Arg Ser Val Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
                20                  25                  30

Gly Ser Arg Phe Phe Asp Ala Asp Glu Ile Asp Ser Val Gly Thr Arg
            35                  40                  45

Trp Ala Ile Leu Leu Ala Gly Ser Asn Gly Tyr Trp Asn Tyr Arg His
        50                  55                  60

Gln Ala Asp Ile Cys His Ala Tyr Gln Leu Leu Lys Lys Gly Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
                100                 105                 110

Asp Val Tyr Asn Gly Val Pro Lys Asp Tyr Thr Gly Asp Asp Val Thr
            115                 120                 125

Val Asp Asn Phe Leu Ala Ala Leu Leu Gly Asn Lys Thr Ala Leu Thr
        130                 135                 140

Gly Gly Ser Gly Lys Val Val Asp Ser Gly Pro Asn Asp His Ile Phe
145                 150                 155                 160

Ile Phe Tyr Ser Asp His Gly Gly Ala Gly Val Leu Gly Met Pro Thr
                165                 170                 175

Asn Pro Tyr Leu Tyr Ala Asn Asp Leu Ile Asp Ala Leu Lys Met Lys
            180                 185                 190

His Ala Ser Gly Thr Tyr Lys Ser Leu Val Phe Tyr Leu Glu Ala Cys
```

```
            195                 200                 205
Glu Ser Gly Ser Met Phe Glu Gly Leu Leu Pro Glu Gly Leu Asn Ile
210                 215                 220

Tyr Ala Thr Thr Ala Ser Asn Ala Asp Glu Ser Ser Trp Gly Thr Tyr
225                 230                 235                 240

Cys Pro Gly Glu Tyr Pro Ser Pro Ile Glu Tyr Asp Thr Cys Leu
                245                 250                 255

Gly Asp Leu Tyr Ser Ile Ser Trp Met Glu Asp Ser Glu Arg His Asn
            260                 265                 270

Leu Arg Thr Glu Ser Leu Lys Gln Gln Tyr His Leu Val Lys Glu Arg
        275                 280                 285

Thr Ala Ser Gly Asn Pro Ala Tyr Gly Ser His Val Met Gln Tyr Gly
290                 295                 300

Asp Val His Leu Ser Lys Asp Ala Val Phe Leu Tyr Met Gly Thr Asp
305                 310                 315                 320

Pro Ala Asn Asp Asn Ser Thr Phe Met Asp Asp Asn Ser Leu Arg Val
                325                 330                 335

Ser Lys Ala Val Asn Gln Arg Asp Ala Asp Leu Val His Phe Trp Tyr
            340                 345                 350

Lys Phe His Lys Ala Pro Glu Gly Ser Val Ser Lys Thr Glu Ala Gln
        355                 360                 365

Lys Arg Leu Asn Glu Ala Ile Ser His Arg Met His Leu Asp Asn Ser
370                 375                 380

Ile Ala Leu Val Gly Lys Leu Leu Phe Gly Ile Lys Lys Gly Pro Glu
385                 390                 395                 400

Val Leu Thr Ser Val Arg Pro Ala Gly Gln Pro Leu Val Asp Asn Trp
                405                 410                 415

Asp Cys Leu Lys Ser Tyr Val Arg Thr Phe Glu Thr His Cys Gly Ser
            420                 425                 430

Leu Ser Gln Tyr Gly Met Lys His Met Arg Ser Val Ala Asn Ile Cys
        435                 440                 445

Asn Ala Gly Ile Lys Met Glu Gln Met Val Glu Ala Ser Ala Gln Ala
450                 455                 460

Cys Pro Ser Val Pro Ser Tyr Thr Trp Ser Ser Leu His Arg Gly Phe
465                 470                 475                 480

Ser Ala
```

<210> SEQ ID NO 43
<211> LENGTH: 494
<212> TYPE: PRT
<213> ORGANISM: Citrus clementina

<400> SEQUENCE: 43

```
Met Thr Arg Leu Ala Ser Gly Val Leu Ile Thr Leu Val Ala Leu
1               5                   10                  15

Ala Gly Ile Ala Asp Gly Ser Arg Asp Ile Ala Gly Asp Ile Leu Lys
            20                  25                  30

Leu Pro Ser Glu Ala Tyr Arg Phe Phe His Asn Gly Gly Gly Ala
        35                  40                  45

Lys Val Asn Asp Asp Asp Ser Val Gly Thr Arg Trp Ala Val Leu
50                  55                  60

Leu Ala Gly Ser Asn Gly Phe Trp Asn Tyr Arg His Gln Ala Asp Ile
65                  70                  75                  80

Cys His Ala Tyr Gln Leu Leu Arg Lys Gly Gly Leu Lys Asp Glu Asn
```

```
                    85                  90                  95
Ile Ile Val Phe Met Tyr Asp Asp Ile Ala Phe Asn Glu Glu Asn Pro
                100                 105                 110
Arg Pro Gly Val Ile Ile Asn His Pro His Gly Asp Val Tyr Lys
            115                 120                 125
Gly Val Pro Lys Asp Tyr Thr Gly Glu Asp Val Thr Val Glu Asn Phe
130                 135                 140
Phe Ala Val Ile Leu Gly Asn Lys Thr Ala Leu Thr Gly Gly Ser Gly
145                 150                 155                 160
Lys Val Val Asp Ser Gly Pro Asn Asp His Ile Phe Ile Phe Tyr Ser
                165                 170                 175
Asp His Gly Gly Pro Gly Val Leu Gly Met Pro Thr Ser Arg Tyr Ile
                180                 185                 190
Tyr Ala Asp Glu Leu Ile Asp Val Leu Lys Lys His Ala Ser Gly
                195                 200                 205
Asn Tyr Lys Ser Leu Val Phe Tyr Leu Glu Ala Cys Glu Ser Gly Ser
            210                 215                 220
Ile Phe Glu Gly Leu Leu Pro Glu Gly Leu Asn Ile Tyr Ala Thr Thr
225                 230                 235                 240
Ala Ser Asn Ala Glu Glu Ser Ser Trp Gly Thr Tyr Cys Pro Gly Glu
                245                 250                 255
Ile Pro Gly Pro Pro Glu Tyr Ser Thr Cys Leu Gly Asp Leu Tyr
            260                 265                 270
Ser Ile Ala Trp Met Glu Asp Ser Asp Ile His Asn Leu Arg Thr Glu
            275                 280                 285
Thr Leu His Gln Gln Tyr Glu Leu Val Lys Thr Arg Thr Ala Ser Tyr
290                 295                 300
Asn Ser Tyr Gly Ser His Val Met Gln Tyr Gly Asp Ile Gly Leu Ser
305                 310                 315                 320
Lys Asn Asn Leu Phe Thr Tyr Leu Gly Thr Asn Pro Ala Asn Asp Asn
                325                 330                 335
Tyr Thr Phe Val Asp Glu Asn Ser Leu Arg Pro Ala Ser Lys Ala Val
                340                 345                 350
Asn Gln Arg Asp Ala Asp Leu Leu His Phe Trp Asp Lys Tyr Arg Lys
            355                 360                 365
Ala Pro Glu Gly Thr Pro Arg Lys Ala Glu Ala Gln Lys Gln Phe Phe
            370                 375                 380
Glu Ala Met Ser His Arg Met His Val Asp His Ser Ile Lys Leu Ile
385                 390                 395                 400
Gly Lys Leu Leu Phe Gly Ile Glu Lys Gly Pro Glu Ile Leu Asn Thr
                405                 410                 415
Val Arg Pro Ala Gly Gln Pro Leu Val Asp Asp Trp Gly Cys Leu Lys
                420                 425                 430
Ser Leu Val Arg Thr Phe Glu Ser His Cys Gly Ala Leu Ser Gln Tyr
            435                 440                 445
Gly Met Lys His Met Arg Ser Leu Ala Asn Ile Cys Asn Thr Gly Ile
            450                 455                 460
Gly Lys Glu Lys Met Ala Glu Ala Ser Ala Gln Ala Cys Glu Asn Ile
465                 470                 475                 480
Pro Ser Gly Pro Trp Ser Ser Leu Asp Lys Gly Phe Ser Ala
                485                 490
```

<210> SEQ ID NO 44

```
<211> LENGTH: 481
<212> TYPE: PRT
<213> ORGANISM: Nicotiana tabacum

<400> SEQUENCE: 44
```

| | | | | | | | | | | | | | | |
|---|---|---|---|---|---|---|---|---|---|---|---|---|---|---|
| Met | Ile | Ser | Tyr | Ala | Ala | Gly | Ile | Phe | Phe | Leu | Val | Gly | Phe | Ser | Ile |
| 1 | | | | 5 | | | | | 10 | | | | | 15 | |
| Ala | Ala | Ala | Ala | Asp | Gly | Arg | Asn | Val | Leu | Lys | Leu | Pro | Ser | Glu | Ala |
| | | | 20 | | | | | 25 | | | | | 30 | | |
| Ser | Arg | Phe | Phe | Asp | Glu | Ala | Asp | Asp | Ser | Val | Gly | Thr | Arg | Trp | Ala |
| | | 35 | | | | | 40 | | | | | 45 | | | |
| Val | Leu | Leu | Ala | Gly | Ser | Asn | Gly | Tyr | Trp | Asn | Tyr | Arg | His | Gln | Ala |
| 50 | | | | | 55 | | | | | 60 | | | | | |
| Asp | Val | Cys | His | Ala | Tyr | Gln | Leu | Leu | Arg | Lys | Gly | Gly | Leu | Lys | Asp |
| 65 | | | | 70 | | | | | 75 | | | | | 80 | |
| Glu | Asn | Ile | Ile | Met | Phe | Met | Tyr | Asp | Asp | Ile | Ala | Tyr | Asn | Glu | Glu |
| | | | | 85 | | | | 90 | | | | | 95 | | |
| Asn | Pro | Arg | Gln | Gly | Val | Ile | Ile | Asn | Ser | Pro | Ala | Gly | Glu | Asp | Val |
| | | | 100 | | | | | 105 | | | | | 110 | | |
| Tyr | Lys | Gly | Val | Pro | Lys | Asp | Tyr | Thr | Gly | Asp | Asp | Val | Asn | Val | Asp |
| | | 115 | | | | | 120 | | | | | 125 | | | |
| Asn | Phe | Leu | Ala | Val | Leu | Leu | Gly | Asn | Lys | Thr | Ala | Leu | Thr | Gly | Gly |
| | 130 | | | | | 135 | | | | | 140 | | | | |
| Ser | Gly | Lys | Val | Val | Asp | Ser | Gly | Pro | Asn | Asp | His | Ile | Phe | Ile | Phe |
| 145 | | | | | 150 | | | | | 155 | | | | | 160 |
| Tyr | Ser | Asp | His | Gly | Gly | Pro | Gly | Val | Leu | Gly | Met | Pro | Thr | Asn | Pro |
| | | | | 165 | | | | | 170 | | | | | 175 | |
| Tyr | Leu | Tyr | Ala | Ser | Asp | Leu | Ile | Asp | Val | Leu | Lys | Lys | Lys | His | Ala |
| | | | 180 | | | | | 185 | | | | | 190 | | |
| Ser | Gly | Thr | Tyr | Lys | Ser | Leu | Val | Leu | Tyr | Ile | Glu | Ala | Cys | Glu | Ser |
| | | | 195 | | | | | 200 | | | | | 205 | | |
| Gly | Ser | Ile | Phe | Glu | Gly | Leu | Leu | Pro | Lys | Gly | Leu | Asn | Ile | Tyr | Ala |
| | 210 | | | | | 215 | | | | | 220 | | | | |
| Thr | Thr | Ala | Ser | Asn | Ala | Val | Glu | Ser | Ser | Trp | Gly | Thr | Tyr | Cys | Pro |
| 225 | | | | | 230 | | | | | 235 | | | | | 240 |
| Gly | Asp | Tyr | Pro | Ser | Leu | Pro | Pro | Gly | Tyr | Glu | Thr | Cys | Leu | Gly | Asp |
| | | | | 245 | | | | | 250 | | | | | 255 | |
| Leu | Tyr | Ala | Val | Ser | Trp | Met | Glu | Asp | Ser | Glu | Met | His | Asn | Leu | Arg |
| | | | 260 | | | | | 265 | | | | | 270 | | |
| Thr | Glu | Asn | Leu | Arg | Gln | Gln | Tyr | His | Leu | Val | Lys | Glu | Arg | Thr | Ala |
| | | 275 | | | | | 280 | | | | | 285 | | | |
| Asn | Gly | Asn | Ser | Ala | Tyr | Gly | Ser | His | Val | Leu | Gln | Phe | Gly | Asp | Leu |
| | 290 | | | | | 295 | | | | | 300 | | | | |
| Gln | Leu | Gly | Met | Asp | Ser | Leu | Phe | Met | Tyr | Met | Gly | Thr | Asn | Pro | Ala |
| 305 | | | | | 310 | | | | | 315 | | | | | 320 |
| Asn | Asp | Asn | Tyr | Thr | Tyr | Val | Asp | Asp | Asn | Ser | Leu | Arg | Ala | Ser | Ser |
| | | | | 325 | | | | | 330 | | | | | 335 | |
| Lys | Ala | Val | Asn | Gln | Arg | Asp | Ala | Asp | Leu | Leu | His | Phe | Trp | Asp | Lys |
| | | | 340 | | | | | 345 | | | | | 350 | | |
| Phe | Arg | Lys | Ala | Pro | Glu | Gly | Ser | Ala | Arg | Lys | Val | Glu | Ala | Gln | Lys |
| | | 355 | | | | | 360 | | | | | 365 | | | |
| Gln | Phe | Thr | Glu | Ala | Met | Ser | His | Arg | Met | His | Leu | Asp | Asn | Ser | Met |
| | 370 | | | | | 375 | | | | | 380 | | | | |
| Ala | Leu | Val | Gly | Lys | Leu | Leu | Phe | Gly | Ile | Gln | Lys | Gly | Pro | Glu | Val |

```
                385                 390                 395                 400
Leu Lys Arg Val Arg Pro Val Gly Gln Pro Leu Val Asp Asp Trp Thr
                    405                 410                 415

Cys Leu Lys Tyr Phe Val Arg Thr Phe Glu Thr His Cys Gly Ser Leu
                420                 425                 430

Ser Gln Tyr Gly Met Lys His Met Arg Ser Ile Ala Asn Ile Cys Asn
                435                 440                 445

Ala Gly Ile Lys Met Glu Gln Met Val Glu Ala Ser Thr Gln Ala Cys
450                 455                 460

Pro Ser Val Pro Thr Asn Ile Trp Ser Ser Leu His Arg Gly Phe Ser
465                 470                 475                 480

Ala

<210> SEQ ID NO 45
<211> LENGTH: 481
<212> TYPE: PRT
<213> ORGANISM: Capsella rubella

<400> SEQUENCE: 45

Met Thr Arg Ile Val Ala Val Ile Val Val Leu Phe Leu Ser Leu
1               5                   10                  15

Val Ala Ala Ser Asp Asn Phe Ile Arg Leu Pro Ser Glu Ala Ser
                20                  25                  30

Lys Phe Phe Arg Pro Asn Asn Glu Asn Asp Asp Ser Thr Arg Trp Ala
                35                  40                  45

Val Leu Val Ala Gly Ser Ser Gly Tyr Trp Asn Tyr Arg His Gln Ala
50                  55                  60

Asp Val Cys His Ala Tyr Gln Leu Leu Lys Lys Gly Gly Val Lys Glu
65                  70                  75                  80

Glu Asn Ile Val Val Phe Met Tyr Asp Asp Ile Ala Asn Asn Glu Glu
                85                  90                  95

Asn Pro Arg Pro Gly Val Ile Ile Asn Ser Pro Asn Gly Glu Asp Val
                100                 105                 110

Tyr Asn Gly Val Pro Lys Asp Tyr Thr Gly Asp Glu Val Asn Val Asn
                115                 120                 125

Asn Phe Phe Ala Val Leu Leu Gly Asn Lys Thr Ala Leu Lys Gly Gly
                130                 135                 140

Ser Gly Lys Val Val Asn Ser Gly Pro Asn Asp His Ile Phe Ile Tyr
145                 150                 155                 160

Tyr Ser Asp His Gly Gly Pro Gly Val Leu Gly Met Pro Thr Ser Pro
                165                 170                 175

Tyr Leu Tyr Ala Lys Asp Leu Asn Asp Val Leu Lys Lys His Ala
                180                 185                 190

Ser Gly Thr Tyr Lys Ser Leu Val Phe Tyr Leu Glu Ala Cys Glu Ser
                195                 200                 205

Gly Ser Ile Phe Glu Gly Leu Leu Pro Glu Gly Leu Asn Ile Tyr Ala
                210                 215                 220

Thr Thr Ala Ser Asn Ala Glu Glu Ser Ser Trp Gly Thr Tyr Cys Pro
225                 230                 235                 240

Gly Glu Asp Pro Ser Pro Ser Glu Tyr Glu Thr Cys Leu Gly Asp
                245                 250                 255

Leu Tyr Ser Val Ala Trp Met Glu Asp Ser Asp Lys His Asn Leu Gln
                260                 265                 270

Thr Glu Ser Leu His Gln Gln Tyr Glu Leu Val Lys Lys Arg Thr Ala
```

```
                275                 280                 285
Gly Thr Gly Ser Ser Tyr Gly Ser His Val Leu Glu Phe Gly Asp Ile
            290                 295                 300
Gly Leu Ser Lys Glu Lys Leu Val Leu Tyr Met Gly Thr Asn Pro Ala
305                 310                 315                 320
Asn Glu Asn Phe Thr Phe Val Asp Glu Asn Ser Ser Leu Arg Leu Pro
                325                 330                 335
Ser Arg Val Thr Asn Gln Arg Asp Ala Asp Leu Val His Phe Trp Asp
            340                 345                 350
Lys Tyr Arg Lys Ala Pro Glu Gly Ser Ala Arg Lys Val Glu Ala Gln
                355                 360                 365
Lys Gln Val Leu Glu Ala Met Ser His Arg Leu His Val Asp Asn Ser
            370                 375                 380
Val Leu Leu Ile Gly Lys Leu Leu Phe Gly Leu Glu Gly Pro Ala Val
385                 390                 395                 400
Leu Asn Lys Val Arg Pro Ser Gly Arg Pro Leu Val Asp Asp Trp Asp
                405                 410                 415
Cys Leu Lys Ser Met Val Arg Ala Phe Glu Arg His Cys Gly Ser Leu
            420                 425                 430
Ser Gln Tyr Gly Ile Lys His Met Arg Ser Ile Ala Asn Ile Cys Asn
                435                 440                 445
Ala Gly Ile Gln Met Gly Leu Met Glu Glu Ala Ala Lys Gln Ala Cys
            450                 455                 460
Pro Ser Ile Pro Ala Gly Pro Trp Ser Ser Leu His Arg Gly Phe Ser
465                 470                 475                 480
Ala

<210> SEQ ID NO 46
<211> LENGTH: 479
<212> TYPE: PRT
<213> ORGANISM: Arabidopsis lyrata subsp. lyrata

<400> SEQUENCE: 46

Met Thr Thr Val Ala Val Thr Phe Leu Ala Leu Phe Leu Tyr Leu Val
1               5                   10                  15
Ala Ala Val Ser Gly Asp Val Ile Lys Leu Pro Ser Gln Ala Ser Lys
                20                  25                  30
Phe Phe His Pro Thr Glu Asn Asp Asp Ser Thr Arg Trp Ala Val
            35                  40                  45
Leu Val Ala Gly Ser Ser Gly Tyr Trp Asn Tyr Arg His Gln Ala Asp
        50                  55                  60
Val Cys His Ala Tyr Gln Leu Leu Lys Lys Gly Gly Val Lys Glu Glu
65                  70                  75                  80
Asn Ile Val Val Phe Met Tyr Asp Asp Ile Ala Lys Asn Glu Glu Asn
                85                  90                  95
Pro Arg Pro Gly Val Ile Ile Asn Ser Pro Asn Gly Glu Asp Val Tyr
            100                 105                 110
Asn Gly Val Pro Lys Asp Tyr Thr Gly Asp Asp Val Asn Val Asp Asn
        115                 120                 125
Leu Leu Ala Val Ile Leu Gly Asn Lys Thr Ala Val Lys Gly Gly Ser
    130                 135                 140
Gly Lys Val Val Asp Ser Gly Pro Asn Asp His Ile Phe Ile Tyr Tyr
145                 150                 155                 160
Ser Asp His Gly Gly Pro Gly Val Leu Gly Met Pro Thr Ser Pro Tyr
```

```
                    165                 170                 175
Leu Tyr Ala Asn Asp Leu Asn Asp Val Leu Lys Lys His Ala Ser
                180                 185                 190

Gly Thr Tyr Lys Ser Leu Val Phe Tyr Leu Glu Ala Cys Glu Ser Gly
            195                 200                 205

Ser Ile Phe Glu Gly Leu Leu Pro Glu Gly Leu Asn Ile Tyr Ala Thr
210                 215                 220

Thr Ala Ser Asn Ala Val Glu Ser Ser Trp Gly Thr Tyr Cys Pro Gly
225                 230                 235                 240

Glu Asp Pro Ser Pro Pro Ser Glu Tyr Glu Thr Cys Leu Gly Asp Leu
                245                 250                 255

Tyr Ser Val Ala Trp Met Glu Asp Ser Asp Ile His Asn Leu Gln Thr
            260                 265                 270

Glu Thr Leu His Gln Gln Tyr Glu Leu Val Lys Lys Arg Thr Ala Gly
        275                 280                 285

Ser Gly Lys Ser Phe Gly Ser His Val Met Glu Phe Gly Asp Ile Gly
    290                 295                 300

Leu Ser Lys Glu Lys Leu Val Leu Tyr Met Gly Thr Asn Pro Ala Asn
305                 310                 315                 320

Glu Asn Phe Thr Phe Val Asn Glu Asn Ser Leu Arg Pro Pro Ser Arg
                325                 330                 335

Val Thr Asn Gln Arg Asp Ala Asp Leu Val His Phe Trp Asp Lys Tyr
            340                 345                 350

Arg Lys Ala Pro Glu Gly Ser Ala Arg Lys Val Glu Ala Gln Lys Gln
        355                 360                 365

Val Leu Glu Ala Met Ser His Arg Leu His Val Asp Asn Ser Ile Leu
    370                 375                 380

Leu Ile Gly Lys Leu Leu Phe Gly Leu Asp Ser Pro Ala Val Leu Asn
385                 390                 395                 400

Asn Val Arg Pro Ser Gly Thr Pro Leu Val Asp Asp Trp Asp Cys Leu
                405                 410                 415

Lys Ser Leu Val Arg Val Phe Glu Met His Cys Gly Ser Leu Ser Gln
            420                 425                 430

Tyr Gly Ile Lys His Met Arg Ser Ile Ala Asn Ile Cys Asn Ala Gly
        435                 440                 445

Ile Gln Met Gly Gln Met Glu Glu Ala Ala Met Gln Ala Cys Pro Thr
    450                 455                 460

Ile Pro Ala Ser Pro Trp Ser Ser Leu Glu Arg Gly Phe Ser Ala
465                 470                 475

<210> SEQ ID NO 47
<211> LENGTH: 482
<212> TYPE: PRT
<213> ORGANISM: Capsella rubella

<400> SEQUENCE: 47

Met Thr Arg Leu Thr Val Gly Val Leu Phe Leu Ser Leu Ile Ala Leu
1               5                   10                  15

Ser Ala Ala Arg Asn Gly Pro Asp Asp Val Ile Lys Leu Pro Ser Gln
                20                  25                  30

Ala Ser Arg Phe Phe Arg Pro Pro Glu Asn Asp Ala Gly Thr Arg Trp
            35                  40                  45

Ala Val Leu Val Ala Gly Ser Ser Gly Tyr Gly Asn Tyr Arg His Gln
        50                  55                  60
```

-continued

```
Ala Asp Ile Cys His Ala Tyr Gln Leu Leu Arg Lys Gly Gly Leu Lys
 65                  70                  75                  80

Glu Glu Asn Ile Val Val Phe Met Tyr Asp Asp Ile Ala Asn Asn Tyr
                 85                  90                  95

Glu Asn Pro Arg Pro Gly Thr Ile Ile Asn Ser Pro His Gly Lys Asp
            100                 105                 110

Val Tyr Gln Gly Val Pro Lys Asp Tyr Thr Gly Asp Asp Val Thr Val
        115                 120                 125

Asp Asn Leu Phe Ala Val Ile Leu Gly Asp Lys Thr Ala Ile Lys Gly
    130                 135                 140

Gly Ser Gly Lys Val Val Asp Ser Gly Pro Asn Asp His Ile Phe Ile
145                 150                 155                 160

Phe Tyr Ser Asp His Gly Gly Pro Gly Val Leu Gly Met Pro Thr Phe
                165                 170                 175

Pro Tyr Ile Tyr Ala Asn Asp Leu Asn Asp Val Leu Lys Lys Lys His
            180                 185                 190

Ala Leu Gly Thr Tyr Lys Ser Leu Val Phe Tyr Leu Glu Ala Cys Glu
        195                 200                 205

Ser Gly Ser Ile Phe Glu Gly Leu Leu Pro Glu Gly Leu Asn Ile Tyr
210                 215                 220

Ala Thr Thr Ala Ser Asn Ala Glu Glu Ser Ser Trp Gly Thr Tyr Cys
225                 230                 235                 240

Pro Gly Glu Glu Pro Ser Pro Pro Glu Tyr Asp Thr Cys Leu Gly
                245                 250                 255

Asp Leu Tyr Ser Val Ala Trp Met Glu Asp Ser Gly Ile His Asn Leu
            260                 265                 270

Gln Thr Glu Thr Leu Gln Gln Gln Tyr Glu Leu Val Lys Lys Arg Thr
        275                 280                 285

Ala Leu Asp Gly Tyr Tyr Tyr Gly Ser His Val Met Gln Tyr Gly Asp
    290                 295                 300

Val Gly Leu Ser Lys Asp Lys Leu Glu Ile Tyr Met Gly Thr Asn Pro
305                 310                 315                 320

Ala Asn Glu Asn Ser Thr Phe Val Asp Ser Asn Ser Leu Lys Leu Pro
                325                 330                 335

Ser Arg Val Thr Asn Gln Arg Asp Ala Asp Leu Val His Phe Trp Glu
            340                 345                 350

Lys Tyr Arg Lys Ala Pro Glu Gly Ser Ser Arg Lys Ala Glu Ala Gln
        355                 360                 365

Lys Gln Val Leu Glu Val Met Ser His Arg Leu His Val Asp Asn Ser
    370                 375                 380

Val Ile Leu Val Gly Lys Ile Leu Phe Gly Ile Ser Lys Gly Pro Gln
385                 390                 395                 400

Val Leu Asn Glu Val Arg Ser Ala Gly Gln Pro Leu Val Asp Asp Trp
                405                 410                 415

Asn Cys Leu Lys Asn Met Val Arg Ala Phe Glu Arg His Cys Gly Ser
            420                 425                 430

Leu Ser Gln Tyr Gly Ile Lys His Met Arg Ser Phe Ala Asn Phe Cys
        435                 440                 445

Asn Ser Gly Ile Gln Met Glu Gln Met Glu Glu Ala Ala Ser Gln Ala
    450                 455                 460

Cys Thr Thr Ile Pro Pro Gly Pro Trp Ser Ser Leu His Arg Gly Phe
465                 470                 475                 480

Ser Ala
```

<210> SEQ ID NO 48
<211> LENGTH: 482
<212> TYPE: PRT
<213> ORGANISM: Vigna mungo

<400> SEQUENCE: 48

```
Met Ala Thr Thr Thr Ser Leu Ser Thr Leu Phe Leu Leu Phe Leu Ala
1               5                   10                  15

Thr Val Ala Leu Val Ala Ala Arg Arg Asp His Val Gly Asp Phe Leu
            20                  25                  30

Arg Leu Pro Ser Asp Ser Gly Asn Asp Asp Asn Val Gln Gly Thr Arg
        35                  40                  45

Trp Ala Ile Leu Phe Ala Gly Ser Asn Gly Tyr Trp Asn Tyr Arg His
    50                  55                  60

Gln Ala Asp Ile Cys His Ala Tyr Gln Ile Leu Arg Lys Gly Gly Leu
65                  70                  75                  80

Lys Glu Glu Asn Ile Ile Val Phe Met Tyr Asp Asp Ile Ala Phe Asn
                85                  90                  95

Trp Asp Asn Pro Arg Pro Gly Val Ile Ile Asn Lys Pro Asp Gly Asp
            100                 105                 110

Asp Val Tyr Glu Gly Val Pro Lys Asp Tyr Thr Gly Glu Asp Ala Thr
        115                 120                 125

Ala His Asn Phe Tyr Ser Ala Leu Leu Gly Asp Lys Ser Ala Leu Thr
    130                 135                 140

Gly Gly Ser Gly Lys Val Val Ser Ser Gly Pro Asp Asp Arg Ile Phe
145                 150                 155                 160

Ile Phe Tyr Ser Asp His Gly Gly Pro Gly Val Leu Gly Thr Pro Ala
                165                 170                 175

Gly Pro Tyr Ile Tyr Ala Ser Asp Leu Val Glu Val Leu Lys Lys Lys
            180                 185                 190

His Ala Ser Gly Thr Tyr Lys Asn Leu Val Phe Tyr Leu Glu Ala Cys
        195                 200                 205

Glu Ala Gly Ser Ile Phe Glu Gly Leu Leu Pro Glu Asp Ile Asn Ile
    210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Pro Glu Tyr Ser Thr Cys Leu
                245                 250                 255

Gly Asp Leu Tyr Ser Val Ala Trp Met Glu Asp Ser Asp Arg His Asn
            260                 265                 270

Leu Arg Thr Glu Ser Leu His Gln Gln Tyr Lys Val Val Lys Asp Arg
        275                 280                 285

Thr Leu Ser Gly Gly Trp Tyr Gly Ser His Val Met Gln Tyr Gly Asp
    290                 295                 300

Val Glu Phe Ser Lys Asp Ala Leu Phe Leu Tyr Leu Gly Thr Asp Pro
305                 310                 315                 320

Ala Asn Asp Asn Leu Thr Phe Val Asp Glu Asn Ser Leu Trp Ser Ser
                325                 330                 335

Ser Thr Ala Val Asn Gln Arg Asp Ala Asp Leu Val His Phe Trp His
            340                 345                 350

Lys Phe Arg Lys Ala Pro Glu Gly Ser Pro Lys Lys Asn Glu Ala Arg
        355                 360                 365

Lys Gln Val Leu Glu Val Met Ser His Arg Met His Ile Asp Asp Ser
```

```
            370                 375                 380
Val Lys Leu Val Gly Lys Leu Leu Phe Gly Phe Glu Lys Ala Pro Glu
385                 390                 395                 400

Val Leu Asn Ala Val Arg Pro Ala Gly Ser Ala Leu Val Asp Asp Trp
                405                 410                 415

Ala Cys Leu Lys Thr Met Val Arg Thr Phe Glu Thr His Cys Gly Ser
                420                 425                 430

Leu Ser Gln Tyr Gly Met Lys His Met Ser Pro Phe Ala Asn Ile Cys
                435                 440                 445

Asn Val Gly Ile Lys Lys Glu Gln Met Ala Glu Ala Ser Ala Gln Ala
            450                 455                 460

Cys Val Thr Val Pro Ala Ser Ser Trp Ser Ser Leu Gln Arg Gly Phe
465                 470                 475                 480

Ser Ala

<210> SEQ ID NO 49
<211> LENGTH: 488
<212> TYPE: PRT
<213> ORGANISM: Eutrema salsugineum

<400> SEQUENCE: 49

Met Thr Ser Val Ala Val Pro Leu Leu Val Leu Leu Ser Leu Ile
1               5                   10                  15

Ala Val Ser Ala Ala Arg Gln Gly Pro Asp Asp Ile Ile Lys Leu Pro
                20                  25                  30

Ser Gln Ala Ser Met Phe Phe Arg Pro Ala Asp Asp Asn Asp Ser
            35                  40                  45

Ser Ala Gly Thr Arg Trp Ala Val Leu Val Ala Gly Ser Asn Gly Tyr
    50                  55                  60

Trp Asn Tyr Arg His Gln Ala Asp Ile Cys His Ala Tyr Gln Leu Leu
65                  70                  75                  80

Arg Lys Gly Gly Val Lys Glu Asp Asn Ile Val Val Phe Met Tyr Asp
                85                  90                  95

Asp Ile Ala Asn Asn Glu Glu Asn Pro Arg Arg Gly Ile Ile Ile Asn
                100                 105                 110

Ser Pro His Gly Lys Asp Val Tyr Gln Gly Val Pro Lys Asp Tyr Thr
            115                 120                 125

Gly Asp Asp Val Thr Val Asp Asn Leu Phe Ala Val Ile Leu Gly Asn
        130                 135                 140

Lys Thr Ala Thr Lys Gly Gly Ser Gly Lys Val Val Asp Ser Gly Pro
145                 150                 155                 160

Asn Asp His Ile Phe Ile Phe Tyr Ser Asp His Gly Gly Pro Gly Val
                165                 170                 175

Leu Gly Met Pro Thr Ser Pro Tyr Leu Tyr Ala Asn Asp Leu Asn Asp
                180                 185                 190

Val Leu Lys Lys Lys His Ala Ser Gly Thr Tyr Lys Ser Leu Val Phe
            195                 200                 205

Tyr Leu Glu Ala Cys Glu Ser Gly Ser Ile Phe Glu Gly Leu Leu Glu
        210                 215                 220

Glu Gly Leu Asn Ile Tyr Ala Thr Thr Ala Ser Asn Ala Val Glu Ser
225                 230                 235                 240

Ser Trp Gly Thr Tyr Cys Pro Gly Glu Asp Pro Ser Leu Pro Pro Glu
                245                 250                 255

Tyr Glu Thr Cys Leu Gly Asp Leu Tyr Ser Val Ser Trp Met Glu Asp
```

-continued

```
                260                 265                 270
Ser Gly Met His Asn Leu Gln Thr Glu Thr Leu Arg Gln Gln Tyr Glu
            275                 280                 285

Leu Val Lys Arg Arg Thr Ala Gly Val Gly Ser Ala Tyr Gly Ser His
        290                 295                 300

Val Met Gln Tyr Gly Asp Val Gly Leu Ser Lys Asp Lys Leu Asp Leu
305                 310                 315                 320

Tyr Met Gly Thr Asn Pro Ala Asn Asp Asn Phe Thr Phe Val Asp Glu
                325                 330                 335

Asn Ser Leu Thr Pro Pro Ser Arg Val Thr Asn Gln Arg Asp Ala Asp
            340                 345                 350

Leu Val His Phe Trp Asp Lys Tyr Arg Lys Ala Pro Glu Gly Ser Thr
        355                 360                 365

Arg Lys Thr Glu Ala Gln Lys Gln Val Leu Ala Met Ser His Arg
370                 375                 380

Leu His Val Asp Asn Ser Val Lys Leu Val Gly Lys Leu Leu Phe Gly
385                 390                 395                 400

Ile Ser Glu Gly Pro Glu Val Leu Asn Lys Val Arg Ser Ala Gly Gln
                405                 410                 415

Pro Leu Val Asp Asp Trp Asn Cys Leu Lys Asn Leu Val Arg Ala Phe
            420                 425                 430

Glu Arg His Cys Gly Ser Leu Ser Gln Tyr Gly Ile Lys His Met Arg
        435                 440                 445

Ser Phe Ala Asn Ile Cys Asn Ala Gly Ile Gln Met Glu Gln Met Glu
    450                 455                 460

Glu Ala Ser Ser Gln Ala Cys Thr Thr Ile Pro Pro Gly Pro Trp Ser
465                 470                 475                 480

Ser Leu His Arg Gly Phe Ser Ala
                485

<210> SEQ ID NO 50
<211> LENGTH: 494
<212> TYPE: PRT
<213> ORGANISM: Citrus sinensis

<400> SEQUENCE: 50

Met Thr Arg Leu Ala Ser Gly Val Leu Ile Thr Leu Leu Val Ala Leu
1               5                   10                  15

Ala Gly Ile Ala Asp Gly Ser Arg Asp Ile Ala Gly Asp Ile Leu Lys
            20                  25                  30

Leu Pro Ser Glu Ala Tyr Arg Phe Phe His Asn Gly Gly Gly Ala
        35                  40                  45

Lys Val Asn Asp Asp Asp Ser Val Gly Thr Arg Trp Ala Val Leu
    50                  55                  60

Leu Ala Gly Ser Asn Gly Phe Trp Asn Tyr Arg His Gln Ala Asp Ile
65                  70                  75                  80

Cys His Ala Tyr Gln Leu Leu Arg Lys Gly Gly Leu Lys Asp Glu Asn
                85                  90                  95

Ile Ile Val Phe Met Tyr Asp Asp Ile Ala Phe Asn Glu Glu Asn Pro
            100                 105                 110

Arg Pro Gly Val Ile Ile Asn His Pro His Gly Asp Asp Val Tyr Lys
        115                 120                 125

Gly Val Pro Lys Asp Tyr Thr Gly Glu Asp Val Thr Val Glu Lys Phe
    130                 135                 140
```

```
Phe Ala Val Val Leu Gly Asn Lys Thr Ala Leu Thr Gly Gly Ser Gly
145                 150                 155                 160

Lys Val Val Asp Ser Gly Pro Asn Asp His Ile Phe Ile Phe Tyr Ser
                165                 170                 175

Asp His Gly Gly Pro Gly Val Leu Gly Met Pro Thr Ser Arg Tyr Ile
            180                 185                 190

Tyr Ala Asp Glu Leu Ile Asp Val Leu Lys Lys His Ala Ser Gly
        195                 200                 205

Asn Tyr Lys Ser Leu Val Phe Tyr Leu Glu Ala Cys Glu Ser Gly Ser
    210                 215                 220

Ile Phe Glu Gly Leu Leu Leu Glu Gly Leu Asn Ile Tyr Ala Thr Thr
225                 230                 235                 240

Ala Ser Asn Ala Glu Glu Ser Ser Trp Gly Thr Tyr Cys Pro Gly Glu
                245                 250                 255

Ile Pro Gly Pro Pro Glu Tyr Ser Thr Cys Leu Gly Asp Leu Tyr
        260                 265                 270

Ser Ile Ala Trp Met Glu Asp Ser Asp Ile His Asn Leu Arg Thr Glu
            275                 280                 285

Thr Leu His Gln Gln Tyr Glu Leu Val Lys Thr Arg Thr Ala Ser Tyr
    290                 295                 300

Asn Ser Tyr Gly Ser His Val Met Gln Tyr Gly Asp Ile Gly Leu Ser
305                 310                 315                 320

Lys Asn Asn Leu Phe Thr Tyr Leu Gly Thr Asn Pro Ala Asn Asp Asn
                325                 330                 335

Tyr Thr Phe Val Asp Glu Asn Ser Leu Arg Pro Ala Ser Lys Ala Val
            340                 345                 350

Asn Gln Arg Asp Ala Asp Leu Leu His Phe Trp Asp Lys Tyr Arg Lys
        355                 360                 365

Ala Pro Glu Gly Thr Pro Arg Lys Ala Glu Ala Gln Lys Gln Phe Phe
    370                 375                 380

Glu Ala Met Ser His Arg Met His Val Asp His Ser Ile Lys Leu Ile
385                 390                 395                 400

Gly Lys Leu Leu Phe Gly Ile Glu Lys Gly Pro Glu Ile Leu Asn Thr
                405                 410                 415

Val Arg Pro Ala Gly Gln Pro Leu Val Asp Asp Trp Gly Cys Leu Lys
            420                 425                 430

Ser Leu Val Arg Thr Phe Glu Ser His Cys Gly Ala Leu Ser Gln Tyr
        435                 440                 445

Gly Met Lys His Met Arg Ser Leu Ala Asn Ile Cys Asn Thr Gly Ile
    450                 455                 460

Gly Lys Glu Lys Met Ala Glu Ala Ser Ala Gln Ala Cys Glu Asn Ile
465                 470                 475                 480

Pro Ser Gly Pro Trp Ser Ser Leu Asp Lys Gly Phe Ser Ala
                485                 490

<210> SEQ ID NO 51
<211> LENGTH: 484
<212> TYPE: PRT
<213> ORGANISM: Capsicum annuum

<400> SEQUENCE: 51

Met Asn Tyr Gln Val Ala Gly Ile Leu Phe Ile Val Gly Leu Ser Val
1               5                   10                  15

Ala Ile Ala Val Thr Ala Val Asp Gly Arg Asn Val Leu Lys Leu Pro
                20                  25                  30
```

-continued

```
Thr Glu Ala Ser Arg Phe Phe Asp His Ala Asp Asp Ser Val Gly
            35                  40                  45
Thr Arg Trp Ala Val Leu Leu Ala Gly Ser Asn Gly Tyr Trp Asn Tyr
 50                  55                  60
Arg His Gln Ala Asp Val Cys His Ala Tyr Gln Leu Leu Arg Lys Gly
 65                  70                  75                  80
Gly Leu Lys Asp Glu Asn Ile Ile Val Phe Met Tyr Asp Asp Ile Ala
                 85                  90                  95
Tyr Asn Glu Glu Asn Pro Arg Pro Gly Val Ile Ile Asn Asn Pro Ala
            100                 105                 110
Ala Glu Asp Val Tyr Glu Gly Val Pro Lys Asp Tyr Thr Arg Asp Glu
            115                 120                 125
Val Asn Val His Asn Phe Leu Ala Val Leu Leu Gly Asn Lys Thr Ala
130                 135                 140
Leu Thr Gly Gly Ser Gly Lys Val Val Asn Ser Gly Pro Asn Asp His
145                 150                 155                 160
Ile Phe Ile Phe Tyr Ser Asp His Gly Gly Pro Gly Val Leu Gly Met
                165                 170                 175
Pro Thr Asn Pro Tyr Leu Tyr Ala Ser Asp Leu Ile Asn Ala Leu Lys
            180                 185                 190
Lys Lys His Ala Ala Gly Ala Tyr Lys Ser Leu Val Leu Tyr Ile Glu
            195                 200                 205
Ala Cys Glu Ser Gly Ser Ile Phe Glu Gly Leu Leu Pro Thr Gly Leu
210                 215                 220
Asn Ile Tyr Ala Thr Thr Ala Ser Asn Ala Val Glu Ser Ser Trp Gly
225                 230                 235                 240
Thr Tyr Cys Pro Gly Glu Tyr Pro Ser Pro Pro Glu Tyr Glu Thr
                245                 250                 255
Cys Leu Gly Asp Leu Tyr Ala Val Ser Trp Met Glu Asp Ser Glu Met
            260                 265                 270
His Asn Leu Arg Thr Glu Asn Leu Arg Gln Gln Tyr His Leu Val Lys
            275                 280                 285
Arg Arg Thr Ala Asn Gly Asn Thr Cys Gly Ser His Val Met Gln Phe
            290                 295                 300
Gly Asp Leu Gln Leu Ser Met Glu Ser Leu Phe Ser Phe Met Gly Thr
305                 310                 315                 320
Asn Pro Ala Asn Asp Asn Tyr Thr Tyr Val Asp Asp Asn Ser Leu Trp
                325                 330                 335
Ala Ser Ser Arg Ala Val Asn Gln Arg Asp Ala Asp Leu Leu His Phe
            340                 345                 350
Trp Asp Lys Phe Arg Lys Ala Pro Glu Gly Ser Ala Arg Lys Val Glu
            355                 360                 365
Ala Gln Lys Gln Phe Thr Glu Ala Met Ser His Arg Met His Leu Asp
            370                 375                 380
Asn Ser Ile Ala Leu Val Gly Lys Leu Leu Phe Gly Ile Gln Lys Gly
385                 390                 395                 400
Pro Glu Val Leu Lys Arg Val Arg Ser Ala Gly Gln Pro Leu Val Asp
                405                 410                 415
Asp Trp Ala Cys Leu Lys Ser Phe Val Arg Thr Phe Glu Thr His Cys
            420                 425                 430
Gly Ser Leu Ser Gln Tyr Gly Met Lys His Met Arg Ser Ile Ala Asn
            435                 440                 445
```

```
Ile Cys Asn Ala Gly Ile His Thr Glu Gln Met Val Glu Ala Ser Ala
    450                 455                 460

Gln Ala Cys Pro Ser Ile Pro Ala Asn Thr Trp Ser Ser Leu His Arg
465                 470                 475                 480

Gly Phe Ser Ala

<210> SEQ ID NO 52
<211> LENGTH: 480
<212> TYPE: PRT
<213> ORGANISM: Solanum lycopersicum

<400> SEQUENCE: 52

Met Val His Val Ala Gly Val Phe Ile Leu Val Gly Ile Ala Val Leu
1               5                   10                  15

Ala Ala Val Glu Gly Arg Asn Val Leu Lys Leu Pro Ser Glu Ala Ser
            20                  25                  30

Arg Phe Phe Asp Asp Ala Asp Asp Ser Val Gly Thr Arg Trp Ala Val
        35                  40                  45

Leu Leu Ala Gly Ser Asn Gly Tyr Trp Asn Tyr Arg His Gln Ala Asp
    50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His His Glu Glu Asn
                85                  90                  95

Pro Arg Pro Gly Val Ile Ile Asn Ser Pro Ala Gly Glu Asp Val Tyr
            100                 105                 110

Glu Gly Val Pro Lys Asp Tyr Thr Gly Asp Asp Val Asn Val His Asn
        115                 120                 125

Phe Leu Ala Val Leu Leu Gly Asn Lys Thr Ala Leu Thr Gly Gly Ser
    130                 135                 140

Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asp Asp Leu Ile Ala Val Leu Lys Lys His Ala Ala
            180                 185                 190

Gly Thr Tyr Lys Ser Leu Val Leu Tyr Ile Glu Ala Cys Glu Ser Gly
        195                 200                 205

Ser Ile Phe Glu Gly Leu Leu Pro Asn Gly Leu Asn Ile Tyr Ala Thr
    210                 215                 220

Thr Ala Ser Asn Ala Glu Ser Ser Trp Gly Thr Tyr Cys Pro Gly
225                 230                 235                 240

Glu Tyr Pro Ser Pro Pro Glu Tyr Glu Thr Cys Leu Gly Asp Leu
                245                 250                 255

Tyr Ala Val Ser Trp Met Glu Asp Ser Glu Met His Asn Leu Arg Thr
            260                 265                 270

Glu Asn Leu Arg Gln Gln Tyr His Leu Val Lys Lys Arg Thr Ala Asn
        275                 280                 285

Gly Asn Thr Ala Tyr Gly Ser His Val Met Gln Phe Gly Asp Leu Gln
    290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asp Asn Ser Leu Leu Ala Ser Ser Lys
                325                 330                 335
```

```
Ala Val Asn Gln Arg Asp Ala Asp Leu Leu His Phe Trp Asp Lys Phe
                340                 345                 350

Arg Lys Ala Pro Glu Gly Ser Ala Arg Lys Val Glu Ala Gln Lys Gln
            355                 360                 365

Phe Thr Glu Ala Met Ser His Arg Met His Leu Asp Glu Arg Ile Ala
370                 375                 380

Leu Val Gly Lys Leu Leu Phe Gly Ile Gln Lys Gly Pro Glu Val Leu
385                 390                 395                 400

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
            420                 425                 430

Gln Tyr Gly Met Lys His Met Arg Ser Ile Ala Asn Ile Cys Asn Ala
        435                 440                 445

Gly Ile Gln Met Glu Gln Met Val Glu Ala Ser Ala Gln Ala Cys Pro
    450                 455                 460

Ser Ile Pro Ser Asn Ile Trp Ser Ser Leu His Arg Gly Phe Ser Ala
465                 470                 475                 480

<210> SEQ ID NO 53
<211> LENGTH: 480
<212> TYPE: PRT
<213> ORGANISM: Solanum tuberosum

<400> SEQUENCE: 53

Met Ile His Val Ala Gly Val Phe Ile Leu Val Gly Val Ala Val Leu
1               5                   10                  15

Ala Ala Val Glu Gly Arg Asn Val Leu Lys Leu Pro Ser Glu Ala Ser
                20                  25                  30

Arg Phe Asp Val Ala Asp Ser Val Gly Thr Arg Trp Ala Val
            35                  40                  45

Leu Leu Ala Gly Ser Asn Gly Tyr Trp Asn Tyr Arg His Gln Ala Asp
50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His His Glu Glu Asn
                85                  90                  95

Pro Arg Pro Gly Val Ile Ile Asn Ser Pro Ala Gly Glu Asp Val Tyr
            100                 105                 110

Glu Gly Val Pro Lys Asp Tyr Thr Gly Asp Asp Val Asn Val His Asn
        115                 120                 125

Phe Leu Thr Val Leu Leu Gly Asn Lys Thr Ala Leu Thr Gly Gly Ser
130                 135                 140

Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asn Asp Leu Ile Ala Val Leu Lys Lys His Ala Ala
            180                 185                 190

Gly Thr Tyr Lys Ser Leu Val Leu Tyr Ile Glu Ala Cys Glu Ser Gly
        195                 200                 205

Ser Ile Phe Glu Gly Leu Leu Pro Lys Gly Leu Asn Ile Tyr Ala Thr
    210                 215                 220

Thr Ala Ser Asn Ala Glu Glu Ser Ser Trp Gly Thr Tyr Cys Pro Gly
225                 230                 235                 240
```

```
Glu Tyr Pro Ser Pro Pro Glu Tyr Glu Thr Cys Leu Gly Asp Leu
            245                 250                 255

Tyr Ala Val Ser Trp Met Glu Asp Ser Glu Met His Asn Leu Arg Thr
        260                 265                 270

Glu Asn Leu Arg Gln Gln Tyr His Leu Val Lys Lys Arg Thr Ala Asn
        275                 280                 285

Gly Asn Thr Ala Tyr Gly Ser His Val Met Gln Phe Gly Asp Leu Gln
        290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asp Asn Ser Leu Trp Ala Ser Ser Lys
                325                 330                 335

Ala Val Asn Gln Arg Asp Ala Asp Leu Leu His Phe Trp Asp Lys Phe
                340                 345                 350

Arg Lys Ala Pro Glu Gly Ser Ala Arg Lys Val Glu Ala Gln Lys Gln
                355                 360                 365

Phe Thr Glu Ala Met Ser His Arg Met His Leu Asp Glu Arg Ile Ala
        370                 375                 380

Leu Val Gly Lys Leu Leu Phe Gly Ile Gln Lys Gly Pro Glu Val Leu
385                 390                 395                 400

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
                420                 425                 430

Gln Tyr Gly Met Lys His Met Arg Ser Ile Ala Asn Ile Cys Asn Ala
        435                 440                 445

Gly Val Gln Met Glu Gln Met Val Glu Ala Ser Val Gln Ala Cys Pro
450                 455                 460

Ser Ile Pro Ser Asn Thr Trp Ser Ser Leu His Arg Gly Phe Ser Ala
465                 470                 475                 480

<210> SEQ ID NO 54
<211> LENGTH: 480
<212> TYPE: PRT
<213> ORGANISM: Solanum lycopersicum

<400> SEQUENCE: 54

Met Val His Val Ala Gly Val Phe Ile Leu Val Gly Ile Ala Val Leu
1               5                   10                  15

Ala Ala Val Glu Gly Arg Asn Val Leu Lys Leu Pro Ser Glu Ala Ser
            20                  25                  30

Arg Phe Phe Asp Asp Ala Asp Asp Ser Val Gly Thr Arg Trp Ala Val
        35                  40                  45

Leu Leu Ala Gly Ser Asn Gly Tyr Trp Asn Tyr Arg His Gln Ala Asp
    50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His His Glu Glu Asn
                85                  90                  95

Pro Arg Pro Gly Val Ile Ile Asn Ser Pro Ala Gly Glu Asp Val Tyr
            100                 105                 110

Glu Gly Val Pro Lys Asp Tyr Thr Gly Asp Asp Val Asn Val His Asn
        115                 120                 125

Phe Leu Ala Val Leu Leu Gly Asn Lys Thr Ala Leu Thr Gly Gly Ser
```

```
        130                 135                 140
Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asp Asp Leu Ile Ala Val Leu Lys Lys His Ala Pro
            180                 185                 190

Gly Thr Tyr Lys Ser Leu Val Leu Tyr Ile Glu Ala Cys Glu Ser Gly
                195                 200                 205

Ser Ile Phe Glu Gly Leu Leu Pro Asn Gly Leu Asn Ile Tyr Ala Thr
            210                 215                 220

Thr Ala Ser Asn Ala Glu Glu Ser Ser Trp Gly Thr Tyr Cys Pro Gly
225                 230                 235                 240

Glu Tyr Pro Ser Pro Pro Glu Tyr Glu Thr Cys Leu Gly Asp Leu
                245                 250                 255

Tyr Ala Val Ser Trp Met Glu Asp Ser Glu Met His Asn Leu Arg Thr
            260                 265                 270

Glu Asn Leu Arg Gln Gln Tyr His Leu Val Lys Lys Arg Thr Ala Asn
                275                 280                 285

Gly Asn Thr Ala Tyr Gly Ser His Val Met Gln Phe Gly Asp Leu Gln
290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asp Asn Ser Leu Leu Ala Ser Ser Lys
                325                 330                 335

Ala Val Asn Gln Arg Asp Ala Asp Leu Leu His Phe Trp Asp Lys Phe
            340                 345                 350

Arg Lys Ala Pro Glu Gly Ser Ala Arg Lys Val Glu Ala Gln Lys Gln
                355                 360                 365

Phe Thr Glu Ala Met Ser His Arg Met His Leu Asp Glu Arg Ile Ala
            370                 375                 380

Leu Val Gly Lys Leu Leu Phe Gly Ile Gln Lys Gly Pro Glu Val Leu
385                 390                 395                 400

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
            420                 425                 430

Gln Tyr Gly Met Lys His Met Arg Ser Ile Ala Asn Ile Cys Asn Ala
                435                 440                 445

Gly Ile Gln Met Glu Gln Met Val Glu Ala Ser Ala Gln Ala Cys Pro
450                 455                 460

Ser Ile Pro Ser Asn Ile Trp Ser Ser Leu His Arg Gly Phe Ser Ala
465                 470                 475                 480

<210> SEQ ID NO 55
<211> LENGTH: 490
<212> TYPE: PRT
<213> ORGANISM: Eutrema salsugineum

<400> SEQUENCE: 55

Met Ser Arg Val Ser Val Thr Val Thr Val Ala Val Ser Phe Leu Ala
1               5                   10                  15

Leu Phe Ile Ser Leu Val Thr Val Ser Cys Asp Val Ile Lys Leu Pro
            20                  25                  30
```

```
Ser Gln Ala Ser Lys Phe Phe Arg Thr Thr Lys His Asn Asp Asp Gly
         35                  40                  45

Asp Ser Ser Ala Gly Thr Lys Trp Ala Val Leu Val Ala Gly Ser Ser
 50                  55                  60

Gly Tyr Trp Asn Tyr Arg His Gln Ala Asp Val Cys His Ala Tyr Gln
 65                  70                  75                  80

Leu Leu Arg Lys Gly Leu Lys Glu Glu Asn Ile Ile Val Phe Met
                 85                  90                  95

Tyr Asp Asp Ile Ala Lys Asn Lys Glu Asn Pro Arg Pro Gly Ile Ile
                100                 105                 110

Ile Asn Ser Pro Asn Gly Asn Asp Val Tyr Asn Gly Val Pro Lys Asp
                115                 120                 125

Tyr Thr Gly Asp Asp Val Asn Val Asp Asn Leu Phe Ala Val Ile Leu
130                 135                 140

Ala Asn Lys Thr Ala Leu Lys Gly Gly Ser Gly Lys Val Val Asp Ser
145                 150                 155                 160

Gly Pro Asp Asp His Ile Phe Ile Tyr Tyr Ser Asp His Gly Gly Pro
                165                 170                 175

Gly Val Leu Gly Met Pro Thr Ser Pro His Leu Tyr Ala Asn Asp Leu
                180                 185                 190

Ile Asp Ile Leu Lys Lys Lys His Ala Ser Gly Thr Tyr Lys Ser Leu
                195                 200                 205

Val Phe Tyr Leu Glu Ala Cys Glu Ser Gly Ser Ile Phe Glu Gly Leu
210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Asp Asp Ser Ser Pro Pro
                245                 250                 255

Lys Glu Tyr Glu Thr Cys Leu Gly Asp Leu Tyr Ser Val Ser Trp Met
                260                 265                 270

Glu Asp Ser Asp Gln His Asn Leu Gln Thr Glu Ser Leu His Gln Gln
                275                 280                 285

Tyr Glu Leu Val Lys Lys Arg Thr Ala Gly Ser Asn Thr Ser Tyr Gly
                290                 295                 300

Ser His Val Met Glu Phe Gly Asp Ile Gly Leu Ser Lys Glu Met Leu
305                 310                 315                 320

Val Leu Tyr Met Gly Thr Asn Pro Asp Asn Glu Asn Tyr Thr Phe Val
                325                 330                 335

Asp Lys Asn Ser Leu Arg Pro Pro Ser Arg Val Thr Asn Gln Arg Asp
                340                 345                 350

Ala Asp Leu Val His Phe Trp Asp Lys Tyr Gln Lys Ala Pro Glu Gly
                355                 360                 365

Ser Ala Arg Lys Ala Glu Ala Gln Lys Gln Val Leu Glu Ala Met Ser
                370                 375                 380

His Arg Leu His Ile Asp Asn Ser Phe Leu Met Ile Gly Lys Leu Leu
385                 390                 395                 400

Phe Gly Ile Ser Glu Gly Pro Leu Val Leu Asn Lys Val Arg Pro Ser
                405                 410                 415

Gly Lys Pro Leu Val Asp Asp Trp Asp Cys Leu Lys Thr Leu Val Arg
                420                 425                 430

Ala Tyr Glu Arg His Cys Gly Ser Leu Ser Gln Tyr Gly Ile Lys His
                435                 440                 445

Met Arg Ser Ile Ala Asn Ile Cys Asn Ala Gly Ile Gln Val Glu Gln
```

```
        450             455             460
Met Glu Glu Ala Ala Met Gln Ala Cys Pro Thr Ile Pro Ala Gly Pro
465                 470                 475                 480

Trp Ser Ser Leu His Arg Gly Phe Ser Ala
                485                 490

<210> SEQ ID NO 56
<211> LENGTH: 492
<212> TYPE: PRT
<213> ORGANISM: Ipomoea batatas

<400> SEQUENCE: 56

Met Ile Arg Ser Val Val Ala Ser Leu Leu Leu Thr Val Ser Ile
1               5                   10                  15

Val Ala Val Ala Asp Gly Arg Gly Phe Leu Lys Leu Pro Ser Glu Ala
                20                  25                  30

Arg Arg Phe Phe Arg Pro Ala Glu Glu Glu Asn Arg Glu Ala Asp Gly
                35                  40                  45

Asp Asp Ser Val Gly Thr Arg Trp Ala Val Leu Ile Ala Gly Ser Asn
        50                  55                  60

Gly Tyr Trp Asn Tyr Arg His Gln Ala Asp Ile Cys His Ala Tyr Gln
65                  70                  75                  80

Ile Leu Lys Ala Gly Gly Leu Lys Asp Glu Asn Ile Val Val Phe Met
                85                  90                  95

Tyr Asp Asp Ile Ala Tyr Asn Glu Glu Asn Pro Arg Lys Gly Ile Ile
                100                 105                 110

Ile Asn Ser Pro His Gly Glu Asp Val Tyr His Gly Val Pro Lys Asp
                115                 120                 125

Tyr Thr Gly Asp Asp Val Thr Ala Asn Asn Leu Leu Ala Val Ile Leu
        130                 135                 140

Gly Asp Lys Ser Ala Val Lys Gly Gly Ser Gly Lys Val Val Asp Ser
145                 150                 155                 160

Gly Pro Asn Asp His Ile Phe Ile Tyr Tyr Ser Asp His Gly Gly Pro
                165                 170                 175

Gly Val Leu Gly Met Pro Thr Ser Pro Tyr Leu Tyr Ala Asp Glu Leu
                180                 185                 190

Asn Ala Ala Leu Lys Lys Lys His Ala Ala Gly Ala Tyr Lys Ser Leu
                195                 200                 205

Val Phe Tyr Leu Glu Ala Cys Glu Ser Gly Ser Ile Phe Glu Gly Ile
        210                 215                 220

Leu Pro Lys Asp Ile Asn Ile Tyr Ala Thr Thr Ala Ser Asn Ala Ile
225                 230                 235                 240

Glu Ser Ser Trp Gly Thr Tyr Cys Pro Gly Glu Tyr Pro Ser Pro Pro
                245                 250                 255

Pro Glu Tyr Glu Thr Cys Leu Gly Asp Leu Tyr Ser Ile Ala Trp Met
                260                 265                 270

Glu Asp Ser Asp Ile His Asn Leu Arg Thr Glu Ser Leu Lys Gln Gln
                275                 280                 285

Tyr Asn Leu Val Lys Asp Arg Thr Leu Asn Gly Asn Thr Ala Tyr Gly
        290                 295                 300

Ser His Val Met Gln Tyr Gly Asp Leu Glu Leu Asn Ala Asp Ser Leu
305                 310                 315                 320

Phe Met Tyr Met Gly Thr Asn Pro Ala Asn Glu Asn Phe Thr Phe Val
                325                 330                 335
```

-continued

```
Asp Glu Lys Ser Leu Lys Leu Ser Ala Pro Arg Arg Ala Val Asn Gln
            340                 345                 350

Arg Asp Ala Asp Leu Leu His Phe Trp Asp Lys Phe Arg Asn Ala Pro
        355                 360                 365

Glu Gly Ser Ala Arg Lys Ser Glu Ala Gln Lys Gln Phe Thr Glu Ala
    370                 375                 380

Ile Thr His Arg Thr His Leu Asp Asn Ser Ile Ala Leu Val Gly Lys
385                 390                 395                 400

Leu Leu Phe Gly Met Glu Lys Gly Pro Glu Val Leu Ser Ser Val Arg
                405                 410                 415

Ala Thr Gly Leu Pro Leu Val Asp Asp Trp Ser Cys Leu Lys Ser Tyr
            420                 425                 430

Val Arg Ala Phe Glu Thr His Cys Gly Ser Leu Ser Gln Tyr Gly Met
        435                 440                 445

Lys His Met Arg Ser Ile Ala Asn Ile Cys Asn Ala Gly Ile Ser Glu
    450                 455                 460

Glu Arg Met Ala Glu Ala Ser Ala Gln Ala Cys Pro Thr Phe Pro Ser
465                 470                 475                 480

Tyr Ser Trp Ser Ser Leu Arg Gly Gly Phe Ser Ala
                485                 490

<210> SEQ ID NO 57
<211> LENGTH: 490
<212> TYPE: PRT
<213> ORGANISM: Nicotiana tabacum

<400> SEQUENCE: 57

Met Ile Arg His Ile Ala Gly Thr Leu Phe Ile Ile Gly Leu Ala Leu
1               5                   10                  15

Asn Val Ala Val Ser Glu Ser Arg Asn Val Leu Lys Leu Pro Ser Glu
            20                  25                  30

Val Ser Arg Phe Phe Gly Ala Asp Lys Ser Asn Val Gly Asp Asp His
        35                  40                  45

Asp Asp Asp Ser Val Gly Thr Arg Trp Ala Ile Leu Leu Ala Gly Ser
    50                  55                  60

Asn Gly Tyr Trp Asn Tyr Arg His Gln Ala Asp Ile Cys His Ala Tyr
65                  70                  75                  80

Gln Leu Leu Lys Lys Gly Gly Leu Lys Asp Glu Asn Ile Val Val Phe
                85                  90                  95

Met Tyr Asp Asp Ile Ala Asn Asn Glu Glu Asn Pro Arg Pro Gly Val
            100                 105                 110

Ile Ile Asn Ser Pro His Gly Glu Asp Val Tyr Lys Gly Val Pro Lys
        115                 120                 125

Asp Tyr Thr Gly Asp Asp Val Thr Val Asn Asn Phe Phe Ala Ala Leu
    130                 135                 140

Leu Gly Asn Lys Thr Ala Leu Ser Gly Gly Ser Gly Lys Val Val Asn
145                 150                 155                 160

Ser Gly Pro Asn Asp His Ile Leu Ile Phe Tyr Ser Asp His Gly Gly
                165                 170                 175

Pro Gly Val Leu Gly Met Pro Thr Asp Pro Tyr Leu Tyr Ala Asn Asp
            180                 185                 190

Leu Ile Asp Val Leu Lys Lys Lys His Ala Ser Gly Thr Tyr Lys Ser
        195                 200                 205

Leu Val Phe Tyr Leu Glu Ala Cys Glu Ser Gly Ser Ile Phe Glu Gly
    210                 215                 220
```

```
Leu Leu Pro Glu Gly Leu Asn Ile Tyr Ala Thr Thr Ala Ser Asn Ala
225                 230                 235                 240

Glu Glu Ser Ser Trp Gly Thr Tyr Cys Pro Gly Glu Tyr Pro Ser Pro
            245                 250                 255

Pro Ile Glu Tyr Glu Thr Cys Leu Gly Asp Leu Tyr Ser Ile Ser Trp
        260                 265                 270

Met Glu Asp Ser Glu Leu His Asn Leu Arg Thr Glu Ser Leu Lys Gln
    275                 280                 285

Gln Tyr His Leu Val Arg Glu Arg Thr Ala Thr Gly Asn Pro Val Tyr
290                 295                 300

Gly Ser His Val Met Gln Tyr Gly Asp Leu His Leu Ser Lys Asp Ala
305                 310                 315                 320

Leu Tyr Leu Tyr Met Gly Thr Asn Pro Ala Asn Asp Asn Tyr Thr Phe
                325                 330                 335

Met Asp Asp Asn Ser Leu Arg Val Ser Lys Ala Val Asn Gln Arg Asp
            340                 345                 350

Ala Asp Leu Leu His Phe Trp Tyr Lys Phe Arg Lys Ala Pro Glu Gly
        355                 360                 365

Ser Val Arg Lys Ile Glu Ala Gln Lys Gln Leu Asn Glu Ala Ile Ser
    370                 375                 380

His Arg Val His Leu Asp Asn Ser Ile Ala Leu Val Gly Lys Leu Leu
385                 390                 395                 400

Phe Gly Ile Lys Lys Gly Pro Glu Val Leu Ser Ser Val Arg Pro Ala
                405                 410                 415

Gly Gln Pro Leu Val Asp Asp Trp Asp Cys Leu Lys Ser Phe Val Arg
            420                 425                 430

Thr Phe Glu Thr His Cys Gly Ser Leu Ser Gln Tyr Gly Met Lys His
        435                 440                 445

Met Arg Ser Ile Ala Asn Ile Cys Asn Val Gly Ile Lys Met Ala Gln
    450                 455                 460

Met Val Glu Ala Ser Ala Gln Ala Cys Pro Ser Phe Ala Ser Asn Thr
465                 470                 475                 480

Trp Ser Ser Leu Gln Arg Gly Phe Ser Ala
                485                 490

<210> SEQ ID NO 58
<211> LENGTH: 494
<212> TYPE: PRT
<213> ORGANISM: Arabidopsis lyrata subsp. lyrata

<400> SEQUENCE: 58

Met Ala Thr Thr Met Thr Arg Val Pro Val Gly Ala Phe Leu Leu Val
1               5                   10                  15

Leu Leu Val Ser Leu Val Ala Val Ser Thr Ala Arg Ser Gly Pro Asp
                20                  25                  30

Asp Val Ile Lys Leu Pro Ser Gln Ala Ser Arg Phe Phe Arg Pro Ala
            35                  40                  45

Gln Asp Asp Asp Ser Asn Ala Gly Thr Arg Trp Ala Val Leu Val
    50                  55                  60

Ala Gly Ser Ser Gly Tyr Trp Asn Tyr Arg His Gln Ala Asp Ile Cys
65                  70                  75                  80

His Ala Tyr Gln Leu Leu Arg Lys Gly Gly Leu Lys Glu Glu Asn Ile
                85                  90                  95

Val Val Phe Met Tyr Asp Asp Ile Ala Asn Asn Tyr Glu Asn Pro Arg
```

```
                100                 105                 110
Pro Gly Thr Leu Ile Asn Ser Pro His Gly Lys Asp Val Tyr Gln Gly
            115                 120                 125

Val Pro Lys Asp Tyr Thr Gly Asp Val Asn Val Asp Asn Leu Phe
130                 135                 140

Ala Val Ile Leu Gly Asp Lys Thr Ala Val Lys Gly Gly Ser Gly Lys
145                 150                 155                 160

Val Val Asp Ser Gly Pro Asn Asp His Ile Phe Ile Phe Tyr Ser Asp
                165                 170                 175

His Gly Gly Pro Gly Val Leu Gly Met Pro Thr Ser Pro Tyr Leu Tyr
                180                 185                 190

Ala Asn Asp Leu Asn Asp Val Leu Lys Lys His Ala Ser Gly Thr
            195                 200                 205

Tyr Lys Ser Leu Val Phe Tyr Leu Glu Ala Cys Glu Ser Gly Ser Ile
    210                 215                 220

Phe Glu Gly Leu Leu Pro Glu Gly Leu Asn Ile Tyr Ala Thr Thr Ala
225                 230                 235                 240

Ser Asn Ala Glu Glu Ser Ser Trp Gly Thr Tyr Cys Pro Gly Glu Glu
                245                 250                 255

Pro Ser Pro Pro Pro Glu Tyr Glu Thr Cys Leu Gly Asp Leu Tyr Ser
            260                 265                 270

Val Ala Trp Met Glu Asp Ser Gly Met His Asn Leu Gln Thr Glu Thr
            275                 280                 285

Leu His Gln Gln Tyr Glu Leu Val Lys Arg Arg Thr Ala Pro Val Gly
    290                 295                 300

Tyr Ser Tyr Gly Ser His Val Met Gln Tyr Gly Asp Val Gly Leu Ser
305                 310                 315                 320

Lys Asp Asn Leu Asp Leu Tyr Met Gly Thr Asn Pro Ala Asn Asp Asn
                325                 330                 335

Phe Thr Phe Ala Asp Ala Asn Ser Leu Lys Pro Pro Ser Arg Val Thr
            340                 345                 350

Asn Gln Arg Asp Ala Asp Leu Val His Phe Trp Glu Lys Tyr Arg Lys
    355                 360                 365

Ala Pro Glu Gly Ser Ala Arg Lys Thr Glu Ala Gln Lys Gln Val Leu
370                 375                 380

Glu Ala Met Ser His Arg Leu His Val Asp Asn Ser Val Ile Leu Val
385                 390                 395                 400

Gly Lys Ile Leu Phe Gly Ile Ser Glu Gly Pro Glu Val Leu Asn Lys
                405                 410                 415

Val Arg Ser Ala Gly Gln Pro Leu Val Asp Asp Trp Asn Cys Leu Lys
            420                 425                 430

Asn Leu Val Arg Ala Phe Glu Arg His Cys Gly Ser Leu Ser Gln Tyr
    435                 440                 445

Gly Ile Lys His Met Arg Ser Phe Ala Asn Ile Cys Asn Ala Gly Ile
450                 455                 460

Arg Thr Glu Gln Met Glu Glu Ala Ala Ser Gln Ala Cys Thr Ser Ile
465                 470                 475                 480

Pro Pro Gly Pro Trp Ser Ser Leu His Arg Gly Phe Ser Ala
            485                 490

<210> SEQ ID NO 59
<211> LENGTH: 478
<212> TYPE: PRT
<213> ORGANISM: Thellungiella halophila
```

<400> SEQUENCE: 59

```
Met Thr Ser Val Ala Val Pro Leu Leu Val Leu Leu Leu Ser Leu Ile
1               5                   10                  15

Ala Val Ser Ala Ala Arg Gln Gly Pro Asp Ile Ile Lys Leu Pro
            20                  25                  30

Ser Gln Ala Ser Met Phe Phe Arg Pro Ala Asp Asp Asn Asp Ser
        35                  40                  45

Ser Ala Gly Thr Arg Trp Ala Val Leu Val Ala Gly Ser Asn Gly Tyr
    50                  55                  60

Trp Asn Tyr Arg His Gln Ala Asp Ile Cys His Ala Tyr Gln Leu Leu
65                  70                  75                  80

Arg Lys Gly Gly Val Lys Glu Asp Asn Ile Val Val Phe Met Tyr Asp
                85                  90                  95

Asp Ile Ala Asn Asn Glu Glu Asn Pro Arg Arg Gly Ile Ile Ile Asn
            100                 105                 110

Ser Pro His Gly Lys Asp Val Tyr Gln Gly Val Pro Lys Asp Tyr Thr
        115                 120                 125

Gly Asp Asp Val Thr Val Asp Asn Leu Phe Ala Val Ile Leu Gly Asn
130                 135                 140

Lys Thr Ala Thr Lys Gly Gly Ser Gly Lys Val Val Asp Ser Gly Pro
145                 150                 155                 160

Asn Asp His Ile Phe Ile Phe Tyr Ser Asp His Gly Gly Pro Gly Val
                165                 170                 175

Leu Gly Met Pro Thr Ser Pro Tyr Leu Tyr Ala Asn Asp Leu Asn Asp
            180                 185                 190

Val Leu Lys Lys Lys His Ala Ser Gly Thr Tyr Lys Ser Leu Val Phe
        195                 200                 205

Tyr Leu Glu Ala Cys Glu Ser Gly Ser Ile Phe Glu Gly Leu Leu Glu
210                 215                 220

Glu Gly Leu Asn Ile Tyr Ala Thr Thr Ala Ser Asn Ala Val Glu Ser
225                 230                 235                 240

Ser Trp Gly Thr Tyr Cys Pro Gly Glu Asp Pro Ser Leu Pro Pro Glu
                245                 250                 255

Tyr Glu Thr Cys Leu Gly Asp Leu Tyr Ser Val Ser Trp Met Glu Asp
            260                 265                 270

Ser Gly Met His Asn Leu Gln Thr Glu Thr Leu Arg Gln Gln Tyr Glu
        275                 280                 285

Leu Val Lys Arg Arg Thr Ala Gly Val Gly Ser Ala Tyr Gly Ser His
290                 295                 300

Val Met Gln Tyr Gly Asp Val Gly Leu Ser Lys Asp Lys Leu Asp Leu
305                 310                 315                 320

Tyr Met Gly Thr Asn Pro Ala Asn Asp Asn Phe Thr Phe Val Asp Glu
                325                 330                 335

Asn Ser Leu Thr Pro Pro Ser Arg Val Thr Asn Gln Arg Asp Ala Asp
            340                 345                 350

Leu Val His Phe Trp Asp Lys Tyr Arg Lys Ala Pro Glu Gly Ser Thr
        355                 360                 365

Arg Lys Thr Glu Ala Gln Lys Gln Val Leu Glu Ala Met Ser His Arg
370                 375                 380

Leu His Val Asp Asn Ser Val Lys Leu Val Gly Lys Leu Leu Phe Gly
385                 390                 395                 400

Ile Ser Glu Gly Pro Glu Val Leu Asn Lys Val Arg Ser Ala Gly Gln
```

```
                       405                 410                 415
Pro Leu Val Asp Asp Trp Asn Cys Leu Lys Asn Leu Val Arg Ala Phe
                420                 425                 430

Glu Arg His Cys Gly Ser Leu Ser Gln Tyr Gly Ile Lys His Met Arg
            435                 440                 445

Ser Phe Ala Asn Ile Cys Asn Ala Gly Ile Gln Met Glu Gln Met Glu
        450                 455                 460

Glu Ala Ser Ser Gln Ala Cys Thr Thr Ile Pro Pro Gly Pro
465                 470                 475

<210> SEQ ID NO 60
<211> LENGTH: 486
<212> TYPE: PRT
<213> ORGANISM: Beta vulgaris

<400> SEQUENCE: 60

Met Met Ile Arg Tyr Thr Ser Gly Val Leu Ile Val Leu Cys Val Leu
1               5                   10                  15

Met Ser Ser Val Val Asp Ser Arg Leu Met Val Asp Asn Leu Ile Arg
                20                  25                  30

Trp Pro Ser Asp His Pro Ser Ile Phe Glu Ser Asp Asp Ser Val
            35                  40                  45

Gly Thr Arg Trp Ala Val Leu Ile Ala Gly Ser Ser Gly Tyr Trp Asn
    50                  55                  60

Tyr Arg His Gln Ala Asp Val Cys His Ala Tyr Gln Val Leu Lys Lys
65                  70                  75                  80

Gly Gly Leu Lys Asp Glu Asn Ile Ile Val Phe Met Tyr Asp Asp Ile
                85                  90                  95

Ala Tyr Asp Glu Glu Asn Pro Arg Pro Gly Val Leu Ile Asn Ser Pro
            100                 105                 110

Tyr Gly His Asp Val Tyr Ala Gly Val Pro Lys Asp Tyr Thr Gly Glu
        115                 120                 125

Asp Val Thr Val Asn Asn Phe Phe Ala Ala Ile Leu Gly Asn Lys Asp
    130                 135                 140

Ala Ile Thr Gly Gly Ser Gly Lys Val Val Asn Ser Gly Pro Asn Asp
145                 150                 155                 160

His Ile Phe Ile Phe Tyr Ser Asp His Gly Gly Ala Gly Val Leu Gly
                165                 170                 175

Met Pro Thr Tyr Pro Tyr Leu Tyr Ala Asp Glu Leu Ile Glu Thr Leu
            180                 185                 190

Lys Glu Lys His Ala Ser Gly Thr Tyr Lys Ser Leu Val Val Tyr Ile
        195                 200                 205

Glu Ala Cys Glu Ser Gly Ser Ile Phe Glu Gly Ile Leu Pro Glu Gly
    210                 215                 220

Leu Asn Ile Tyr Ala Thr Thr Ala Ser Asn Ala Val Glu Ser Ser Trp
225                 230                 235                 240

Gly Thr Tyr Cys Pro Gly Gln Asp Pro Asn Val Pro Pro Glu Tyr Asp
                245                 250                 255

Thr Cys Leu Gly Asp Leu Tyr Ser Val Ser Trp Ile Glu Asp Ser Glu
            260                 265                 270

Arg His Asn Leu His Thr Glu Ser Leu Lys Gln Gln Tyr Glu Val Val
        275                 280                 285

Lys Thr Lys Thr Ala Glu Lys Pro Phe Tyr Gly Ser His Val Met Gln
    290                 295                 300
```

Tyr Gly Asp Lys Glu Leu Thr Gln Asp Met Leu Tyr Leu Tyr Met Gly
305                 310                 315                 320

Thr Asn Pro Asn Glu Asn Tyr Thr Tyr Val Asp Asp Asn Ser Leu
            325                 330                 335

His Pro Thr Ser Ser Asn Ala Val Asn Gln Arg Asp Ala Asp Leu Ile
            340                 345                 350

His Phe Trp Asn Lys Phe Arg Lys Ala Ser Glu Gly Ser Gln Arg Lys
            355                 360                 365

Ile Asn Ala Gln Lys Gln Phe Met Glu Val Met Ser His Arg Val His
            370                 375                 380

Leu Asp Asp Ser Ile Lys Leu Ile Gly Lys Leu Leu Phe Gly Ile Glu
385                 390                 395                 400

Lys Gly Leu Gly Val Leu Gln Thr Val Arg Pro Thr Gly Gln Pro Leu
                405                 410                 415

Val Asp Asp Trp Asn Cys Leu Lys Thr Leu Val Arg Thr Phe Glu Lys
                420                 425                 430

His Cys Gly Ser Leu Ser Gln Tyr Gly Met Lys His Met Arg Ser Ile
                435                 440                 445

Ala Asn Ile Cys Asn Ala Gly Ile Thr Thr Asn Gln Met Ala Glu Ala
450                 455                 460

Ser Ala Gln Ala Cys Pro Ser Phe Pro Ser Gly Pro Trp Ser Ser Leu
465                 470                 475                 480

His Arg Gly Phe Ser Ala
                485

<210> SEQ ID NO 61
<211> LENGTH: 494
<212> TYPE: PRT
<213> ORGANISM: Arabidopsis thaliana

<400> SEQUENCE: 61

Met Ala Thr Thr Met Thr Arg Val Ser Val Gly Val Val Leu Phe Val
1               5                   10                  15

Leu Leu Val Ser Leu Val Ala Val Ser Ala Ala Arg Ser Gly Pro Asp
                20                  25                  30

Asp Val Ile Lys Leu Pro Ser Gln Ala Ser Arg Phe Phe Arg Pro Ala
            35                  40                  45

Glu Asn Asp Asp Ser Asn Ser Gly Thr Arg Trp Ala Val Leu Val
        50                  55                  60

Ala Gly Ser Ser Gly Tyr Trp Asn Tyr Arg His Gln Ala Asp Ile Cys
65                  70                  75                  80

His Ala Tyr Gln Leu Leu Arg Lys Gly Leu Lys Glu Glu Asn Ile
            85                  90                  95

Val Val Phe Met Tyr Asp Asp Ile Ala Asn Asn Tyr Glu Asn Pro Arg
                100                 105                 110

Pro Gly Thr Ile Ile Asn Ser Pro His Gly Lys Asp Val Tyr Gln Gly
            115                 120                 125

Val Pro Lys Asp Tyr Thr Gly Asp Asp Val Asn Val Asp Asn Leu Phe
            130                 135                 140

Ala Val Ile Leu Gly Asp Lys Thr Ala Val Lys Gly Ser Gly Lys
145                 150                 155                 160

Val Val Asp Ser Gly Pro Asn Asp His Ile Phe Ile Phe Tyr Ser Asp
                165                 170                 175

His Gly Gly Pro Gly Val Leu Gly Met Pro Thr Ser Pro Tyr Leu Tyr
                180                 185                 190

```
Ala Asn Asp Leu Asn Asp Val Leu Lys Lys His Ala Leu Gly Thr
            195                 200                 205

Tyr Lys Ser Leu Val Phe Tyr Leu Glu Ala Cys Glu Ser Gly Ser Ile
210                 215                 220

Phe Glu Gly Leu Leu Pro Glu Gly Leu Asn Ile Tyr Ala Thr Thr Ala
225                 230                 235                 240

Ser Asn Ala Glu Glu Ser Ser Trp Gly Thr Tyr Cys Pro Gly Glu Glu
            245                 250                 255

Pro Ser Pro Pro Glu Tyr Glu Thr Cys Leu Gly Asp Leu Tyr Ser
            260                 265                 270

Val Ala Trp Met Glu Asp Ser Gly Met His Asn Leu Gln Thr Glu Thr
            275                 280                 285

Leu His Gln Gln Tyr Glu Leu Val Lys Arg Arg Thr Ala Pro Val Gly
            290                 295                 300

Tyr Ser Tyr Gly Ser His Val Met Gln Tyr Gly Asp Val Gly Ile Ser
305                 310                 315                 320

Lys Asp Asn Leu Asp Leu Tyr Met Gly Thr Asn Pro Ala Asn Asp Asn
            325                 330                 335

Phe Thr Phe Ala Asp Ala Asn Ser Leu Lys Pro Pro Ser Arg Val Thr
            340                 345                 350

Asn Gln Arg Asp Ala Asp Leu Val His Phe Trp Glu Lys Tyr Arg Lys
            355                 360                 365

Ala Pro Glu Gly Ser Ala Arg Lys Thr Glu Ala Gln Lys Gln Val Leu
            370                 375                 380

Glu Ala Met Ser His Arg Leu His Ile Asp Asn Ser Val Ile Leu Val
385                 390                 395                 400

Gly Lys Ile Leu Phe Gly Ile Ser Arg Gly Pro Glu Val Leu Asn Lys
            405                 410                 415

Val Arg Ser Ala Gly Gln Pro Leu Val Asp Asp Trp Asn Cys Leu Lys
            420                 425                 430

Asn Gln Val Arg Ala Phe Glu Arg His Cys Gly Ser Leu Ser Gln Tyr
            435                 440                 445

Gly Ile Lys His Met Arg Ser Phe Ala Asn Ile Cys Asn Ala Gly Ile
            450                 455                 460

Gln Met Glu Gln Met Glu Glu Ala Ala Ser Gln Ala Cys Thr Thr Leu
465                 470                 475                 480

Pro Thr Gly Pro Trp Ser Ser Leu Asn Arg Gly Phe Ser Ala
            485                 490

<210> SEQ ID NO 62
<211> LENGTH: 490
<212> TYPE: PRT
<213> ORGANISM: Arabidopsis thaliana

<400> SEQUENCE: 62

Met Thr Arg Val Ser Val Gly Val Leu Phe Val Leu Leu Val Ser
1               5                   10                  15

Leu Val Ala Val Ser Ala Ala Arg Ser Gly Pro Asp Asp Val Ile Lys
            20                  25                  30

Leu Pro Ser Gln Ala Ser Arg Phe Phe Arg Pro Ala Glu Asn Asp Asp
            35                  40                  45

Asp Ser Asn Ser Gly Thr Arg Trp Ala Val Leu Val Ala Gly Ser Ser
50                  55                  60

Gly Tyr Trp Asn Tyr Arg His Gln Ala Asp Ile Cys His Ala Tyr Gln
```

```
            65                  70                  75                  80
Leu Leu Arg Lys Gly Gly Leu Lys Glu Glu Asn Ile Val Val Phe Met
                85                  90                  95

Tyr Asp Asp Ile Ala Asn Asn Tyr Glu Asn Pro Arg Pro Gly Thr Ile
                100                 105                 110

Ile Asn Ser Pro His Gly Lys Asp Val Tyr Gln Gly Val Pro Lys Asp
                115                 120                 125

Tyr Thr Gly Asp Asp Val Asn Val Asp Asn Leu Phe Ala Val Ile Leu
                130                 135                 140

Gly Asp Lys Thr Ala Val Lys Gly Gly Ser Gly Lys Val Val Asp Ser
145                 150                 155                 160

Gly Pro Asn Asp His Ile Phe Ile Phe Tyr Ser Asp His Gly Gly Pro
                165                 170                 175

Gly Val Leu Gly Met Pro Thr Ser Pro Tyr Leu Tyr Ala Asn Asp Leu
                180                 185                 190

Asn Asp Val Leu Lys Lys Lys His Ala Leu Gly Thr Tyr Lys Ser Leu
                195                 200                 205

Val Phe Tyr Leu Glu Ala Cys Glu Ser Gly Ser Ile Phe Glu Gly Leu
                210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Glu Glu Pro Ser Pro Pro
                245                 250                 255

Pro Glu Tyr Glu Thr Cys Leu Gly Asp Leu Tyr Ser Val Ala Trp Met
                260                 265                 270

Glu Asp Ser Gly Met His Asn Leu Gln Thr Glu Thr Leu His Gln Gln
                275                 280                 285

Tyr Glu Leu Val Lys Arg Arg Thr Ala Pro Val Gly Tyr Ser Tyr Gly
                290                 295                 300

Ser His Val Met Gln Tyr Gly Asp Val Gly Ile Ser Lys Asp Asn Leu
305                 310                 315                 320

Asp Leu Tyr Met Gly Thr Asn Pro Ala Asn Asp Asn Phe Thr Phe Ala
                325                 330                 335

Asp Ala Asn Ser Leu Lys Pro Pro Ser Arg Val Thr Asn Gln Arg Asp
                340                 345                 350

Ala Asp Leu Val His Phe Trp Glu Lys Tyr Arg Lys Ala Pro Glu Gly
                355                 360                 365

Ser Ala Arg Lys Thr Glu Ala Gln Lys Gln Val Leu Glu Ala Met Ser
                370                 375                 380

His Arg Leu His Ile Asp Asn Ser Val Ile Leu Val Gly Lys Ile Leu
385                 390                 395                 400

Phe Gly Ile Ser Arg Gly Pro Glu Val Leu Asn Lys Val Arg Ser Ala
                405                 410                 415

Gly Gln Pro Leu Val Asp Asp Trp Asn Cys Leu Lys Asn Gln Val Arg
                420                 425                 430

Ala Phe Glu Arg His Cys Gly Ser Leu Ser Gln Tyr Gly Ile Lys His
                435                 440                 445

Met Arg Ser Phe Ala Asn Ile Cys Asn Ala Gly Ile Gln Met Glu Gln
450                 455                 460

Met Glu Glu Ala Ala Ser Gln Ala Cys Thr Thr Leu Pro Thr Gly Pro
465                 470                 475                 480

Trp Ser Ser Leu Asn Arg Gly Phe Ser Ala
                485                 490
```

<210> SEQ ID NO 63
<211> LENGTH: 484
<212> TYPE: PRT
<213> ORGANISM: Nicotiana tabacum

<400> SEQUENCE: 63

```
Met Ile Val Arg Tyr Val Val Ser Ala Ile Leu Ile Gly Leu Ser
1               5                   10                  15

Val Val Ala Ala Val Asp Gly Arg Asp Val Leu Lys Leu Pro Ser Glu
            20                  25                  30

Ala Ser Thr Phe Phe Ser Gly Asn Tyr Asp Asp Ser Ile Gly Thr
            35                  40                  45

Lys Trp Ala Val Leu Val Ala Gly Ser Arg Gly Tyr Trp Asn Tyr Arg
50                  55                  60

His Gln Ala Asp Val Cys His Ala Tyr Gln Leu Leu Lys Lys Gly Gly
65                  70                  75                  80

Leu Lys Asp Glu Asn Ile Ile Val Phe Met Tyr Asp Asp Ile Ala His
                85                  90                  95

Asn Phe Glu Asn Pro Arg Pro Gly Val Ile Ile Asn Ser Pro Asn Gly
                100                 105                 110

Asp Asp Val Tyr Lys Gly Val Pro Lys Asp Tyr Thr Gly His His Val
            115                 120                 125

Thr Ala Asn Asn Phe Leu Ala Val Ile Leu Gly Asn Lys Ala Ala Leu
130                 135                 140

Ser Gly Gly Ser Gly Lys Val Val Glu Ser Gly Pro Asn Asp His Ile
145                 150                 155                 160

Phe Ile Phe Tyr Ser Asp His Gly Gly Pro Gly Val Leu Gly Met Pro
                165                 170                 175

Ser Gly Pro Tyr Leu Tyr Ala Asp Asp Leu Ile Asp Val Leu Lys Arg
            180                 185                 190

Lys His Ala Ser Gly Thr Tyr Lys Ser Leu Val Phe Tyr Ile Glu Ala
        195                 200                 205

Cys Glu Ser Gly Ser Ile Phe Glu Gly Leu Leu Pro Glu Gly Leu Asn
210                 215                 220

Ile Tyr Ala Thr Thr Ala Ser Asn Ala Glu Glu Asp Ser Trp Gly Thr
225                 230                 235                 240

Tyr Cys Pro Gly Asp Tyr Pro Gly Pro Pro Glu Tyr Gln Thr Cys
                245                 250                 255

Leu Gly Asp Leu Tyr Ala Val Ser Trp Met Glu Asp Ser Glu Lys His
            260                 265                 270

Asn Leu Arg Arg Glu Thr Leu Gly Met Gln Tyr Glu Leu Val Lys Arg
        275                 280                 285

Arg Thr Ala Asn Ser Phe Pro Tyr Ala Ser Ser His Val Met Gln Tyr
290                 295                 300

Gly Asp Leu Lys Leu Met Asp Asp Pro Leu Ser Leu Tyr Met Gly Thr
305                 310                 315                 320

Asn Pro Ala Asn Asp Asn Tyr Thr Phe Leu Asp Glu Asn Ser Ser Leu
                325                 330                 335

Leu Ser Ala Lys Pro Val Asn Gln Arg Asp Ala Asp Leu Leu His Phe
            340                 345                 350

Trp Asp Lys Phe Leu Lys Ala Pro Gln Gly Ser Val Arg Lys Val Glu
        355                 360                 365

Ala Gln Lys Gln Leu Ser Glu Ala Met Ser His Arg Met His Ile Asp
```

```
            370                 375                 380
Asp Ser Ile Ala Leu Val Gly Arg Leu Leu Phe Gly Ile Glu Lys Gly
385                 390                 395                 400

Pro Asp Val Leu Ile Arg Val Arg Pro Thr Gly Glu Pro Leu Val Asp
                405                 410                 415

Asp Trp Asn Cys Leu Lys Ser Phe Val Arg Thr Phe Glu Thr Arg Cys
                420                 425                 430

Gly Ser Leu Ser Gln Tyr Gly Met Lys His Met Arg Ala Val Ala Asn
            435                 440                 445

Ile Cys Asn Ser Cys Ile Thr Met Glu Gln Ile Ala Lys Ala Ser Ala
            450                 455                 460

Gln Ala Cys Val Ser Ile Pro Ser Asn Ser Trp Ser Ser Leu Asp Glu
465                 470                 475                 480

Gly Phe Ser Ala

<210> SEQ ID NO 64
<211> LENGTH: 478
<212> TYPE: PRT
<213> ORGANISM: Arabidopsis thaliana

<400> SEQUENCE: 64

Met Thr Thr Val Val Ser Phe Leu Ala Leu Phe Leu Phe Leu Val Ala
1               5                   10                  15

Ala Val Ser Gly Asp Val Ile Lys Leu Pro Ser Leu Ala Ser Lys Phe
            20                  25                  30

Phe Arg Pro Thr Glu Asn Asp Asp Ser Thr Lys Trp Ala Val Leu
        35                  40                  45

Val Ala Gly Ser Ser Gly Tyr Trp Asn Tyr Arg His Gln Ala Asp Val
50                  55                  60

Cys His Ala Tyr Gln Leu Leu Lys Lys Gly Val Lys Glu Glu Asn
65                  70                  75                  80

Ile Val Val Phe Met Tyr Asp Asp Ile Ala Lys Asn Glu Glu Asn Pro
                85                  90                  95

Arg Pro Gly Val Ile Ile Asn Ser Pro Asn Gly Glu Asp Val Tyr Asn
            100                 105                 110

Gly Val Pro Lys Asp Tyr Thr Gly Asp Glu Val Asn Val Asp Asn Leu
        115                 120                 125

Leu Ala Val Ile Leu Gly Asn Lys Thr Ala Leu Lys Gly Gly Ser Gly
130                 135                 140

Lys Val Val Asp Ser Gly Pro Asn Asp His Ile Phe Ile Tyr Tyr Ser
145                 150                 155                 160

Asp His Gly Gly Pro Gly Val Leu Gly Met Pro Thr Ser Pro Asn Leu
                165                 170                 175

Tyr Ala Asn Asp Leu Asn Asp Val Leu Lys Lys Tyr Ala Ser Gly
            180                 185                 190

Thr Tyr Lys Ser Leu Val Phe Tyr Leu Glu Ala Cys Glu Ser Gly Ser
        195                 200                 205

Ile Phe Glu Gly Leu Leu Pro Glu Gly Leu Asn Ile Tyr Ala Thr Thr
210                 215                 220

Ala Ser Asn Ala Glu Glu Ser Ser Trp Gly Thr Tyr Cys Pro Gly Glu
225                 230                 235                 240

Asp Pro Ser Pro Pro Ser Glu Tyr Glu Thr Cys Leu Gly Asp Leu Tyr
                245                 250                 255

Ser Val Ala Trp Ile Glu Asp Ser Glu Lys His Asn Leu Gln Thr Glu
```

```
                260                 265                 270
Thr Leu His Glu Gln Tyr Glu Leu Val Lys Lys Arg Thr Ala Gly Ser
            275                 280                 285
Gly Lys Ser Tyr Gly Ser His Val Met Glu Phe Gly Asp Ile Gly Leu
        290                 295                 300
Ser Lys Glu Lys Leu Val Leu Phe Met Gly Thr Asn Pro Ala Asp Glu
305                 310                 315                 320
Asn Phe Thr Phe Val Asn Glu Asn Ser Ile Arg Pro Pro Ser Arg Val
                325                 330                 335
Thr Asn Gln Arg Asp Ala Asp Leu Val His Phe Trp His Lys Tyr Gln
            340                 345                 350
Lys Ala Pro Glu Gly Ser Ala Arg Lys Val Glu Ala Gln Lys Gln Val
        355                 360                 365
Leu Glu Ala Met Ser His Arg Leu His Val Asp Asn Ser Ile Leu Leu
    370                 375                 380
Ile Gly Ile Leu Leu Phe Gly Leu Glu Gly His Ala Val Leu Asn Lys
385                 390                 395                 400
Val Arg Pro Ser Gly Glu Pro Leu Val Asp Asp Trp Asp Cys Leu Lys
                405                 410                 415
Ser Leu Val Arg Ala Phe Glu Arg His Cys Gly Ser Leu Ser Gln Tyr
            420                 425                 430
Gly Ile Lys His Met Arg Ser Ile Ala Asn Met Cys Asn Ala Gly Ile
        435                 440                 445
Gln Met Arg Gln Met Glu Glu Ala Ala Met Gln Ala Cys Pro Thr Ile
    450                 455                 460
Pro Thr Ser Pro Trp Ser Ser Leu Asp Arg Gly Phe Ser Ala
465                 470                 475

<210> SEQ ID NO 65
<211> LENGTH: 478
<212> TYPE: PRT
<213> ORGANISM: Genlisea aurea

<400> SEQUENCE: 65

Ile Val Leu Leu Leu Ser Val Ser Ile Leu Thr Ser Asp Cys Arg
1               5                   10                  15
Asn Gln Phe Ile Lys Leu Pro Ser Glu Val Phe Ser Tyr Gly Gly Glu
            20                  25                  30
Ser Glu Asp Asp Ser Val Gly Thr Arg Trp Ala Val Leu Val Ala Gly
        35                  40                  45
Ser Ser Gly Tyr Trp Asn Tyr Arg His Gln Ala Asp Val Cys His Ala
    50                  55                  60
Tyr Gln Ile Leu Lys Arg Gly Gly Leu Lys Asp Glu Asn Ile Ile Val
65                  70                  75                  80
Phe Met Tyr Asp Asp Ile Ala Gln Asn Leu Glu Asn Pro Arg Pro Gly
                85                  90                  95
Ile Val Ile Asn Asn Pro His Gly Glu Asp Val Tyr His Gly Val Pro
            100                 105                 110
Lys Asp Tyr Val Gly Arg Gln Val Thr Ala His Asn Phe Tyr Ser Val
        115                 120                 125
Leu Leu Gly Asp Lys Ala Gly Leu Thr Gly Gly Ser Gly Lys Val Ile
    130                 135                 140
Glu Ser Gly Pro Asn Asp His Ile Phe Ile Tyr Tyr Thr Asp His Gly
145                 150                 155                 160
```

```
Gly Pro Gly Val Leu Gly Met Pro Ser Gly Pro Tyr Ile Tyr Ala Asp
                165                 170                 175

Asp Leu Asn Asp Val Leu Lys Lys His Ala Ser Gly Thr Tyr Lys
            180                 185                 190

Ser Leu Val Phe Tyr Leu Glu Ala Cys Glu Ser Gly Ser Ile Phe Glu
            195                 200                 205

Gly Ile Leu Pro Asp Asn Leu Asn Ile Tyr Ala Thr Thr Ala Ser Asn
            210                 215                 220

Ala Glu Glu Ser Ser Trp Gly Thr Tyr Cys Pro Gly Asp Ile Ile Ala
225                 230                 235                 240

Pro Pro Leu Glu Tyr Asp Thr Cys Leu Gly Asp Leu Tyr Ser Ile Ala
            245                 250                 255

Trp Met Glu Asp Ser Asp Ile His Asn Leu Arg Thr Glu Ser Leu Glu
            260                 265                 270

Gln Gln Tyr Gln Val Val Lys Lys Arg Thr Ala Asn Gly Asp Ser Tyr
            275                 280                 285

Tyr Gly Ser His Val Met Gln Tyr Gly Glu Leu Lys Leu Asp Leu Glu
            290                 295                 300

Asn Leu Phe Leu Tyr Leu Gly Thr Asp Pro Ala Asn Asp Asn Tyr Thr
305                 310                 315                 320

Phe Val Glu Gly Asn Ser Leu Ser Thr Ser Pro Ser Gly Arg Val Asn
            325                 330                 335

Gln Arg Asp Ala Asp Leu Leu His Phe Trp His Lys Phe Trp Lys Ala
            340                 345                 350

Pro Glu Arg Ser Ser Glu Lys Asp Glu Ala Gln Arg Arg Leu Ala Glu
            355                 360                 365

Val Val Ser His Arg Ser His Ile Asp Asp Ser Ile Glu Leu Ile Gly
            370                 375                 380

Asp Leu Leu Phe Gly Ser Thr Glu Gly Thr Arg Val Leu Lys His Val
385                 390                 395                 400

Arg Pro Ser Gly Arg Pro Val Val Asp Asp Trp Asp Cys Leu Arg Ser
            405                 410                 415

Leu Val Arg Thr Phe Glu Thr Tyr Cys Gly Ser Leu Ser Gln Tyr Gly
            420                 425                 430

Met Lys His Met Arg Ser Phe Ala Asn Ile Cys Asn Ser Gly Val Lys
            435                 440                 445

Ala Glu Lys Met Gly Glu Ala Thr Gln Gln Val Cys Thr Ala Phe Pro
            450                 455                 460

Ser His Asn Pro Trp Ser Ser Leu His Arg Gly Phe Ser Ala
465                 470                 475

<210> SEQ ID NO 66
<211> LENGTH: 486
<212> TYPE: PRT
<213> ORGANISM: Zea mays

<400> SEQUENCE: 66

Met Val Ala Ala Arg Leu Arg Leu Ala Leu Leu Leu Ser Val Cys Leu
1               5                   10                  15

Cys Ser Ala Trp Ala Arg Pro Arg Leu Glu Thr Ala Ile Arg Leu Pro
            20                  25                  30

Ser Gln Arg Ala Ala Ala Ala Asp Glu Thr Asp Asp Gly Ala Val Gly
            35                  40                  45

Thr Arg Trp Ala Val Leu Ile Ala Gly Ser Ser Gly Tyr Tyr Asn Tyr
            50                  55                  60
```

```
Arg His Gln Ala Asp Ile Cys His Ala Tyr Gln Ile Met Lys Lys Gly
 65                  70                  75                  80

Gly Leu Lys Asp Glu Asn Ile Ile Val Phe Met Tyr Asp Asp Ile Ala
                 85                  90                  95

His Ser Pro Glu Asn Pro Arg Pro Gly Val Ile Ile Asn His Pro Gln
            100                 105                 110

Gly Gly Asp Val Tyr Ala Gly Val Pro Lys Asp Tyr Thr Gly Arg Asp
        115                 120                 125

Val Asn Val Asp Asn Phe Phe Ala Val Leu Leu Gly Asn Lys Thr Ala
130                 135                 140

Leu Arg Gly Gly Ser Gly Lys Val Val Asp Ser Gly Pro Asp Asp His
145                 150                 155                 160

Ile Phe Val Phe Tyr Ser Asp His Gly Gly Pro Gly Val Leu Gly Met
                165                 170                 175

Pro Thr Tyr Pro Tyr Leu Tyr Gly Asp Asp Leu Val Asp Val Leu Lys
            180                 185                 190

Lys Lys His Ala Ala Gly Thr Tyr Lys Ser Leu Val Phe Tyr Leu Glu
        195                 200                 205

Ala Cys Glu Ser Gly Ser Ile Phe Glu Gly Leu Leu Pro Asn Asp Ile
210                 215                 220

Asn Val Tyr Ala Thr Thr Ala Ser Asn Ala Glu Glu Ser Ser Trp Gly
225                 230                 235                 240

Thr Tyr Cys Pro Gly Glu Phe Pro Ser Pro Pro Glu Tyr Asp Thr
                245                 250                 255

Cys Leu Gly Asp Leu Tyr Ser Val Ala Trp Met Glu Asp Ser Asp Phe
                260                 265                 270

His Asn Leu Arg Thr Glu Ser Leu Lys Gln Gln Tyr Lys Leu Val Lys
            275                 280                 285

Asp Arg Thr Ala Val His Asp Thr Phe Ser Tyr Gly Ser His Val Met
290                 295                 300

Gln Tyr Gly Ala Leu Glu Leu Asn Val Gln Arg Leu Phe Ser Tyr Ile
305                 310                 315                 320

Gly Thr Asp Pro Ala Asn Asp Gly Asn Thr Phe Ile Glu Asp Asn Ser
                325                 330                 335

Leu Pro Ser Phe Ser Lys Ala Val Asn Gln Arg Asp Ala Asp Leu Val
            340                 345                 350

Tyr Phe Trp Gln Lys Tyr Arg Lys Leu Ala Asp Ser Ser Pro Pro Lys
        355                 360                 365

Ser Glu Ala Arg Lys Glu Leu Leu Glu Val Met Ala His Arg Ser His
370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
                405                 410                 415

Val Asp Asp Trp Ser Cys Leu Lys Ser Ile Val Arg Thr Phe Glu Ala
            420                 425                 430

Arg Cys Gly Ser Leu Ala Gln Tyr Gly Met Lys His Met Arg Ser Phe
        435                 440                 445

Ala Asn Met Cys Asn Ala Gly Ile Leu Pro Glu Ala Val Ser Lys Val
450                 455                 460

Thr Ala Gln Ala Cys Ser Ser Ile Pro Ser Asn Pro Trp Ser Ser Ile
465                 470                 475                 480
```

```
His Lys Gly Phe Ser Ala
            485

<210> SEQ ID NO 67
<211> LENGTH: 486
<212> TYPE: PRT
<213> ORGANISM: Zea mays

<400> SEQUENCE: 67

Met Val Ala Ala Arg Leu Arg Leu Ser Leu Leu Ser Val Cys Leu
1               5                   10                  15

Ser Ser Ala Trp Ala Arg Pro Arg Leu Glu Pro Ala Ile Arg Leu Pro
                20                  25                  30

Ser Gln Arg Ala Ala Ala Asp Glu Thr Asp Asp Gly Asp Val Gly
            35                  40                  45

Thr Arg Trp Ala Val Leu Ile Ala Gly Ser Ser Gly Tyr Tyr Asn Tyr
        50                  55                  60

Arg His Gln Ala Asp Ile Cys His Ala Tyr Gln Ile Met Lys Lys Gly
65                  70                  75                  80

Gly Leu Lys Asp Glu Asn Ile Ile Val Phe Met Tyr Asp Asp Ile Ala
                85                  90                  95

His Ser Pro Glu Asn Pro Arg Pro Gly Val Ile Ile Asn His Pro Gln
            100                 105                 110

Gly Gly Asp Val Tyr Ala Gly Val Pro Lys Asp Tyr Thr Gly Arg Asp
        115                 120                 125

Val Asn Val Asp Asn Phe Phe Ala Val Leu Leu Gly Asn Lys Thr Ala
130                 135                 140

Leu Arg Gly Gly Ser Gly Lys Val Val Asp Ser Gly Pro Asn Asp His
145                 150                 155                 160

Ile Phe Val Phe Tyr Ser Asp His Gly Gly Pro Gly Val Leu Gly Met
                165                 170                 175

Pro Thr Tyr Pro Tyr Leu Tyr Gly Asp Asp Leu Val Asp Val Leu Lys
            180                 185                 190

Lys Lys His Ala Ala Gly Thr Tyr Lys Ser Leu Val Phe Tyr Leu Glu
        195                 200                 205

Ala Cys Glu Ser Gly Ser Ile Phe Glu Gly Leu Leu Pro Asn Asp Ile
210                 215                 220

Asn Val Tyr Ala Thr Thr Ala Ser Asn Ala Asp Glu Ser Ser Trp Gly
225                 230                 235                 240

Thr Tyr Cys Pro Gly Glu Phe Pro Ser Pro Pro Glu Tyr Asp Thr
                245                 250                 255

Cys Leu Gly Asp Leu Tyr Ser Val Ala Trp Met Glu Asp Ser Asp Phe
            260                 265                 270

His Asn Leu Arg Thr Glu Ser Leu Lys Gln Gln Tyr Lys Leu Val Lys
        275                 280                 285

Asp Arg Thr Ala Val His Asp Thr Phe Ser Tyr Gly Ser His Val Met
290                 295                 300

Gln Tyr Gly Ala Leu Glu Leu Asn Val Gln Arg Leu Phe Ser Tyr Ile
305                 310                 315                 320

Gly Thr Asp Pro Ala Asn Asp Gly Asn Thr Phe Ile Glu Asp Asn Ser
                325                 330                 335

Leu Pro Ser Phe Ser Lys Ala Val Asn Gln Arg Asp Ala Asp Leu Val
            340                 345                 350

Tyr Phe Trp Gln Lys Tyr Arg Lys Leu Ala Asp Ser Ser His Ala Lys
        355                 360                 365
```

```
Asn Glu Ala Arg Lys Glu Leu Leu Glu Val Met Ala His Arg Ser His
    370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
                405                 410                 415

Val Asp Asp Trp Ser Cys Leu Lys Ser Ile Val Arg Thr Phe Glu Ala
            420                 425                 430

Arg Cys Gly Ser Leu Ala Gln Tyr Gly Met Lys His Met Arg Ser Phe
        435                 440                 445

Ala Asn Met Cys Asn Ala Gly Ile Leu Pro Glu Ala Val Ser Lys Val
    450                 455                 460

Ala Ala Gln Ala Cys Ser Ser Ile Pro Ser Asn Pro Trp Ser Ser Ile
465                 470                 475                 480

His Lys Gly Phe Ser Ala
                485

<210> SEQ ID NO 68
<211> LENGTH: 488
<212> TYPE: PRT
<213> ORGANISM: Saccharum officinarum

<400> SEQUENCE: 68

Met Val Thr Ala Arg Leu Arg Leu Ala Leu Leu Leu Ser Val Phe
1               5                   10                  15

Leu Cys Ser Ala Trp Ala Arg Pro Arg Leu Glu Pro Thr Ile Arg Leu
            20                  25                  30

Pro Ser Glu Arg Ala Ala Ala Ala Gly Asp Glu Thr Asp Asp Ala
        35                  40                  45

Val Gly Thr Arg Trp Ala Val Leu Val Ala Gly Ser Ser Gly Tyr Tyr
    50                  55                  60

Asn Tyr Arg His Gln Ala Asp Ile Cys His Ala Tyr Gln Ile Met Lys
65                  70                  75                  80

Lys Gly Gly Leu Lys Asp Glu Asn Ile Ile Val Phe Met Tyr Asp Asp
                85                  90                  95

Ile Ala His Ser Ala Glu Asn Pro Arg Pro Gly Val Val Ile Asn His
            100                 105                 110

Pro Gln Gly Gly Asp Val Tyr Ala Gly Val Pro Lys Asp Tyr Thr Gly
        115                 120                 125

Arg Gln Val Ser Val Asn Asn Phe Phe Ala Val Leu Leu Gly Asn Lys
    130                 135                 140

Thr Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
            180                 185                 190

Leu Lys Lys Lys His Ala Ala Gly Ser Tyr Lys Ser Leu Val Phe Tyr
        195                 200                 205

Leu Glu Ala Cys Glu Ser Gly Ser Ile Phe Glu Gly Leu Leu Pro Asp
    210                 215                 220

Asp Ile Asn Val Tyr Ala Thr Thr Ala Ser Asn Ala Glu Glu Ser Ser
225                 230                 235                 240

Trp Gly Thr Tyr Cys Pro Gly Glu Phe Pro Ser Pro Pro Pro Glu Tyr
```

```
            245                 250                 255
Asp Thr Cys Leu Gly Asp Leu Tyr Ser Val Ser Trp Met Glu Asp Ser
            260                 265                 270

Asp Phe His Asn Leu Arg Thr Glu Ser Leu Lys Gln Gln Tyr Lys Leu
            275                 280                 285

Val Lys Asp Arg Thr Ala Ala Gln Asp Thr Phe Ser Tyr Gly Ser His
            290                 295                 300

Val Met Gln Tyr Gly Ser Leu Glu Leu Asn Val Gln Lys Leu Phe Ser
305                 310                 315                 320

Tyr Ile Gly Thr Asn Pro Ala Asn Asp Gly Asn Thr Phe Val Glu Asp
                    325                 330                 335

Asn Ser Leu Pro Ser Phe Ser Lys Ala Val Asn Gln Arg Asp Ala Asp
                    340                 345                 350

Leu Val Tyr Phe Trp Gln Lys Tyr Arg Lys Leu Ala Asp Gly Ser Ser
                    355                 360                 365

Lys Lys Asn Glu Ala Arg Lys Glu Leu Leu Glu Val Met Ser His Arg
            370                 375                 380

Ser His Val Asp Asn Ser Val Glu Leu Ile Gly Ser Leu Leu Phe Gly
385                 390                 395                 400

Ser Glu Asp Gly Pro Arg Val Leu Lys Ala Val Arg Ala Ala Gly Glu
                    405                 410                 415

Pro Leu Val Asp Asp Trp Ser Cys Leu Lys Ser Met Val Arg Thr Phe
                    420                 425                 430

Glu Ala Gln Cys Gly Ser Leu Ala Gln Tyr Gly Met Lys His Met Arg
            435                 440                 445

Thr Phe Ala Asn Ile Cys Asn Ala Gly Ile Leu Pro Glu Ala Val Ser
            450                 455                 460

Lys Val Ala Ala Gln Ala Cys Thr Ser Ile Pro Ser Asn Pro Trp Ser
465                 470                 475                 480

Ser Ile Asp Lys Gly Phe Ser Ala
                    485

<210> SEQ ID NO 69
<211> LENGTH: 486
<212> TYPE: PRT
<213> ORGANISM: Zea mays

<400> SEQUENCE: 69

Met Val Ala Ala Arg Leu Arg Leu Ala Leu Leu Leu Ser Val Cys Leu
1               5                   10                  15

Cys Ser Ala Trp Ala Arg Pro Arg Leu Glu Thr Ala Ile Arg Leu Pro
            20                  25                  30

Ser Gln Arg Ala Ala Ala Asp Glu Thr Asp Asp Gly Ala Val Gly
            35                  40                  45

Thr Arg Trp Ala Val Leu Ile Ala Gly Ser Ser Gly Tyr Tyr Asn Tyr
        50                  55                  60

Arg His Gln Ala Asp Ile Cys His Ala Tyr Gln Ile Met Lys Lys Gly
65                  70                  75                  80

Gly Leu Lys Asp Glu Asn Ile Ile Val Phe Met Tyr Asp Asp Ile Ala
                85                  90                  95

His Ser Pro Glu Asn Pro Arg Pro Gly Val Ile Ile Asn His Pro Gln
            100                 105                 110

Gly Gly Asp Val Tyr Ala Gly Val Pro Lys Asp Tyr Thr Gly Arg Asp
            115                 120                 125
```

Val Asn Val Asp Asn Phe Phe Ala Val Leu Leu Gly Asn Lys Thr Ala
            130                 135                 140

Leu Arg Gly Gly Ser Gly Lys Val Val Asp Ser Gly Pro Asp Asp His
145                 150                 155                 160

Ile Phe Val Phe Tyr Ser Asp His Gly Pro Gly Val Leu Gly Met
                165                 170                 175

Pro Thr Tyr Pro Tyr Leu Tyr Gly Asp Asp Leu Val Asp Val Leu Lys
                180                 185                 190

Lys Lys His Ala Ala Gly Thr Tyr Lys Ser Leu Val Phe Tyr Leu Glu
            195                 200                 205

Ala Cys Glu Ser Gly Ser Ile Phe Glu Gly Leu Leu Pro Asn Asp Ile
210                 215                 220

Asn Val Tyr Ala Thr Thr Ala Ser Asn Ala Glu Glu Ser Ser Trp Gly
225                 230                 235                 240

Thr Tyr Cys Pro Gly Glu Phe Pro Ser Pro Pro Glu Tyr Asp Thr
                245                 250                 255

Cys Leu Gly Asp Leu Tyr Ser Val Ala Trp Met Glu Asp Ser Asp Phe
                260                 265                 270

His Asn Leu Arg Thr Glu Ser Leu Lys Gln Gln Tyr Lys Leu Val Lys
            275                 280                 285

Asp Arg Thr Ala Val His Asp Thr Phe Ser Tyr Gly Ser His Val Met
290                 295                 300

Gln Tyr Gly Ala Leu Glu Leu Asn Val Gln His Leu Phe Ser Tyr Ile
305                 310                 315                 320

Gly Thr Asp Pro Ala Asn Asp Gly Asn Thr Phe Ile Glu Asp Asn Ser
                325                 330                 335

Leu Pro Ser Phe Ser Lys Ala Val Asn Gln Arg Asp Ala Asp Leu Val
                340                 345                 350

Tyr Phe Trp Gln Lys Tyr Arg Lys Phe Ala Asp Ser Pro Ala Lys
            355                 360                 365

Ser Glu Ala Arg Lys Glu Leu Leu Glu Val Met Ala His Arg Ser His
            370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
                405                 410                 415

Val Asp Asp Trp Ser Cys Leu Lys Ser Ile Val Arg Thr Phe Glu Ala
                420                 425                 430

Arg Cys Gly Ser Leu Ala Gln Tyr Gly Met Lys His Met Arg Ser Phe
            435                 440                 445

Ala Asn Met Cys Asn Ala Gly Ile Leu Pro Glu Ala Val Ser Lys Val
450                 455                 460

Ala Ala Gln Ala Cys Ser Ser Ile Pro Ser Asn Pro Trp Ser Ser Ile
465                 470                 475                 480

His Lys Gly Phe Ser Ala
                485

<210> SEQ ID NO 70
<211> LENGTH: 481
<212> TYPE: PRT
<213> ORGANISM: Sorghum bicolor

<400> SEQUENCE: 70

Met Val Ala Ala Arg Leu Arg Leu Ala Leu Leu Leu Leu Leu Pro Val
1               5                   10                  15

```
Phe Leu Cys Ser Ala Trp Ala Arg Pro Arg Leu Glu Pro Thr Ile Arg
             20                  25                  30

Leu Pro Ser Asp Arg Ala Asp Ala Val Gly Thr Arg Trp Ala Val
         35                  40                  45

Leu Val Ala Gly Ser Asn Gly Tyr Tyr Asn Tyr Arg His Gln Ala Asp
     50                  55                  60

Ile Cys His Ala Tyr Gln Ile Met Lys Lys Gly Gly Leu Lys Asp Glu
65                   70                  75                  80

Asn Ile Ile Val Phe Met Tyr Asp Asp Ile Ala His Ser Pro Glu Asn
                 85                  90                  95

Pro Arg Pro Gly Val Leu Ile Asn His Pro Gln Gly Gly Asp Val Tyr
             100                 105                 110

Ala Gly Val Pro Lys Asp Tyr Thr Gly Arg Glu Val Ser Val Asn Asn
             115                 120                 125

Phe Phe Ala Val Leu Leu Gly Asn Lys Thr Ala Leu Lys Gly Gly Ser
130                 135                 140

Gly Lys Val Val Asp Ser Gly Pro Asn Asp His Ile Phe Val Phe Tyr
145                 150                 155                 160

Ser Asp His Gly Gly Pro Gly Val Leu Gly Met Pro Thr Tyr Pro Tyr
                 165                 170                 175

Leu Tyr Gly Asp Asp Leu Val Asp Val Leu Lys Lys Lys His Ala Ala
             180                 185                 190

Gly Thr Tyr Lys Ser Leu Val Phe Tyr Leu Glu Ala Cys Glu Ser Gly
             195                 200                 205

Ser Ile Phe Glu Gly Leu Leu Pro Asp Asp Ile Asn Val Tyr Ala Thr
             210                 215                 220

Thr Ala Ser Asn Ala Glu Glu Ser Ser Trp Gly Thr Tyr Cys Pro Gly
225                 230                 235                 240

Glu Phe Pro Ser Pro Pro Glu Tyr Asp Thr Cys Leu Gly Asp Leu
                 245                 250                 255

Tyr Ser Val Ser Trp Met Glu Asp Ser Asp Phe His Asn Leu Arg Thr
             260                 265                 270

Glu Ser Leu Lys Gln Gln Tyr Lys Leu Val Lys Asp Arg Thr Ala Val
             275                 280                 285

Gln Asp Thr Phe Ser Tyr Gly Ser His Val Met Gln Tyr Gly Ser Leu
290                 295                 300

Glu Leu Asn Val Gln Lys Leu Phe Ser Tyr Ile Gly Thr Asn Pro Ala
305                 310                 315                 320

Asn Asp Gly Asn Thr Phe Val Glu Asp Asn Ser Leu Pro Ser Phe Ser
                 325                 330                 335

Lys Ala Val Asn Gln Arg Asp Ala Asp Leu Val Tyr Phe Trp Gln Lys
             340                 345                 350

Tyr Arg Lys Leu Ala Asp Asp Ser Ser Lys Lys Asn Glu Ala Arg Lys
             355                 360                 365

Glu Leu Leu Glu Val Met Ala His Arg Ser His Val Asp Asn Ser Val
             370                 375                 380

Glu Leu Ile Gly Ser Leu Leu Phe Gly Ser Glu Asp Gly Pro Arg Val
385                 390                 395                 400

Leu Lys Ala Val Arg Ala Ala Gly Glu Pro Leu Val Asp Asp Trp Ser
                 405                 410                 415

Cys Leu Lys Ser Met Val Arg Thr Phe Glu Ala Gln Cys Gly Ser Leu
             420                 425                 430
```

```
Ala Gln Tyr Gly Met Lys His Met Arg Ser Phe Ala Asn Ile Cys Asn
            435                 440                 445

Ala Gly Ile Leu Pro Glu Ala Val Ser Lys Val Ala Ala Gln Ala Cys
    450                 455                 460

Thr Ser Ile Pro Ser Asn Pro Trp Ser Ile Asp Lys Gly Phe Ser
465                 470                 475                 480

Ala

<210> SEQ ID NO 71
<211> LENGTH: 488
<212> TYPE: PRT
<213> ORGANISM: Saccharum hybrid cultivar SP80-3280

<400> SEQUENCE: 71

Met Val Ala Ala Arg Leu Arg Leu Ala Leu Leu Leu Ser Val Cys
1               5                   10                  15

Leu Cys Ser Ala Trp Ala Arg Pro Arg Leu Glu Pro Thr Ile Arg Leu
            20                  25                  30

Pro Ser Glu Arg Ala Ala Ala Ala Gly Asp Glu Thr Asp Asp Ala
            35                  40                  45

Val Gly Thr Arg Trp Ala Val Leu Val Ala Gly Ser Ser Gly Tyr Tyr
    50                  55                  60

Asn Tyr Arg His Gln Ala Asp Ile Cys His Ala Tyr Gln Ile Met Lys
65                  70                  75                  80

Lys Gly Gly Leu Lys Asp Glu Asn Ile Ile Val Phe Met Tyr Asp Asp
                85                  90                  95

Ile Ala His Ser Ala Glu Asn Pro Arg Pro Gly Val Val Ile Asn His
            100                 105                 110

Pro Gln Gly Gly Asp Val Tyr Ala Gly Val Pro Lys Asp Tyr Thr Gly
        115                 120                 125

Arg Gln Val Ser Val Asn Asn Phe Phe Ala Val Leu Leu Gly Asn Lys
130                 135                 140

Thr Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
            180                 185                 190

Leu Lys Lys Lys His Ala Ala Gly Thr Tyr Lys Ser Leu Val Phe Tyr
        195                 200                 205

Leu Glu Ala Cys Glu Ser Gly Ser Ile Phe Glu Gly Leu Leu Pro Asp
    210                 215                 220

Asp Ile Asn Val Tyr Ala Thr Thr Ala Ser Asn Ala Glu Glu Ser Ser
225                 230                 235                 240

Trp Gly Thr Tyr Cys Pro Gly Glu Phe Pro Ser Pro Pro Glu Tyr
                245                 250                 255

Asp Thr Cys Leu Gly Asp Leu Tyr Ser Val Ser Trp Met Glu Asp Ser
            260                 265                 270

Asp Phe His Asn Leu Arg Thr Glu Ser Leu Lys Gln Gln Tyr Lys Leu
        275                 280                 285

Val Lys Asp Arg Thr Ala Ala Gln Asp Thr Phe Ser Tyr Gly Ser His
    290                 295                 300

Val Met Gln Tyr Gly Ser Leu Glu Leu Asn Val Gln Lys Leu Phe Ser
305                 310                 315                 320
```

Tyr Ile Gly Thr Asn Pro Ala Asn Asp Gly Asn Thr Phe Val Glu Asp
                325                 330                 335

Asn Ser Leu Pro Ser Phe Phe Lys Ser Cys Asn Gln Arg Asp Ala Asp
            340                 345                 350

Leu Val Tyr Phe Trp Gln Lys Tyr Arg Lys Leu Ala Asp Gly Ser Ser
        355                 360                 365

Lys Lys Asn Glu Ala Arg Lys Glu Leu Leu Glu Val Met Ser His Arg
370                 375                 380

Ser His Val Asp Asn Ser Val Glu Leu Ile Gly Ser Leu Leu Phe Gly
385                 390                 395                 400

Ser Glu Asp Gly Pro Arg Val Leu Lys Ala Val Arg Ala Ala Gly Glu
                405                 410                 415

Pro Leu Val Asp Asp Trp Ser Cys Leu Lys Ser Met Val Arg Thr Phe
            420                 425                 430

Glu Ala Gln Cys Gly Ser Leu Ala Gln Tyr Gly Met Lys His Met Arg
        435                 440                 445

Thr Phe Ala Asn Ile Cys Asn Ala Gly Ile Leu Pro Glu Ala Val Ser
    450                 455                 460

Lys Val Ala Ala Gln Ala Cys Thr Ser Ile Pro Ser Asn Pro Trp Ser
465                 470                 475                 480

Ser Ile Asp Lys Gly Phe Ser Ala
                485

<210> SEQ ID NO 72
<211> LENGTH: 503
<212> TYPE: PRT
<213> ORGANISM: Oryza sativa Japonica Group

<400> SEQUENCE: 72

Met Ala Ala Arg Ala Ser Ala Phe Arg Leu Val Leu Pro Pro Ala Arg
1               5                   10                  15

Gly Ala Ala Pro Ser Phe Ala His Leu Ala Ala Val Ala Val Ala Arg
                20                  25                  30

Pro Arg Trp Glu Glu Glu Gly Ser Asn Leu Arg Leu Pro Ser Glu Arg
        35                  40                  45

Ala Val Ala Ala Gly Ala Ala Asp Asp Ala Ala Glu Ala Ala Glu
    50                  55                  60

Gly Thr Arg Trp Ala Val Leu Ile Ala Gly Ser Asn Gly Tyr Tyr Asn
65                  70                  75                  80

Tyr Arg His Gln Ala Asp Val Cys His Ala Tyr Gln Ile Met Lys Arg
                85                  90                  95

Gly Gly Leu Lys Asp Glu Asn Ile Ile Val Phe Met Tyr Asp Asp Ile
                100                 105                 110

Ala His Asn Pro Glu Asn Pro Arg Pro Gly Val Ile Ile Asn His Pro
            115                 120                 125

Gln Gly Gly Asp Val Tyr Ala Gly Val Pro Lys Asp Tyr Thr Gly Lys
        130                 135                 140

Glu Val Asn Val Lys Asn Leu Phe Ala Val Leu Leu Gly Asn Lys Thr
145                 150                 155                 160

Ala Val Lys Gly Gly Ser Gly Lys Val Leu Asp Ser Gly Pro Asn Asp
                165                 170                 175

His Ile Phe Ile Phe Tyr Ser Asp His Gly Gly Pro Gly Val Leu Gly
            180                 185                 190

Met Pro Thr Tyr Pro Tyr Leu Tyr Gly Asp Asp Leu Val Asp Val Leu
        195                 200                 205

```
Lys Lys Lys His Ala Ala Gly Thr Tyr Lys Ser Leu Val Phe Tyr Leu
        210                 215                 220

Glu Ala Cys Glu Ser Gly Ser Ile Phe Glu Gly Leu Leu Pro Asn Gly
225                 230                 235                 240

Ile Asn Val Tyr Ala Thr Thr Ala Ser Asn Ala Asp Glu Ser Ser Trp
                245                 250                 255

Gly Thr Tyr Cys Pro Gly Glu Tyr Pro Ser Pro Pro Glu Tyr Asp
                260                 265                 270

Thr Cys Leu Gly Asp Leu Tyr Ser Val Ala Trp Met Glu Asp Ser Asp
        275                 280                 285

Val His Asn Leu Arg Thr Glu Ser Leu Lys Gln Gln Tyr Asn Leu Val
        290                 295                 300

Lys Glu Arg Thr Ser Val Gln His Thr Tyr Tyr Ser Gly Ser His Val
305                 310                 315                 320

Met Glu Tyr Gly Ser Leu Glu Leu Asn Ala His His Val Phe Met Tyr
                325                 330                 335

Met Gly Ser Asn Pro Ala Asn Asp Asn Ala Thr Phe Val Glu Asp Asn
                340                 345                 350

Ser Leu Pro Ser Phe Ser Arg Ala Val Asn Gln Arg Asp Ala Asp Leu
        355                 360                 365

Val Tyr Phe Trp Gln Lys Tyr Arg Lys Leu Pro Glu Ser Ser Pro Glu
        370                 375                 380

Lys Asn Glu Ala Arg Lys Gln Leu Leu Glu Met Met Ala His Arg Ser
385                 390                 395                 400

His Val Asp Asn Ser Val Glu Leu Ile Gly Asn Leu Leu Phe Gly Ser
                405                 410                 415

Glu Glu Gly Pro Arg Val Leu Lys Ala Val Arg Ala Thr Gly Glu Pro
                420                 425                 430

Leu Val Asp Asp Trp Ser Cys Leu Lys Ser Met Val Arg Thr Phe Glu
        435                 440                 445

Ala Gln Cys Gly Ser Leu Ala Gln Tyr Gly Met Lys His Met Arg Ser
        450                 455                 460

Phe Ala Asn Ile Cys Asn Ala Gly Ile Ser Ala Glu Ala Met Ala Lys
465                 470                 475                 480

Val Ala Ala Gln Ala Cys Thr Ser Ile Pro Ser Asn Pro Trp Ser Ser
                485                 490                 495

Thr His Arg Gly Phe Ser Ala
                500

<210> SEQ ID NO 73
<211> LENGTH: 481
<212> TYPE: PRT
<213> ORGANISM: Zea mays

<400> SEQUENCE: 73

Met Val Ala Asp Arg Leu Arg Leu Ala Leu Leu Ser Ala Cys Leu
1               5                   10                  15

Cys Ser Ala Trp Ala Arg Pro Arg Leu Glu Pro Thr Ile Arg Leu Pro
                20                  25                  30

Ser Glu Arg Ala Ala Ala Asp Asp Ala Val Gly Thr Arg Trp Ala Val
                35                  40                  45

Leu Ile Ala Gly Ser Asn Gly Tyr Tyr Asn Tyr Arg His Gln Ala Asp
        50                  55                  60

Ile Cys His Ala Tyr Gln Ile Met Lys Lys Gly Gly Leu Lys Asp Glu
```

```
            65                  70                  75                  80
Asn Ile Val Val Phe Met Tyr Asp Asp Ile Ala His Ser Pro Glu Asn
                85                  90                  95

Pro Arg Pro Gly Val Ile Ile Asn His Pro Gln Gly Gly Asp Val Tyr
               100                 105                 110

Ala Gly Val Pro Lys Asp Tyr Thr Gly Arg Glu Val Asn Val Asp Asn
               115                 120                 125

Phe Phe Ala Val Leu Leu Gly Asn Lys Thr Ala Leu Arg Gly Gly Ser
130                 135                 140

Gly Lys Val Val Asp Ser Gly Pro Asn Asp His Ile Phe Val Phe Tyr
145                 150                 155                 160

Ser Asp His Gly Gly Pro Gly Val Leu Gly Met Pro Thr Tyr Pro Tyr
                165                 170                 175

Leu Tyr Gly Asp Asp Leu Val Asp Val Leu Lys Lys His Ala Ala
                180                 185                 190

Gly Thr Tyr Lys Ser Leu Val Phe Tyr Leu Glu Ala Cys Glu Ser Gly
                195                 200                 205

Ser Ile Phe Glu Gly Leu Leu Pro Asn Asp Ile Asn Val Tyr Ala Thr
210                 215                 220

Thr Ala Ser Asn Ala Glu Glu Ser Ser Trp Gly Thr Tyr Cys Pro Gly
225                 230                 235                 240

Glu Phe Pro Ser Pro Pro Glu Tyr Asp Thr Cys Leu Gly Asp Leu
                245                 250                 255

Tyr Ser Val Ala Trp Met Glu Asp Ser Asp Phe His Asn Leu Arg Thr
                260                 265                 270

Glu Ser Leu Lys Gln Gln Tyr Asn Leu Val Lys Asp Arg Thr Ala Val
                275                 280                 285

Gln Asp Thr Phe Ser Tyr Gly Ser His Val Met Gln Tyr Gly Ser Leu
                290                 295                 300

Glu Leu Asn Val Lys His Leu Phe Ser Tyr Ile Gly Thr Asn Pro Ala
305                 310                 315                 320

Asn Asp Asp Asn Thr Phe Ile Glu Asp Asn Ser Leu Pro Ser Phe Ser
                325                 330                 335

Lys Ala Val Asn Gln Arg Asp Ala Asp Leu Val Tyr Phe Trp Gln Lys
                340                 345                 350

Tyr Arg Lys Leu Ala Asp Ser Ser Pro Glu Lys Asn Glu Ala Arg Lys
                355                 360                 365

Glu Leu Leu Glu Val Met Ala His Arg Ser His Val Asp Ser Ser Val
370                 375                 380

Glu Leu Ile Gly Ser Leu Leu Phe Gly Ser Glu Asp Gly Pro Arg Val
385                 390                 395                 400

Leu Lys Ala Val Arg Ala Ala Gly Glu Pro Leu Val Asp Asp Trp Ser
                405                 410                 415

Cys Leu Lys Ser Thr Val Arg Thr Phe Glu Ala Gln Cys Gly Ser Leu
                420                 425                 430

Ala Gln Tyr Gly Met Lys His Met Arg Ser Phe Ala Asn Ile Cys Asn
                435                 440                 445

Ala Gly Ile Leu Pro Glu Ala Val Ser Lys Val Ala Ala Gln Ala Cys
                450                 455                 460

Thr Ser Ile Pro Ser Asn Pro Trp Ser Ser Ile His Lys Gly Phe Ser
465                 470                 475                 480

Ala
```

<210> SEQ ID NO 74
<211> LENGTH: 481
<212> TYPE: PRT
<213> ORGANISM: Zea mays

<400> SEQUENCE: 74

```
Met Val Ala Asp Arg Leu Arg Leu Ala Leu Leu Ser Ala Cys Leu
1               5                   10                  15

Cys Ser Ala Trp Ala Arg Pro Arg Leu Glu Pro Thr Ile Arg Leu Pro
            20                  25                  30

Ser Asp Arg Ala Ala Ala Asp Ala Val Gly Thr Arg Trp Ala Val
        35                  40                  45

Leu Ile Ala Gly Ser Asn Gly Tyr Tyr Asn Tyr Arg His Gln Ala Asp
    50                  55                  60

Ile Cys His Ala Tyr Gln Ile Met Lys Lys Gly Gly Leu Lys Asp Glu
65                  70                  75                  80

Asn Ile Val Val Phe Met Tyr Asp Asp Ile Ala His Ser Pro Glu Asn
                85                  90                  95

Pro Arg Pro Gly Val Ile Ile Asn His Pro Gln Gly Gly Asp Val Tyr
            100                 105                 110

Ala Gly Val Pro Lys Asp Tyr Thr Gly Arg Asp Val Asn Val Asp Asn
        115                 120                 125

Phe Phe Ala Val Leu Leu Gly Asn Lys Thr Ala Leu Arg Gly Gly Ser
130                 135                 140

Gly Lys Val Val Asp Ser Gly Pro Asn Asp His Ile Ser Val Phe Tyr
145                 150                 155                 160

Ser Asp His Gly Gly Pro Gly Val Leu Gly Met Pro Thr Tyr Pro Tyr
                165                 170                 175

Leu Tyr Gly Asp Asp Leu Val Asp Val Leu Lys Lys His Ala Ala
            180                 185                 190

Gly Thr Tyr Lys Ser Leu Val Phe Tyr Leu Glu Ala Cys Glu Ser Gly
        195                 200                 205

Ser Ile Phe Glu Gly Leu Leu Pro Asn Asp Ile Asn Val Tyr Ala Thr
210                 215                 220

Thr Ala Ser Asn Ala Glu Glu Ser Ser Trp Gly Thr Tyr Cys Pro Gly
225                 230                 235                 240

Glu Phe Pro Ser Pro Pro Glu Tyr Asp Thr Cys Leu Gly Asp Leu
                245                 250                 255

Tyr Ser Val Ala Trp Met Glu Asp Ser Asp Phe His Asn Leu Arg Thr
            260                 265                 270

Glu Ser Leu Lys Gln Gln Tyr Asn Leu Val Lys Asp Arg Thr Ala Val
        275                 280                 285

Gln Asp Thr Phe Ser Tyr Gly Ser His Val Met Gln Tyr Gly Ser Leu
290                 295                 300

Gly Leu Asn Val Lys His Leu Phe Ser Tyr Ile Gly Thr Asn Pro Ala
305                 310                 315                 320

Asn Asp Asp Asn Thr Phe Ile Glu Asp Asn Ser Leu Pro Ser Phe Ser
                325                 330                 335

Lys Ala Val Asn Gln Arg Asp Ala Asp Leu Val Tyr Phe Trp Gln Lys
            340                 345                 350

Tyr Arg Lys Leu Ala Asp Ser Ser Pro Glu Lys Asn Glu Ala Arg Arg
        355                 360                 365

Glu Leu Leu Glu Val Met Ala His Arg Ser His Val Asp Ser Ser Val
370                 375                 380
```

```
Glu Leu Ile Gly Ser Leu Phe Gly Ser Glu Asp Gly Pro Arg Val
385                 390                 395                 400

Leu Lys Ala Val Arg Ala Gly Glu Pro Leu Val Asp Asp Trp Ser
                405                 410                 415

Cys Leu Lys Ser Thr Val Arg Thr Phe Glu Ala Gln Cys Gly Ser Leu
                420                 425                 430

Ala Gln Tyr Gly Met Lys His Met Arg Ser Phe Ala Asn Ile Cys Asn
            435                 440                 445

Ala Gly Ile Leu Pro Glu Ala Val Ser Lys Val Ala Ala Gln Ala Cys
        450                 455                 460

Thr Ser Ile Pro Ser Asn Pro Trp Ser Ser Ile His Lys Gly Phe Ser
465                 470                 475                 480

Ala

<210> SEQ ID NO 75
<211> LENGTH: 501
<212> TYPE: PRT
<213> ORGANISM: Oryza sativa Japonica Group

<400> SEQUENCE: 75

Met Ala Ala Arg Ala Arg Leu Arg Leu Val Leu Pro Pro Leu Ala Ala
1               5                   10                  15

Leu Leu Leu Phe Ala His Leu Ala Ala Val Ala Val Ala Arg Pro Arg
                20                  25                  30

Trp Glu Glu Glu Gly Ser Asn Leu Arg Leu Pro Ser Glu Arg Ala Val
            35                  40                  45

Ala Ala Gly Ala Ala Ala Asp Asp Ala Ala Glu Ala Ala Glu Gly Thr
        50                  55                  60

Arg Trp Ala Val Leu Ile Ala Gly Ser Asn Gly Tyr Tyr Asn Tyr Arg
65                  70                  75                  80

His Gln Ala Asp Val Cys His Ala Tyr Gln Ile Met Lys Arg Gly Gly
                85                  90                  95

Leu Lys Asp Glu Asn Ile Ile Val Phe Met Tyr Asp Asp Ile Ala His
                100                 105                 110

Asn Pro Glu Asn Pro Arg Pro Gly Val Ile Ile Asn His Pro Gln Gly
            115                 120                 125

Gly Asp Val Tyr Ala Gly Val Pro Lys Asp Tyr Thr Gly Lys Glu Val
        130                 135                 140

Asn Val Lys Asn Leu Phe Ala Val Leu Leu Gly Asn Lys Thr Ala Val
145                 150                 155                 160

Lys Gly Gly Ser Gly Lys Val Leu Asp Ser Gly Pro Asn Asp His Ile
                165                 170                 175

Phe Ile Phe Tyr Ser Asp His Gly Gly Pro Gly Val Leu Gly Met Pro
                180                 185                 190

Thr Tyr Pro Tyr Leu Tyr Gly Asp Asp Leu Val Asp Val Leu Lys Lys
            195                 200                 205

Lys His Ala Ala Gly Thr Tyr Lys Ser Leu Val Phe Tyr Leu Glu Ala
        210                 215                 220

Cys Glu Ser Gly Ser Ile Phe Glu Gly Leu Leu Pro Asn Gly Ile Asn
225                 230                 235                 240

Val Tyr Ala Thr Thr Ala Ser Asn Ala Asp Glu Ser Ser Trp Gly Thr
                245                 250                 255

Tyr Cys Pro Gly Glu Tyr Pro Ser Pro Pro Glu Tyr Asp Thr Cys
                260                 265                 270
```

```
Leu Gly Asp Leu Tyr Ser Val Ala Trp Met Glu Asp Ser Asp Val His
            275                 280                 285

Asn Leu Arg Thr Glu Ser Leu Lys Gln Gln Tyr Asn Leu Val Lys Glu
    290                 295                 300

Arg Thr Ser Val Gln His Thr Tyr Tyr Ser Gly Ser His Val Met Glu
305                 310                 315                 320

Tyr Gly Ser Leu Glu Leu Asn Ala His His Val Phe Met Tyr Met Gly
                325                 330                 335

Ser Asn Pro Ala Asn Asp Asn Ala Thr Phe Val Glu Asp Asn Ser Leu
            340                 345                 350

Pro Ser Phe Ser Arg Ala Val Asn Gln Arg Asp Ala Asp Leu Val Tyr
        355                 360                 365

Phe Trp Gln Lys Tyr Arg Lys Leu Pro Glu Ser Ser Pro Glu Lys Asn
370                 375                 380

Glu Ala Arg Lys Gln Leu Leu Glu Met Met Ala His Arg Ser His Val
385                 390                 395                 400

Asp Asn Ser Val Glu Leu Ile Gly Asn Leu Leu Phe Gly Ser Glu Glu
                405                 410                 415

Gly Pro Arg Val Leu Lys Ala Val Arg Ala Thr Gly Glu Pro Leu Val
            420                 425                 430

Asp Asp Trp Ser Cys Leu Lys Ser Met Val Arg Thr Phe Glu Ala Gln
        435                 440                 445

Cys Gly Ser Leu Ala Gln Tyr Gly Met Lys His Met Arg Ser Phe Ala
450                 455                 460

Asn Ile Cys Asn Ala Gly Ile Ser Ala Glu Ala Met Ala Lys Val Ala
465                 470                 475                 480

Ala Gln Ala Cys Thr Ser Ile Pro Ser Asn Pro Trp Ser Ser Thr His
                485                 490                 495

Arg Gly Phe Ser Ala
            500

<210> SEQ ID NO 76
<211> LENGTH: 485
<212> TYPE: PRT
<213> ORGANISM: Zea mays

<400> SEQUENCE: 76

Met Val Ala Asp Arg Leu Arg Leu Ala Leu Leu Ser Ala Cys Leu
1               5                   10                  15

Cys Ser Ala Trp Ala Arg Pro Arg Leu Glu Pro Thr Ile Arg Leu Pro
            20                  25                  30

Ser Glu Arg Ala Ala Ala Asp Glu Thr Asp Asp Ala Val Gly Thr
        35                  40                  45

Arg Trp Ala Val Leu Ile Ala Gly Ser Asn Gly Tyr Tyr Asn Tyr Arg
50                  55                  60

His Gln Ala Asp Ile Cys His Ala Tyr Gln Ile Met Lys Lys Gly Gly
65                  70                  75                  80

Leu Lys Asp Glu Asn Ile Val Val Phe Met Tyr Asp Asp Ile Ala His
                85                  90                  95

Ser Pro Glu Asn Pro Arg Pro Gly Val Ile Ile Asn His Pro Gln Gly
            100                 105                 110

Gly Asp Val Tyr Ala Gly Val Pro Lys Asp Tyr Thr Gly Arg Asp Val
        115                 120                 125

Asn Val Asp Asn Phe Phe Ala Val Leu Leu Gly Asn Lys Thr Ala Leu
```

130                 135                 140
Arg Gly Ser Gly Lys Val Asp Ser Gly Pro Asn Asp His Ile
145                 150                 155                 160

Phe Val Phe Tyr Ser Asp His Gly Pro Gly Val Leu Gly Met Pro
                    165                 170                 175

Thr Tyr Pro Tyr Leu Tyr Gly Asp Asp Leu Val Asp Val Leu Lys Lys
                    180                 185                 190

Lys His Ala Ala Gly Thr Tyr Lys Ser Leu Val Phe Tyr Leu Glu Ala
                195                 200                 205

Cys Glu Ser Gly Ser Ile Phe Glu Gly Leu Leu Pro Asn Asp Ile Asn
            210                 215                 220

Val Tyr Ala Thr Thr Ala Ser Asn Ala Glu Glu Ser Ser Trp Gly Thr
225                 230                 235                 240

Tyr Cys Pro Gly Glu Phe Pro Ser Pro Pro Glu Tyr Asp Thr Cys
                    245                 250                 255

Leu Gly Asp Leu Tyr Ser Val Ala Trp Met Glu Asp Ser Asp Phe His
                260                 265                 270

Asn Leu Arg Thr Glu Ser Leu Lys Gln Gln Tyr Asn Leu Val Lys Asp
            275                 280                 285

Arg Thr Ala Val Gln Asp Thr Phe Ser Tyr Gly Ser His Val Met Gln
290                 295                 300

Tyr Gly Ser Leu Glu Leu Asn Val Lys His Leu Phe Ser Tyr Ile Gly
305                 310                 315                 320

Thr Asn Pro Ala Asn Asp Asp Asn Thr Phe Ile Glu Asp Asn Ser Leu
                    325                 330                 335

Pro Ser Leu Ser Lys Ala Val Asn Gln Arg Asp Ala Asp Leu Val Tyr
                340                 345                 350

Phe Trp Gln Lys Tyr Arg Lys Leu Ala Asp Ser Ser Pro Glu Lys Asn
            355                 360                 365

Glu Ala Arg Arg Glu Leu Leu Glu Val Met Ala His Arg Ser His Val
        370                 375                 380

Asp Ser Ser Val Glu Leu Ile Gly Ser Leu Leu Phe Gly Ser Glu Asp
385                 390                 395                 400

Gly Pro Arg Val Leu Lys Ala Val Arg Ala Ala Gly Glu Pro Leu Val
                    405                 410                 415

Asp Asp Trp Ser Cys Leu Lys Ser Thr Val Arg Thr Phe Glu Ala Gln
                420                 425                 430

Cys Gly Ser Leu Ala Gln Tyr Gly Met Lys His Met Arg Ser Phe Ala
            435                 440                 445

Asn Ile Cys Asn Ala Gly Ile Leu Pro Glu Ala Val Ser Lys Val Ala
450                 455                 460

Ala Gln Ala Cys Thr Ser Ile Pro Ser Asn Pro Trp Ser Ser Ile His
465                 470                 475                 480

Lys Gly Phe Ser Ala
                485

<210> SEQ ID NO 77
<211> LENGTH: 488
<212> TYPE: PRT
<213> ORGANISM: Brachypodium distachyon

<400> SEQUENCE: 77

Met Ala Ser Phe Arg Leu Leu Pro Leu Ala Leu Leu Leu Cys Ala Cys
1               5                   10                  15

```
Leu Ser Ala His Ala Arg Thr Ser Leu Leu Glu Gln Thr Ile Arg Leu
             20                  25                  30

Pro Ser Gln Arg Gly Ala Ala Gly Gln Gln Glu Val Asp Asp Asp Ser
         35                  40                  45

Val Gly Thr Arg Trp Ala Val Leu Ile Ala Gly Ser Asn Gly Tyr Tyr
     50                  55                  60

Asn Tyr Arg His Gln Ala Asp Ile Cys His Ala Tyr Gln Ile Met Lys
 65                  70                  75                  80

Lys Gly Gly Leu Lys Asp Glu Asn Ile Ile Val Phe Met Tyr Asp Asp
                 85                  90                  95

Ile Ala His Asn Pro Glu Asn Pro Arg Pro Gly Val Ile Ile Asn His
             100                 105                 110

Pro Gln Gly Gly Asp Val Tyr Ala Gly Val Pro Lys Asp Tyr Thr Gly
         115                 120                 125

Lys Glu Val Asn Val Lys Asn Phe Phe Ala Val Leu Leu Gly Asn Lys
    130                 135                 140

Ala Ala Val Ser Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
            180                 185                 190

Leu Lys Lys Lys His Ala Ala Gly Thr Tyr Lys Ser Leu Val Phe Tyr
        195                 200                 205

Leu Glu Ala Cys Glu Ser Gly Ser Ile Phe Glu Gly Leu Leu Pro Asn
    210                 215                 220

Asp Ile Gly Ile Tyr Ala Thr Thr Ala Ser Asn Ala Glu Glu Ser Ser
225                 230                 235                 240

Trp Gly Thr Tyr Cys Pro Gly Glu Tyr Pro Ser Pro Pro Glu Tyr
                245                 250                 255

Asp Thr Cys Leu Gly Asp Leu Tyr Ser Ile Ala Trp Met Glu Asp Ser
            260                 265                 270

Asp Val His Asn Leu Arg Thr Glu Ser Leu Lys Gln Gln Tyr Asp Leu
        275                 280                 285

Val Lys Lys Arg Thr Ala Pro Glu Asn Ser Tyr Ser Tyr Gly Ser His
    290                 295                 300

Val Met Gln Tyr Gly Ser Leu Asp Leu Asn Ala Glu His Leu Phe Leu
305                 310                 315                 320

Tyr Ile Gly Ser Asn Pro Ala Asn Asp Asn Thr Thr Phe Val Glu Gly
                325                 330                 335

Asn Ser Leu Pro Ser Phe Ser Arg Ala Val Asn Gln Arg Asp Ala Asp
            340                 345                 350

Leu Val Tyr Phe Trp Gln Lys Tyr Arg Lys Leu Ala Glu Ser Ser Pro
        355                 360                 365

Ala Lys Asn Asp Ala Arg Lys Glu Leu Leu Glu Met Met Ala His Arg
    370                 375                 380

Ser His Val Asp Asn Ser Val Glu Leu Thr Gly Asn Leu Leu Phe Gly
385                 390                 395                 400

Ser Glu Asp Gly Pro Met Val Leu Lys Thr Val Arg Thr Ala Gly Glu
                405                 410                 415

Pro Leu Val Asp Asp Trp Gly Cys Leu Lys Ser Thr Val Arg Ala Phe
            420                 425                 430

Glu Ser Gln Cys Gly Ser Leu Ala Gln Tyr Gly Met Lys His Met Arg
```

```
            435                 440                 445
Ser Phe Ala Asn Ile Cys Asn Ala Gly Ile Leu Pro Glu Ala Thr Ala
450                 455                 460

Lys Val Ala Ala Gln Ala Cys Pro Ser Ile Pro Ala Asn Pro Trp Ser
465                 470                 475                 480

Ala Thr His Lys Gly Phe Ser Ala
                485

<210> SEQ ID NO 78
<211> LENGTH: 484
<212> TYPE: PRT
<213> ORGANISM: Hordeum vulgare subsp. vulgare

<400> SEQUENCE: 78

Met Ala Met Ala Ser Phe Arg Leu Leu Pro Leu Ala Leu Leu Leu Ser
1               5                   10                  15

Val Ala His Ala Arg Thr Pro Arg Leu Glu Pro Thr Ile Arg Leu Pro
                20                  25                  30

Ser Gln Arg Ala Ala Gly Gln Glu Asp Asp Asp Ser Val Gly Thr Arg
            35                  40                  45

Trp Ala Val Leu Ile Ala Gly Ser Asn Gly Tyr Tyr Asn Tyr Arg His
        50                  55                  60

Gln Ala Asp Ile Cys His Ala Tyr Gln Ile Met Lys Lys Gly Gly Leu
65                  70                  75                  80

Lys Asp Glu Asn Ile Ile Val Phe Met Tyr Asp Asp Ile Ala Arg Asn
                85                  90                  95

Pro Glu Asn Pro Arg Pro Gly Val Ile Ile Asn His Pro Gln Gly Gly
            100                 105                 110

Asp Val Tyr Ala Gly Val Pro Lys Asp Tyr Thr Gly Lys Glu Val Asn
        115                 120                 125

Val Lys Asn Phe Phe Ala Val Leu Leu Gly Asn Lys Thr Ala Val Asn
130                 135                 140

Gly Gly Ser Gly Lys Val Val Asp Ser Gly Pro Asn Asp His Ile Phe
145                 150                 155                 160

Val Phe Tyr Ser Asp His Gly Gly Pro Gly Val Leu Gly Met Pro Thr
                165                 170                 175

Tyr Pro Tyr Leu Tyr Gly Asp Asp Leu Val Asp Val Leu Lys Lys Lys
            180                 185                 190

His Ala Ala Gly Thr Tyr Lys Ser Leu Val Phe Tyr Leu Glu Ala Cys
        195                 200                 205

Glu Ser Gly Ser Ile Phe Glu Gly Leu Leu Pro Asn Asp Ile Gly Val
210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Pro Glu Tyr Asp Thr Cys Leu
                245                 250                 255

Gly Asp Leu Tyr Ser Ile Ser Trp Met Glu Asp Ser Asp Val His Asn
            260                 265                 270

Leu Arg Thr Glu Ser Leu Lys Gln Gln Tyr Asn Leu Val Lys Lys Arg
        275                 280                 285

Thr Ala Ala Gln Asp Ser Tyr Ser Tyr Gly Ser His Val Met Gln Tyr
        290                 295                 300

Gly Ser Leu Asp Leu Asn Ala Glu His Leu Phe Ser Tyr Ile Gly Ser
305                 310                 315                 320
```

```
Asn Pro Ala Asn Glu Asn Thr Thr Phe Val Glu Asp Asn Ala Leu Pro
                325                 330                 335

Ser Leu Ser Arg Ala Val Asn Gln Arg Asp Ala Asp Leu Val Tyr Phe
            340                 345                 350

Trp Gln Lys Tyr Arg Lys Leu Ala Glu Ser Pro Ala Lys Asn Asn
        355                 360                 365

Ala Arg Lys Gln Leu Leu Glu Met Met Gly His Arg Ser His Ile Asp
    370                 375                 380

Ser Ser Val Glu Leu Ile Gly Asn Leu Leu Phe Gly Ser Ala Gly Gly
385                 390                 395                 400

Pro Met Val Leu Lys Thr Val Arg Pro Ala Gly Glu Pro Leu Val Asp
                405                 410                 415

Asp Trp Ser Cys Leu Lys Ser Thr Val Arg Thr Phe Glu Ser Gln Cys
            420                 425                 430

Gly Ser Leu Ala Gln Tyr Gly Met Lys His Met Arg Ser Phe Ala Asn
        435                 440                 445

Met Cys Asn Ala Gly Ile Val Pro Glu Ala Met Ala Lys Val Ala Ala
    450                 455                 460

Gln Ala Cys Thr Ser Phe Pro Thr Asn Pro Trp Ser Ala Thr His Lys
465                 470                 475                 480

Gly Phe Ser Ala

<210> SEQ ID NO 79
<211> LENGTH: 493
<212> TYPE: PRT
<213> ORGANISM: Aegilops tauschii

<400> SEQUENCE: 79

Met Ala Met Ala Ser Phe Arg Pro Leu Pro Leu Ala Leu Leu Leu Ala
1               5                   10                  15

Ala Cys Leu Ser Ala Phe Val Leu Ala Val Ala His Ala Arg Thr Pro
            20                  25                  30

Arg Leu Glu Pro Thr Ile Arg Leu Pro Ser Gln Arg Ala Ala Gly Gln
        35                  40                  45

Glu Asp Asp Asp Ser Val Gly Thr Arg Trp Ala Val Leu Ile Ala Gly
    50                  55                  60

Ser Asn Gly Tyr Tyr Asn Tyr Arg His Gln Ala Asp Ile Cys His Ala
65                  70                  75                  80

Tyr Gln Ile Met Lys Lys Gly Leu Lys Asp Glu Asn Ile Ile Val
                85                  90                  95

Phe Met Tyr Asp Asp Ile Ala His Asn Pro Glu Asn Pro Arg Pro Gly
                100                 105                 110

Val Ile Ile Asn His Pro Gln Gly Gly Asp Val Tyr Ala Gly Val Pro
            115                 120                 125

Lys Asp Tyr Thr Gly Lys Glu Val Asn Val Lys Asn Phe Phe Ala Val
    130                 135                 140

Leu Leu Gly Asn Lys Thr Ala Val Ser Gly Gly Ser Gly Lys Val Val
145                 150                 155                 160

Asp Ser Gly Pro Asn Asp His Ile Phe Val Phe Tyr Ser Asp His Gly
                165                 170                 175

Gly Pro Gly Val Leu Gly Met Pro Thr Tyr Pro Tyr Leu Tyr Gly Asp
            180                 185                 190

Asp Leu Val Asp Val Leu Lys Lys Lys His Ala Ala Gly Thr Tyr Lys
        195                 200                 205
```

```
Ser Leu Val Phe Tyr Leu Glu Ala Cys Glu Ser Gly Ser Ile Phe Glu
    210                 215                 220

Gly Leu Leu Pro Asn Asp Ile Gly Val Tyr Ala Thr Thr Ala Ser Asn
225                 230                 235                 240

Ala Glu Glu Ser Ser Trp Gly Thr Tyr Cys Pro Gly Glu Tyr Pro Ser
            245                 250                 255

Pro Pro Pro Glu Tyr Asp Thr Cys Leu Gly Asp Leu Tyr Ser Ile Ser
            260                 265                 270

Trp Met Glu Asp Ser Asp Val His Asn Leu Arg Thr Glu Ser Leu Lys
            275                 280                 285

Gln Gln Tyr Asn Leu Val Lys Lys Arg Thr Ala Ala Gln Asp Ser Tyr
290                 295                 300

Ser Tyr Gly Ser His Val Met Gln Tyr Gly Ser Leu Asp Leu Asn Ala
305                 310                 315                 320

Glu His Leu Phe Ser Tyr Ile Gly Ser Asn Pro Ala Asn Glu Asn Thr
                325                 330                 335

Thr Phe Val Glu Asp Asn Ala Leu Pro Ser Phe Ser Arg Ala Val Asn
            340                 345                 350

Gln Arg Asp Ala Asp Leu Val Tyr Phe Trp Gln Lys Tyr Arg Lys Leu
            355                 360                 365

Ala Glu Ser Ser Pro Glu Lys Asn Asp Ala Arg Lys Gln Leu Leu Glu
370                 375                 380

Met Met Gly His Arg Ser His Ile Asp Asn Ser Val Glu Pro Ile Gly
385                 390                 395                 400

Asn Leu Leu Phe Gly Ser Ala Gly Gly Pro Met Val Leu Lys Ala Val
                405                 410                 415

Arg Pro Ala Gly Glu Pro Leu Val Asp Asp Trp Ser Cys Leu Lys Ser
            420                 425                 430

Thr Val Arg Thr Phe Glu Ser Gln Cys Gly Ser Leu Ala Gln Tyr Gly
            435                 440                 445

Met Lys His Met Arg Ser Phe Ala Asn Ile Cys Asn Ala Gly Ile Val
450                 455                 460

Pro Glu Ala Met Ala Lys Val Ala Ala Gln Ala Arg Thr Ser Ile Pro
465                 470                 475                 480

Thr Asn Pro Trp Ser Ala Thr His Lys Gly Phe Ser Ala
                485                 490

<210> SEQ ID NO 80
<211> LENGTH: 493
<212> TYPE: PRT
<213> ORGANISM: Triticum monococcum

<400> SEQUENCE: 80

Met Ala Met Ala Ser Phe Arg Pro Leu Pro Leu Ala Leu Leu Leu Ala
1               5                   10                  15

Ala Cys Leu Ser Ala Leu Val Leu Ala Val Ala His Ala Arg Ser Pro
                20                  25                  30

Arg Leu Glu Pro Thr Ile Arg Leu Pro Ser Gln Arg Ala Ala Gly Gln
            35                  40                  45

Glu Asp Asp Asp Ser Val Gly Thr Arg Trp Ala Val Leu Ile Ala Gly
50                  55                  60

Ser Asn Gly Tyr Tyr Asn Tyr Arg His Gln Ala Asp Ile Cys His Ala
65                  70                  75                  80

Tyr Gln Ile Met Lys Lys Gly Gly Leu Lys Asp Glu Asn Ile Ile Val
                85                  90                  95
```

Phe Met Tyr Asp Asp Ile Ala His Asn Leu Glu Asn Pro Gly Pro Gly
                100                 105                 110

Val Ile Ile Asn His Pro Gln Gly Gly Asp Val Tyr Ala Gly Val Pro
            115                 120                 125

Lys Asp Tyr Thr Gly Lys Glu Val Asn Val Lys Asn Leu Phe Ala Val
        130                 135                 140

Leu Leu Gly Asn Lys Thr Ala Val Ser Gly Ser Gly Lys Val Val
145                 150                 155                 160

Asp Ser Gly Pro Asn Asp His Ile Phe Val Phe Tyr Ser Asp His Gly
                165                 170                 175

Gly Pro Gly Val Leu Gly Met Pro Thr Tyr Pro Tyr Leu Tyr Gly Asp
            180                 185                 190

Asp Leu Val Asp Val Leu Lys Lys His Ala Ala Gly Thr Tyr Lys
        195                 200                 205

Ser Leu Val Phe Tyr Leu Glu Ala Cys Glu Ser Gly Ser Ile Phe Glu
    210                 215                 220

Gly Leu Leu Pro Asn Asp Ile Gly Val Tyr Ala Thr Thr Ala Ser Asn
225                 230                 235                 240

Ala Glu Glu Ser Ser Trp Gly Thr Tyr Cys Pro Gly Glu Tyr Pro Ser
                245                 250                 255

Pro Pro Pro Glu Tyr Asp Thr Cys Leu Gly Asp Leu Tyr Ser Ile Ser
            260                 265                 270

Trp Met Glu Asp Ser Asp Val His Asn Leu Arg Thr Glu Ser Leu Lys
        275                 280                 285

Gln Gln Tyr Asn Leu Val Lys Lys Arg Thr Ala Ala Gln Asp Ser Tyr
    290                 295                 300

Ser Tyr Gly Ser His Val Met Gln Tyr Gly Ser Leu Asp Leu Asn Ala
305                 310                 315                 320

Glu His Leu Phe Ser Tyr Ile Gly Ser Asn Pro Ala Asn Glu Asn Thr
                325                 330                 335

Thr Phe Val Glu Asp Asn Ala Leu Pro Ser Phe Ser Arg Ala Val Asn
            340                 345                 350

Gln Arg Asp Ala Asp Leu Val Tyr Phe Trp Gln Lys Tyr Arg Lys Leu
        355                 360                 365

Ala Glu Ser Ser Pro Glu Lys Asn Asp Ala Arg Lys Gln Leu Leu Glu
    370                 375                 380

Met Met Gly His Arg Ser His Ile Asp Asn Ser Val Glu Leu Ile Gly
385                 390                 395                 400

Asn Leu Leu Phe Gly Ser Ala Gly Gly Pro Met Val Leu Lys Ala Val
                405                 410                 415

Arg Pro Ala Gly Glu Pro Leu Val Asp Asp Trp Ser Cys Leu Lys Ser
            420                 425                 430

Thr Val Arg Thr Phe Glu Ser Gln Cys Gly Ser Leu Ala Gln Tyr Gly
        435                 440                 445

Met Lys His Met Arg Ser Phe Ala Asn Ile Cys Asn Ala Gly Ile Val
    450                 455                 460

Pro Glu Ala Thr Ala Lys Val Ala Ala Gln Ala Cys Thr Ser Ile Pro
465                 470                 475                 480

Thr Asn Pro Trp Ser Ala Thr His Lys Gly Phe Ser Ala
                485                 490

<210> SEQ ID NO 81
<211> LENGTH: 493

<212> TYPE: PRT
<213> ORGANISM: Aegilops speltoides

<400> SEQUENCE: 81

Met Ala Met Ala Ser Phe Arg Pro Leu Pro Leu Ala Leu Leu Leu Ala
1               5                   10                  15

Ala Cys Leu Ser Glu Leu Val Leu Ala Val Ala His Ala Arg Thr Pro
            20                  25                  30

Arg Leu Glu Pro Thr Ile Arg Leu Pro Ser Gln Arg Ala Ala Gly Gln
        35                  40                  45

Glu Asp Asp Ser Val Gly Thr Arg Trp Ala Val Leu Ile Ala Gly
    50                  55                  60

Ser Asn Gly Tyr Tyr Asn Tyr Arg His Gln Ala Asp Ile Cys His Ala
65                  70                  75                  80

Tyr Gln Ile Met Lys Lys Gly Gly Leu Lys Asp Glu Asn Ile Ile Ile
                85                  90                  95

Phe Met Tyr Asp Asp Ile Ala His Asn Pro Glu Asn Pro Arg Pro Gly
            100                 105                 110

Val Ile Ile Asn His Pro Gln Gly Gly Asp Val Tyr Ala Gly Val Pro
        115                 120                 125

Lys Asp Tyr Thr Gly Lys Glu Val Asn Val Lys Asn Phe Phe Ala Val
    130                 135                 140

Leu Leu Gly Asn Arg Thr Ala Val Ser Gly Ser Gly Lys Val Val
145                 150                 155                 160

Asp Ser Gly Pro Asn Asp His Ile Phe Val Phe Tyr Ser Asp His Gly
                165                 170                 175

Gly Pro Gly Val Leu Gly Met Pro Thr Tyr Pro Tyr Leu Tyr Gly Asp
            180                 185                 190

Asp Leu Val Asp Val Leu Lys Lys Lys His Ala Ala Gly Thr Tyr Lys
        195                 200                 205

Ser Leu Val Phe Tyr Leu Glu Ala Cys Glu Ser Gly Ser Ile Phe Glu
    210                 215                 220

Gly Leu Leu Pro Asn Asp Ile Gly Val Tyr Ala Thr Thr Ala Ser Asn
225                 230                 235                 240

Ala Glu Glu Ser Ser Trp Gly Thr Tyr Cys Pro Gly Glu Tyr Pro Ser
                245                 250                 255

Pro Pro Pro Glu Tyr Asp Thr Cys Leu Gly Asp Leu Tyr Ser Ile Ser
            260                 265                 270

Trp Met Glu Asp Ser Asp Val His Asn Leu Arg Thr Glu Ser Leu Lys
        275                 280                 285

Gln Gln Tyr Asn Leu Val Lys Lys Arg Thr Ala Ala Gln Asp Ser Tyr
    290                 295                 300

Ser Tyr Gly Ser His Val Met Gln Tyr Gly Ser Leu Asp Leu Asn Ala
305                 310                 315                 320

Glu His Leu Phe Ser Tyr Ile Gly Ser Asn Pro Ala Asn Glu Asn Thr
                325                 330                 335

Thr Phe Val Glu Asp Asn Ala Leu Pro Ser Phe Ser Gly Ala Val Asn
            340                 345                 350

Gln Arg Asp Ala Asp Leu Val Tyr Phe Trp Gln Lys Tyr Arg Lys Leu
        355                 360                 365

Ala Glu Ser Ser Pro Glu Lys Asn Asp Ala Arg Lys Gln Leu Leu Glu
    370                 375                 380

Met Met Gly His Arg Ser His Ile Asp Asn Ser Val Glu Leu Ile Gly
385                 390                 395                 400

```
Asn Leu Leu Phe Gly Ser Ala Gly Pro Met Val Leu Lys Ala Val
            405                 410                 415

Arg Pro Ala Gly Glu Pro Leu Val Asp Asp Trp Ser Cys Leu Lys Ser
            420                 425                 430

Thr Val Arg Thr Phe Glu Ser Gln Cys Gly Ser Leu Ala Gln Tyr Gly
            435                 440                 445

Met Lys His Met Arg Ser Phe Ala Asn Ile Cys Asn Val Gly Ile Val
450                 455                 460

Pro Glu Ala Met Ala Lys Val Ala Ala Gln Ala Cys Thr Asn Ile Pro
465                 470                 475                 480

Thr Asn Pro Trp Ser Ala Thr His Lys Gly Phe Ser Ala
            485                 490
```

<210> SEQ ID NO 82
<211> LENGTH: 469
<212> TYPE: PRT
<213> ORGANISM: Amborella trichopoda

<400> SEQUENCE: 82

```
Met Ala Phe Ser Gly Lys Ser Val Leu Phe Ala Val Phe Met Ala
1               5                   10                  15

Phe Ser Gly Val Tyr Gly Arg Tyr Ser Thr Trp Ser Asp Phe Leu Arg
            20                  25                  30

Met Pro Gln Thr Glu Asp Ser Val Gly Thr Arg Trp Ala Val Leu Val
            35                  40                  45

Ala Gly Ser Ser Gly Tyr Gly Asn Tyr Arg His Gln Ala Asp Ile Cys
50                  55                  60

His Ala Tyr Gln Thr Met Ile Arg Gly Gly Leu Lys Glu Lys Asn Ile
65                  70                  75                  80

Val Val Phe Met Tyr Asp Asp Ile Ala Tyr Asn Glu Asn Pro Arg
            85                  90                  95

Pro Gly Val Ile Ile Asn Arg Pro His Gly Glu Asp Val Tyr Ala Gly
            100                 105                 110

Val Pro Lys Asp Tyr Val Gly Asp Asp Val Asn Val Asp Asn Leu Phe
            115                 120                 125

Ala Val Ile Leu Gly Asn Lys Ser Ala Leu Thr Gly Gly Ser Gly Lys
130                 135                 140

Val Val Asp Ser Gly Pro Asp Asp His Ile Phe Ile Phe Tyr Ser Asp
145                 150                 155                 160

His Gly Gly Ala Gly Val Leu Gly Met Pro Thr Tyr Pro Tyr Leu Tyr
            165                 170                 175

Ala Asp Asp Leu Val Asn Val Leu Lys Lys Lys His Val Ser Gly Thr
            180                 185                 190

Tyr Lys Ser Leu Val Phe Tyr Leu Glu Ala Cys Glu Ser Gly Ser Ile
            195                 200                 205

Phe Glu Gly Leu Leu Pro Glu Gly Leu Asn Ile Tyr Ala Thr Thr Ala
            210                 215                 220

Ser Asn Ala Val Glu Ser Ser Trp Gly Thr Tyr Cys Pro Asp Ser
225                 230                 235                 240

Pro Asp Phe Pro Gln Glu Tyr Asp Thr Cys Leu Gly Asp Leu Tyr Ser
            245                 250                 255

Val Ser Trp Met Glu Asp Ser Asp Ile His Asn Leu Gln Phe Glu Thr
            260                 265                 270

Leu Lys Gln Gln Tyr Glu Leu Val Lys Met Arg Thr Ser Asn Phe Glu
```

```
                275                 280                 285
Thr Tyr Met Phe Gly Ser His Val Met Gln Tyr Gly Asp Ser Gly Leu
290                 295                 300
Gly Lys Glu Gln Leu Val Leu Tyr Met Gly Ser Asn Pro Ala Asn Asp
305                 310                 315                 320
Asn Ser Thr Phe Ile Ser Arg Asn Glu Leu Pro Ser Phe Ser Lys Ala
                325                 330                 335
Val Asn Gln Arg Asp Ala Asp Leu Val Tyr Phe Trp Asn Lys Tyr Arg
                340                 345                 350
Lys Ser Pro Val Gly Ser Ile Lys Lys Arg Asn Ala Gln Lys Glu Leu
                355                 360                 365
Phe Asp Val Met Ala His Arg Leu His Leu Asp Asn Ser Ile Glu Leu
370                 375                 380
Ile Gly Lys Leu Leu Phe Gly Ser Glu Lys Gly Pro Glu Ile Leu Lys
385                 390                 395                 400
Thr Val Arg Thr Thr Gly Leu Pro Leu Val Asp Asp Trp Asp Cys Leu
                405                 410                 415
Lys Ala Met Val Arg Thr Phe Glu Thr Lys Cys Gly Ser Ile Ser Gln
                420                 425                 430
Tyr Gly Met Lys His Met Arg Ser Met Ala Asn Ile Cys Asn Ala Gly
                435                 440                 445
Ile Ser Lys Glu Val Met Ala Glu Ala Ser Ala Glu Ala Cys Thr Arg
                450                 455                 460
Ile Pro Thr Thr Ser
465

<210> SEQ ID NO 83
<211> LENGTH: 489
<212> TYPE: PRT
<213> ORGANISM: Hordeum vulgare subsp. vulgare

<400> SEQUENCE: 83

Met Ala Met Ala Ser Phe His Leu Leu Pro Leu Ser Leu Leu Leu Leu
1               5                   10                  15
Leu Leu Val Val Ala Asn Ala Gly Thr Pro Pro Leu Glu Pro Gly Leu
                20                  25                  30
Arg Leu Pro Ser Gln Arg Ala Ala Gly Arg Gln Glu Asn Asp Gly
            35                  40                  45
Ser Val Gly Thr Lys Trp Ala Val Leu Val Ala Gly Ser Asn Gly Tyr
50                  55                  60
Gln Asn Tyr Arg His Gln Ala Asp Val Cys His Ala Tyr Gln Ile Ile
65                  70                  75                  80
Lys Lys Gly Gly Leu Lys Asp Glu Asn Ile Ile Val Phe Met Tyr Asp
                85                  90                  95
Asp Ile Ala His Asn Pro Glu Asn Pro Arg Pro Gly Val Ile Ile Asn
                100                 105                 110
His Pro Gln Gly Gly Asp Val Tyr Ala Gly Val Pro Lys Asp Tyr Thr
            115                 120                 125
Gly Lys Glu Val Asn Ala Lys Asn Leu Phe Ala Val Leu Leu Gly Asn
130                 135                 140
Lys Thr Ala Val Ser Gly Gly Ser Gly Lys Val Val Asp Ser Gly Pro
145                 150                 155                 160
Asn Asp His Ile Phe Val Phe Tyr Ser Asp His Gly Gly Pro Gly Val
                165                 170                 175
```

```
Ile Gly Met Pro Thr Tyr Pro Tyr Ile Tyr Gly Asp Asp Leu Val Asp
            180                 185                 190

Val Leu Lys Lys Lys His Ala Ala Gly Thr Tyr Lys Ser Leu Val Phe
        195                 200                 205

Tyr Leu Glu Ala Cys Glu Ala Gly Ser Val Phe Glu Gly Leu Leu Pro
    210                 215                 220

Asn Asp Ile Gly Val Tyr Ala Thr Thr Ala Ser Asn Ala Glu Glu Ser
225                 230                 235                 240

Ser Trp Gly Ala Tyr Cys Pro Gly Glu Tyr Pro Ser Pro Pro Pro Glu
                245                 250                 255

Tyr Asp Thr Cys Leu Gly Asp Leu Tyr Ser Ile Ser Trp Met Glu Asp
            260                 265                 270

Ser Asp Val His Asn Leu Arg Thr Glu Ser Leu Lys Glu Gln Tyr Asn
        275                 280                 285

Leu Val Lys Lys Arg Thr Ala Ala Gln Asp Ser Tyr Ser Tyr Gly Ser
    290                 295                 300

His Val Met Gln Tyr Gly Ser Leu Asp Leu Asn Ala Gln His Leu Phe
305                 310                 315                 320

Leu Tyr Ile Gly Ser Asn Pro Ala Asn Asp Asn Ala Thr Phe Val Glu
                325                 330                 335

Glu Asn Ser Leu Pro Ser Phe Ser Arg Ala Val Asn Gln Arg Asp Ala
            340                 345                 350

Asp Leu Val Tyr Phe Trp His Lys Tyr Arg Lys Leu Ala Glu Ser Ser
        355                 360                 365

Pro Glu Lys Asn Asn Ala Arg Lys Gln Leu Leu Glu Met Met Gly His
    370                 375                 380

Arg Ser His Val Asp Asn Ser Val Glu Leu Ile Gly Asn Leu Leu Phe
385                 390                 395                 400

Gly Ser Ala Asp Gly Pro Met Val Leu Lys Ser Val Arg Pro Ala Gly
                405                 410                 415

Glu Pro Leu Val Asp Asp Trp Asn Cys Leu Lys Ser Thr Val His Thr
            420                 425                 430

Phe Glu Ser Gln Cys Gly Ser Leu Ala Gln Tyr Gly Met Lys His Met
        435                 440                 445

Arg Ser Phe Ala Asn Ile Cys Asn Ala Gly Ile Leu Pro Glu Thr Met
    450                 455                 460

Val Lys Val Ala Ala Gln Ala Cys Thr Ser Ile Pro Thr Asn Pro Trp
465                 470                 475                 480

Ser Gly Thr His Lys Gly Phe Ser Ala
                485

<210> SEQ ID NO 84
<211> LENGTH: 485
<212> TYPE: PRT
<213> ORGANISM: Zea mays

<400> SEQUENCE: 84

Met Val Ala Asp Arg Leu Arg Leu Ala Leu Leu Leu Ser Ala Cys Leu
1               5                   10                  15

Cys Ser Ala Trp Ala Arg Pro Arg Leu Glu Pro Thr Ile Arg Leu Pro
            20                  25                  30

Ser Glu Arg Ala Ala Ala Asp Glu Thr Asp Asp Ala Val Gly Thr
        35                  40                  45

Arg Trp Ala Val Leu Ile Ala Gly Ser Asn Gly Tyr Tyr Asn Tyr Arg
    50                  55                  60
```

```
His Gln Ala Asp Ile Cys His Ala Tyr Gln Ile Met Lys Lys Gly Gly
 65                  70                  75                  80

Leu Lys Asp Glu Asn Ile Val Val Phe Met Tyr Asp Asp Ile Ala His
                 85                  90                  95

Ser Pro Glu Asn Pro Arg Pro Gly Val Ile Asn His Pro Gln Gly
                100                 105                 110

Gly Asp Val Tyr Ala Gly Val Pro Lys Asp Tyr Thr Gly Arg Glu Val
                115                 120                 125

Asn Val Asp Asn Phe Phe Ala Val Leu Leu Gly Asn Lys Thr Ala Leu
                130                 135                 140

Arg Gly Gly Ser Gly Lys Val Val Asp Ser Gly Pro Asn Asp His Ile
145                 150                 155                 160

Phe Val Phe Tyr Ser Asp His Gly Gly Pro Gly Val Leu Gly Met Pro
                165                 170                 175

Thr Tyr Pro Tyr Leu Tyr Gly Asp Asp Leu Val Asp Val Leu Lys Lys
                180                 185                 190

Lys His Ala Ala Gly Thr Tyr Lys Ser Leu Val Phe Tyr Leu Glu Ala
                195                 200                 205

Cys Glu Ser Gly Ser Ile Phe Glu Gly Leu Leu Pro Asn Asp Ile Asn
210                 215                 220

Val Tyr Ala Thr Thr Ala Ser Asn Ala Glu Glu Ser Ser Trp Gly Thr
225                 230                 235                 240

Tyr Cys Pro Gly Glu Phe Pro Ser Pro Pro Glu Tyr Asp Thr Cys
                245                 250                 255

Leu Gly Asp Leu Tyr Ser Val Ala Trp Met Glu Asp Ser Asp Phe His
                260                 265                 270

Asn Leu Arg Thr Glu Ser Leu Lys Gln Gln Tyr Asn Leu Val Lys Asp
                275                 280                 285

Arg Thr Ala Val Gln Asp Thr Phe Ser Tyr Gly Ser His Val Met Gln
290                 295                 300

Tyr Gly Ser Leu Glu Leu Asn Val Lys His Leu Phe Ser Tyr Ile Gly
305                 310                 315                 320

Thr Asn Pro Ala Asn Asp Asn Thr Ser Ile Glu Asp Asn Ser Leu
                325                 330                 335

Pro Ser Phe Ser Lys Ala Val Asn Gln Arg Asp Ala Asp Leu Val Tyr
                340                 345                 350

Phe Trp Gln Lys Tyr Arg Lys Leu Ala Asp Ser Ser His Glu Lys Asn
                355                 360                 365

Glu Ala Arg Arg Glu Leu Leu Glu Val Met Ala His Arg Ser His Val
                370                 375                 380

Asp Ser Ser Val Glu Leu Ile Gly Ser Leu Leu Phe Gly Ser Glu Asp
385                 390                 395                 400

Gly Pro Arg Val Leu Lys Ala Val Arg Ala Ala Gly Glu Pro Leu Val
                405                 410                 415

Asp Asp Trp Ser Cys Leu Lys Ser Thr Val Arg Thr Phe Glu Ala Gln
                420                 425                 430

Cys Gly Ser Leu Ala His Tyr Gly Met Lys His Met Arg Ser Phe Pro
                435                 440                 445

Asn Ile Cys Asn Ala Gly Ile Leu Pro Glu Ala Val Ser Lys Val Ala
                450                 455                 460

Ala Gln Ala Cys Thr Ser Ile Pro Ser Asn Pro Trp Ser Ser Ile His
465                 470                 475                 480
```

Lys Gly Phe Ser Ala
            485

<210> SEQ ID NO 85
<211> LENGTH: 487
<212> TYPE: PRT
<213> ORGANISM: Setaria italica

<400> SEQUENCE: 85

Met Met Ala Ala Ala Arg Leu Arg Leu Ala Leu Leu Leu Tyr Val Phe
1               5                   10                  15

Met Cys Ala Ala Trp Ala Arg Pro Gly Leu Glu Pro Ala Ile Arg Leu
            20                  25                  30

Pro Ser Glu Arg Ala Ala Ala Gly Glu Gly Thr Asp Asp Ala Val
        35                  40                  45

Gly Thr Arg Trp Ala Val Leu Ile Ala Gly Ser Asn Gly Tyr Tyr Asn
    50                  55                  60

Tyr Arg His Gln Ala Asp Ile Cys His Ala Tyr Gln Ile Leu Lys Lys
65                  70                  75                  80

Gly Gly Leu Lys Asp Glu Asn Ile Ile Val Phe Met Tyr Asp Asp Ile
                85                  90                  95

Ala His Ser Pro Glu Asn Pro Arg Pro Gly Val Ile Ile Asn His Pro
            100                 105                 110

Gln Gly Gly Asp Val Tyr Ala Gly Val Pro Lys Asp Tyr Thr Gly Arg
        115                 120                 125

Glu Val Asn Val Asn Asn Phe Phe Ala Val Leu Leu Gly Asn Lys Thr
    130                 135                 140

Ala Val Ser Gly Gly Ser Gly Lys Val Val Asp Ser Gly Pro Asn Asp
145                 150                 155                 160

His Ile Phe Val Phe Tyr Ser Asp His Gly Gly Pro Gly Val Leu Gly
                165                 170                 175

Met Pro Thr Tyr Pro Tyr Leu Tyr Gly Asp Asp Leu Val Asn Val Leu
            180                 185                 190

Lys Lys Lys His Ala Ala Gly Thr Tyr Lys Ser Leu Val Phe Tyr Leu
        195                 200                 205

Glu Ala Cys Glu Ser Gly Ser Ile Phe Glu Gly Leu Leu Pro Asn Asp
    210                 215                 220

Ile Asn Val Tyr Ala Thr Thr Ala Ser Asn Ala Asp Glu Ser Ser Trp
225                 230                 235                 240

Gly Thr Tyr Cys Pro Gly Glu Ser Pro Ser Pro Pro Glu Tyr Asp
                245                 250                 255

Thr Cys Leu Gly Asp Leu Tyr Ser Val Ala Trp Met Glu Asp Ser Asp
            260                 265                 270

Phe His Asn Leu Arg Thr Glu Ser Leu Lys Gln Gln Tyr Asn Leu Val
        275                 280                 285

Lys Asp Arg Thr Ser Val His Asn Thr Phe Thr Tyr Gly Ser His Val
    290                 295                 300

Met Gln Tyr Gly Ser Leu Asn Leu Asn Val Gln His Leu Phe Ser Tyr
305                 310                 315                 320

Ile Gly Thr Asn Pro Ala Asn Asp Asp Asn Lys Phe Val Glu Gly Asn
                325                 330                 335

Ser Leu Pro Ser Phe Thr Arg Ala Val Asn Gln Arg Asp Ala Asp Leu
            340                 345                 350

Val Tyr Phe Trp Gln Lys Tyr Arg Lys Val Ala Glu Gly Ser Pro Gly
        355                 360                 365

```
Lys Asn Asp Ala Arg Lys Glu Leu Leu Glu Val Met Ala His Arg Ser
            370                 375                 380

His Val Asp Asn Ser Val Glu Leu Ile Gly Ser Leu Leu Phe Gly Ser
385                 390                 395                 400

Glu Asp Gly Pro Arg Val Leu Lys Ala Val Arg Ala Ala Gly Glu Pro
                405                 410                 415

Leu Val Asp Asp Trp Ser Cys Leu Lys Ser Met Val Arg Ala Phe Glu
            420                 425                 430

Ala Gln Cys Gly Ser Leu Ser Gln Tyr Gly Met Lys His Met Arg Ser
            435                 440                 445

Phe Ala Asn Ile Cys Asn Ala Gly Ile Leu Pro Asp Ala Val Ser Lys
            450                 455                 460

Val Ala Ala Gln Ala Cys Thr Ser Ile Pro Ser Asn Pro Trp Ser Ser
465                 470                 475                 480

Ile His Met Gly Phe Ser Ala
                485

<210> SEQ ID NO 86
<211> LENGTH: 460
<212> TYPE: PRT
<213> ORGANISM: Medicago truncatula

<400> SEQUENCE: 86

Met Asp Phe Ser Gln Phe Ser Thr Ile Leu Phe Leu Thr Val Ile Leu
1               5                   10                  15

Thr Ile Phe Ala Ala Val Ser Gly Ser Arg Asp Leu Pro Gly Asp Tyr
            20                  25                  30

Ile Arg Leu Pro Ser Gln Ser Gln Ala Ser Arg Phe Phe His Glu Pro
            35                  40                  45

Glu Asn Asp Asp Asn Asp Gln Gly Thr Arg Trp Ala Ile Leu Leu Ala
50                  55                  60

Gly Ser Asn Gly Tyr Trp Asn Tyr Arg His Gln Ala Asp Val Cys His
65                  70                  75                  80

Ala Tyr Gln Leu Leu Arg Lys Gly Gly Leu Lys Glu Glu Asn Ile Ile
            85                  90                  95

Val Phe Met Tyr Asp Asp Ile Ala Ser Asn Val Glu Asn Pro Arg Pro
            100                 105                 110

Gly Val Ile Ile Asn Lys Pro Asp Gly Gly Asp Val Tyr Glu Gly Val
            115                 120                 125

Pro Lys Asp Tyr Thr Gly Ala Glu Val His Ala Asp Asn Phe Tyr Ala
            130                 135                 140

Ala Leu Leu Gly Asn Lys Ser Ala Leu Thr Gly Gly Ser Gly Lys Val
145                 150                 155                 160

Val Asp Ser Gly Pro Asn Asp His Ile Phe Val Tyr Tyr Thr Asp His
                165                 170                 175

Gly Gly Pro Gly Val Leu Gly Met Pro Val Gly Pro Tyr Leu Tyr Ala
            180                 185                 190

Ser Asp Leu Asn Glu Val Leu Lys Lys His Ala Ser Gly Ser Tyr
            195                 200                 205

Lys Ser Leu Val Phe Tyr Leu Glu Lys Ile Ser Ile Ser Met Arg Gln
            210                 215                 220

Thr Ala Ser Asn Ala Val Glu Ser Ser Trp Gly Thr Tyr Cys Pro Gly
225                 230                 235                 240

Glu Tyr Pro Pro Pro Pro Pro Glu Tyr Ser Thr Cys Leu Gly Asp Leu
```

```
            245                 250                 255
Tyr Ser Ile Ala Trp Met Glu Asp Ser Asp Ile His Asn Leu Arg Thr
            260                 265                 270

Glu Ser Leu His Gln Gln Tyr Lys Leu Val Lys Asp Arg Thr Ile Asn
            275                 280                 285

Gly Tyr Tyr Gly Ser His Val Met Glu Tyr Gly Asp Val Gly Leu Ser
            290                 295                 300

Asn Asn His Leu Phe Leu Tyr Leu Gly Thr Asn Pro Ala Asn Asp Asn
305                 310                 315                 320

Ile Ser Phe Val Asp Glu Ser Ser Leu Lys Leu Arg Ser Pro Ser Thr
                    325                 330                 335

Ala Val Asn Gln Arg Asp Ala Asp Leu Ile His Phe Trp Asp Lys Phe
                    340                 345                 350

Arg Lys Ala Pro Glu Gly Ser Leu Arg Lys Asn Glu Ala Gln Lys Glu
                    355                 360                 365

Val Leu Glu Ala Met Ser His Arg Met His Val Asp Asn Ser Val Lys
                    370                 375                 380

Leu Ile Gly Lys Leu Leu Phe Gly Ile Glu Lys Gly Thr Glu Leu Leu
385                 390                 395                 400

Asp Asn Val Arg Pro Ala Gly Ser Pro Leu Val Asp Asn Trp Asp Cys
                    405                 410                 415

Leu Lys Thr Met Val Lys Thr Phe Glu Thr His Cys Gly Ser Leu Ser
                    420                 425                 430

Gln Tyr Gly Met Lys His Met Arg Ser Phe Ala Asn Ile Cys Asn Ala
                    435                 440                 445

Gly Ile Gln Thr Glu Gln Met Ala Glu Ala Ser Ala
450                 455                 460

<210> SEQ ID NO 87
<211> LENGTH: 478
<212> TYPE: PRT
<213> ORGANISM: Populus trichocarpa

<400> SEQUENCE: 87

Met Thr Gly Leu Ala Thr Gly Ala Ile Phe Leu Leu Ile Ser Leu Cys
1               5                   10                  15

Gly Ile Ala Ala Ala Gly Arg Asp Thr Val Gly Asp Val Leu Arg Leu
                20                  25                  30

Pro Ser Glu Ala Ser Arg Phe Phe His Asn Asp Asn Ser Asp Asp
            35                  40                  45

Asp Ser Thr Gly Thr Arg Trp Ala Ile Leu Leu Ala Gly Ser Asn Gly
        50                  55                  60

Tyr Trp Asn Tyr Arg His Gln Ala Asp Val Cys His Ala Tyr Gln Leu
65                  70                  75                  80

Leu Arg Lys Gly Gly Leu Lys Glu Glu Asn Ile Ile Val Phe Met Tyr
                85                  90                  95

Asp Asp Ile Ala Tyr Asn Ser Glu Asn Pro Arg Arg Gly Val Ile Ile
                100                 105                 110

Asn Ser Pro Gln Gly Glu Asp Val Tyr Lys Gly Val Pro Lys Asp Tyr
                115                 120                 125

Thr Gly Glu Asp Val Thr Val Gly Asn Phe Phe Ala Ala Ile Leu Gly
            130                 135                 140

Asn Lys Thr Ala Leu Thr Gly Gly Ser Gly Lys Val Val Asp Ser Gly
145                 150                 155                 160
```

-continued

Pro Asn Asp His Ile Phe Ile Tyr Tyr Thr Asp His Gly Gly Pro Gly
                165                 170                 175

Val Leu Gly Met Pro Thr Asn Pro Tyr Leu Tyr Ala Asp Asp Leu Ile
            180                 185                 190

Asp Val Leu Lys Lys Lys His Ala Ser Gly Thr Tyr Lys Ser Leu Val
        195                 200                 205

Phe Tyr Leu Glu Ala Cys Glu Ser Gly Ser Ile Phe Glu Gly Leu Leu
    210                 215                 220

Pro Gln Gly Leu Asn Ile Tyr Ala Thr Thr Ala Ser Asn Ala Glu Glu
225                 230                 235                 240

Ser Ser Trp Gly Thr Tyr Cys Pro Gly Glu Asn Pro Ser Pro Pro Pro
                245                 250                 255

Glu Tyr Glu Thr Cys Leu Gly Asp Leu Tyr Ser Val Ala Trp Met Glu
            260                 265                 270

Asp Ser Asp Ile His Asn Leu Gln Thr Glu Thr Leu His Gln Gln Tyr
        275                 280                 285

Glu Leu Val Lys Arg Arg Thr Ser Asn Asp Asn Ser Pro Tyr Gly Ser
    290                 295                 300

His Val Met Gln Tyr Gly Asp Val Gly Leu Ser Lys Asp Asn Ile Phe
305                 310                 315                 320

Leu Tyr Met Gly Thr Asn Pro Ala Asn Asp Asn Phe Thr Phe Met Asp
                325                 330                 335

Glu Asn Leu Leu Arg Pro Arg Ser Lys Ala Val Asn Gln Arg Asp Ala
            340                 345                 350

Asp Leu Val His Phe Trp Asp Lys Tyr Arg Lys Ala Pro Glu Gly Ser
        355                 360                 365

Ser Arg Lys Val Glu Ala Gln Lys Gln Phe Val Glu Ala Met Ser His
    370                 375                 380

Arg Met His Ile Asp His Ser Ile Lys Leu Ile Gly Lys Leu Leu Phe
385                 390                 395                 400

Gly Ile Glu Lys Ala Ser Glu Val Leu Asn Ala Ile Arg Pro Ala Gly
                405                 410                 415

Gln Pro Leu Val Asp Asp Trp Asp Cys Leu Lys Thr Leu Val Lys Phe
            420                 425                 430

Tyr Gly Ser Gln Pro Leu Leu Tyr His Arg Leu Thr Cys Leu Phe Ser
        435                 440                 445

Leu Ile Ala Ser Pro Ala Gly Asp Thr Ser Lys Asp Ser Phe Pro Phe
    450                 455                 460

Leu Arg Lys Cys Leu Leu Phe Phe Tyr Ala Gly Glu Asp Phe
465                 470                 475

<210> SEQ ID NO 88
<211> LENGTH: 431
<212> TYPE: PRT
<213> ORGANISM: Genlisea aurea

<400> SEQUENCE: 88

Asp Asp Asp Ile Val Gly Thr Arg Trp Ala Val Leu Val Ala Gly Ser
1               5                   10                  15

Asn Gly Tyr Trp Asn Tyr Arg His Gln Ala Asp Val Cys His Ala Tyr
                20                  25                  30

Gln Thr Leu Lys Lys Gly Gly Leu Lys Asp Glu Asn Ile Ile Val Phe
            35                  40                  45

Met Tyr Asp Asp Ile Ala Tyr Asn Asp Glu Asn Pro Arg Pro Gly Val
        50                  55                  60

```
Ile Ile Asn His Pro His Gly Glu Asn Val Tyr Asp Gly Val Pro Lys
 65                  70                  75                  80

Asp Tyr Val Gly Asp Val Thr Val Asp Asn Phe Phe Ala Val Leu
                 85                  90                  95

Leu Gly Asn Lys Thr Ala Leu Ser Gly Ser Gly Lys Val Val Asp
            100                 105                 110

Ser Gly Pro Asn Asp His Ile Phe Val Tyr Ser Asp His Gly Gly
            115                 120                 125

Pro Gly Val Leu Gly Met Pro Thr Asp Pro Tyr Leu Tyr Ala Asn Asp
            130                 135                 140

Leu Ile Asp Val Leu Lys Arg Lys His Ala Ser Gly Thr Tyr Lys Ser
145                 150                 155                 160

Leu Val Phe Tyr Val Glu Ala Cys Glu Ser Gly Ser Ile Phe Glu Gly
                165                 170                 175

Leu Leu Pro Glu Gly Leu Asn Ile Phe Ala Thr Thr Ala Ser Asn Ala
            180                 185                 190

Glu Glu Asn Ser Trp Gly Thr Tyr Cys Pro Gly Asp Asp Ile Gly Pro
            195                 200                 205

Pro Pro Glu Tyr Glu Thr Cys Leu Gly Asp Met Tyr Ser Val Ser Trp
            210                 215                 220

Met Glu Asp Ser Asp Gln His Asn Leu Arg Thr Glu Thr Leu Arg Gln
225                 230                 235                 240

Gln Tyr His Val Val Arg Glu Arg Thr Ala Arg Asp Asn Ser His Arg
                245                 250                 255

Tyr Gly Ser His Val Met Gln Tyr Gly Asp Leu Lys Leu Ser Val Asp
            260                 265                 270

Lys Leu Phe Leu Tyr Met Gly Ser Asn Pro Ser Asn Asp Asn Ser Thr
            275                 280                 285

Phe Gly Gly Ser Val His Leu Ser Gly Asn Ser Ser Trp Pro Ser Ser
            290                 295                 300

Met Ala Val Ser Gln Arg Asp Ala Asp Val Leu His Phe Trp Asp Lys
305                 310                 315                 320

Phe Arg Lys Ala Pro Glu Gly Ser Ser Arg Lys Ala Glu Ala Gln Lys
                325                 330                 335

Gln Leu Ala Glu Val Met Val Arg Arg Ser Arg Val Asp Ile Ser Val
            340                 345                 350

Val Ser Ile Gly Lys Leu Leu Phe Gly Ser Ser Glu Ile Met Asn Ala
            355                 360                 365

Ile Arg Pro Ser Gly Lys Ser Leu Val Asp Asp Trp Asp Cys Leu Lys
            370                 375                 380

Ser Leu Val Arg Ile Phe Glu Thr Tyr Cys Ser Ser Leu Ser Gly Tyr
385                 390                 395                 400

Gly Met Lys His Met Arg Ser Ile Ala Asn Met Cys Asn Ala Gly Val
                405                 410                 415

Ser Glu Glu Gln Met Ser Glu Ala Ser Ser Gln Val Cys Ser Ser
            420                 425                 430

<210> SEQ ID NO 89
<211> LENGTH: 422
<212> TYPE: PRT
<213> ORGANISM: Triticum urartu

<400> SEQUENCE: 89

Met Ser Arg Ala Asp Ile Cys His Ala Tyr Gln Ile Leu Lys Lys Gly
```

-continued

```
1               5                   10                  15
Gly Leu Lys Asp Glu Asn Ile Ile Val Phe Met Tyr Asp Asp Ile Ala
                20                  25                  30

His Asn Leu Glu Asn Pro Arg Pro Gly Val Ile Ile Asn His Pro Gln
            35                  40                  45

Gly Gly Asp Val Tyr Ala Gly Val Pro Lys Asp Tyr Thr Gly Lys Glu
        50                  55                  60

Val Asn Val Lys Asn Leu Phe Ala Val Leu Leu Gly Asn Lys Thr Ala
65                  70                  75                  80

Val Asn Gly Gly Ser Gly Lys Val Leu Asp Ser Gly Pro Asn Asp His
                85                  90                  95

Ile Phe Val Phe Tyr Ser Asp His Gly Gly Pro Gly Val Ile Gly Met
                100                 105                 110

Pro Thr Asn Pro Tyr Val Tyr Gly Asp Asp Leu Val Asp Val Leu Lys
            115                 120                 125

Lys Lys His Ala Ala Gly Ser Tyr Lys Ser Leu Val Phe Tyr Leu Glu
        130                 135                 140

Ala Cys Glu Ala Gly Ser Val Phe Glu Gly Leu Leu Pro Asn Asp Ile
145                 150                 155                 160

Gly Val Tyr Ala Thr Thr Ala Ser Asp Ala Glu Glu Ser Ser Trp Gly
                165                 170                 175

Thr Tyr Cys Pro Gly Glu Tyr Pro Ser Pro Pro Glu Tyr Asp Thr
            180                 185                 190

Cys Leu Gly Asp Leu Tyr Ser Ile Ser Trp Met Glu Asp Ser Asp Val
        195                 200                 205

His Asn Leu Arg Thr Glu Ser Leu Lys Gln Gln Tyr Asp Leu Val Lys
    210                 215                 220

Lys Arg Thr Ala Ala Gln Asp Ser Tyr Ser Tyr Gly Ser His Val Met
225                 230                 235                 240

Gln Tyr Gly Ser Leu Asp Leu Asn Ala Gln Gln Leu Phe Leu Tyr Ile
                245                 250                 255

Gly Ser Asn Pro Ala Asn Asn Asn Thr Thr Phe Val Glu Asp Asn Ser
            260                 265                 270

Leu Pro Ser Phe Ser Arg Ala Val Asn Gln Arg Asp Ala Asp Leu Val
        275                 280                 285

Tyr Phe Trp His Lys Tyr Arg Lys Leu Ala Glu Ser Ser Pro Glu Lys
        290                 295                 300

Asn Asp Ala Arg Lys Gln Leu Leu Glu Met Thr Ser His Arg Ser His
305                 310                 315                 320

Ile Asp Asn Ser Val Glu Leu Ile Gly Asn Leu Leu Phe Gly Phe Ala
                325                 330                 335

Asp Gly Pro Met Val Leu Lys Thr Val Arg Pro Ala Gly Glu Pro Leu
            340                 345                 350

Val Asp Asp Trp Ser Cys Leu Lys Ser Thr Val Arg Ala Phe Glu Ser
        355                 360                 365

Gln Cys Gly Ser Leu Ala Gln Tyr Gly Met Lys His Met Arg Ser Phe
    370                 375                 380

Ala Asn Ile Cys Asn Ala Gly Val Leu Pro Glu Ala Met Val Lys Val
385                 390                 395                 400

Ala Ala Gln Ala Cys Lys Ser Ile Pro Thr Asn Pro Trp Ser Ala Thr
                405                 410                 415

His Lys Gly Phe Ser Ala
            420
```

<210> SEQ ID NO 90
<211> LENGTH: 474
<212> TYPE: PRT
<213> ORGANISM: Hordeum vulgare subsp. vulgare

<400> SEQUENCE: 90

```
Met Ala Arg Leu Pro Cys Ser Pro Leu Leu Leu Leu Val Leu Ser
1               5                   10                  15

Ser Gln Leu Ala Leu Leu Val Ala Gly Glu Phe Leu Arg Leu Pro Ser
                20                  25                  30

Glu Lys Asp Val Val Gly Thr Arg Trp Ala Val Leu Ile Ala Gly Ser
            35                  40                  45

Asn Gly Tyr Tyr Asn Tyr Arg His Gln Ala Asp Val Cys His Ala Tyr
        50                  55                  60

Gln Ile Met Lys Lys Gly Gly Leu Lys Asp Glu Asn Ile Ile Val Phe
65                  70                  75                  80

Met Tyr Asp Asp Ile Ala Asn Asn Arg Asp Asn Pro Arg Pro Gly Val
                85                  90                  95

Ile Ile Asn His Pro Lys Gly Gly Asp Val Tyr Ala Gly Val Pro Lys
            100                 105                 110

Asp Tyr Thr Gly Ala Asp Val Asn Thr Asn Asn Phe Leu Ala Ala Leu
        115                 120                 125

Leu Gly Asp Lys Ser Lys Leu Thr Gly Ser Gly Ser Gly Lys Val Val
130                 135                 140

Ser Ser Gly Pro Asp Asp His Ile Phe Val Tyr Tyr Ala Asp His Gly
145                 150                 155                 160

Gly Pro Gly Ile Leu Gly Met Pro Glu Asp Glu Glu Tyr Leu Tyr Ala
                165                 170                 175

Asn Asp Leu Val Arg Thr Leu Glu Lys Lys His Ala Gly Gly Ala Gly
            180                 185                 190

Tyr Lys Ser Leu Val Phe Tyr Leu Glu Ala Cys Glu Ser Gly Ser Ile
        195                 200                 205

Phe Glu Gly Leu Leu Pro Gly Asn Ile Ser Val Tyr Ala Thr Thr Ala
210                 215                 220

Ala Asn Ala Glu Glu Ser Ser Trp Gly Thr Tyr Cys Pro Gly Asp Asp
225                 230                 235                 240

Glu Gly Ala Pro Pro Pro Glu Tyr Asp Thr Cys Leu Gly Asp Leu Tyr
                245                 250                 255

Ser Val Ala Trp Met Glu Asp Ser Asp Ala His Asn Leu Asn Ala Glu
            260                 265                 270

Ser Leu Lys Gln Gln Tyr Glu Arg Val Arg Asn Arg Thr Ser Ala Asp
        275                 280                 285

Gly Thr Tyr Ser Leu Gly Ser His Val Met Gln Tyr Gly Asp Leu Gly
290                 295                 300

Leu Asn Asp Gln Ser Leu Phe Gln Tyr Ile Gly Thr Asn Pro Ala Asn
305                 310                 315                 320

Asp Asn Ala Thr Phe Val Gln Ser Ser Ser Ser Arg Gln Leu Pro
                325                 330                 335

Gly Ala Arg Val Asn Gln Arg Asp Ala Asp Leu Val His Phe Trp His
            340                 345                 350

Lys Tyr Arg Arg Ser Ala Glu Gly Ser Ala Glu Lys Val Glu Ala Arg
        355                 360                 365

Arg Arg Leu Val Glu Thr Met Ala Arg Arg Ser Arg Val Asp Ser Ser
```

```
                370             375             380
Val Glu Leu Ile Gly Gly Leu Phe Gly Ser Glu Glu Gly Ala Lys
385                 390                 395                 400

Val Leu Gly Thr Val Arg Pro Ala Gly Gln Pro Val Val Asp Asp Trp
                405                 410                 415

Gly Cys Leu Lys Ser Val Val Arg Arg Phe Glu Arg Cys Gly Pro
                420                 425                 430

Leu Thr Gln Tyr Gly Met Lys His Met Arg Ser Leu Ala Asn Ile Cys
                435                 440                 445

Asn Ala Gly Val Arg Glu Glu Val Met Asp Lys Ala Ala Ser Gln Ala
450                 455                 460

Cys Ala Ala Ser Pro Ser Ser Leu Ile Ile
465                 470

<210> SEQ ID NO 91
<211> LENGTH: 424
<212> TYPE: PRT
<213> ORGANISM: Aegilops tauschii

<400> SEQUENCE: 91

Met Ser Gln Val Arg Ala Asp Ile Cys His Ala Tyr Gln Ile Leu Lys
1               5                   10                  15

Thr Gly Gly Leu Lys Asp Glu Asn Ile Ile Val Phe Met Tyr Asp Asp
                20                  25                  30

Ile Ala His Asn Leu Glu Asn Pro Arg Pro Gly Val Ile Ile Asn His
                35                  40                  45

Pro Gln Gly Gly Asp Val Tyr Ala Gly Val Pro Lys Asp Tyr Thr Gly
            50                  55                  60

Lys Glu Val Asn Val Lys Asn Leu Phe Ala Val Leu Leu Gly Asn Lys
65                  70                  75                  80

Thr Ala Val Ser Gly Gly Ser Gly Lys Val Val Asp Ser Gly Pro Asn
                85                  90                  95

Asp His Ile Phe Val Phe Tyr Ser Asp His Gly Gly Pro Gly Val Ile
                100                 105                 110

Gly Met Pro Thr Tyr Pro Tyr Val Tyr Gly Asp Asp Leu Val Asp Val
                115                 120                 125

Leu Lys Lys Lys His Ala Ala Gly Thr Tyr Lys Ser Leu Val Phe Tyr
130                 135                 140

Leu Glu Ala Cys Glu Ala Gly Ser Val Phe Glu Gly Leu Leu Pro Asn
145                 150                 155                 160

Asp Ile Gly Val Tyr Ala Thr Thr Ala Ser Asn Ala Glu Glu Ser Ser
                165                 170                 175

Trp Gly Thr Tyr Cys Pro Gly Glu Tyr Pro Ser Pro Pro Ser Glu Tyr
                180                 185                 190

Asp Thr Cys Leu Gly Asp Leu Tyr Ser Ile Ser Trp Met Glu Asp Ser
                195                 200                 205

Asp Val His Asn Leu Arg Thr Glu Ser Leu Lys Gln Gln Tyr Asp Leu
210                 215                 220

Val Lys Lys Arg Thr Ala Ala Gln Asp Ser Tyr Ser Tyr Gly Ser His
225                 230                 235                 240

Val Met Gln Tyr Gly Ser Leu Asp Leu Asn Asp Gln His Leu Phe Leu
                245                 250                 255

Tyr Ile Gly Ser Asn Pro Ala Asn Asp Asn Thr Thr Phe Val Glu Asp
                260                 265                 270
```

```
Asn Ser Leu Pro Ser Phe Ser Arg Ala Val Asn Gln Arg Asp Ala Asp
            275                 280                 285

Leu Val Tyr Phe Trp Arg Lys Tyr Gln Lys Leu Ala Glu Ser Ser Thr
    290                 295                 300

Glu Lys Asn Asp Ala Arg Lys Gln Leu Leu Glu Met Met Gly His Arg
305                 310                 315                 320

Ser His Ile Asp Asn Ser Val Glu Leu Ile Gly Asn Leu Leu Phe Gly
                325                 330                 335

Phe Ala Asp Gly Pro Met Val Leu Lys Thr Val Arg Pro Ala Gly Glu
            340                 345                 350

Pro Leu Ala Asp Asp Trp Ser Cys Leu Lys Ser Met Val Arg Ala Phe
        355                 360                 365

Glu Ser Gln Cys Gly Ser Leu Ala Gln Tyr Gly Met Lys His Met Arg
    370                 375                 380

Ser Phe Ala Asn Ile Cys Asn Ala Gly Ile Leu Pro Glu Ala Met Val
385                 390                 395                 400

Lys Met Ala Ala Gln Ala Cys Thr Ser Ile Pro Thr Asn Pro Trp Ser
                405                 410                 415

Ala Thr His Asn Gly Phe Ser Ala
            420

<210> SEQ ID NO 92
<211> LENGTH: 461
<212> TYPE: PRT
<213> ORGANISM: Solanum tuberosum

<400> SEQUENCE: 92

Met Asn Arg Ser Ile Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
            20                  25                  30

Gly Ser Arg Phe Phe Asp Ala Asp Glu Ser Asp Ser Val Gly Thr Arg
        35                  40                  45

Trp Ala Ile Leu Leu Ala Gly Ser Asn Gly Tyr Trp Asn Tyr Arg His
    50                  55                  60

Gln Ala Asp Ile Cys His Ala Tyr Gln Leu Leu Lys Lys Gly Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
            100                 105                 110

Asp Val Tyr Lys Gly Val Pro Lys Asp Tyr Thr Gly Asp Asp Val Thr
        115                 120                 125

Val Asn Asn Phe Leu Ala Leu Leu Gly Asn Lys Thr Ala Leu Thr
    130                 135                 140

Gly Gly Ser Gly Lys Val Val Asp Ser Gly Pro Asn Asp His Ile Phe
145                 150                 155                 160

Ile Phe Cys Ser Asp His Gly Gly Ala Gly Val Ile Gly Met Pro Thr
                165                 170                 175

Asp Pro Tyr Leu Tyr Ala Asn Asp Leu Ile Asp Ala Leu Lys Lys Lys
            180                 185                 190

His Ala Ser Gly Thr Tyr Lys Ser Leu Val Phe Tyr Leu Glu Ala Cys
        195                 200                 205

Glu Ser Gly Ser Met Ser Glu Gly Leu Leu Pro Glu Gly Leu Asn Val
    210                 215                 220
```

```
Tyr Ala Thr Thr Ala Ser Asn Ala Asp Glu Ser Ser Trp Gly Thr Tyr
225                 230                 235                 240

Cys Pro Gly Glu Tyr Pro Ser Pro Pro Ile Glu Tyr Gly Thr Cys Leu
            245                 250                 255

Gly Asp Leu Tyr Ser Ile Ser Trp Met Glu Asp Ser Asp Arg His Asn
        260                 265                 270

Leu Arg Thr Glu Thr Leu Lys Gln Gln Tyr His Leu Val Lys Glu Arg
    275                 280                 285

Thr Ala Ser Gly Asn Pro Ala Tyr Gly Ser His Val Met Gln Tyr Gly
290                 295                 300

Asp Val His Leu Ser Lys Asp Ala Leu Phe Leu Tyr Met Gly Thr Asp
305                 310                 315                 320

Pro Ala Asn Asp Asn Tyr Thr Phe Val Asp Asp Asn Ser Leu Arg Val
                325                 330                 335

Ser Lys Ala Val Asn Gln Arg Asp Ala Asp Leu Val His Phe Trp Tyr
            340                 345                 350

Lys Phe His Lys Ala Pro Glu Gly Ser Val Arg Lys Thr Glu Ala Gln
        355                 360                 365

Lys Gln Leu Asn Glu Ala Ile Ser His Arg Met His Leu Asp Asn Ser
    370                 375                 380

Ile Ala Leu Val Gly Lys Leu Leu Phe Gly Ile Lys Lys Gly Pro Glu
385                 390                 395                 400

Val Leu Thr Ser Val Arg Pro Ala Gly Gln Pro Leu Val Asp Asp Trp
                405                 410                 415

Asp Cys Leu Lys Ser Tyr Val Ser Thr Pro Thr Pro Phe Ser Ser Ile
            420                 425                 430

Ser Phe Glu Phe Ser Gln Ile Tyr Ser Cys Ile Ser Leu Tyr Gly Gly
        435                 440                 445

Met Arg Leu Arg Ser Leu Val Leu Asp Ile Leu Leu Val
    450                 455                 460

<210> SEQ ID NO 93
<211> LENGTH: 441
<212> TYPE: PRT
<213> ORGANISM: Triticum urartu

<400> SEQUENCE: 93

Met Ala Met Ala Ser Phe Arg Pro Pro Leu Ala Leu Leu Leu Ala
1               5                   10                  15

Ala Cys Leu Ser Ala Leu Ala Asp Ile Cys His Ala Tyr Gln Ile Met
            20                  25                  30

Lys Lys Gly Gly Leu Lys Asp Glu Asn Ile Ile Val Phe Met Tyr Asp
        35                  40                  45

Asp Ile Ala His Asn Pro Glu Asn Pro Arg Pro Gly Val Ile Ile Asn
50                  55                  60

His Pro Gln Gly Gly Asp Val Tyr Ala Gly Val Pro Lys Asp Tyr Thr
65                  70                  75                  80

Gly Lys Glu Val Asn Val Lys Asn Phe Phe Ala Val Leu Leu Gly Asn
                85                  90                  95

Lys Thr Ala Val Ser Gly Gly Asn Gly Lys Val Val Asp Ser Gly Pro
            100                 105                 110

Asn Asp His Ile Phe Val Phe Tyr Ser Asp His Gly Gly Pro Gly Val
        115                 120                 125

Leu Gly Met Pro Thr Tyr Pro Tyr Leu Tyr Gly Asp Asp Leu Val Asp
```

```
                130             135             140
Val Leu Lys Lys His Ala Ala Gly Thr Tyr Lys Ser Leu Val Phe
145                 150                 155                 160

Tyr Leu Glu Ala Cys Glu Ser Gly Ser Ile Phe Glu Gly Leu Leu Pro
                165                 170                 175

Asn Asp Ile Gly Val Tyr Ala Thr Thr Ala Ser Asn Ala Glu Glu Ser
                180                 185                 190

Ser Trp Gly Thr Tyr Cys Pro Gly Glu Tyr Pro Ser Pro Pro Pro Glu
                195                 200                 205

Tyr Asp Thr Cys Leu Gly Asp Leu Tyr Ser Ile Ser Trp Met Glu Asp
                210                 215                 220

Ser Asp Val His Asn Leu Arg Thr Glu Ser Leu Lys Gln Gln Tyr Asn
225                 230                 235                 240

Leu Val Lys Lys Arg Thr Ala Ala Gln Asp Ser Tyr Ser Tyr Gly Ser
                245                 250                 255

His Val Met Gln Tyr Gly Ser Leu Asp Leu Asn Ala Glu His Leu Phe
                260                 265                 270

Ser Tyr Ile Gly Ser Asn Pro Ala Asn Glu Asn Thr Thr Phe Val Glu
                275                 280                 285

Asp Asn Ala Leu Pro Ser Phe Ser Arg Ala Val Asn Gln Arg Asp Ala
                290                 295                 300

Asp Leu Val Tyr Phe Trp Gln Lys Tyr Arg Lys Leu Ala Glu Ser Ser
305                 310                 315                 320

Pro Glu Lys Asn Asp Ala Arg Lys Gln Leu Leu Glu Met Met Gly His
                325                 330                 335

Arg Ser His Ile Asp Asn Ser Ile Glu Leu Ile Gly Asn Leu Leu Phe
                340                 345                 350

Gly Ser Ala Gly Gly Pro Met Val Leu Lys Ala Val Arg Pro Ala Gly
                355                 360                 365

Glu Pro Leu Val Asp Asp Trp Ser Cys Leu Lys Ser Thr Val Arg Thr
                370                 375                 380

Phe Glu Ser Gln Cys Gly Ser Leu Ala Gln Tyr Gly Met Lys His Met
385                 390                 395                 400

Arg Ser Phe Ala Asn Ile Cys Asn Ala Gly Ile Val Pro Glu Ala Thr
                405                 410                 415

Ala Lys Val Ala Ala Gln Ala Cys Thr Ser Ile Pro Thr Asn Pro Trp
                420                 425                 430

Ser Ala Thr His Lys Gly Phe Ser Ala
                435                 440

<210> SEQ ID NO 94
<211> LENGTH: 394
<212> TYPE: PRT
<213> ORGANISM: Citrus clementina

<400> SEQUENCE: 94

Met Tyr Asp Asp Ile Ala Phe Asn Glu Glu Asn Pro Arg Pro Gly Val
1               5                   10                  15

Ile Ile Asn His Pro His Gly Asp Asp Val Tyr Lys Gly Val Pro Lys
                20                  25                  30

Asp Tyr Thr Gly Glu Asp Val Thr Val Glu Asn Phe Phe Ala Val Ile
                35                  40                  45

Leu Gly Asn Lys Thr Ala Leu Thr Gly Gly Ser Gly Lys Val Val Asp
                50                  55                  60
```

```
Ser Gly Pro Asn Asp His Ile Phe Ile Phe Tyr Ser Asp His Gly Gly
 65                  70                  75                  80

Pro Gly Val Leu Gly Met Pro Thr Ser Arg Tyr Ile Tyr Ala Asp Glu
                 85                  90                  95

Leu Ile Asp Val Leu Lys Lys His Ala Ser Gly Asn Tyr Lys Ser
            100                 105                 110

Leu Val Phe Tyr Leu Glu Ala Cys Glu Ser Gly Ser Ile Phe Glu Gly
            115                 120                 125

Leu Leu Pro Glu Gly Leu Asn Ile Tyr Ala Thr Thr Ala Ser Asn Ala
            130                 135                 140

Glu Glu Ser Ser Trp Gly Thr Tyr Cys Pro Gly Glu Ile Pro Gly Pro
145                 150                 155                 160

Pro Pro Glu Tyr Ser Thr Cys Leu Gly Asp Leu Tyr Ser Ile Ala Trp
                165                 170                 175

Met Glu Asp Ser Asp Ile His Asn Leu Arg Thr Glu Thr Leu His Gln
                180                 185                 190

Gln Tyr Glu Leu Val Lys Thr Arg Thr Ala Ser Tyr Asn Ser Tyr Gly
            195                 200                 205

Ser His Val Met Gln Tyr Gly Asp Ile Gly Leu Ser Lys Asn Asn Leu
            210                 215                 220

Phe Thr Tyr Leu Gly Thr Asn Pro Ala Asn Asp Asn Tyr Thr Phe Val
225                 230                 235                 240

Asp Glu Asn Ser Leu Arg Pro Ala Ser Lys Ala Val Asn Gln Arg Asp
                245                 250                 255

Ala Asp Leu Leu His Phe Trp Asp Lys Tyr Arg Lys Ala Pro Glu Gly
                260                 265                 270

Thr Pro Arg Lys Ala Glu Ala Gln Lys Gln Phe Phe Glu Ala Met Ser
            275                 280                 285

His Arg Met His Val Asp His Ser Ile Lys Leu Ile Gly Lys Leu Leu
            290                 295                 300

Phe Gly Ile Glu Lys Gly Pro Glu Ile Leu Asn Thr Val Arg Pro Ala
305                 310                 315                 320

Gly Gln Pro Leu Val Asp Asp Trp Gly Cys Leu Lys Ser Leu Val Arg
                325                 330                 335

Thr Phe Glu Ser His Cys Gly Ala Leu Ser Gln Tyr Gly Met Lys His
                340                 345                 350

Met Arg Ser Leu Ala Asn Ile Cys Asn Thr Gly Ile Gly Lys Glu Lys
            355                 360                 365

Met Ala Glu Ala Ser Ala Gln Ala Cys Glu Asn Ile Pro Ser Gly Pro
            370                 375                 380

Trp Ser Ser Leu Asp Lys Gly Phe Ser Ala
385                 390

<210> SEQ ID NO 95
<211> LENGTH: 473
<212> TYPE: PRT
<213> ORGANISM: Setaria italica

<400> SEQUENCE: 95

Met Ala Thr Ala Thr Thr Arg Leu Arg Cys Leu Leu Leu Leu Phe Leu
  1               5                  10                  15

Val Gln Leu Leu Leu Leu Ser Ala Ala Gly Ala Arg Trp Gln
             20                  25                  30

Asp Phe Leu Arg Leu Pro Ser Glu Gly Gly Asp Ala Ala Ala Gly Thr
             35                  40                  45
```

```
Arg Trp Ala Val Leu Ile Ala Gly Ser Asn Gly Tyr Tyr Asn Tyr Arg
 50                  55                  60
His Gln Ala Asp Val Cys His Ala Tyr Gln Ile Met Lys Lys Gly Gly
 65                  70                  75                  80
Leu Lys Asp Glu Asn Ile Ile Val Phe Met Tyr Asp Asp Ile Ala Ser
                 85                  90                  95
Ser Pro Asp Asn Pro Arg Pro Gly Val Ile Asn His Pro Ser Gly
            100                 105                 110
Gly Asp Val Tyr Ala Gly Val Pro Lys Asp Tyr Thr Gly Glu Asp Val
        115                 120                 125
Thr Val Asn Asn Phe Leu Ala Val Leu Leu Gly Asn Arg Ser Ala Val
    130                 135                 140
Ser Gly Gly Ser Gly Lys Val Val Ala Ser Gly Pro Gly Asp His Val
145                 150                 155                 160
Phe Val Tyr Tyr Ser Asp His Gly Gly Pro Gly Val Leu Gly Met Pro
                165                 170                 175
Ser Gly Asp Tyr Leu Tyr Ala Lys Asp Leu Val Gly Ala Leu Glu Arg
            180                 185                 190
Lys His Asp Ala Gly Gly Tyr Arg Ser Leu Val Phe Tyr Leu Glu Ala
        195                 200                 205
Cys Glu Ser Gly Ser Ile Phe Glu Gly Leu Leu Pro Glu Gly Ile Asn
    210                 215                 220
Val Tyr Ala Thr Thr Ala Ala Asn Ala Glu Glu Ser Ser Trp Gly Thr
225                 230                 235                 240
Tyr Cys Pro Gly Asp Asp Gln Gly Pro Pro Glu Phe Asp Thr Cys
                245                 250                 255
Leu Gly Asp Leu Tyr Ser Val Ala Trp Met Glu Asp Ser Asp Val His
            260                 265                 270
Asn Leu Arg Thr Glu Ser Leu Lys Gln Gln Tyr Glu Val Val Lys Asp
        275                 280                 285
Arg Thr Ser Ala His Gly Thr Tyr Ser Leu Gly Ser His Val Met Gln
    290                 295                 300
Tyr Gly Asp Gln Ser Leu Asn Gly Gln Ser Leu Tyr Gln Phe Ile Gly
305                 310                 315                 320
Thr Asp Pro Ala Asn Asp Asn Ala Thr Phe Gly Arg Asp Asn Ser Leu
                325                 330                 335
Arg Arg Arg Ser Ser Gly Thr Val Asn Gln Arg Asp Ala Asp Leu Val
            340                 345                 350
Tyr Phe Trp Gln Lys Tyr Lys Lys Ser Ala Glu Gly Thr Pro Glu Lys
        355                 360                 365
Ala Glu Ala Arg Lys Arg Leu Leu Gln Val Met Ser Arg Arg Ser Arg
    370                 375                 380
Val Asp Ser Ser Met Glu Leu Ile Gly Ser Leu Leu Phe Gly Ser Asp
385                 390                 395                 400
Glu Gly Pro Lys Val Leu Gly Ala Val Arg Pro Ala Gly Gln Pro Leu
                405                 410                 415
Ala Asp Asp Trp Asp Cys Leu Lys Ala Met Val His Ala Tyr Glu Ala
            420                 425                 430
Gln Cys Gly Pro Leu Lys Gln Tyr Gly Met Lys His Met Arg Ser Phe
        435                 440                 445
Ala Asn Ile Cys Asn Ala Gly Val Gly Glu Asp Ala Met Ala Lys Val
    450                 455                 460
```

```
Ala Ser Gln Ala Cys Ala Ala Arg
465             470

<210> SEQ ID NO 96
<211> LENGTH: 543
<212> TYPE: PRT
<213> ORGANISM: Aegilops tauschii

<400> SEQUENCE: 96

Met Ala Ser Asn Arg Leu Leu Pro Leu Ala Leu Leu Leu Leu Leu Leu
1               5                   10                  15

Ala Met Ala His Ala Asp Thr Pro Arg Leu Glu Pro Thr Val Arg Leu
            20                  25                  30

Pro Ser Gln Arg Met Ala Ala Gly Gln Gly Asp Asp Gly Ser Val Gly
        35                  40                  45

Thr Arg Trp Ala Ala Leu Val Ala Gly Ser Asn Gly Tyr Gln Asn Tyr
    50                  55                  60

Arg His Gln Gly Arg Thr Leu Tyr His Gly Phe Tyr Ser Leu Leu Val
65                  70                  75                  80

Gly Val Ser Ser Arg Asp Pro Pro Thr Phe Phe Leu Ser Val Lys
                85                  90                  95

Ser Ile Pro Ser Trp Glu Ile Arg Trp Val Asp Asp Asn Glu Val Leu
                100                 105                 110

Cys Leu Ile Cys Gly Ala Lys Leu Cys Thr Val Gln Ala Asp Ile Cys
            115                 120                 125

His Ala Tyr Gln Ile Leu Lys Lys Gly Gly Leu Lys Asp Glu Asn Ile
        130                 135                 140

Ile Val Phe Met Tyr Asp Asp Ile Ala His Asn Leu Glu Asn Pro Arg
145                 150                 155                 160

Pro Gly Val Ile Ile Asn His Pro Gln Gly Gly Asp Val Tyr Ser Gly
                165                 170                 175

Val Pro Met Asp Tyr Thr Gly Lys Glu Val Asn Val Lys Asn Leu Phe
            180                 185                 190

Ala Val Leu Leu Gly Asn Lys Thr Ala Val Ser Gly Gly Ser Gly Lys
        195                 200                 205

Val Leu Asp Ser Gly Pro Asn Asp His Ile Phe Val Phe Tyr Ser Asp
    210                 215                 220

His Gly Gly Pro Gly Val Ile Gly Met Pro Thr Asn Pro Tyr Val Tyr
225                 230                 235                 240

Gly Asp Asp Leu Val Asp Val Leu Lys Lys His Ala Ala Gly Thr
                245                 250                 255

Tyr Arg Ser Leu Val Phe Tyr Leu Glu Ala Cys Glu Ala Gly Ser Val
            260                 265                 270

Phe Glu Gly Leu Leu Pro Asn Asp Ile Ser Val Tyr Thr Thr Thr Ala
        275                 280                 285

Ser Asn Ala Glu Glu Ser Ser Trp Gly Thr Tyr Cys Pro Gly Glu Tyr
    290                 295                 300

Pro Ser Pro Pro Glu Tyr Asp Thr Cys Leu Gly Asp Leu Tyr Ser
305                 310                 315                 320

Ile Ser Trp Met Glu Asp Ser Asp Val His Asn Leu Arg Thr Glu Ser
                325                 330                 335

Leu Lys Gln Gln Tyr Asp Leu Val Lys Lys Arg Thr Ala Ala Gln Asp
            340                 345                 350

Ser Tyr Asn Tyr Gly Ser His Val Met Gln Tyr Gly Ser Leu Asp Leu
        355                 360                 365
```

```
Asn Ala Gln Gln Leu Phe Leu Tyr Ile Gly Ser Asn Pro Ala Asn Asn
            370                 375                 380

Lys Thr Thr Phe Val Glu Asp Asn Ser Leu Pro Ser Phe Ser Arg Val
385                 390                 395                 400

Val Asn Gln Arg Asp Ala Asp Leu Val Tyr Phe Trp His Lys Tyr Arg
                405                 410                 415

Lys Leu Ala Glu Ser Ser Pro Glu Lys Asn Asp Ala Arg Lys Gln Leu
            420                 425                 430

Leu Glu Met Met Ser His Arg Ser His Ile Asp Asn Ser Val Glu Leu
            435                 440                 445

Ile Gly Asn Leu Leu Phe Gly Ser Ala Asp Gly Pro Met Val Leu Lys
450                 455                 460

Thr Val Arg Pro Ala Gly Glu Pro Leu Val Asp Asp Trp Ser Cys Leu
465                 470                 475                 480

Lys Ser Thr Val Arg Ala Phe Glu Ser Gln Cys Gly Ser Leu Ala Gln
                485                 490                 495

Tyr Gly Met Lys His Met Arg Ser Phe Ala Asn Ile Cys Asn Ala Gly
            500                 505                 510

Val Leu Pro Glu Ala Thr Val Lys Val Ala Ala Gln Ala Cys Lys Ser
            515                 520                 525

Ile Pro Thr Asn Pro Trp Ser Ala Thr His Lys Gly Phe Ser Ala
530                 535                 540
```

<210> SEQ ID NO 97
<211> LENGTH: 493
<212> TYPE: PRT
<213> ORGANISM: Picea sitchensis

<400> SEQUENCE: 97

```
Met Gly Ser Ser Lys Gly Phe Gln Leu Gly Leu Leu Cys Tyr Phe Leu
1               5                   10                  15

Leu Leu Ser Leu Asp Ser Ser Lys Val Ala Asp Gly Ala Arg Arg Asp
            20                  25                  30

Trp Asn Ser Leu Leu Lys Leu Pro Thr Asn His Val Asp Ala Asp Ser
        35                  40                  45

Asp Arg Ile Gly Thr Glu Trp Ala Val Leu Leu Ala Gly Ser Ser Gly
    50                  55                  60

Tyr Trp Asn Tyr Arg His Gln Ala Asp Val Cys His Ala Tyr Gln Ile
65                  70                  75                  80

Leu Arg Arg Gly Gly Leu Lys Glu Glu Asn Ile Val Val Phe Met Tyr
                85                  90                  95

Asp Asp Ile Ala Tyr Asp Glu Glu Asn Pro His Pro Gly Thr Ile Ile
            100                 105                 110

Asn His Pro Gln Gly Ser Asp Val Tyr Ala Gly Val Pro Lys Asp Tyr
        115                 120                 125

Thr Gly Glu Asp Val Thr Val Asn Asn Phe Phe Ala Ala Ile Leu Gly
    130                 135                 140

Asn Lys Ser Leu Val Thr Gly Gly Ser Gly Lys Val Val Glu Ser Gly
145                 150                 155                 160

Pro Asn Asp Arg Ile Phe Ile Tyr Tyr Ser Asp His Gly Gly Pro Gly
                165                 170                 175

Val Leu Gly Met Pro Leu Pro Pro Tyr Leu Tyr Ala Asn Asp Phe Val
            180                 185                 190

Gln Val Leu Lys Lys Lys His Asp Ala Gly Ser Tyr Arg Glu Met Val
```

```
                195                 200                 205
Ile Tyr Val Glu Ala Cys Glu Ser Gly Ser Ile Phe Glu Gly Leu Leu
210                 215                 220

Pro Thr Asp Leu Asn Ile Tyr Val Thr Thr Ala Ser Asn Ala Glu Glu
225                 230                 235                 240

Asn Ser Trp Gly Thr Tyr Cys Pro Gly Met Asp Pro Pro Pro Pro
            245                 250                 255

Glu Tyr Asp Thr Cys Leu Gly Asp Leu Tyr Ser Val Ala Trp Met Glu
            260                 265                 270

Asp Ser Glu Ile Asn Asn Leu Lys Glu Thr Leu Leu Gln Gln Tyr
            275                 280                 285

Asp Leu Val Lys Leu Arg Thr Ser Asn His Asn Thr Tyr Met Ser Gly
290                 295                 300

Ser His Val Met Gln Tyr Gly Asn Ile Thr Ile Ser Gln Glu Glu Leu
305                 310                 315                 320

Tyr Leu Tyr Met Gly Phe Asp Ser Ala Asn Ser Asn Ala Ser Leu Val
                325                 330                 335

Leu Glu Asn Ser Pro Leu Leu Glu Lys Thr Glu Ala Lys Ala Ile Asn
            340                 345                 350

Gln Arg Asp Ala Asp Leu Leu Tyr Met Trp Gln Lys Tyr Lys Lys Ser
            355                 360                 365

Lys Glu Asp Ser Pro Glu Arg Leu Thr Ala Gln Thr Gln Leu Leu Glu
370                 375                 380

Phe Met Ala His Arg Met His Val Asp Lys Ser Val Lys Leu Val Gly
385                 390                 395                 400

Asn Leu Leu Phe Gly Pro Glu Lys Gly Pro Ala Val Phe Asn Ala Val
                405                 410                 415

Arg Pro Gln Gly Glu Pro Leu Val Asp Asp Trp Asp Cys Leu Lys Lys
            420                 425                 430

Met Val Arg Thr Phe Glu Gly His Cys Gly Ser Leu Ala Gln Tyr Gly
            435                 440                 445

Met Lys His Met Arg Ala Leu Ala Asn Ile Cys Asn Glu Gly Ile Ser
450                 455                 460

Met Asp Thr Met Ala Thr Val Ser Ala Glu Ala Cys Thr Gln Phe Pro
465                 470                 475                 480

Ala Gly Ser Trp Ser Ser Leu Gln Arg Gly Phe Ser Ala
                485                 490

<210> SEQ ID NO 98
<211> LENGTH: 380
<212> TYPE: PRT
<213> ORGANISM: Vicia narbonensis

<400> SEQUENCE: 98

Asp Val Cys His Ala Tyr Gln Leu Leu Arg Lys Gly Gly Leu Lys Glu
1               5                   10                  15

Glu Asn Ile Ile Val Phe Met Tyr Asp Asp Ile Ala Tyr Ser Glu Glu
                20                  25                  30

Asn Pro Arg Pro Gly Val Ile Ile Asn Ser Pro His Gly Glu Asn Val
            35                  40                  45

Tyr Glu Gly Val Pro Lys Asp Tyr Thr Gly Glu Asp Val Thr Val Gly
    50                  55                  60

Asn Phe Phe Ala Ala Leu Leu Gly Asn Lys Ser Ala Leu Ser Gly Gly
65                  70                  75                  80
```

Ser Gly Lys Val Val Asp Ser Gly Pro Asn Asp Arg Ile Phe Val Phe
                85                  90                  95

Tyr Ser Asp His Gly Pro Gly Val Leu Gly Met Pro Thr Ser Pro
            100                 105                 110

Tyr Met Tyr Ala Ser Asp Leu Val Glu Val Leu Lys Ile Lys His Ala
            115                 120                 125

Ala Gly Thr Tyr Lys Ser Leu Val Phe Tyr Leu Glu Ala Cys Glu Ser
            130                 135                 140

Gly Ser Ile Phe Glu Gly Leu Leu Pro Glu Gly Leu Asn Ile Tyr Ala
145                 150                 155                 160

Thr Thr Ala Ala Asn Ala Glu Glu Ser Ser Trp Gly Thr Tyr Cys Pro
                165                 170                 175

Gly Glu Asn Pro Ser Pro Pro Glu Tyr Glu Thr Cys Leu Ala Asp
            180                 185                 190

Leu Tyr Ser Val Ala Trp Met Glu Asp Ser Asp Ile His Asn Leu Gln
            195                 200                 205

Thr Glu Thr Leu His Gln Gln Tyr Glu Leu Val Lys Glu Arg Thr Ser
            210                 215                 220

Asn Gly Asn Ser Asn Tyr Gly Ser His Val Met Gln Tyr Gly Asp Ile
225                 230                 235                 240

Glu Leu Ser Lys Asp Ser Leu Phe Leu Tyr Leu Gly Ser Asn Pro Ser
                245                 250                 255

Asn Glu Asn Phe Thr Phe Val Gly Arg Asn Ser Leu Val Pro Pro Ser
            260                 265                 270

Lys Ala Ile Asn Gln Arg Asp Ala Asp Leu Ile His Phe Trp Asp Lys
            275                 280                 285

Phe Arg Lys Ala Pro Gln Gly Ser Pro Arg Lys Ala Ala Gln Lys
            290                 295                 300

Glu Val Leu Glu Ala Met Ser His Arg Met His Ile Asp Asp Ser Ile
305                 310                 315                 320

Lys Leu Val Gly Lys Leu Leu Phe Gly Met Lys Lys Gly Pro Glu Val
                325                 330                 335

Leu Thr Ser Val Arg Pro Ala Gly Gln Pro Leu Val Asp Asp Trp Asp
            340                 345                 350

Cys Leu Lys Thr Leu Val Arg Thr Phe Glu Thr Tyr Cys Gly Ser Leu
            355                 360                 365

Ser Gln Tyr Gly Met Lys His Met Arg Ser Phe Ala
            370                 375                 380

<210> SEQ ID NO 99
<211> LENGTH: 455
<212> TYPE: PRT
<213> ORGANISM: Nicotiana tabacum

<400> SEQUENCE: 99

Met Ile Arg Lys Asn Gly Val Val Pro Phe Leu Val Ala Leu Phe Val
1               5                   10                  15

Leu Val Cys Thr Ala Glu Gly Arg Asn Leu Leu Glu Ser Ile Val Glu
                20                  25                  30

Asp Asp Asn Pro Thr Gly Thr Lys Trp Ala Val Leu Val Ala Gly Ser
            35                  40                  45

Asn Glu Trp Asp Asn Tyr Arg His Gln Ala Asp Val Cys His Ala Tyr
        50                  55                  60

Gln Leu Leu Lys Lys Gly Gly Leu Lys Asp Glu Asn Ile Ile Val Phe
65                  70                  75                  80

```
Met Tyr Asp Asp Ile Ala Tyr Asn Lys Asn Pro Arg Pro Gly Ile
                85                  90                  95

Ile Ile Asn Ser Pro His Gly His Asp Val Tyr Lys Gly Val Pro Lys
    100                 105                 110

Asp Tyr Thr Gly Lys Asp Cys Asn Ala Asp Asn Phe Phe Ala Val Ile
        115                 120                 125

Leu Gly Asn Lys Ser Ala Leu Thr Gly Gly Ser Gly Lys Val Val Glu
    130                 135                 140

Asn Gly Pro Asn Asp Tyr Ile Phe Ile Tyr Tyr Ala Asp His Gly Ala
145                 150                 155                 160

Pro Gly Leu Ile Gly Met Pro Ser Gly Asp Val Val Tyr Ala Asp Asp
                165                 170                 175

Leu Asn Arg Val Leu Ile Lys Lys His Thr Phe Gly Thr Tyr Ser Lys
        180                 185                 190

Leu Val Phe Tyr Met Glu Ala Cys Glu Ser Gly Ser Met Phe Asp Gly
    195                 200                 205

Leu Leu Pro Lys Gly Leu Asn Ile Tyr Val Thr Ala Ala Ser Lys Pro
    210                 215                 220

Asp Glu Ser Ser Trp Ala Thr Tyr Cys Ile Arg Leu Gly Asp Glu Asp
225                 230                 235                 240

Gln Cys Leu Gly Asp Leu Tyr Ser Val Ser Trp Leu Glu Asp Ser Asp
                245                 250                 255

Leu His Asp Arg Gln Val Glu Thr Leu Glu Lys Gln Tyr Gln Leu Val
        260                 265                 270

Arg Lys Arg Thr Leu Asn Asn Gly Thr Glu Glu Gly Ser His Val Met
    275                 280                 285

Gln Tyr Gly Asp Leu His Ile Ser Glu Asp Pro Leu Phe Arg Tyr Met
    290                 295                 300

Gly Ser Asn Ser Ala Lys Asn Ser Tyr Asn Thr Ser Asn Asn Asp Glu
305                 310                 315                 320

Ser Trp Leu Pro Ser Arg Thr Val Asn Gln Arg Asp Val His Leu Met
                325                 330                 335

His Leu Trp Ser Lys Phe Arg Ser Ala Pro Glu Gly Ser Ala Arg Lys
        340                 345                 350

Ala Glu Ala His Arg Gln Leu Ser Glu Ala Leu Ser Gln Arg Glu Asp
    355                 360                 365

Val Asp Asn Ser Val Arg His Ile Gly Glu Val Leu Phe Gly Val Glu
    370                 375                 380

Lys Ser His Lys Leu Leu Asn Thr Val Arg Pro Ala Gly Gln Pro Leu
385                 390                 395                 400

Val Asp Asp Trp Asp Cys Leu Lys Ser Phe Val Lys Ile Phe Glu Ser
                405                 410                 415

Gln Cys Gly Thr Leu Thr Pro Tyr Gly Arg Lys His Val Arg Gly Phe
        420                 425                 430

Ala Asn Leu Cys Asn Ala Gly Ile Arg Arg Glu Gln Met Ala Ala Ala
    435                 440                 445

Ala Lys Gln Ala Cys Pro Pro
    450                 455

<210> SEQ ID NO 100
<211> LENGTH: 492
<212> TYPE: PRT
<213> ORGANISM: Aegilops tauschii
```

-continued

```
<400> SEQUENCE: 100

Met Ala Arg Leu Ser Cys Ser Pro Leu Leu Leu Leu Phe Leu Ser
1               5                   10                  15

Ser Gln Leu Ala Leu Leu Val Ala Gly Glu Phe Leu Arg Leu Pro Ser
            20                  25                  30

Glu Lys Asp Val Val Gly Thr Arg Trp Ala Val Leu Ile Ala Gly Ser
            35                  40                  45

Asn Gly Tyr Tyr Asn Tyr Arg His Gln Ala Gly Thr Lys Phe Pro Ile
50                  55                  60

Lys Tyr Ser Ser Leu Ile Thr Leu Met Glu Asn Ala Asp Val Cys His
65                  70                  75                  80

Ala Tyr Gln Ile Met Lys Lys Gly Leu Lys Asp Glu Asn Ile Ile
                85                  90                  95

Val Phe Met Tyr Asp Asp Ile Ala Gly Asn Arg Asp Asn Pro Arg Pro
            100                 105                 110

Gly Val Ile Ile Asn His Pro Lys Gly Asp Val Tyr Ala Gly Val
            115                 120                 125

Pro Lys Asp Tyr Thr Gly Ala Asp Val Asn Ala Asn Asn Phe Leu Ala
    130                 135                 140

Ala Leu Leu Gly Asp Lys Ser Lys Leu Thr Gly Ser Gly Ser Gly Lys
145                 150                 155                 160

Val Val Ser Ser Gly Ser Asp Asp His Ile Phe Val Tyr Tyr Ala Asp
                165                 170                 175

His Gly Gly Pro Gly Ile Leu Gly Met Pro Gly Asp Glu Glu Tyr Leu
            180                 185                 190

Tyr Ala Asn Asp Leu Val Arg Thr Leu Glu Lys Lys His Ala Gly Gly
        195                 200                 205

Ala Gly Tyr Lys Ser Leu Val Phe Tyr Leu Glu Ala Cys Glu Ser Gly
    210                 215                 220

Ser Ile Phe Glu Gly Leu Leu Pro Gly Asn Ile Gly Val Tyr Ala Thr
225                 230                 235                 240

Thr Ala Ala Asn Ala Glu Glu Ser Ser Trp Gly Thr Tyr Cys Pro Gly
                245                 250                 255

Asp Asp Glu Gly Ala Pro Pro Glu Tyr Asp Thr Cys Leu Gly Asp
            260                 265                 270

Leu Tyr Ser Val Ala Trp Met Glu Asp Ser Asp Ala His Asn Leu Asn
        275                 280                 285

Ala Glu Ser Leu Lys Gln Gln Tyr Glu Arg Val Arg Asp Arg Thr Ser
    290                 295                 300

Ala Ala Gly Thr Tyr Ser Leu Gly Ser His Val Met Gln Tyr Gly Asp
305                 310                 315                 320

Leu Asp Leu Asn Asp Gln Ser Leu Phe Leu Tyr Ile Gly Thr Asn Pro
                325                 330                 335

Ala Asn Asp Asn Ala Ser Phe Val Gln Gly Ser Ser Thr Ser Arg
            340                 345                 350

Gln Leu Pro Gly Gly Arg Val Asn Gln Arg Asp Ala Asp Leu Val His
        355                 360                 365

Phe Trp His Lys Tyr Arg Arg Ser Ala Glu Gly Ser Ala Lys Lys Gly
    370                 375                 380

Glu Ala Arg Arg Arg Leu Val Glu Thr Met Ala Arg Arg Ser Arg Val
385                 390                 395                 400

Asp Ser Ser Val Glu Leu Ile Gly Gly Leu Leu Phe Gly Ser Glu Gln
                405                 410                 415
```

Gly Ala Lys Val Leu Gly Ala Val Arg Pro Ala Gly Gln Pro Val Val
            420                 425                 430

Ala Asp Trp Asp Cys Leu Lys Ser Val Val Arg Arg Phe Gln Glu Arg
            435                 440                 445

Cys Gly Pro Leu Thr Gln Tyr Gly Met Lys His Met Arg Ser Leu Ala
450                 455                 460

Asn Leu Cys Asn Ala Gly Val Arg Glu Glu Ala Met Asp Lys Ala Ala
465                 470                 475                 480

Ala Gln Ala Cys Ala Ala Asn Pro Ser Ser Leu Phe
            485                 490

<210> SEQ ID NO 101
<211> LENGTH: 467
<212> TYPE: PRT
<213> ORGANISM: Brachypodium distachyon

<400> SEQUENCE: 101

Met Ala Arg Leu Ser Cys Phe Leu Leu Leu Gln Ala Gln Leu Phe
1               5                   10                  15

Leu Leu Val Ala Gly Glu Phe Leu Arg Leu Pro Ser Glu Gln Asp Val
            20                  25                  30

Ala Gly Thr Arg Trp Ala Val Leu Ile Ala Gly Ser Asn Asp Tyr Tyr
            35                  40                  45

Asn Tyr Arg His Gln Ala Asp Val Cys His Ala Tyr Gln Ile Met Lys
            50                  55                  60

Lys Gly Gly Leu Lys Asp Glu Asn Ile Ile Val Phe Met Tyr Asp Asp
65                  70                  75                  80

Ile Ala Asn Asn Pro Asp Asn Pro Arg Pro Gly Val Ile Ile Asn His
                85                  90                  95

Pro Thr Gly Gly Asp Val Tyr Ala Gly Val Pro Lys Asp Tyr Thr Gly
            100                 105                 110

Lys Asp Val Asn Ala Asn Asn Phe Leu Ala Ala Leu Leu Gly Asp Lys
            115                 120                 125

Ser Lys Leu Thr Gly Ser Gly Ser Gly Lys Val Val Ser Ser Gly Pro
130                 135                 140

Asn Asp His Ile Phe Val Tyr Tyr Ala Asp His Gly Gly Pro Gly Val
145                 150                 155                 160

Leu Gly Met Pro Glu Asp Ser Tyr Leu Tyr Ala Asn Asp Leu Val
                165                 170                 175

Arg Ala Leu Glu Lys Lys His Ala Gly Ala Gly Tyr Lys Ser Leu
            180                 185                 190

Val Phe Tyr Leu Glu Ala Cys Glu Ser Gly Ser Ile Phe Glu Gly Leu
            195                 200                 205

Leu Pro Gly Asn Ile Ser Val Tyr Ala Thr Thr Ala Ser Asn Ala Glu
210                 215                 220

Glu Ser Ser Trp Gly Thr Tyr Cys Pro Gly Asp Val Asp Gly Ala Pro
225                 230                 235                 240

Pro Ala Glu Phe Asp Thr Cys Leu Gly Asp Leu Tyr Ser Val Ala Trp
                245                 250                 255

Met Glu Asp Ser Asp Ala His Asn Leu Lys Ala Glu Ser Leu Lys Gln
                260                 265                 270

Gln Tyr Asp Arg Val Arg Asp Arg Thr Ser Ala His Glu Thr Tyr Asn
            275                 280                 285

Leu Gly Ser His Val Met Gln Tyr Gly Asp Leu Gly Ile Asn Ala Gln

```
                        290                 295                 300
Ser Leu Asp Ile Phe Ile Gly Ser Asn Pro Ala Asn Asp Lys Ser Asn
305                 310                 315                 320

Ser Ser Val Ser Ser Leu Leu Arg Asn Ala Arg Ala Gly Val Val His
                325                 330                 335

Gln Arg Asp Ala Asp Leu Leu His Phe Trp His Lys Tyr Lys Arg Ser
                340                 345                 350

Ala Glu Gly Ser Ala Arg Lys His Glu Ala Arg Arg Leu Val Glu
                355                 360                 365

Met Met Ala Arg Arg Ala Arg Val Asp Gly Ser Val Glu Leu Leu Gly
        370                 375                 380

Gly Leu Leu Phe Gly Ser Glu Glu Gly Ala Lys Val Met Asn Ala Val
385                 390                 395                 400

Arg Pro Ala Gly Gln Ala Leu Val Asp Asp Trp Asp Cys Leu Lys Asp
                405                 410                 415

Val Val Arg Arg Phe Glu Ala Arg Cys Gly Pro Leu Thr Gln Tyr Gly
                420                 425                 430

Met Lys His Met Arg Ala Leu Ala Asn Val Cys Asn Ala Gly Val Gly
                435                 440                 445

Val Glu Ala Val Asp Arg Ala Ala Ser Gln Ala Cys Ala Val His Pro
        450                 455                 460

Ser Val Phe
465

<210> SEQ ID NO 102
<211> LENGTH: 493
<212> TYPE: PRT
<213> ORGANISM: Sorghum bicolor

<400> SEQUENCE: 102

Met Ala Ala Ala Ala Trp Leu Cys Gly Leu Leu Trp Leu Leu Ala His
1               5                   10                  15

Ala Ala Ala Val Ala Ser Ala Ala Asp Gly Ala Asp Gly Gly Trp Glu
                20                  25                  30

Pro Leu Ile Arg Met Pro Thr Gly Lys Gly Gly Asp Ala Ala Ala Arg
            35                  40                  45

Ala Val Glu Glu Asp Asp Glu Val Gly Thr Arg Trp Ala Val Leu Val
        50                  55                  60

Ala Gly Ser Ser Gly Tyr Gly Asn Tyr Arg His Gln Ala Asp Val Cys
65                  70                  75                  80

His Ala Tyr Gln Ile Leu Arg Lys Gly Gly Val Lys Glu Glu Asn Ile
                85                  90                  95

Val Val Phe Met Tyr Asp Asp Ile Ala His Asn Ile Leu Asn Pro Arg
            100                 105                 110

Pro Gly Val Ile Ile Asn His Pro Lys Gly Glu Asn Val Tyr Asn Gly
        115                 120                 125

Val Pro Lys Asp Tyr Thr Gly Asp Gln Val Thr Thr Glu Asn Phe Phe
130                 135                 140

Ala Val Leu Leu Gly Asn Lys Ser Ala Ile Thr Gly Gly Ser Lys Lys
145                 150                 155                 160

Val Ile Asp Ser Lys Pro Asn Asp His Ile Phe Ile Tyr Tyr Ser Asp
                165                 170                 175

His Gly Gly Pro Gly Val Leu Gly Met Pro Asn Leu Pro Tyr Leu Tyr
            180                 185                 190
```

```
Ala Gly Asp Phe Ile Lys Val Leu Lys Lys His Ala Cys Asn Ser
            195                 200                 205

Tyr Ser Lys Met Val Ile Tyr Val Glu Ala Cys Glu Ser Gly Ser Ile
210                 215                 220

Phe Glu Gly Leu Met Pro Glu Asp Leu Asn Ile Tyr Val Thr Thr Ala
225                 230                 235                 240

Ser Asn Pro Val Glu Asn Ser Trp Gly Thr Tyr Cys Pro Gly Met Glu
                245                 250                 255

Pro Ser Pro Pro Glu Tyr Ile Thr Cys Leu Gly Asp Leu Tyr Ser
            260                 265                 270

Val Ser Trp Met Glu Asp Ser Gln Thr His Asn Leu Lys Lys Glu Thr
            275                 280                 285

Ile Lys Asp Gln Tyr Glu Val Val Lys Thr Arg Thr Ser Asn Ser Asn
290                 295                 300

Lys Tyr Lys Glu Gly Ser His Val Met Glu Tyr Gly Asp Lys Thr Phe
305                 310                 315                 320

Lys Asp Glu Lys Leu Phe Leu Tyr Gln Gly Phe Asp Pro Ala Asn Ala
                325                 330                 335

Asn Ile Ala Asn Met Leu Leu Trp Pro Gly Pro Lys Gly Ala Val Asn
            340                 345                 350

Gln Arg Asp Ala Asp Leu Leu Phe Met Trp Lys Arg Tyr Glu Gln Leu
            355                 360                 365

Asn Gly Glu Ser Val Glu Lys Leu Arg Ala Leu Ile Glu Ile Lys Glu
            370                 375                 380

Thr Val Gln His Arg Lys His Leu Asp Ser Ser Ile Asp Phe Ile Gly
385                 390                 395                 400

Arg Leu Leu Phe Gly Phe Glu Lys Gly Pro Ser Met Leu Glu Ala Val
                405                 410                 415

Arg Ala Ser Gly Leu Pro Leu Val Asp Asp Trp Asp Cys Leu Lys Arg
            420                 425                 430

Met Val Arg Ile Phe Glu Ser Gln Cys Gly Ser Leu Thr Gln Tyr Gly
            435                 440                 445

Met Lys Tyr Met Arg Ala Phe Ala Asn Ile Cys Asn Ser Gly Ile Ser
450                 455                 460

Glu Met Lys Met Arg Glu Ser Ser Ile Ser Ala Cys Ser Ser Tyr Asn
465                 470                 475                 480

Ser Ala Arg Trp Ser Pro Met Ala Gln Gly His Ser Ala
                485                 490

<210> SEQ ID NO 103
<211> LENGTH: 491
<212> TYPE: PRT
<213> ORGANISM: Triticum monococcum

<400> SEQUENCE: 103

Met Ala Pro Arg Trp Cys Phe Ala Leu Leu Leu Leu Cys Ala Ala
1               5                   10                  15

Ala Arg Pro Gly Ala Asp Ala Ser Lys Gly Lys Trp Asp Pro Val Ile
                20                  25                  30

Arg Met Pro Gly Glu Glu Pro Ala Thr Gly Asp Glu Ser Ser Glu
            35                  40                  45

Glu Gly Glu Asp Gly Val Gly Thr Arg Trp Ala Val Leu Val Ala Gly
        50                  55                  60

Ser Ser Gly Tyr Gly Asn Tyr Arg His Gln Ala Asp Ile Cys His Ala
65                  70                  75                  80
```

```
Tyr Gln Ile Leu Arg Lys Gly Val Lys Glu Asn Ile Val Val
                85              90              95
Phe Met Tyr Asp Asp Ile Ala Asn Asn Pro Leu Asn Pro Arg Pro Gly
            100                 105                 110
Val Ile Ile Asn His Pro Glu Gly Asp Val Tyr Ala Gly Val Pro
            115                 120                 125
Lys Asp Tyr Thr Gly Glu Glu Val Thr Ala Lys Asn Phe Tyr Ala Val
    130                 135                 140
Leu Leu Gly Asn Lys Thr Ala Val Thr Gly Gly Ser Lys Lys Val Ile
145                 150                 155                 160
Asp Ser Lys Pro Asn Asp His Ile Phe Ile Tyr Tyr Ser Asp His Gly
                165                 170                 175
Gly Pro Gly Val Leu Gly Met Pro Asn Leu Pro Tyr Leu Tyr Ala Ala
            180                 185                 190
Asp Phe Ile Lys Val Leu Gln Glu Lys His Ala Ser Asn Thr Tyr Ala
            195                 200                 205
Lys Met Val Ile Tyr Val Glu Ala Cys Glu Ser Gly Ser Ile Phe Glu
    210                 215                 220
Gly Leu Met Pro Ala Asp Leu Asn Ile Tyr Val Thr Thr Ala Ser Asn
225                 230                 235                 240
Ala Glu Glu Ser Ser Trp Gly Thr Tyr Cys Pro Gly Met Glu Pro Ser
                245                 250                 255
Pro Pro Ser Glu Tyr Ile Thr Cys Leu Gly Asp Leu Tyr Ser Ile Ser
            260                 265                 270
Trp Met Glu Asp Ser Glu Thr Asn Asn Leu Lys Glu Thr Ile Lys
    275                 280                 285
Lys Gln Tyr Glu Val Val Lys Lys Arg Thr Ser Asp Met Asn Ser Tyr
    290                 295                 300
Ser Ala Gly Ser His Val Met Glu Tyr Gly Asp Lys Thr Phe Lys Asp
305                 310                 315                 320
Glu Lys Leu Tyr Leu Tyr Gln Gly Phe Asn Pro Ala Asn Thr Asn Ile
                325                 330                 335
Thr Asn Met Leu Leu Leu Gln Ala Pro Lys Ala Ala Ile Asn Gln Arg
            340                 345                 350
Asp Ala Asp Leu Leu Phe Leu Trp Arg Arg Tyr Glu Leu Leu His Glu
            355                 360                 365
Lys Ser Lys Glu Lys Gly Asn Val Leu Arg Glu Ile Ser Glu Thr Val
    370                 375                 380
Thr His Arg Lys His Leu Asp Ser Ser Ile Asp Phe Ile Gly Lys Leu
385                 390                 395                 400
Leu Phe Gly Phe Glu Asn Gly Pro Ser Val Leu Gln Ala Val Arg Pro
                405                 410                 415
Ser Gly Lys Pro Leu Val Asp Asp Trp Asp Cys Leu Lys Arg Met Val
            420                 425                 430
Arg Ile Phe Glu Ser His Cys Gly Ser Leu Thr Gln Tyr Gly Met Lys
            435                 440                 445
His Met Arg Ala Phe Ala Asn Ile Cys Asn Asn Gly Ile Ser Gly Thr
    450                 455                 460
Thr Met Lys Glu Ala Ser Ile Gly Ala Cys Gly Val Gln Asn Ser Ala
465                 470                 475                 480
Arg Trp Ser Ser Leu Ile Gln Gly Tyr Ser Ala
                485                 490
```

<210> SEQ ID NO 104
<211> LENGTH: 491
<212> TYPE: PRT
<213> ORGANISM: Aegilops speltoides

<400> SEQUENCE: 104

```
Met Ala Pro Arg Trp Cys Phe Ala Leu Leu Leu Leu Cys Ala Ala
1               5                   10                  15

Ala Gly Ala Gly Ala Asp Ala Ser Lys Gly Lys Trp Asp Pro Val Ile
            20                  25                  30

Arg Met Pro Gly Glu Glu Pro Ala Thr Gly Asp Glu Ser Ser Glu
            35                  40                  45

Glu Gly Glu Asp Gly Val Gly Thr Arg Trp Ala Val Leu Val Ala Gly
    50                  55                  60

Ser Ser Gly Tyr Gly Asn Tyr Arg His Gln Ala Asp Ile Cys His Ala
65                  70                  75                  80

Tyr Gln Ile Leu Arg Lys Gly Gly Val Lys Glu Glu Asn Ile Val Val
                85                  90                  95

Phe Met Tyr Asp Asp Ile Ala Asn Asn Pro Leu Asn Pro Arg Pro Gly
            100                 105                 110

Val Ile Ile Asn His Pro Glu Gly Glu Asp Val Tyr Ala Gly Val Pro
            115                 120                 125

Lys Asp Tyr Thr Gly Glu Ala Val Thr Ala Lys Asn Phe Tyr Ala Val
    130                 135                 140

Leu Leu Gly Asn Asn Thr Ala Val Thr Gly Gly Ser Lys Lys Val Ile
145                 150                 155                 160

Asp Ser Lys Pro Asn Asp His Ile Phe Ile Tyr Tyr Ser Asp His Gly
                165                 170                 175

Gly Pro Gly Val Leu Gly Met Pro Asn Leu Pro Tyr Leu Tyr Ala Ala
            180                 185                 190

Asp Phe Ile Lys Val Leu Gln Glu Lys His Ala Ser Asn Thr Tyr Ala
            195                 200                 205

Lys Met Val Ile Tyr Val Glu Ala Cys Glu Ser Gly Ser Ile Phe Glu
    210                 215                 220

Gly Leu Met Pro Ala Asp Leu Asn Ile Tyr Val Thr Thr Ala Ser Asn
225                 230                 235                 240

Ala Glu Glu Ser Ser Trp Gly Thr Tyr Cys Pro Gly Met Glu Pro Ser
                245                 250                 255

Pro Pro Ser Glu Tyr Ile Thr Cys Leu Gly Asp Leu Tyr Ser Ile Ser
            260                 265                 270

Trp Met Glu Asp Ser Glu Thr Asn Asn Leu Lys Glu Glu Thr Ile Lys
    275                 280                 285

Lys Gln Tyr Glu Val Val Lys Lys Arg Thr Ser Asp Met Asn Ser Tyr
    290                 295                 300

Ser Ala Gly Ser His Val Met Glu Tyr Gly Asp Lys Thr Phe Lys Asp
305                 310                 315                 320

Glu Lys Leu Tyr Leu Tyr Gln Gly Phe Asn Pro Ala Asn Thr Asn Ile
                325                 330                 335

Thr Asn Lys Leu Phe Leu Gln Ala Pro Lys Ala Ala Ile Asn Gln Arg
            340                 345                 350

Asp Ala Asp Leu Leu Phe Leu Trp Arg Arg Tyr Glu Leu Leu His Glu
            355                 360                 365

Lys Ser Lys Glu Lys Ala Asn Val Leu Arg Glu Ile Ser Glu Thr Val
    370                 375                 380
```

```
Ala His Arg Lys His Leu Asp Ser Ser Ile Asp Phe Ile Gly Lys Leu
385                 390                 395                 400

Leu Phe Gly Phe Glu Asn Gly Pro Trp Glu Leu Gln Ala Val Arg Pro
            405                 410                 415

Ser Gly Lys Pro Leu Val Asp Asp Trp Asp Cys Leu Lys Arg Met Val
            420                 425                 430

Arg Ile Phe Glu Ser His Cys Gly Ser Leu Thr Gln Tyr Gly Met Lys
            435                 440                 445

His Met Arg Ala Phe Ala Asn Ile Cys Asn Asn Gly Val Ser Gly Thr
    450                 455                 460

Thr Met Asn Glu Ala Ser Ile Gly Ala Cys Gly Val Gln Asn Ser Ala
465                 470                 475                 480

Arg Trp Ser Thr Leu Ile Gln Gly Tyr Ser Ala
            485                 490

<210> SEQ ID NO 105
<211> LENGTH: 489
<212> TYPE: PRT
<213> ORGANISM: Aegilops tauschii

<400> SEQUENCE: 105

Met Ala Pro Arg Trp Cys Phe Ala Leu Leu Leu Leu Cys Ala Ala
1               5                   10                  15

Ala Gly Ala Asp Ala Ser Lys Gly Lys Trp Asp Pro Val Ile Arg Met
            20                  25                  30

Pro Gly Glu Glu Glu Pro Ala Thr Gly Asp Asp Ser Ser Glu Glu Gly
            35                  40                  45

Glu Asp Gly Val Gly Thr Arg Trp Ala Val Leu Val Ala Gly Ser Ser
    50                  55                  60

Gly Tyr Gly Asn Tyr Arg His Gln Ala Asp Ile Cys His Ala Tyr Gln
65                  70                  75                  80

Ile Leu Arg Lys Gly Gly Val Lys Glu Glu Asn Ile Val Val Phe Met
                85                  90                  95

Tyr Asp Asp Ile Ala Asn Asn Pro Leu Asn Pro Arg Pro Gly Val Ile
            100                 105                 110

Ile Asn His Pro Glu Gly Glu Asp Val Tyr Ala Gly Val Pro Lys Asp
        115                 120                 125

Tyr Thr Gly Glu Ala Val Thr Ala Lys Asn Phe Tyr Ala Val Leu Leu
    130                 135                 140

Gly Asn Lys Thr Ala Val Thr Gly Gly Ser Lys Lys Val Ile Asp Ser
145                 150                 155                 160

Lys Pro Asn Asp His Ile Phe Ile Tyr Tyr Ser Asp His Gly Gly Pro
                165                 170                 175

Gly Val Leu Gly Met Pro Asn Leu Pro Tyr Leu Tyr Ala Ala Asp Phe
            180                 185                 190

Ile Lys Val Leu Gln Glu Lys His Ala Ser Asn Thr Tyr Ala Lys Met
        195                 200                 205

Val Ile Tyr Val Glu Ala Cys Glu Ser Gly Ser Ile Phe Glu Gly Leu
    210                 215                 220

Met Pro Ala Asp Leu Asn Ile Tyr Val Thr Thr Ala Ser Asn Ala Glu
225                 230                 235                 240

Glu Ser Ser Trp Gly Thr Tyr Cys Pro Gly Met Glu Pro Ser Pro Pro
                245                 250                 255

Ser Glu Tyr Ile Thr Cys Leu Gly Asp Leu Tyr Ser Ile Ser Trp Met
```

-continued

```
               260                 265                 270
Glu Asp Ser Glu Thr Asn Asn Leu Lys Glu Thr Ile Lys Lys Gln
            275                 280                 285
Tyr Glu Val Val Lys Lys Arg Thr Ser Asp Met Asn Ser Tyr Ser Ala
        290                 295                 300
Gly Ser His Val Met Glu Tyr Gly Asp Met Thr Phe Lys Asp Glu Lys
305                 310                 315                 320
Leu Tyr Leu Tyr Gln Gly Phe Asn Pro Ala Asn Thr Asn Ile Thr Asn
                325                 330                 335
Lys Leu Phe Leu Gln Ala Pro Lys Ala Ala Ile Asn Gln Arg Asp Ala
            340                 345                 350
Asp Leu Leu Phe Leu Trp Arg Arg Tyr Glu Leu Leu His Gly Lys Ser
        355                 360                 365
Lys Glu Lys Ala Asn Val Leu Thr Glu Ile Gly Glu Thr Val Ala His
            370                 375                 380
Arg Lys His Leu Asp Asn Ser Ile Asp Phe Ile Gly Lys Leu Leu Phe
385                 390                 395                 400
Gly Phe Glu Asn Gly Pro Ser Glu Leu Gln Ala Val Arg Pro Ser Gly
                405                 410                 415
Lys Pro Leu Val Asp Asp Trp Asp Cys Leu Lys Arg Met Val Arg Ile
            420                 425                 430
Phe Glu Ser His Cys Gly Ser Leu Thr Gln Tyr Gly Met Lys His Met
        435                 440                 445
Arg Ala Phe Ala Asn Ile Cys Asn Asn Gly Val Ser Gly Thr Thr Met
    450                 455                 460
Lys Glu Ala Ser Ile Asn Thr Cys Gly Gly His Asn Ser Ala Arg Leu
465                 470                 475                 480
Ser Thr Leu Ile Gln Gly Tyr Ser Ala
                485
```

<210> SEQ ID NO 106
<211> LENGTH: 460
<212> TYPE: PRT
<213> ORGANISM: Solanum tuberosum

<400> SEQUENCE: 106

```
Met Ile Phe Lys Tyr Asn Val Phe Val Ala Leu Val Val Leu Ser
1               5                   10                  15
Ile Trp Asp Asn Ile Glu Gly Arg Ser Val Ser Lys Phe Leu Thr Glu
            20                  25                  30
Glu Thr Val Gly Thr Lys Trp Ala Val Leu Val Ala Gly Ser Asn Gly
        35                  40                  45
Trp Phe Asn Tyr Arg His Gln Ala Asp Val Cys His Ala Tyr Gln Ile
    50                  55                  60
Leu Lys Lys Gly Gly Leu Lys Asp Glu Asn Ile Ile Val Phe Met Tyr
65                  70                  75                  80
Asp Asp Ile Ala Asn Asn Thr Met Asn Pro Arg Pro Gly Val Ile Ile
                85                  90                  95
Asn Asn Pro His Gly Gln Asp Val Tyr Lys Gly Val Pro Lys Asp Tyr
            100                 105                 110
Val Gly Glu Asp Val Asn Ala Glu Asn Phe Phe Asn Val Ile Leu Ala
        115                 120                 125
Asn Lys Ser Gly Ile Thr Gly Gly Ser Gly Lys Val Leu Asn Ser Gly
    130                 135                 140
```

```
Pro Asn Asp His Ile Phe Ile Tyr Tyr Thr Asp His Gly Gly Pro Gly
145                 150                 155                 160

Ile Ile Ser Met Pro Thr Gly Leu Val Tyr Ala Asn Asp Leu Ile Asn
            165                 170                 175

Val Leu Lys Lys Lys His Ala Ser Gly Thr Tyr Ser Lys Leu Val Phe
        180                 185                 190

Tyr Leu Glu Ala Cys Glu Ser Gly Met Phe Asp Gly Leu Leu Pro
    195                 200                 205

Glu Gly Leu Asn Ile Tyr Val Thr Thr Ala Ser Asn Pro Asn Glu Ser
210                 215                 220

Ser Trp Gly Thr Tyr Cys Gln Met Gly Ala Gly Pro Cys Leu Val
225                 230                 235                 240

Glu Cys Pro Pro Pro Glu Phe Gln Gly Val Cys Leu Gly Asp Leu Tyr
                245                 250                 255

Ser Val Ala Trp Met Glu Asp Ser Glu Ala Glu Asp Arg Gln Thr Glu
            260                 265                 270

Thr Leu Asn Asp Gln Tyr Asn Thr Val Ala Asn Arg Thr Ala Ala Asn
        275                 280                 285

Leu Thr Tyr Gly Ser His Val Met Gln Tyr Gly Asp Thr Val Leu Ser
    290                 295                 300

Val Asp Val Leu Phe Gln Tyr Met Gly Ala Ala Ser Val Asn His Ser
305                 310                 315                 320

His Val Ser Met Asn Ser Glu Ser Ser Ser Gln Asn Val Asp Gln Arg
                325                 330                 335

Asp Val Glu Leu Phe Tyr Leu Thr Ser Lys Tyr Gln Asp Ala Pro Glu
            340                 345                 350

Gly Ser Asp Glu His Phe Glu Thr Arg Val Lys Leu Ile Lys Thr Ile
        355                 360                 365

Ala Glu Arg Ser Gln Val Asp Asn Ser Val Lys His Ile Gly Asp Leu
    370                 375                 380

Leu Phe Gly Val Glu Lys Gly Ser Glu Val Leu Gln His Val Arg Pro
385                 390                 395                 400

Ala Gly Gln Pro Leu Val Asp Asn Trp Asp Cys Leu Lys Ser Tyr Ile
                405                 410                 415

Glu Thr Phe Glu Val His Cys Gly Lys Leu Ser Ser Tyr Gly Lys Lys
            420                 425                 430

His Ile Arg Gly Ile Ala Asn Ile Cys Asn Ala Gly Ile Lys Ser Glu
        435                 440                 445

Gln Met Ala Ser Ala Thr Ala Gln Ala Cys Ser Ser
450                 455                 460

<210> SEQ ID NO 107
<211> LENGTH: 490
<212> TYPE: PRT
<213> ORGANISM: Brachypodium distachyon

<400> SEQUENCE: 107

Met Ala Ala Trp Trp Cys Phe Ala Leu Leu Leu Val Leu Cys Ala Pro
1               5                   10                  15

Ala Gly Ala Asp Val Ser Lys Gly Lys Trp Glu Pro Leu Ile Arg Met
            20                  25                  30

Pro Gly Glu Lys Glu Pro Ala Thr Ala Arg Gly Phe Glu Gly Pro Glu
        35                  40                  45

Glu Glu Asp Gly Val Gly Thr Arg Trp Ala Val Leu Ile Ala Gly Ser
50                  55                  60
```

```
Ser Gly Tyr Gly Asn Tyr Arg His Gln Ala Asp Ile Cys His Ala Tyr
 65                  70                  75                  80

Gln Val Leu Arg Lys Gly Gly Leu Lys Glu Asn Ile Val Val Phe
             85                  90                  95

Met Tyr Asp Asp Ile Ala Asn Ser Ala Leu Asn Pro Arg Pro Gly Val
            100                 105                 110

Ile Ile Asn His Pro Gln Gly Glu Asp Val Tyr Ala Gly Val Pro Lys
            115                 120                 125

Asp Tyr Thr Gly Glu Gln Val Thr Ala Lys Asn Leu Tyr Ala Val Leu
            130                 135                 140

Leu Gly Asn Lys Thr Ala Val Thr Gly Gly Ser Lys Lys Val Ile Asp
145                 150                 155                 160

Ser Gln Pro Lys Asp His Ile Phe Ile Tyr Tyr Ser Asp His Gly Gly
                165                 170                 175

Pro Gly Val Leu Gly Met Pro Asn Leu Pro Tyr Leu Tyr Ala Gly Asp
            180                 185                 190

Phe Ile Lys Ile Leu Gln Gln Lys His Ala Ser Asn Thr Tyr Ala Lys
            195                 200                 205

Met Val Ile Tyr Val Glu Ala Cys Glu Ser Gly Ser Ile Phe Glu Gly
            210                 215                 220

Leu Met Pro Ala Asp Leu Asn Ile Tyr Val Thr Thr Ala Ser Asn Ala
225                 230                 235                 240

Glu Glu Ser Ser Trp Gly Thr Tyr Cys Pro Gly Met Glu Pro Ser Pro
                245                 250                 255

Pro Ser Glu Tyr Ile Thr Cys Leu Gly Asp Leu Tyr Ser Val Ser Trp
            260                 265                 270

Met Glu Asp Ser Glu Asn His Asn Leu Lys Glu Glu Thr Ile Lys Lys
            275                 280                 285

Gln Tyr Glu Val Val Lys Arg Arg Thr Ser Asp Leu Asn Ser Tyr Ser
            290                 295                 300

Ala Gly Ser His Val Met Glu Tyr Gly Asp Lys Thr Phe Lys Asp Glu
305                 310                 315                 320

Lys Leu Tyr Leu Tyr Gln Gly Phe Asn Pro Ala Asn Ala Asn Ile Thr
                325                 330                 335

Asn Lys Leu Phe Trp Gln Ala Pro Arg Ala Ala Ile Asn Gln Arg Asp
            340                 345                 350

Ala Asp Leu Leu Phe Leu Trp Arg Arg Tyr Glu Met Leu His Glu Lys
            355                 360                 365

Ser Lys Glu Lys Val Lys Val Leu Arg Glu Ile Ser Glu Thr Val Met
            370                 375                 380

His Arg Lys His Leu Asp Asn Ser Val Asp Leu Ile Gly Gln Leu Leu
385                 390                 395                 400

Phe Gly Phe Glu Asn Gly Pro Ser Val Leu Gln Ala Val Arg Pro Ser
                405                 410                 415

Gly Lys Pro Leu Val Asp Asp Trp Asp Cys Leu Lys Arg Met Val Arg
            420                 425                 430

Ile Phe Glu Ser His Cys Gly Pro Leu Thr Gln Tyr Gly Met Lys His
            435                 440                 445

Met Arg Ala Phe Ala Asn Ile Cys Asn Asn Gly Ile Pro Gly Ser Thr
            450                 455                 460

Met Lys Glu Gly Ser Ile Ser Ala Cys Gly Ser Arg Asn Ile Ala Arg
465                 470                 475                 480
```

```
Trp Ser Pro Leu Ile Gln Gly Tyr Ser Ala
            485                 490
```

```
<210> SEQ ID NO 108
<211> LENGTH: 493
<212> TYPE: PRT
<213> ORGANISM: Zea mays

<400> SEQUENCE: 108

Met Met Ala Ala Ala Trp Leu Cys Gly Leu Leu Ser Leu Leu Ala
1               5                   10                  15

Leu Ala Gly Ala Ala Ser Ala Ala Asp Gly Ala Glu Gly Glu Trp Glu
                20                  25                  30

Pro Leu Ile Arg Met Pro Thr Ala Lys Gly Ser Asp Ala Ala Ser Ala
            35                  40                  45

Pro Ala Ala Glu Asp Asp Glu Val Gly Thr Arg Trp Ala Val Leu Val
50                  55                  60

Ala Gly Ser Phe Gly Tyr Gly Asn Tyr Arg His Gln Ala Asp Val Cys
65                  70                  75                  80

His Ala Tyr Gln Ile Leu Gln Lys Gly Gly Val Lys Lys Glu Asn Ile
                85                  90                  95

Val Val Phe Met Tyr Asp Asp Ile Ala His Asn Ile Leu Asn Pro Arg
            100                 105                 110

Pro Gly Val Ile Ile Asn His Pro Lys Gly Ala Asn Val Tyr Asp Gly
            115                 120                 125

Val Pro Lys Asp Tyr Thr Gly Asp Gln Val Thr Thr Glu Asn Phe Phe
130                 135                 140

Ala Val Leu Leu Gly Asn Arg Ser Ala Thr Thr Gly Gly Ser Lys Lys
145                 150                 155                 160

Val Ile Asp Ser Lys Pro Asn Asp His Ile Phe Ile Tyr Tyr Ser Asp
                165                 170                 175

His Gly Gly Pro Gly Val Leu Gly Met Pro Asn Leu Pro Tyr Leu Tyr
            180                 185                 190

Ala Gly Asp Phe Ile Lys Val Leu Lys Lys Lys His Ala Ser Asn Ser
            195                 200                 205

Tyr Ser Lys Met Val Ile Tyr Val Glu Ala Cys Glu Ser Gly Ser Ile
            210                 215                 220

Phe Glu Gly Leu Met Pro Glu Asp Leu Asn Ile Tyr Val Thr Thr Ala
225                 230                 235                 240

Ser Asn Pro Val Glu Asn Ser Trp Gly Thr Tyr Cys Pro Gly Met Glu
                245                 250                 255

Pro Ser Pro Pro Pro Glu Tyr Ile Thr Cys Leu Gly Asp Leu Tyr Ser
            260                 265                 270

Val Ser Trp Met Glu Asp Ser Glu Thr His Asn Leu Lys Lys Glu Thr
            275                 280                 285

Ile Lys Asp Gln Tyr Glu Val Val Lys Thr Arg Thr Ser Asn Ser Asn
            290                 295                 300

Lys Tyr Lys Glu Gly Ser His Val Met Glu Tyr Gly Asp Lys Thr Phe
305                 310                 315                 320

Lys Asp Glu Lys Leu Ser Phe Tyr Gln Gly Phe Asp Pro Ala Asn Ala
                325                 330                 335

Asn Ile Ala Asn Met Leu Leu Trp Pro Gly Pro Lys Gly Ala Val Asn
            340                 345                 350

Gln Arg Asp Ala Asp Leu Leu Phe Met Trp Lys Arg Tyr Glu Gln Leu
            355                 360                 365
```

Asn Gly Gly Thr Glu Glu Lys Leu Arg Ala Leu Ile Glu Ile Lys Glu
        370                 375                 380

Thr Val Gln His Arg Lys His Leu Asp Ser Ser Ile Asp Phe Val Gly
385                 390                 395                 400

Arg Leu Val Phe Gly Phe Glu Lys Gly Pro Ser Met Leu Glu Ala Val
                405                 410                 415

Arg Thr Ser Gly Gln Pro Leu Val Asp Asp Trp Asp Cys Leu Lys Arg
            420                 425                 430

Met Val Arg Ile Phe Glu Ser Gln Cys Gly Ser Leu Thr Gln Tyr Gly
                435                 440                 445

Met Lys Tyr Met Arg Ala Phe Ala Asn Ile Cys Asn Ser Gly Ile Ser
        450                 455                 460

Glu Met Lys Met Arg Glu Ser Ser Ile Ser Ala Cys Ser Ser Tyr Asn
465                 470                 475                 480

Ser Ala Arg Trp Ser Pro Met Ala Arg Gly His Ser Ala
                485                 490

<210> SEQ ID NO 109
<211> LENGTH: 492
<212> TYPE: PRT
<213> ORGANISM: Setaria italica

<400> SEQUENCE: 109

Met Ala Ala Ala Ala Trp Leu Cys Gly Leu Leu Ser Leu Leu Ala Val
1               5                   10                  15

Ala Ala Ala Ala Ser Val Asp Gly Ala Glu Glu Glu Trp Glu Pro Leu
            20                  25                  30

Ile Arg Met Pro Thr Glu Lys Gly Gly Asn Ala Ala Ala Ala Ala Pro
        35                  40                  45

Ala Ala Glu Glu Asp Glu Val Gly Thr Arg Trp Ala Val Leu Val Ala
    50                  55                  60

Gly Ser Ser Gly Tyr Gly Asn Tyr Arg His Gln Ala Asp Val Cys His
65                  70                  75                  80

Ala Tyr Gln Ile Leu Leu Lys Gly Gly Val Lys Glu Glu Asn Ile Val
                85                  90                  95

Val Phe Met Tyr Asp Asp Ile Ala His Asn Ile Leu Asn Pro Arg Pro
            100                 105                 110

Gly Val Ile Ile Asn His Pro Lys Gly Glu Asn Val Tyr Pro Gly Val
        115                 120                 125

Pro Lys Asp Tyr Thr Gly Asp Gln Val Thr Thr Glu Asn Phe Phe Ala
    130                 135                 140

Val Leu Leu Gly Asn Arg Ser Ala Ile Thr Gly Gly Ser Lys Lys Val
145                 150                 155                 160

Ile Asp Ser Lys Pro Asn Asp His Ile Phe Ile Tyr Tyr Ser Asp His
                165                 170                 175

Gly Gly Pro Gly Val Leu Gly Met Pro Asn Leu Pro Tyr Leu Tyr Ala
            180                 185                 190

Gly Asp Phe Ile Lys Val Leu Lys Lys His Ala Ser Asn Ser Tyr
        195                 200                 205

Ser Lys Met Val Ile Tyr Val Glu Ala Cys Glu Ser Gly Ser Ile Phe
    210                 215                 220

Glu Gly Leu Met Pro Gln Asp Leu Asn Ile Tyr Val Thr Thr Ala Ser
225                 230                 235                 240

Asn Pro Val Glu Asn Ser Trp Gly Thr Tyr Cys Pro Gly Met Asp Pro

```
            245                 250                 255
Ser Pro Pro Pro Glu Tyr Ile Thr Cys Leu Gly Asp Leu Tyr Ser Val
            260                 265                 270

Ser Trp Met Glu Asp Ser Gln Thr His Asn Leu Met Lys Glu Thr Ile
            275                 280                 285

Lys Asp Gln Tyr Glu Val Val Lys Thr Arg Thr Ser Asn Leu Lys Lys
            290                 295                 300

Tyr Lys Glu Gly Ser His Val Met Glu Tyr Gly Asp Lys Thr Phe Thr
305                 310                 315                 320

Asn Glu Lys Leu Phe Leu Tyr Gln Gly Phe Asp Pro Ala Asn Ala Asn
                325                 330                 335

Ala Ala Asn Thr Leu Leu Trp Pro Gly Pro Lys Gly Ala Val Asn Gln
            340                 345                 350

Arg Asp Ala Asp Leu Leu Phe Met Trp Lys Arg Tyr Glu Gln Leu Asp
                355                 360                 365

Gly Gly Ser Glu Glu Lys Leu Arg Ala Leu Arg Glu Ile Lys Glu Thr
370                 375                 380

Val Gln His Arg Lys His Leu Asp Ser Ser Ile Asp Phe Ile Gly Arg
385                 390                 395                 400

Leu Val Phe Gly Phe Glu Asn Gly Pro Lys Met Leu Glu Ala Val Arg
                405                 410                 415

Ala Ser Gly Gln Pro Leu Val Asp Asp Trp Asp Cys Leu Lys Arg Met
                420                 425                 430

Val Arg Ile Phe Glu Ala Gln Cys Gly Ser Leu Thr Gln Tyr Gly Met
                435                 440                 445

Lys Tyr Met Arg Ala Phe Ala Asn Ile Cys Asn Ser Gly Ile Ser Glu
            450                 455                 460

Ala Lys Met Arg Glu Ser Ser Ile Ser Ala Cys Gly Tyr Asn Ser
465                 470                 475                 480

Ala Arg Trp Ser Pro Met Ala Gln Gly His Ser Ala
                485                 490

<210> SEQ ID NO 110
<211> LENGTH: 5
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (4)..(4)
<223> OTHER INFORMATION: Xaa is Gly with -NH- being replaced by -S-.

<400> SEQUENCE: 110

Tyr Lys Asn Xaa Val
1               5

<210> SEQ ID NO 111
<211> LENGTH: 5
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (4)..(4)
<223> OTHER INFORMATION: Xaa is Gly with -NH- being replaced by -O-.

<400> SEQUENCE: 111

Tyr Lys Asn Xaa Val
```

```
1               5

<210> SEQ ID NO 112
<211> LENGTH: 5
<212> TYPE: PRT
<213> ORGANISM: artificial construct
<220> FEATURE:
<223> OTHER INFORMATION: synthesized peptide

<400> SEQUENCE: 112

Tyr Lys Asn His Val
1               5

<210> SEQ ID NO 113
<211> LENGTH: 5
<212> TYPE: PRT
<213> ORGANISM: artificial construct
<220> FEATURE:
<223> OTHER INFORMATION: synthetic peptide

<400> SEQUENCE: 113

Tyr Lys Asn Gly Val
1               5

<210> SEQ ID NO 114
<211> LENGTH: 6
<212> TYPE: PRT
<213> ORGANISM: artificial construct
<220> FEATURE:
<223> OTHER INFORMATION: synthesized peptide

<400> SEQUENCE: 114

Gly Ile Gly Gly Ile Arg
1               5

<210> SEQ ID NO 115
<211> LENGTH: 5
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is Gly with -NH2 being replaced by -OH

<400> SEQUENCE: 115

Xaa Val Tyr Lys Val
1               5

<210> SEQ ID NO 116
<211> LENGTH: 14
<212> TYPE: PRT
<213> ORGANISM: artificial construct
<220> FEATURE:
<223> OTHER INFORMATION: synthetic peptide

<400> SEQUENCE: 116

Glu Arg Leu Tyr Arg Gly Arg Leu Tyr Arg Arg Asn His Val
1               5                   10

<210> SEQ ID NO 117
<211> LENGTH: 6
<212> TYPE: PRT
<213> ORGANISM: artificial construct
<220> FEATURE:
<223> OTHER INFORMATION: synthetic peptide
<220> FEATURE:
```

```
<221> NAME/KEY: MISC_FEATURE
<222> LOCATION: (1)..(1)
<223> OTHER INFORMATION: Xaa is Thr conjugated to biotin.
<220> FEATURE:
<221> NAME/KEY: MISC_FEATURE
<222> LOCATION: (5)..(5)
<223> OTHER INFORMATION: Xaa is Gly with -NH- being replaced by -O-.

<400> SEQUENCE: 117

Xaa Tyr Lys Asn Xaa Val
1               5

<210> SEQ ID NO 118
<211> LENGTH: 7
<212> TYPE: PRT
<213> ORGANISM: artificial construct
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa ia acetyl Arg.
<220> FEATURE:
<221> NAME/KEY: MISC_FEATURE
<222> LOCATION: (6)..(6)
<223> OTHER INFORMATION: Xaa ia Gly with -NH- being replaced by -S-.

<400> SEQUENCE: 118

Xaa Tyr Arg Leu Asn Xaa Val
1               5

<210> SEQ ID NO 119
<211> LENGTH: 7
<212> TYPE: PRT
<213> ORGANISM: artificial construct
<220> FEATURE:
<223> OTHER INFORMATION: synthetic peptide

<400> SEQUENCE: 119

Arg Tyr Arg Leu Asn His Val
1               5

<210> SEQ ID NO 120
<211> LENGTH: 7
<212> TYPE: PRT
<213> ORGANISM: artificial construct
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is acetyl Arg.
<220> FEATURE:
<221> NAME/KEY: MISC_FEATURE
<222> LOCATION: (6)..(6)
<223> OTHER INFORMATION: Xaa is Gly with -NH- being replaced by -S-.

<400> SEQUENCE: 120

Xaa Leu Tyr Arg Asn Xaa Val
1               5

<210> SEQ ID NO 121
<211> LENGTH: 4
<212> TYPE: PRT
<213> ORGANISM: artificial construct
<220> FEATURE:
<223> OTHER INFORMATION: synthetic peptide

<400> SEQUENCE: 121

Arg Leu Tyr Arg
```

<210> SEQ ID NO 122
<211> LENGTH: 85
<212> TYPE: PRT
<213> ORGANISM: artificial construct
<220> FEATURE:
<223> OTHER INFORMATION: artificial construct

<400> SEQUENCE: 122

Met Gly Ile Met Gln Ile Phe Val Lys Thr Leu Thr Gly Lys Thr Ile
1               5                   10                  15

Thr Leu Glu Val Glu Pro Ser Asp Thr Ile Glu Asn Val Lys Ala Lys
            20                  25                  30

Ile Gln Asp Lys Glu Gly Ile Pro Pro Asp Gln Gln Arg Leu Ile Phe
        35                  40                  45

Ala Gly Lys Gln Leu Glu Asp Gly Arg Thr Leu Ser Asp Tyr Asn Ile
    50                  55                  60

Gln Lys Glu Ser Thr Leu His Leu Val Leu Arg Leu Arg Gly Gly His
65                  70                  75                  80

His His His His His
            85

<210> SEQ ID NO 123
<211> LENGTH: 260
<212> TYPE: PRT
<213> ORGANISM: artificial construct
<220> FEATURE:
<223> OTHER INFORMATION: artificial construct

<400> SEQUENCE: 123

Met Ile His His His His His His Ser Gly Val Asp Leu Gly Thr Glu
1               5                   10                  15

Asn Leu Tyr Phe Gln Ser Met Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
            85                  90                  95

Pro Asp His Met Lys Gln His Asp Phe Phe Lys Ser Ala Met Pro Glu
        100                 105                 110

Gly Tyr Val Gln Glu Arg Thr Ile Phe Phe Lys Asp Asp Gly Asn Tyr
    115                 120                 125

Lys Thr Arg Ala Glu Val Lys Phe Glu Gly Asp Thr Leu Val Asn Arg
130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
            165                 170                 175

Asp Lys Gln Lys Asn Gly Ile Lys Val Asn Phe Lys Ile Arg His Asn
        180                 185                 190

Ile Glu Asp Gly Ser Val Gln Leu Ala Asp His Tyr Gln Gln Asn Thr
    195                 200                 205

```
Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys
            260

<210> SEQ ID NO 124
<211> LENGTH: 89
<212> TYPE: PRT
<213> ORGANISM: artificial construct
<220> FEATURE:
<223> OTHER INFORMATION: artificial construct

<400> SEQUENCE: 124

Met Gly Ile Ser Gly Ser Gly Ser Gln Ile Phe Val Lys Thr Leu Thr
1               5                   10                  15

Gly Lys Thr Ile Thr Leu Glu Val Glu Pro Ser Asp Thr Ile Glu Asn
            20                  25                  30

Val Lys Ala Lys Ile Gln Asp Lys Glu Gly Ile Pro Pro Asp Gln Gln
        35                  40                  45

Arg Leu Ile Phe Ala Gly Lys Gln Leu Glu Asp Gly Arg Thr Leu Ser
    50                  55                  60

Asp Tyr Asn Ile Gln Lys Glu Ser Thr Leu His Leu Val Leu Arg Leu
65                  70                  75                  80

Arg Gly Gly His His His His His His
                85

<210> SEQ ID NO 125
<211> LENGTH: 8
<212> TYPE: PRT
<213> ORGANISM: artificial construct
<220> FEATURE:
<223> OTHER INFORMATION: synthetic peptide

<400> SEQUENCE: 125

Lys Ala Leu Val Ile Asn His Val
1               5

<210> SEQ ID NO 126
<211> LENGTH: 5
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (4)..(4)
<223> OTHER INFORMATION: Xaa is thio- or glycolic acid, His and Gly,
      respectively.

<400> SEQUENCE: 126

Tyr Lys Asn Xaa Val
1               5

<210> SEQ ID NO 127
<211> LENGTH: 9
<212> TYPE: PRT
<213> ORGANISM: artificial construct
<220> FEATURE:
<223> OTHER INFORMATION: synthesized peptide
```

```
<400> SEQUENCE: 127

Tyr Lys Asn Gly Ile Gly Gly Ile Arg
1               5

<210> SEQ ID NO 128
<211> LENGTH: 6
<212> TYPE: PRT
<213> ORGANISM: artificial construct
<220> FEATURE:
<223> OTHER INFORMATION: synthesized peptide

<400> SEQUENCE: 128

Leu Pro Glu Thr Gly Gly
1               5

<210> SEQ ID NO 129
<211> LENGTH: 7
<212> TYPE: PRT
<213> ORGANISM: artificial construct
<220> FEATURE:
<223> OTHER INFORMATION: synthesized peptide

<400> SEQUENCE: 129

Gly Ile Ser Gly Ser Gly Ser
1               5

<210> SEQ ID NO 130
<211> LENGTH: 7
<212> TYPE: PRT
<213> ORGANISM: artificial construct
<220> FEATURE:
<223> OTHER INFORMATION: synthesized peptide

<400> SEQUENCE: 130

Gly Gly Ser Gly Ser Gly Ser
1               5

<210> SEQ ID NO 131
<211> LENGTH: 8
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is Acetyl Arg
<220> FEATURE:
<221> NAME/KEY: MISC_FEATURE
<222> LOCATION: (8)..(8)
<223> OTHER INFORMATION: Xaa is  beta-Ala

<400> SEQUENCE: 131

Xaa Leu Tyr Arg Asn Arg Ile Xaa
1               5

<210> SEQ ID NO 132
<211> LENGTH: 14
<212> TYPE: PRT
<213> ORGANISM: artificial construct
<220> FEATURE:
<223> OTHER INFORMATION: synthesized peptide

<400> SEQUENCE: 132

Trp Arg Leu Tyr Arg Gly Arg Leu Tyr Arg Arg Asn His Val
1               5                   10
```

```
<210> SEQ ID NO 133
<211> LENGTH: 12
<212> TYPE: PRT
<213> ORGANISM: artificial construct
<220> FEATURE:
<223> OTHER INFORMATION: synthesized peptide

<400> SEQUENCE: 133

Trp Arg Leu Tyr Arg Gly Arg Leu Tyr Arg Arg Asn
1               5                   10

<210> SEQ ID NO 134
<211> LENGTH: 12
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is W which also forms a peptide bond with
      N at position 12
<220> FEATURE:
<221> NAME/KEY: MISC_FEATURE
<222> LOCATION: (12)..(12)
<223> OTHER INFORMATION: Xaa is N which also forms a peptide bond with W
      at position 1

<400> SEQUENCE: 134

Xaa Arg Leu Tyr Arg Gly Arg Leu Tyr Arg Arg Xaa
1               5                   10

<210> SEQ ID NO 135
<211> LENGTH: 12
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (12)..(12)
<223> OTHER INFORMATION: Xaa is ASN-OCH2(OH)CH2OH

<400> SEQUENCE: 135

Trp Arg Leu Tyr Arg Gly Arg Leu Tyr Arg Arg Xaa
1               5                   10

<210> SEQ ID NO 136
<211> LENGTH: 7
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (6)..(6)
<223> OTHER INFORMATION: Xaa ia Gly with -NH- being replaced by -S-.
<220> FEATURE:
<221> NAME/KEY: MISC_FEATURE
<222> LOCATION: (7)..(7)
<223> OTHER INFORMATION: Xaa is amidated Val.

<400> SEQUENCE: 136

Arg Tyr Arg Leu Asn Xaa Xaa
1               5

<210> SEQ ID NO 137
<211> LENGTH: 7
<212> TYPE: PRT
<213> ORGANISM: artificial construct
<220> FEATURE:
```

```
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is acetyl Arg.
<220> FEATURE:
<221> NAME/KEY: MISC_FEATURE
<222> LOCATION: (6)..(6)
<223> OTHER INFORMATION: Xaa is Gly with -NH- being replaced by -S-.
<220> FEATURE:
<221> NAME/KEY: MISC_FEATURE
<222> LOCATION: (7)..(7)
<223> OTHER INFORMATION: Xaa is amidated Val.

<400> SEQUENCE: 137

Xaa Tyr Arg Leu Asn Xaa Xaa
1               5

<210> SEQ ID NO 138
<211> LENGTH: 7
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is acetyl Arg.
<220> FEATURE:
<221> NAME/KEY: MISC_FEATURE
<222> LOCATION: (6)..(6)
<223> OTHER INFORMATION: Xaa is Gly with its -NH- being replaced with
      -S-.
<220> FEATURE:
<221> NAME/KEY: MISC_FEATURE
<222> LOCATION: (7)..(7)
<223> OTHER INFORMATION: Xaa is amidated Val.

<400> SEQUENCE: 138

Xaa Leu Tyr Arg Asn Xaa Xaa
1               5

<210> SEQ ID NO 139
<211> LENGTH: 4
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (4)..(4)
<223> OTHER INFORMATION: Xaa is amidated Arg.

<400> SEQUENCE: 139

Arg Leu Tyr Xaa
1

<210> SEQ ID NO 140
<211> LENGTH: 7
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (7)..(7)
<223> OTHER INFORMATION: Xaa is amidated Val.

<400> SEQUENCE: 140

Arg Tyr Arg Leu Asn His Xaa
1               5
```

```
<210> SEQ ID NO 141
<211> LENGTH: 16
<212> TYPE: PRT
<213> ORGANISM: artificial construct
<220> FEATURE:
<223> OTHER INFORMATION: synthesized peptide

<400> SEQUENCE: 141

Gly Arg Cys Thr Lys Ile Ser Pro Pro Ile Cys Phe Pro Asn His Val
1               5                   10                  15

<210> SEQ ID NO 142
<211> LENGTH: 7
<212> TYPE: PRT
<213> ORGANISM: artificial construct
<220> FEATURE:
<223> OTHER INFORMATION: synthesized peptide
<220> FEATURE:
<221> NAME/KEY: MISC_FEATURE
<222> LOCATION: (6)..(6)
<223> OTHER INFORMATION: Xaa is Gly with its -NH- being replaced by -S-.

<400> SEQUENCE: 142

Arg Tyr Arg Leu Asn Xaa Val
1               5
```